United States Patent
Nguyen et al.

(10) Patent No.: US 12,390,237 B2
(45) Date of Patent: *Aug. 19, 2025

(54) NEUROVASCULAR CLOT RETRIEVING SYSTEM

(71) Applicant: Cerebrova KP Medical, Inc., Irvine, CA (US)

(72) Inventors: Thanh Van Nguyen, Irvine, CA (US); Rajan Hansji, Irvine, CA (US); Duy Nguyen, Irvine, CA (US)

(73) Assignee: Cerebrova KP Medical, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 19/020,361

(22) Filed: Jan. 14, 2025

(65) Prior Publication Data

US 2025/0195095 A1 Jun. 19, 2025

Related U.S. Application Data

(63) Continuation of application No. 18/583,727, filed on Feb. 21, 2024, now Pat. No. 12,226,112.
(Continued)

(51) Int. Cl.
*A61B 17/221* (2006.01)
*A61B 17/00* (2006.01)

(52) U.S. Cl.
CPC .. *A61B 17/221* (2013.01); *A61B 2017/00778* (2013.01); *A61B 2017/00862* (2013.01); *A61B 2017/2212* (2013.01)

(58) Field of Classification Search
CPC ............ A61B 17/221; A61B 17/22031; A61B 2017/00778; A61B 2017/2212;
(Continued)

(56) References Cited

U.S. PATENT DOCUMENTS 3,506,011 A 4/1970 Silverman
4,727,873 A 3/1988 Mobin-Uddin
(Continued)

FOREIGN PATENT DOCUMENTS

CN 102036611 4/2011
CN 103841905 6/2014
(Continued)

OTHER PUBLICATIONS

US 8,668,714 B2, 03/2014, Cully et al. (withdrawn)
(Continued)

*Primary Examiner* — Kankindi Rwego
(74) *Attorney, Agent, or Firm* — Knobbe, Martens, Olson & Bear, LLP

(57) ABSTRACT

Various embodiments of devices and methods of use are provided. The device can include a catheter shaft having a proximal end and a distal end. The device can include an extractor. The extractor can include engagement panels located at a first longitudinal location and engagement panels located at a second longitudinal location. The extractor can include a spacer between engagement panels located at the first longitudinal location and engagement panels located at the second longitudinal location. The device can include a sheath, wherein the extractor comprises a collapsed state within the sheath for delivery and an expanded state within a blood vessel. In the expanded state, the engagement panels are configured to engage material between engagement panels located at a first longitudinal location and engagement panels located at a second longitudinal location.

20 Claims, 88 Drawing Sheets

Related U.S. Application Data

(60) Provisional application No. 63/617,321, filed on Jan. 3, 2024, provisional application No. 63/610,696, filed on Dec. 15, 2023.

(58) Field of Classification Search
CPC .... A61B 2017/2215; A61B 2017/2217; A61B 2017/22034; A61B 2017/22035
USPC .................................................. 606/127, 128
See application file for complete search history.

(56) References Cited

U.S. PATENT DOCUMENTS

| | | |
|---|---|---|
| 5,011,488 A | 4/1991 | Ginsburg |
| 5,102,415 A | 4/1992 | Guenther et al. |
| 5,135,484 A | 8/1992 | Wright |
| 5,846,251 A | 12/1998 | Hart |
| 5,868,708 A | 2/1999 | Hart |
| 5,895,398 A | 4/1999 | Wensel et al. |
| 5,935,139 A | 8/1999 | Bates |
| 5,947,985 A | 9/1999 | Imran |
| 6,036,720 A | 3/2000 | Abrams et al. |
| 6,066,149 A | 5/2000 | Samson et al. |
| 6,126,635 A | 10/2000 | Simpson et al. |
| 6,165,196 A | 12/2000 | Stack et al. |
| 6,179,859 B1 | 1/2001 | Bates et al. |
| 6,210,370 B1 | 4/2001 | Chi-Sing et al. |
| 6,221,006 B1 | 4/2001 | Dubrul et al. |
| 6,264,663 B1 | 7/2001 | Cano |
| 6,270,477 B1 | 8/2001 | Bagaoisan et al. |
| 6,319,242 B1 | 11/2001 | Patterson et al. |
| 6,391,044 B1 | 5/2002 | Yadav et al. |
| 6,432,122 B1 | 8/2002 | Gilson et al. |
| 6,458,139 B1 | 10/2002 | Palmer et al. |
| 6,569,181 B1 | 5/2003 | Burns |
| 6,605,102 B1 | 8/2003 | Mazzocchi et al. |
| 6,620,182 B1 | 9/2003 | Khosravi et al. |
| 6,635,070 B2 | 10/2003 | Leeflang et al. |
| 6,645,224 B2 | 11/2003 | Gilson et al. |
| 6,663,650 B2 | 12/2003 | Sepetka et al. |
| 6,824,545 B2 | 11/2004 | Sepetka et al. |
| 6,840,950 B2 | 1/2005 | Stanford et al. |
| 6,945,977 B2 | 9/2005 | Demarais et al. |
| 7,094,249 B1 | 8/2006 | Broome et al. |
| 7,179,273 B1 | 2/2007 | Palmer et al. |
| 7,220,271 B2 | 5/2007 | Clubb et al. |
| 7,232,432 B2 | 6/2007 | Fulton et al. |
| 7,491,210 B2 | 2/2009 | Dubrul et al. |
| 7,621,870 B2 | 11/2009 | Berrada et al. |
| 7,662,165 B2 | 2/2010 | Gilson et al. |
| 7,766,921 B2 | 8/2010 | Sepetka et al. |
| 7,780,696 B2 | 8/2010 | Daniel et al. |
| 7,785,342 B2 | 8/2010 | Gilson et al. |
| 7,901,426 B2 | 3/2011 | Gilson et al. |
| 7,914,549 B2 | 3/2011 | Morsi |
| 8,070,769 B2 | 12/2011 | Broome |
| 8,092,486 B2 | 1/2012 | Berrada et al. |
| 8,236,024 B2 | 8/2012 | Stanford et al. |
| 8,252,017 B2 | 8/2012 | Paul, Jr. et al. |
| 8,255,193 B2 | 8/2012 | Humphrey et al. |
| 8,298,252 B2 | 10/2012 | Krolik et al. |
| 8,313,503 B2 | 11/2012 | Cully et al. |
| 8,337,520 B2 | 12/2012 | Cully et al. |
| 8,361,095 B2 | 1/2013 | Osborne |
| 8,388,644 B2 | 3/2013 | Parker |
| 8,444,661 B2 | 5/2013 | Nair et al. |
| 8,460,335 B2 | 6/2013 | Carpenter |
| 8,475,487 B2 | 7/2013 | Bonnette et al. |
| 8,491,623 B2 | 7/2013 | Vogel et al. |
| 8,545,526 B2 | 10/2013 | Martin et al. |
| 8,613,717 B2 | 12/2013 | Aklog et al. |
| 8,657,849 B2 | 2/2014 | Parker |
| 8,696,622 B2 | 4/2014 | Fiorella |
| 8,734,374 B2 | 5/2014 | Aklog et al. |
| 8,771,289 B2 | 7/2014 | Mohiuddin et al. |
| 8,777,976 B2 | 7/2014 | Brady et al. |
| 8,795,305 B2 | 8/2014 | Martin et al. |
| 8,795,322 B2 | 8/2014 | Cully et al. |
| 8,801,748 B2 | 8/2014 | Martin |
| 8,864,792 B2 | 10/2014 | Eckhouse et al. |
| 8,919,389 B2 | 12/2014 | Gries |
| 8,926,642 B2 | 1/2015 | Nelson |
| 8,932,319 B2 | 1/2015 | Martin et al. |
| 8,948,848 B2 | 2/2015 | Merhi |
| 8,956,384 B2 | 2/2015 | Berrada et al. |
| 8,968,330 B2 | 3/2015 | Rosenbluth et al. |
| 8,998,944 B2 | 4/2015 | Thornton |
| 9,254,371 B2 | 2/2016 | Martin et al. |
| 9,283,066 B2 | 3/2016 | Hopkins et al. |
| 9,301,769 B2 | 4/2016 | Brady et al. |
| 9,308,007 B2 | 4/2016 | Cully et al. |
| 9,358,022 B2 | 6/2016 | Morsi |
| 9,398,946 B2 | 7/2016 | Valaie |
| 9,408,620 B2 | 8/2016 | Rosenbluth et al. |
| 9,427,244 B2 | 8/2016 | Lund-Clausen et al. |
| 9,463,036 B2 | 10/2016 | Brady et al. |
| 9,526,864 B2 | 12/2016 | Quick |
| 9,579,116 B1 | 2/2017 | Nguyen et al. |
| 9,636,206 B2 | 5/2017 | Nguyen et al. |
| 9,744,024 B2 | 8/2017 | Nguyen et al. |
| 9,844,386 B2 | 12/2017 | Nguyen et al. |
| 9,931,495 B2 | 4/2018 | Aboytes |
| 9,999,493 B2 | 6/2018 | Nguyen et al. |
| 10,045,790 B2 | 8/2018 | Cox et al. |
| 10,070,879 B2 | 9/2018 | Nguyen et al. |
| 10,076,347 B2 | 9/2018 | Sepetka et al. |
| 10,143,482 B2 | 12/2018 | Nguyen et al. |
| 10,238,482 B2 | 3/2019 | Nguyen et al. |
| 10,271,863 B2 | 4/2019 | Marks et al. |
| 10,292,723 B2 | 5/2019 | Brady |
| 10,314,600 B2 | 6/2019 | Morsi |
| 10,376,275 B2 | 8/2019 | Nguyen et al. |
| 10,456,236 B2 | 10/2019 | Nguyen et al. |
| 10,512,479 B2 | 12/2019 | Nguyen et al. |
| 10,517,708 B2 | 12/2019 | Gorochow |
| 10,660,645 B2 | 5/2020 | Allen et al. |
| 10,687,834 B2 | 6/2020 | Follmer et al. |
| 10,716,586 B2 | 7/2020 | Krolik et al. |
| 10,939,931 B2 | 3/2021 | Grandfield et al. |
| 11,090,057 B2 | 8/2021 | Allen et al. |
| 11,259,820 B2 | 3/2022 | Walzman |
| 11,471,175 B2 | 10/2022 | Nguyen et al. |
| 11,490,913 B2 | 11/2022 | Nguyen et al. |
| 11,504,150 B2 | 11/2022 | Marks et al. |
| 11,510,691 B2 | 11/2022 | Nguyen et al. |
| 11,793,531 B2 | 10/2023 | Nguyen et al. |
| 12,029,443 B2 | 7/2024 | Nguyen et al. |
| 12,226,112 B1 * | 2/2025 | Nguyen ............... A61B 17/221 |
| 2002/0095171 A1 | 7/2002 | Belef |
| 2002/0123765 A1 | 9/2002 | Sepetka et al. |
| 2002/0147458 A1 | 10/2002 | Hiblar et al. |
| 2002/0169474 A1 | 11/2002 | Kusleika et al. |
| 2003/0176884 A1 | 9/2003 | Berrada et al. |
| 2003/0216770 A1 | 11/2003 | Persidsky et al. |
| 2004/0039411 A1 | 2/2004 | Gilson et al. |
| 2004/0073198 A1 | 4/2004 | Gilson et al. |
| 2004/0087971 A1 | 5/2004 | Arnott |
| 2004/0098025 A1 | 5/2004 | Sepetka et al. |
| 2004/0098033 A1 | 5/2004 | Leeflang et al. |
| 2005/0085826 A1 | 4/2005 | Nair et al. |
| 2005/0085846 A1 | 4/2005 | Carrison et al. |
| 2006/0025804 A1 | 2/2006 | Krolik et al. |
| 2006/0155305 A1 | 7/2006 | Freudenthal et al. |
| 2006/0212062 A1 | 9/2006 | Farascioni |
| 2006/0282111 A1 | 12/2006 | Morsi |
| 2007/0010702 A1 | 1/2007 | Wang et al. |
| 2007/0088382 A1 | 4/2007 | Bei et al. |
| 2007/0093744 A1 | 4/2007 | Elmaleh |
| 2007/0112374 A1 | 5/2007 | Paul et al. |
| 2007/0191866 A1 | 8/2007 | Palmer et al. |
| 2007/0282303 A1 | 12/2007 | Nash et al. |
| 2008/0167678 A1 | 7/2008 | Morsi |
| 2008/0262487 A1 | 10/2008 | Wensel et al. |
| 2009/0292307 A1 | 11/2009 | Razack |

(56) References Cited

U.S. PATENT DOCUMENTS

| | | |
|---|---|---|
| 2010/0211095 A1 | 8/2010 | Carpenter |
| 2010/0249815 A1 | 9/2010 | Jantzen et al. |
| 2010/0268264 A1 | 10/2010 | Bonnette et al. |
| 2010/0268265 A1 | 10/2010 | Krolik et al. |
| 2011/0125181 A1 | 5/2011 | Brady et al. |
| 2011/0166586 A1 | 7/2011 | Sepetka et al. |
| 2011/0196414 A1 | 8/2011 | Porter et al. |
| 2012/0172915 A1 | 7/2012 | Fifer et al. |
| 2012/0197285 A1 | 8/2012 | Martin et al. |
| 2012/0271403 A1 | 10/2012 | Gries |
| 2012/0310251 A1 | 12/2012 | Sepetka et al. |
| 2012/0330346 A1 | 12/2012 | Frimerman |
| 2012/0330350 A1 | 12/2012 | Jones et al. |
| 2013/0102996 A1 | 4/2013 | Strauss |
| 2013/0144326 A1 | 6/2013 | Brady et al. |
| 2013/0178891 A1 | 7/2013 | Russell et al. |
| 2013/0184738 A1 | 7/2013 | Laroya et al. |
| 2013/0184741 A1 | 7/2013 | Laroya et al. |
| 2013/0197567 A1 | 8/2013 | Brady et al. |
| 2013/0238009 A9 | 9/2013 | Hopkins et al. |
| 2013/0267993 A1 | 10/2013 | Carpenter |
| 2013/0338703 A1 | 12/2013 | Hansen et al. |
| 2013/0345739 A1 | 12/2013 | Brady et al. |
| 2014/0005712 A1 | 1/2014 | Martin |
| 2014/0005717 A1 | 1/2014 | Martin et al. |
| 2014/0046358 A1 | 2/2014 | Cully et al. |
| 2014/0052103 A1 | 2/2014 | Cully et al. |
| 2014/0128894 A1 | 5/2014 | Sepetka et al. |
| 2014/0155908 A1 | 6/2014 | Rosenbluth et al. |
| 2014/0249566 A1 | 9/2014 | Quinn et al. |
| 2014/0249568 A1 | 9/2014 | Adams et al. |
| 2014/0276403 A1 | 9/2014 | Follmer et al. |
| 2014/0276922 A1 | 9/2014 | McLain et al. |
| 2014/0277013 A1 | 9/2014 | Sepetka et al. |
| 2014/0350593 A1 | 11/2014 | Laroya et al. |
| 2014/0371781 A1 | 12/2014 | Morgan |
| 2015/0005781 A1 | 1/2015 | Lund-Clausen et al. |
| 2015/0018929 A1 | 1/2015 | Martin et al. |
| 2015/0088190 A1 | 3/2015 | Jensen |
| 2015/0196380 A1 | 7/2015 | Berrada et al. |
| 2015/0265299 A1 | 9/2015 | Cooper et al. |
| 2015/0297251 A1 | 10/2015 | Sos |
| 2015/0306311 A1 | 10/2015 | Pinchuk et al. |
| 2016/0022290 A1 | 1/2016 | Johnson et al. |
| 2016/0022291 A1 | 1/2016 | Johnson et al. |
| 2016/0022292 A1 | 1/2016 | Stigall et al. |
| 2016/0038271 A1 | 2/2016 | Johnsen et al. |
| 2016/0113666 A1 | 4/2016 | Quick et al. |
| 2016/0143721 A1 | 5/2016 | Rosenbluth et al. |
| 2016/0192953 A1 | 7/2016 | Brady |
| 2016/0256180 A1 | 9/2016 | Vale et al. |
| 2017/0035445 A1 | 2/2017 | Nguyen et al. |
| 2017/0086960 A1 | 3/2017 | Nguyen et al. |
| 2017/0143359 A1 | 5/2017 | Nguyen et al. |
| 2017/0224366 A1 | 8/2017 | Nguyen et al. |
| 2017/0259042 A1 | 9/2017 | Nguyen et al. |
| 2018/0055619 A1 | 3/2018 | Nguyen et al. |
| 2018/0125512 A1 | 5/2018 | Nguyen et al. |
| 2018/0296315 A1 | 10/2018 | Nguyen et al. |
| 2019/0015122 A1 | 1/2019 | Nguyen et al. |
| 2019/0021750 A1* | 1/2019 | Heilman ............... A61B 17/221 |
| 2019/0099194 A1 | 4/2019 | Nguyen et al. |
| 2019/0142445 A1 | 5/2019 | Morsi |
| 2019/0216589 A1 | 7/2019 | Nguyen et al. |
| 2020/0029985 A1 | 1/2020 | Nguyen et al. |
| 2020/0197031 A1 | 6/2020 | Nguyen et al. |
| 2020/0222171 A1 | 7/2020 | Nguyen et al. |
| 2021/0128185 A1 | 5/2021 | Nguyen et al. |
| 2021/0307767 A1 | 10/2021 | Gifford, III et al. |
| 2023/0066304 A1 | 3/2023 | Nguyen et al. |
| 2023/0103647 A1 | 4/2023 | Nguyen et al. |
| 2023/0285040 A1 | 9/2023 | Cunniffe et al. |
| 2024/0032954 A1 | 2/2024 | Nguyen et al. |
| 2024/0173045 A1 | 5/2024 | Nguyen et al. |
| 2024/0293134 A1 | 9/2024 | Nguyen et al. |

FOREIGN PATENT DOCUMENTS

| | | |
|---|---|---|
| CN | 104042304 | 9/2014 |
| CN | 113440214 | 9/2021 |
| EP | 1221307 | 7/2002 |
| EP | 3 539 486 | 9/2019 |
| EP | 3 681 418 | 7/2020 |
| EP | 3 718 492 | 10/2020 |
| FR | 2 694 687 | 2/1994 |
| JP | 2011-508635 | 3/2011 |
| WO | WO 99/39648 | 8/1999 |
| WO | WO 02/36025 | 5/2002 |
| WO | WO 03/077799 | 9/2003 |
| WO | WO 2006/138391 | 12/2006 |
| WO | WO 2007/047818 | 4/2007 |
| WO | WO 2008/070996 | 6/2008 |
| WO | WO 2009/055782 | 4/2009 |
| WO | WO 2009/086482 | 7/2009 |
| WO | WO 2015079401 | 6/2015 |
| WO | WO 2017/024258 | 2/2017 |
| WO | WO 2018/148174 | 8/2018 |
| WO | WO 2021/092235 | 5/2021 |
| WO | WO 2022/236265 | 11/2022 |

OTHER PUBLICATIONS

Invitation to Pay Additional Fees dated May 20, 2024 in PCT/US2024/016740 in 3 pages.

Tendency Definition and Meaning Britannica Dictionary; 4 pages (2024).

International Search Report and Written Opinion in PCT/US2024/016740 dated Aug. 27, 2024; 29 pages.

* cited by examiner 110, 112, 114

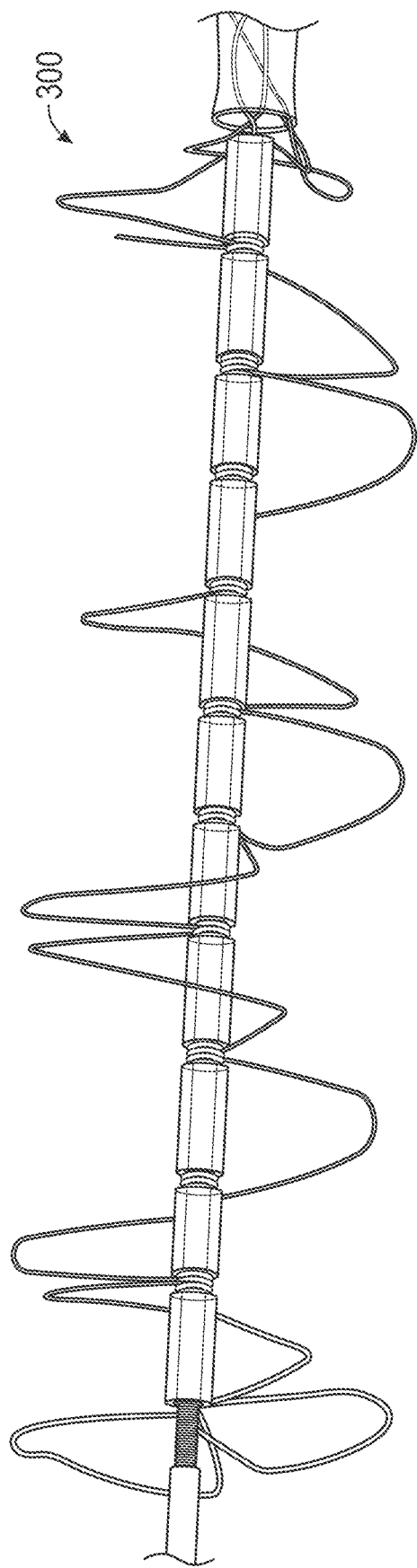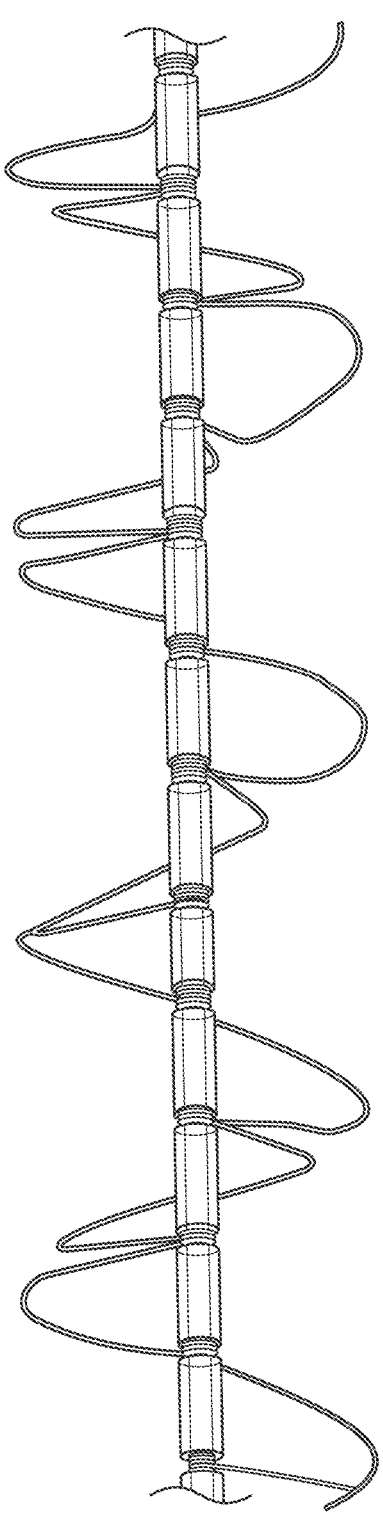
FIG. 40
FIG. 41

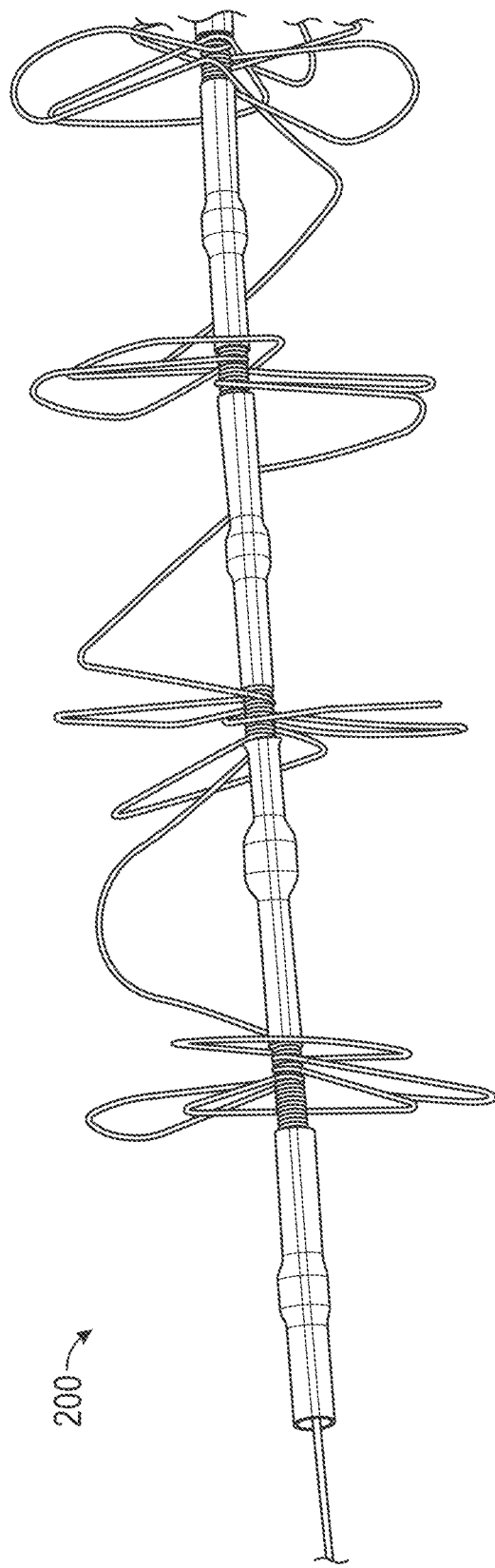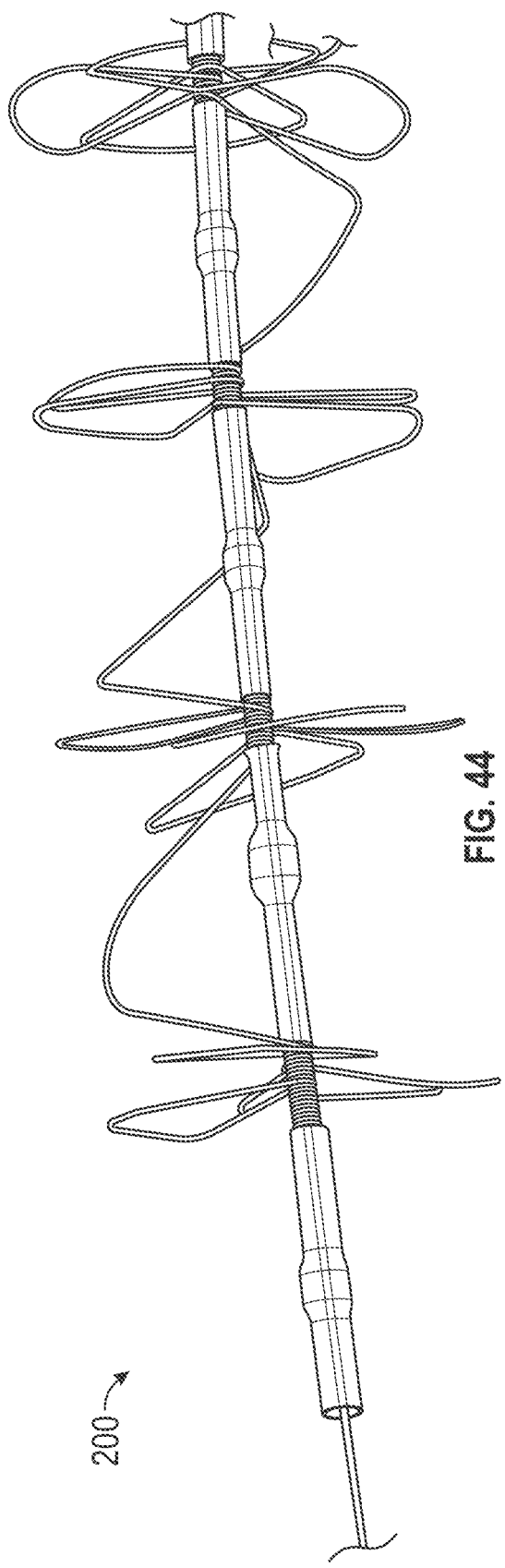

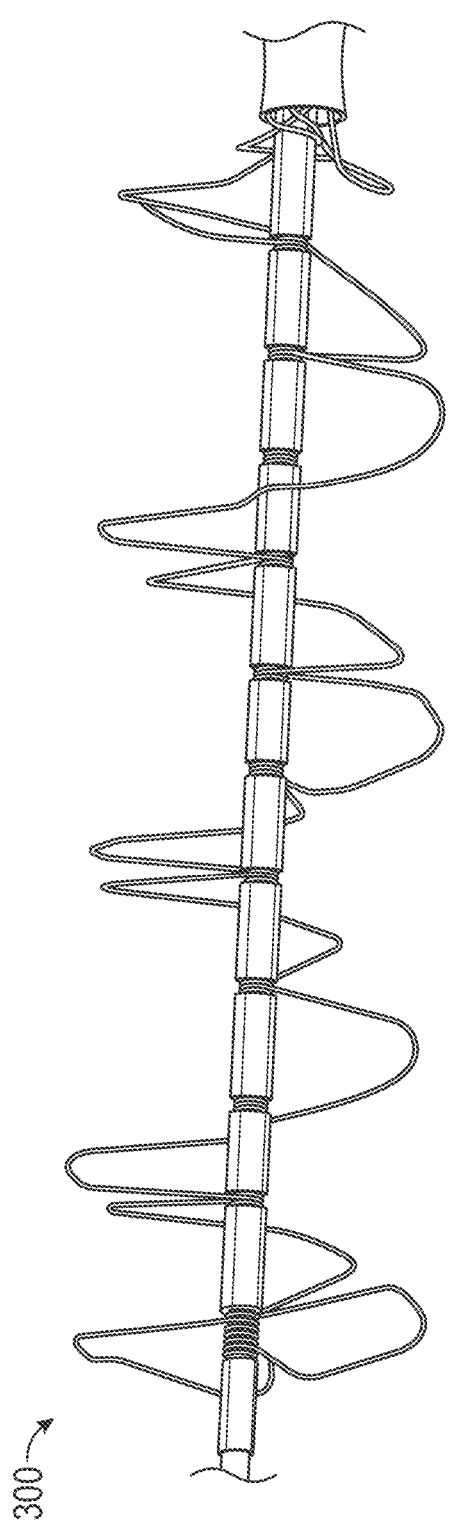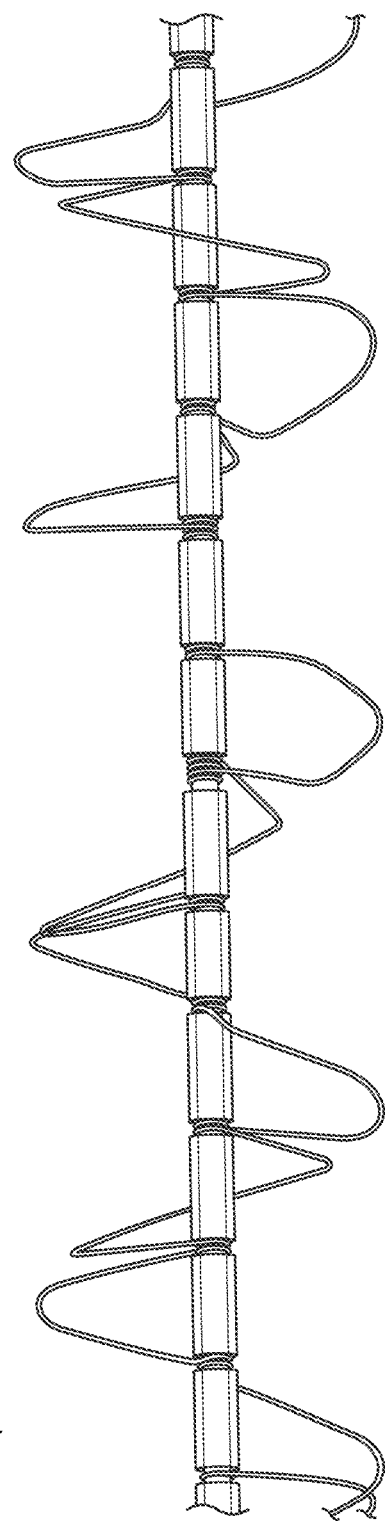
FIG. 48
FIG. 49

NEUROVASCULAR CLOT RETRIEVING SYSTEM

CROSS-REFERENCE TO RELATED APPLICATIONS

This application is a continuation of U.S. patent application Ser. No. 18/583,727, filed Feb. 21, 2024, which claims priority benefit to U.S. Provisional Patent Application No. 63/610,696, filed Dec. 15, 2023 and U.S. Provisional Patent Application No. 63/617,321, filed Jan. 3, 2024, the entirety of each is hereby incorporated by reference herein.

BACKGROUND

Field

Some embodiments described herein relate generally to systems and methods for removing a material, such as a blood clot, or foreign materials in the body and, in particular, to methods for treating a neurovascular embolism.

Description of the Related Art

Stroke is the third most common cause of death in the United States and the most disabling neurologic disorder. Approximately 700,000 patients suffer from stroke annually. Stroke is characterized by the acute onset of a neurological deficit that persists for at least 24 hours and is the result of a disturbance of the cerebral circulation. Stroke incidence increases with age. There are hemorrhagic stroke and ischemic stroke. Hemorrhagic stroke accounts for 20% of the stroke population and occurs due to rupture of an aneurysm or arteriovenous malformation bleeding into the brain tissue resulted in cerebral infarction. Ischemic stroke occurs in 80% of the population and is caused by occluded vessels that deprive the brain of oxygen-carrying blood. Ischemic strokes are caused by emboli that have dislodged from different areas of the body or from the cerebral vessels themselves to occlude in the narrow cerebral arteries more distally. Many such occlusions occur in the middle cerebral artery (MCA), although such is not the only site where emboli come to rest.

Traditionally, medical management of acute ischemic stroke consisted mainly of general supportive care. In 1996, the Food and Drug Administration approved the use of thrombolytic drug, tissue plasminogen activator (t-PA) for treating acute stroke. A randomized, double-blind trial, the National Institute of Neurological Disorders and t-PA Stroke Study, revealed a statistically significant improvement in stroke scale scores at 24 hours in the group of patients receiving intravenous t-PA within 3 hours of the onset of an ischemic stroke. Since the approval of t-PA, an emergency room physician could offer stroke patients an effective treatment besides supportive care.

However, treatment with systemic t-PA is associated with increased risk of intracerebral hemorrhage and other hemorrhagic complications. Patients treated with t-PA were more likely to sustain a symptomatic intracerebral hemorrhage during the first 36 hours of treatment. The frequency of symptomatic hemorrhage increases when t-PA is administered beyond 3 hours from the onset of a stroke. Besides the time constraint in using t-PA in acute ischemic stroke, other contraindications include for example if the patient has had a previous stroke or serious head trauma in the preceding 3 months, if the patient has a systolic blood pressure above 185 mmHg or diastolic blood pressure above 110 mmHg, if the patient requires aggressive treatment to reduce the blood pressure to the specified limits, if the patient is taking anticoagulants or has a propensity to hemorrhage, and/or if the patient has had a recent invasive surgical procedure. As a result, there is only a small percentage of stroke patients are qualified to receive t-PA.

Another treatment to remove the emboli is to mechanically remove the clot or emboli from the vessel. However, the need remains to effectively mechanically remove the clot, such as to completely remove the clot from the vessel. As such, the need remains to efficiently mechanically remove the clot, such as by requiring only a single pass with a clot remover. There are additional needs related to the small scale of the neurovascular vessels.

SUMMARY

Devices and methods are disclosed for treating vessels, including blood vessels and other body lumen other than blood vessels. In some embodiments, the devices and methods are tailored to neurovascular vessels. Currently, there are various stent retriever designs attempts to remove clot from the vessel. However, there are several disadvantages with the current stent retriever or mechanical removal devices. When conventional stent retriever deploys, the entire stent retriever has to deploy in order for the stent retriever to be effective. When deploying, the stent retriever is required to expand inside the clot to engage or secure into the clot. First, this requires time to expand which then prohibits immediate blood flow thus prevents immediate recanalization. Second, if the clot is tough or organized, the stent retriever may not have enough radial force to engage into the clot thereby preventing good engagement rendering the stent retriever ineffective. Another disadvantage is that once the stent retriever is deployed and allowed to engage into the clot, the stent retriever is then retracted or pulled proximally to remove the clot. During the retraction or pulling the stent retriever, the stent retriever tends to axially lengthen or elongate under tension thereby pulling away from the clot and therefore the stent retriever does not hold well onto the clot. As a result, it is required to have multiple passes to retrieve and remove the clot with the stent retriever. The multiple passes results in longer time to recanalization and reduces the potential for good clinical outcomes. The current stent retriever designs do not completely secure the clot when retrieving the clot due to the tension causing axially lengthening and the clot potentially releasing downstream emboli. Under tension, these stent retrievers axially lengthen and elongate allowing clot material to escape. Additionally, the current stent retrievers have high vessel surface area contact when the stent retriever is fully expanded. The outer surface of the stent-like structure of the stent retriever contacts the vessel wall and that contact can potentially cause vessel trauma during removing the stent retriever.

Specifically, the current mechanical thrombectomy designs such as stent retrievers used to remove the clot from the neurovascular system have several shortcomings. The stent retrievers when deployed require some time in order for the stent retriever to fully expand. This results in a longer time to restore blood flow. Once deployed, the stent retriever expands and should engage into the clot. However, full engagement with the clot is not always achieved. This engagement of the stent retriever can be achieved with soft acute clot. If there are organized tough clot, then the stent retriever is unable to engage the clot. Furthermore, when the stent retriever retracts proximally to remove the clot, the stent retriever has tendency to stretch or elongate. The stent elongation causes the stent retriever to reduce in diameter thereby pulling away from the clot and potentially disengaging from the clot, thus resulting in downstream emboli. The stent retrievers also have high surface contact to the vessel resulting in high friction force that can potentially cause trauma to the vessel wall.

Advantages of certain embodiments described herein include that the extractor can be effective when partially deployed. For instance, only a distal portion of the extractor can be deployed for smaller clots. The engagement panels at the first longitudinal location can be deployed, but engagement panels at another longitudinal location can remain collapsed. The extractor is effective whether engagement panels at one longitudinal location are deployed or engagement panels at a plurality of longitudinal locations are deployed. When deploying, the extractor can expand distal to the clot and the extractor can be pulled proximally to engage the clot. The extractor does not necessarily need to be expanded inside the clot to engage or secure into the clot. The deployment process of the extractor can save time compared to stent retrievers. Time is of the essence to restore blood flow. The extractor can allow immediate blood flow thus immediate recanalization, and in some cases, within about 120, 90, 60, 45, 40, 30, 20, 10 seconds or less, or ranges including any two of the aforementioned values. Further, the extractor is designed to have enough radial force to engage into tough or organized clot. The engagement panels can be supported in the radial direction. The engagement panels can be stacked. The radial force of the extractor allows good engagement rendering the extractor very effective. The extractor can be engaged with the clot and retracted or pulled proximally to remove the clot. During the retraction or pulling the extractor the extractor resists axially lengthening or elongating under tension. The extractor does not pull away from the clot when retracted and therefore holds onto the clot. The extractor may effectively remove the clot in a single pass. The single pass results in a shorter time to recanalization and increases the potential for good clinical outcomes. The extractor completely secures the clot when retrieving the clot due to the tension and thus reduces the risk that the clot releases downstream emboli. Under tension, the extractor does not axially lengthen and elongate in some cases. Additionally, the extractor has low vessel surface area contact when the engagement panels are fully expanded. The outer surface of the extractor minimally contacts the vessel wall which reduces the risk of vessel trauma during removing the extractor.

The extractor or engager has several advantages, including any number of the following. The extractor or engager when deployed requires little time in order for the extractor to fully expand. This resulted in a shorter time to restore blood flow. Once deployed, the extractor expands and engages into the clot or is pulled into engagement with the clot. The extractor can effectively capture soft acute clot. The extractor can effectively capture organized tough clot. The extractor can capture harder clots that the stent retriever is unable to engage. Furthermore, the extractor does not have a tendency to stretch or elongate. The extractor does not reduce in diameter when retracted. The engagement panels retain their shape when pulled. The engagement panels conform to the vessel wall while maintaining good clot engagement. In some embodiments, the diameter of the engagement panels does not change. In some embodiments, the diameter of the engagement panels conforms to the vessel wall. In some embodiments, the diameter of the engagement panels conforms to the vessel diameter. In some embodiments, the engagement panels are constrained for delivery and open within a vessel to conform to the vessel. The engagement panels can pass along the vessel wall without reducing in diameter. Thereby, the extractor has less tendency to pull away from the clot and potentially disengage from the clot. The extractor has less tendency to create downstream emboli. The extractor also has little surface contact with the vessel resulting in a low friction force that reduces the risk of trauma to the vessel wall. The extractor herein is able to deploy and is fully functional once deployed. Upon retraction of the extractor to remove clot, the engagement panels act independently and do not stretch or elongate under tension thus securing the clot during transit. The engagement panels also have minimal vessel surface contact which reduces the friction between the extractor and vessel, thereby potentially causing less vessel trauma. In some embodiments, the devices and methods completely remove a material from the vessel. In some embodiments, the devices and methods remove a material in a single pass. In some embodiments, the devices and methods can remove a material from other parts of the vascular system such as arterial disease, filtering chronic total occlusion, arteriovenous fistulas, deep vein thrombosis or pulmonary embolism.

In some embodiments, a device for removing material from a patient is provided. The device can include a catheter shaft. The device can include an extractor comprising engagement panels located at a first longitudinal location and engagement panels located at a second longitudinal location. In some embodiments, the extractor comprises a collapsed state for delivery and an expanded state within a blood vessel. In some embodiments, in the expanded state the engagement panels are configured to engage material between engagement panels located at a first longitudinal location and engagement panels located at a second longitudinal location.

In some embodiments, the extractor or engager is unitarily formed from one member. In some embodiments, the extractor can be formed from two or more members. In some embodiments, the member can be a wire. In some embodiments, the member can be solid, tubular and other geometric configurations such as flat ribbon and oval. In some embodiments, the extractor is unitarily formed from one member. In some embodiments, each engagement panel comprises two legs and an arc therebetween. In some embodiments, each engagement panel comprises an eyelet. In some embodiments, legs of the engagement panels at the first longitudinal location do not overlap. In some embodiments, legs of each engagement panels have a constant angle therebetween. In some embodiments, legs of each engagement panels have a different angle therebetween. In some embodiments, legs of each engagement panels extend straight and outwardly. In some embodiments, legs of each engagement panels can have any pattern. In some embodiments, legs of each engagement panels have a curve. In some embodiments, legs of each engagement panels are a zig zag. In some embodiments, each engagement panel comprises an eyelet to receive the catheter shaft. In some embodiments, engagement panels located at the first longitudinal location and engagement panels located at the second longitudinal location are moveable relative to the catheter shaft. In some embodiments, engagement panels located at the first longitudinal location and engagement panels located at the second longitudinal location are fixed relative to the catheter shaft. In some embodiments, engagement panels located at the first longitudinal location comprise three engagement panels. In some embodiments, engagement panels located at the first longitudinal location comprise four engagement panels. In some embodiments, the engagement panels located at the first longitudinal location comprise two engagement panels. In some embodiments, engagement panels located at the first longitudinal location comprise a single helical engagement panel. In some embodiments, engagement panels located at the first longitudinal location comprise a double helical engagement panel. In some embodiments, engagement panels located at the first longitudinal location comprise a plurality helical engagement panels. In some embodiments, the engagement panels initial expanded portion revert proximally when the engagement panels first deploy. In some embodiments, the engagement panels second expanded portion extend outward. In some embodiments, engagement panels located at the first longitudinal location comprise of five, six, seven or more engagement panels. In some embodiments, engagement panels have space between them. In some embodiments, engagement panels can be next to each other in series with no spacer (thereby minimal to no gap). In some embodiments, the engagement panels' initial expanded portion revert proximally when the engagement panels first deploy. In some embodiments, the engagement panels' second expanded portion extend outward. In some embodiments, engagement panels located at the first longitudinal location deploy simultaneously. In some embodiments, the extractor further comprises a spacer between engagement panels located at the first longitudinal location and engagement panels located at the second longitudinal location. In some embodiments, the spacer comprises a tube. In some embodiments, the spacer comprises a coil. In some embodiments, the spacer comprises a single ring or a plurality of rings. In some embodiments, the spacer is integrally formed with the engagement panels located at the first longitudinal location and engagement panels located at the second longitudinal location. In some embodiments, the spacer provides an open space between the engagement panels located at the first longitudinal location and engagement panels located at the second longitudinal location. In some embodiments, the spacer is movable relative to the catheter shaft. In some embodiments, the spacer is fixed relative to the catheter shaft. In some embodiments, engagement panels located at the first longitudinal location are configured to engage a clot while the engagement panels located at the second longitudinal location are collapsed. In some embodiments, engagement panels located at the first longitudinal location and engagement panels located at the second longitudinal location are configured to engage a clot while additional engagement panels are collapsed. In some embodiments, the device can include a connecting member between engagement panels located at the first longitudinal location and engagement panels located at the second longitudinal location. In some embodiments, the connecting member is radially offset from a central axis of the catheter shaft. In some embodiments, the catheter shaft is a core wire. In some embodiments, the core wire has a taper at the distal end. The core wire can be produced in the form of laser cut hypotube or any geometric configurations. In some embodiments, the engagement panels do not comprise sharp edges and are configured to be atraumatic with respect to the blood vessel. In some embodiments, a device for removing material from a patient, comprising any number of features as disclosed herein.

In some embodiments, a device for removing material from a patient is provided. The device can include a catheter shaft or core wire. The device can include an extractor comprising engagement panels located at a first longitudinal location and engagement panels located at a second longitudinal location. The device can include a sheath. In some embodiments, the extractor comprises a collapsed state within the sheath for delivery and an expanded state within a blood vessel. In some embodiments, in the expanded state the engagement panels are configured to engage material between engagement panels located at a first longitudinal location and engagement panels located at a second longitudinal location.

In some embodiments, engagement panels located at the first longitudinal location are configured to engage a clot while the engagement panels located at the second longitudinal location are collapsed within the sheath. In some embodiments, engagement panels located at the first longitudinal location and engagement panels located at the second longitudinal location are configured to engage a clot while additional engagement panels are collapsed within the sheath. In some embodiments, the engagement panels do not comprise sharp edges and are configured to be atraumatic with respect to the blood vessel. In some embodiments, the extractor further comprises a spacer between engagement panels located at the first longitudinal location and engagement panels located at the second longitudinal location.

In some embodiments, a device for removing material from a patient is provided. The device can include a catheter shaft or core wire. The device can include a distal member. The device can include an extractor comprising engagement panels located at a first longitudinal location and engagement panels located at a second longitudinal location. In some embodiments, the extractor further comprises an open space or spacer between engagement panels located at the first longitudinal location and engagement panels located at the second longitudinal location. In some embodiments, the distal member and the extractor comprise a collapsed state for delivery and an expanded state within a blood vessel. In some embodiments, in the expanded state the engagement panels are configured to engage material between engagement panels located at a first longitudinal location and engagement panels located at a second longitudinal location. The device can include a sheath. In some embodiments, the extractor comprises a collapsed state within the sheath for delivery and an expanded state within a blood vessel.

In some embodiments, engagement panels located at the first longitudinal location are configured to engage a clot while the engagement panels located at the second longitudinal location are collapsed within the sheath. In some embodiments, engagement panels located at the first longitudinal location and engagement panels located at the second longitudinal location are configured to engage a clot while additional engagement panels are collapsed within the sheath. In some embodiments, the extractor further comprises a spacer between engagement panels located at the first longitudinal location and engagement panels located at the second longitudinal location.

In some embodiments, a device for removing material from a patient is provided. The device can include a distal member. The device can include an extractor comprising engagement panels located at a first longitudinal location and engagement panels located at a second longitudinal location. In some embodiments, the distal member and the extractor comprise a collapsed state for delivery and an expanded state within a blood vessel. In some embodiments, in the expanded state the engagement panels are configured to engage material between engagement panels located at a first longitudinal location and engagement panels located at a second longitudinal location.

In some embodiments, the distal member is positioned distal, within, or proximal to the extractor. In some embodiments, the distal member is configured to straighten in the collapsed state. In some embodiments, the distal member is comprised of plurality of members. In some embodiments, the engagement panels located at the first longitudinal location form a relatively complete circle configured to be in contact with a vessel. In some embodiments, the engagement panels located at the first longitudinal location and the engagement panels are configured to have minimal surface contact with a vessel wall. In some embodiments, the engagement panels located at the first longitudinal location and the engagement panels are separated longitudinally by a connecting member. In some embodiments, the engagement panels located at the first longitudinal location are configured to expand without stretching or shortening.

In some embodiments, a device for removing material from a patient is provided. The device can include a distal member. The device can include an extractor comprising engagement panels located at a first longitudinal location and engagement panels located at a second longitudinal location. In some embodiments, the distal member and the extractor comprise a collapsed state for delivery and an expanded state within a blood vessel. In some embodiments, in the expanded state the engagement panels are configured to engage material between engagement panels located at a first longitudinal location and engagement panels located at a second longitudinal location.

In some embodiments, the distal member is positioned distal to the extractor. In some embodiments, the distal member is configured to collect loose clot, soft clot and/or in transit clot. In some embodiments, the distal member is configured to straighten in the collapsed state. In some embodiments, the distal member comprises a tubular portion and an expanded portion in the expanded state. In some embodiments, there are three or four engagement panels located at the first location. In some embodiments, there are three or four engagement panels located at the second location. In some embodiments, the engagement panels located at the first longitudinal location comprise a first eyelet and the engagement panels located at the second longitudinal location comprise a second eyelet. In some embodiments, the engagement panels located at the first longitudinal location are formed from a single wire. In some embodiments, the engagement panels located at the first longitudinal location and the engagement panels at the second longitudinal location are formed from a single wire. In some embodiments, the engagement panels located at the first longitudinal location form a relatively complete circle configured to be in contact with a vessel. In some embodiments, the engagement panels located at the first longitudinal location are configured to have minimal surface contact with a vessel wall. In some embodiments, the engagement panels located at the first longitudinal location and the engagement panels located at the second longitudinal location are configured to have minimal surface contact with a vessel wall. In some embodiments, the engagement panels located at the first longitudinal location and the engagement panels located at the second longitudinal location are configured to move relative to each other. In some embodiments, the engagement panels located at the first longitudinal location comprise pores radially inward from the perimeter of the engagement panels. In some embodiments, the engagement panels located at the first longitudinal location and the engagement panels located at the second longitudinal location are separated longitudinally by a connecting member. In some embodiments, the engagement panels located at the first longitudinal location are configured to expand without stretching or shortening. In some embodiments, the engagement panels located at the first longitudinal location are configured to radially expand to open. In some embodiments, the engagement panels located at the first longitudinal location comprise a double wire.

In some embodiments, a device for removing material from a patient is provided. The device can include a catheter shaft. The device can include an extractor comprising a first array of engagement panels located at a first longitudinal location and a second array of engagement panels located at a second longitudinal location. In some embodiments, the extractor further comprises a spacer between the first array of engagement panels located at the first longitudinal location and the second array engagement panels located at the second longitudinal location. In some embodiments, the extractor comprises a collapsed state for delivery and an expanded state within a blood vessel. In some embodiments, in the expanded state the engagement panels are configured to engage material between the first array of engagement panels located at the first longitudinal location and the second array of engagement panels located at the second longitudinal location.

In some embodiments, the first array of engagement panels comprises a first engagement panel and a second engagement panel operably coupled to the catheter shaft, wherein the first engagement panel and the second engagement panel are configured to at least partially contact each other when the extractor is in the expanded state. In some embodiments, the second array of engagement panels comprises a first engagement panel and a second engagement panel operably coupled to the catheter shaft, wherein the first engagement panel and the second engagement panel are configured to at least partially contact each other when the extractor is in the expanded state. In some embodiments, the first array of engagement panels comprises at least four engagement panels. In some embodiments, the second array of engagement panels comprises at least four engagement panels.

In some embodiments, the device can include a distal member. In some embodiments, the catheter shaft comprises a plurality of segments. In some embodiments, the plurality of segments of the catheter shaft are operably connected via a sleeve connector. In some embodiments, each of the arrays of engagement panels comprises at least one radiopaque marker. In some embodiments, the at least one radiopaque marker is operably connected to a leg of an engagement panel. In some embodiments, the at least one radiopaque marker is operably connected to an arc of an engagement panel. In some embodiments, the engagement panels do not comprise sharp edges and are configured to be atraumatic with respect to the blood vessel.

In some embodiments, a method of removing a thrombus from a target cerebral blood vessel is provided. The method can include deploying a guidewire into an access vessel. The method can include advancing the guidewire into the target cerebral blood vessel and across the thrombus. The method can include advancing a catheter across the thrombus. In some embodiments, the catheter houses an extractor comprising a first array of engagement panels located at a first longitudinal location and a second array of engagement panels located at a second longitudinal location. The method can include deploying at least a portion of the extractor such that the first array of engagement panels is positioned distal to the thrombus and the second array of engagement panels is positioned within the thrombus or proximal to the thrombus. The method can include withdrawing the extractor from the target cerebral vessel, thereby capturing at least a portion of the thrombus.

In some embodiments, the extractor further comprises a spacer or free space between the first array of engagement panels location at the first longitudinal location and the second array engagement panels located at the second longitudinal location. In some embodiments, the second array of engagement panels located at the second longitudinal location are configured to engage the thrombus while additional engagement panels are collapsed. In some embodiments, the thrombus is located within the middle cerebral artery. In some embodiments, as the catheter is retracted proximally, the first array of engagement panels revert proximally. In some embodiments, as the catheter is retracted proximally, the first array of engagement panels move outward until the engagement panels are relatively aligned with a respective eyelet. In some embodiments, as the catheter is retracted proximally, the first array of engagement panels expand to the diameter of the target cerebral blood vessel.

In some embodiments, the extractor or engager is unitarily formed from one member. In some embodiments, the extractor can be formed from two or more members. In some embodiments, the extractor can be formed of two or more elongated members. In some embodiments, the member can be a wire. In some embodiments, the member can be a single wire. In some embodiments, the member can be a double wire. In some embodiments, the member can be a triple wire. In some embodiments, the elongate members are side-by-side. In some embodiments, the elongated members are twisted or woven. In some embodiments, the wire can be made of solid super elastic nitinol wire. In some embodiments, the wire can be made of DFT wire (drawing filled tubing) Nitinol with platinum core. In some embodiments, the member can be solid, tubular, and other geometric configurations such as flat ribbon and oval. In some embodiments, each engagement panel comprises two legs and an arc therebetween. In some embodiments, each engagement panel comprises an eyelet. In some embodiments, legs of the engagement panels at the first longitudinal location do not overlap. In some embodiments, legs of each engagement panels have a constant angle therebetween. In some embodiments, legs of each engagement panels have a different angle therebetween. In some embodiments, legs of each engagement panels extend straight and outwardly. In some embodiments, legs of each engagement panels can have any pattern. In some embodiments, legs of each engagement panels have a curve. In some embodiments, the panel has radiopaque marker bands. In some embodiments, the radiopaque marker band is a coil. The marker bands can be made of platinum/iridium tube or coils. In some embodiments, the radiopaque marker band is cylindrical or circular. In some embodiments, there is one marker band. In some embodiments, there are a plurality of marker bands. In some embodiment, there is one or more marker bands along the length of the distal end of the catheter. In some embodiment, there is one or more marker bands along the length of the proximal end of the catheter. In some embodiments, legs of each engagement panels are a zig zag. In some embodiments, the engagement panels at each longitudinal location comprises an eyelet to receive the catheter shaft. In some embodiments, the engagement panels located at the first longitudinal location and the engagement panels located at the second longitudinal location are moveable relative to the catheter shaft. In some embodiments, the engagement panels located at the first longitudinal location and the engagement panels located at the second longitudinal location are fixed relative to the catheter shaft. In some embodiments, the engagement panels located at the first longitudinal location comprise three engagement panels. In some embodiments, the engagement panels located at the first longitudinal location comprise four engagement panels. In some embodiments, the engagement panels located at the first longitudinal location comprise a single helical engagement panel. In some embodiments, the engagement panels located at the first longitudinal location comprise a double helical engagement panel. In some embodiments, the engagement panels located at the first longitudinal location comprise a plurality helical engagement panels.

In some embodiments, an initial expanded portion of engagement panels revert proximally when the engagement panels first deploy. In some embodiments, a second expanded portion of engagement panels extend outward. In some embodiments, the arcs of the engagement panels at the first longitudinal location are in a first, constrained position where the arcs of the engagement panels are distal to the eyelet at the first longitudinal location. The arcs of the engagement panels can be folded downward toward the catheter shaft or core wire. The arcs of the engagement panels can lie down. The arcs of the engagement panels can be coaxial with the catheter shaft or core wire. The arcs of the engagement panels can extend distally. The arcs of the engagement panels can extend toward the distal member. The arcs of the engagement panels can be within a loading tube assembly or microcatheter in in the first, constrained position. In some embodiments, the arcs of the engagement panels at the second longitudinal location are in the first, constrained position where the arcs of the engagement panels are distal to the eyelet at the second longitudinal location. In some embodiments, the arcs of the engagement panels at the third longitudinal location are in the first, constrained position where the arcs of the engagement panels are distal to the eyelet at the third longitudinal location. The engagement panels at the first longitudinal location and the second longitudinal location can fold in the same direction, such as distally. The engagement panels at the second longitudinal location and the third longitudinal location can fold in the same direction, such as distally. The engagement panels at the first longitudinal location and the third longitudinal location can fold in the same direction, such as distally. The engagement panels at the first longitudinal location and the second longitudinal location can fold in opposite directions, such as distally for the engagement panels at the first longitudinal location and proximally for the engagement panels at the second longitudinal location. The engagement panels at the second longitudinal location and the third longitudinal location can fold in opposite directions, such as distally for the engagement panels at the second longitudinal location and proximally for the engagement panels at the third longitudinal location. The engagement panels at the first longitudinal location and the third longitudinal location can fold in opposite directions, such as distally for the engagement panels at the first longitudinal location and proximally for the engagement panels at the third longitudinal location.

In some embodiments, the arcs of the engagement panels at the first longitudinal location are in the second, expanded position where the arcs revert proximally and outwardly. The arcs of the engagement panels at the first longitudinal location can be relatively inline with the eyelet at the first longitudinal location. The arcs of the engagement panels can be substantially perpendicular to the catheter shaft or core wire. The arcs of the engagement panels can be radially outward from the eyelet. The arcs of the engagement panels can be substantially perpendicular to the eyelet. The arcs of the engagement panels can extend to the vessel wall. The arcs of the engagement panels can extend can expand to the diameter of the vessel. The arcs of the engagement panels can be distal to a loading tube assembly or microcatheter in the second, expanded position. In some methods, reverting from the first, constrained position to the second, expanded position will scrap along the vessel wall and/or grab the material as the engagement panels move from the first, constrained position to the second, expanded position. In some embodiments, the legs of the engagement panels at the first longitudinal location are next to each other along the length of the catheter or core wire in the first, constrained position. The legs of the engagement panels are folded inward along the catheter or core wire. The legs of the engagement panels can lie down. In some embodiments, the legs of the engagement panels at the first longitudinal location are farther apart in the second, expanded position. The legs of the engagement panels extend outward from the respective eyelet in the second, expanded position.

For example, the arc of the engagement panels initially expands proximally, where the arc portions of the engagement panels move proximally or revert proximally as the loading tube assembly or microcatheter or delivery catheter is retracted. Reverting the arcs of the engagement panels proximally will allow the engagement panels to capture and secure the clot better. As the delivery catheter is further retracted, the legs of the engagement panels extends outward in the second, expanded position. In some embodiments, the engagement panels located at the first longitudinal location comprise of two, three, four, five, six, seven, eight, nine, ten, or more engagement panels.

In some embodiments, the engagement panels have space between them. In some embodiments, the engagement panels can be next to each other in series with no spacer (thereby minimal to no gap). In some embodiments, the engagement panels located at the first longitudinal location deploy simultaneously. In some embodiments, the engagement panels located at the first longitudinal location deploy independently. In some embodiments, the engagement panels located at the first longitudinal location deploy sequentially. In some embodiments, the eyelet of the engagement panels is stacked together with no gap. The elongate member or wire forms a portion of the eyelet, the leg of the first engagement panel at the first longitudinal location, the arc of the first engagement panel, and the leg of the first engagement panel. Then, with little to no gap, the elongate member forms a portion of the eyelet, the leg of the second engagement panel at the first longitudinal location, the arc of the second engagement panel, and the leg of the second engagement panel. Then, with little to no gap, the elongate member can form additional engagement panels at the first longitudinal location. The eyelet can be formed such that the engagement panels at the first longitudinal location deploy together or substantially together from the first, constrained position to the second, expanded position. In some embodiments, the eyelet of the engagement panels has a gap so that the engagement panels at the first longitudinal location deploy independently. The elongate member or wire forms a portion of the eyelet, the leg of the first engagement panel at the first longitudinal location, the arc of the first engagement panel, and the leg of the first engagement panel. Then, in some embodiments, the elongate member can form multiple coils to form a gap. Then, after the gap, the elongate member forms a portion of the eyelet, the leg of the second engagement panel at the first longitudinal location, the arc of the second engagement panel, and the leg of the second engagement panel. Then, with additional gaps therebetween, the elongate member can form additional engagement panels at the first longitudinal location. The eyelet can be formed such that the engagement panels at the first longitudinal location deploy independently from the first, constrained position to the second, expanded position. The eyelet can be formed such that the engagement panels at the first longitudinal location deploy sequentially from the first, constrained position to the second, expanded position. In some embodiments, the engagement panels located at the first longitudinal location and the engagement panels at the second longitudinal location deploy independently. In some embodiments, the engagement panels located at the first longitudinal location and the engagement panels at the second longitudinal location deploy sequentially.

In some embodiments, the extractor includes a spacer between the engagement panels at the first longitudinal location and the engagement panels at the second longitudinal location. In some embodiments, the spacer comprises a tube. In some embodiments, the spacer comprises a coil. In some embodiments, the spacer is located between the engagement panels at the first longitudinal location and the engagement panels at the second longitudinal location. In some embodiments, the spacer is continuous with the eyelets. In some embodiments, the spacer is integrally formed with the engagement panels located at the first longitudinal location and the engagement panels located at the second longitudinal location. In some embodiments, the spacer provides an open space between the engagement panels located at the first longitudinal location and the engagement panels located at the second longitudinal location. In some embodiments, the engagement panels located at the first longitudinal location are configured to engage a clot while the engagement panels located at the second longitudinal location are collapsed. In some embodiments, the engagement panels located at the first longitudinal location and the engagement panels located at the second longitudinal location are configured to engage a clot while additional engagement panels are collapsed. In some embodiments, the device can include a connecting member between the engagement panels located at the first longitudinal location and the engagement panels located at the second longitudinal location. In some embodiments, the spacer is movable relative to the catheter shaft. In some embodiments, the spacer is fixed relative to the catheter shaft. In some embodiments, the catheter shaft is a core wire. In some embodiments, the core wire has a taper at the distal end. In some embodiments, the core wire can be produced in the form of laser cut hypotube or any geometric configurations. In some embodiment, the extractor includes a distal member or distal plug. The distal member is positioned distal to the extractor to collect loose clot, soft clot and/or in transit clot.

In some embodiments, a device for removing material from a patient is provided. The device can include a catheter shaft or core wire. The device can include an extractor comprising engagement panels located at a first longitudinal location and engagement panels located at a second longitudinal location. In some embodiments, the extractor further comprises a spacer between engagement panels located at the first longitudinal location and engagement panels located at the second longitudinal location. The device can include a distal member. The device can include a loading tube or sheath or a tubular member. In some embodiments, the extractor comprises a collapsed state within the sheath or tubular member for delivery and an expanded state within a blood vessel. In some embodiments, in the expanded state the engagement panels are configured to engage material between engagement panels located at a first longitudinal location and engagement panels located at a second longitudinal location.

In some embodiments, engagement panels located at the first longitudinal location are configured to engage a clot while the engagement panels located at the second longitudinal location are collapsed within the sheath or tubular member. In some embodiments, engagement panels located at the first longitudinal location and engagement panels located at the second longitudinal location are configured to engage a clot while additional engagement panels are collapsed within the sheath or tubular member. In some embodiments, the extractor further comprises a spacer between engagement panels located at the first longitudinal location and engagement panels located at the second longitudinal location. In some embodiments, systems and methods as disclosed herein can include any number of the following advantages. In some embodiments, clots or other unwanted material within a body lumen can be removed without requiring deployment, expansion, and/or unsheathing of the entire length of the extractor as sets of engagement panels can act independently relative to other sets of engagement panels. In some embodiments, the atraumatic sets of engagement panels can control clot removal by pinching or otherwise exerting forces, such as axial forces, between adjacent sets of longitudinally spaced-apart engagement panels. In some embodiments, the spacer between engagement panels can control the distance and force exerted between adjacent sets of longitudinally spaced-apart engagement panels. In some embodiments, the engagement panels can be integrally formed from a single wire, a single material and/or a tubular member for improved durability and manufacturing. In some embodiments, each engagement panel forms a perimeter surrounding a free space or pore devoid of material. The pore advantageously reduces size and weight of the extractor and improves maneuverability of the extractor without adversely affecting control of clot removal. In some embodiments, each set of engagement panels are operably connected to each other with one or more connecting elements. The connecting elements can be discrete from and radially offset from the catheter or core wire. The arrangement of the connecting elements can further modulate actuation between adjacent sets of engagement panels while still allowing each set of engagement panels to act independently of one another. In some embodiments, one or more of the engagement panels have radiopaque markers or material to improve visualization. In some embodiments, the engagement panel has a distal member to prevent clot distal migration. In some embodiments, the engagement panels can be adjusted at the proximal ends to increase the space or opening between the engagement panels at the first and second longitudinal locations or decrease the space or opening between the engagement panels at the first and second longitudinal locations. In some embodiments, a system, device, or method can include any number of features as disclosed herein. In some embodiments, a system, device, or method does not comprise one or more features disclosed herein.

BRIEF DESCRIPTION OF THE DRAWINGS

The structure and method of use will be better understood with the following detailed description of embodiments, along with the accompanying illustrations, in which:

FIGS. 40-42 are views of the third embodiment of the helical engagement panel extractor with spacer in between the engagement panel.

FIGS. 43-44 are view of the second embodiment of the four engagement panel extractor with spacer in between the engagement panels and eyelets.

FIGS. 48-52 are views of the third embodiment of the helical engagement panel extractor with spacers between the engagement panels and eyelets.

DETAILED DESCRIPTION

Figure 1:
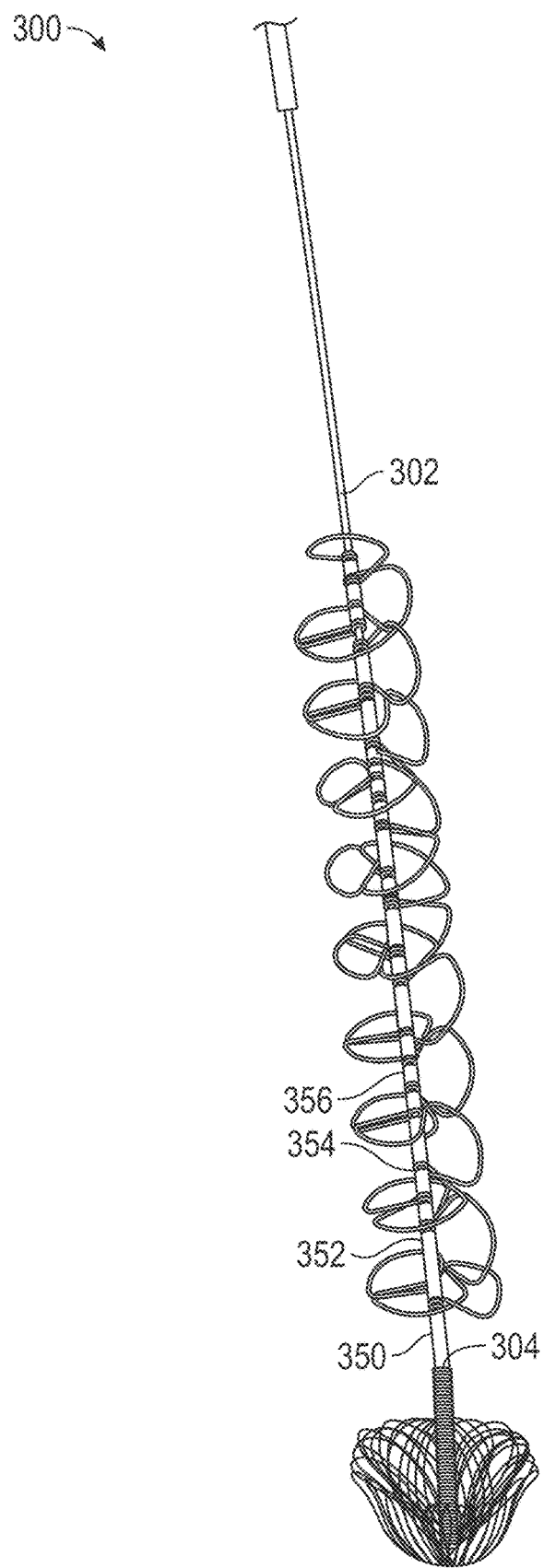
FIG. 1 is a side view of an embodiment of a helical engagement panel extractor.

Mechanical therapies can be provided such as capturing and removing a clot or emboli, dissolving the clot, disrupting and suctioning the clot, and/or creating a flow channel through the clot. The MERCI Retriever System was one of the first mechanical devices developed for stroke treatment. The retriever consists of a wire with a helical coil formed at the distal end. For the procedure, a guide catheter with a balloon at the tip is placed in the internal carotid artery (ICA). A microcatheter is threaded through the balloon guide catheter and used to introduce the MERCI retriever across the clot. The microcatheter is then pulled back to deploy the retriever around the clot or emboli. The microcatheter and retriever are then pulled back together, along with the clot or emboli, into the balloon guide catheter. The balloon of the guide catheter is inflated, and a syringe is connected to the balloon guide catheter to aspirate the guide catheter while the clot or emboli are inside the guide catheter. There remains a need for mechanical systems to retrieve clots. Some systems and methods do not include any balloon members.

Physicians currently perform thrombectomies with new generation stent retrievers to resolve ischemic stroke. Stent retrievers can be stent-like devices to capture material. Generally, the physician deploys the stent retriever into the clot to engage within the clot. The physician then withdraws the stent retriever while it is expanded against and engaging within the clot. The physician must be able to withdraw the clot through the vasculature into a guide catheter positioned within vessels. Even in successful procedures, a physician's objective is to prevent the vessel wall or lumen from experiencing trauma. The physician also desirably prevents dislodging the clot or emboli as the stent retriever passes through the vasculature when removing the stent retriever. Another risk in such a procedure is that the clot or emboli can break free from the stent retriever and lodge in smaller downstream vessels causing more concern than the original blockage. If the clot or emboli breaks free from the device and flows downstream, the loose clot or emboli may become trapped in smaller and more tortuous vessels. This will be difficult for the physician to use the same stent retriever device to again remove the clot because the device may be too large in the new obstruction location. There remain some disadvantages using this approach. There remains a need for better mechanical systems to retrieve clots.

One challenge with designing clot or emboli removal devices is the nature of the neurovascular vasculature around the clot or emboli. The neurovascular vasculature system is fragile and delicate. Neurovascular vessels are more fragile than similarly sized vessels in other parts of the body. Applying excessive force to these vessels could result in perforations and hemorrhage. Another challenge is the wide range of clot composition and morphologies. More mature and organized subacute clot material is less compressible than softer, fresher acute clot. In some instances, the organized clot is tightly wedged in the blood vessel due to the flow of blood and pressure exerted onto the clot or emboli. This further causes additional difficulties and challenges for retriever devices, such as for extraction and aspiration devices, to pull the clot or emboli away. Aspiration may require additional suction pressure which tends to be not effective with small bore catheters. Extraction devices, like the stent retriever, may have shortcomings since the radial force may not be high enough to engage or grab the clot securely especially if the clot is robust and organized. In situations where the clot is more organized, the stent retriever device may tend to slide against the vessel wall and not engage the clot or emboli. With the higher radial force produced by the stent retriever device, there is a risk of extending the vessel causing further difficulty retrieving the clot and potentially creating vessel trauma. Additionally, during retraction of the stent retriever device, the radial force exerted on the vessel wall causes the vessel perforators to extend and potentially cause vessel damage and hemorrhage. Thus, the current devices are typically not suited for material removal in the neurovascular vasculature.

Current devices include stent retrievers, stent-like devices, that are being used to remove clots. Stent retrievers are self-expanding devices attached to the end of a long catheter shaft, which are advanced through a microcatheter and deployed across clot obstructions to engage and remove the clot.

One disadvantage of some stent retrievers is that they can mainly rely on an outward radial force to retain and grip on the clot. If the radial force is too low, then the stent retrievers is unable to encapsulate or engage the clot radially, particularly when the clot is tough and/or organized. The stent retrievers may lose their grip on the clot. If the radial force is too high, then the stent retrievers can damage the vessel wall and also the stent retrievers may require excessive force to withdraw or pull the stent retrievers from the vessel. The stent retrievers that apply sufficient radial force to deal with all clot types may cause vessel trauma and the stent retrievers that have low radial force to remain atraumatic may not effectively retrieve all clot types. Furthermore, during retraction of the stent retriever through tortuous anatomy, the stent retriever will axially lengthen or elongate, and this stretching causes the stent retriever diameter to reduce in size thereby pulling away from the clot and causing potential emboli.

Another potential disadvantage with some stent retrievers is with the pinning mechanism itself. The stent retrievers that rely exclusively on pinning clots against a vessel wall may not restrain the clot effectively when retrieving the clot, passing a branch vessel or when passing into a vessel that is larger than the fully expanded diameter of the stent retrievers.

Another disadvantage with the stent retrievers is the lack of distal protection. During retrieval, the stent retrievers may have potential clot fragments that are released downstream into smaller vessel causing further damage.

Another potential disadvantage is that the stent retriever may not sufficiently retain the clot as it pulls the clot to the catheter. In such a case, some or all of the clot or emboli might remain in the vasculature. As the stent retriever moves the clot, the clot might not adhere to the stent retriever as the stent retriever is withdrawn. Even if the clot is successfully withdrawn to the tip of the guide catheter, the clot may be sheared from the stent retriever as the stent retriever is retrieved along with the clot into the guide catheter. Withdrawing the expanded stent retriever, either fully or partially expanded, by itself can result in undesired trauma to the vessel. In most cases, since the stent retriever is oversized compared to the vessel, dragging a fixed metallic structure can pull the arteries and/or strip the inner lining of the vessel causing further trauma such as a hemorrhagic stroke or leakage of blood from a cerebral vessel. The stent retriever can get stuck on plaque on the vessel walls resulting in further vascular damage.

Another potential disadvantage is that the stent retriever axially lengthen or elongates and stretches under tension. Specifically, when the stent retriever is retracted to capture the clot, the stent retriever tends to axially lengthen or elongate and stretch due to the tension exerted onto the stent retriever. The tension will cause the stent retriever to axially lengthen and reduce its diameter and cause the stent retriever to release or pull away from the clot. This will potentially loosen the grip of the stent retriever on the clot and allow the clot to dislodge.

Another potential disadvantage are concerns about dislodged or fragmented clot. The migration of dislodged fragments can increase the time of the procedure. During a procedure, restoration of blood flow is critical. Furthermore, a physician might be unaware of one or more fragments that dislodge from the initial obstruction and cause blockage of smaller more distal vessels.

While utilizing mechanical thrombectomy may lead to clot removal, there are several potential risks and disadvantages. There is a high occurrence of patients that do not achieved adequate reperfusion after the first pass through the vessel due to the clot not being retrieved completely. This is due to the structural and functional disadvantages of many existing and previous stent retrievers. There is a need for, among other things, an improved retriever device that can improve the grip on, or otherwise effectively control the removal of an occlusive clot without necessarily increasing the outward radial force on the clot, thereby protecting the surrounding vasculature. Some embodiments described herein address one, two, or more of the shortcomings and disadvantages of the stent retrievers.

Although certain embodiments and examples are disclosed below, it will be understood by those in the art that the disclosure extends beyond the specifically disclosed embodiments and/or uses of the invention and obvious modifications and equivalents thereof. Thus, it is intended that the scope should not be limited by the particular disclosed embodiments described herein.

The systems and methods described herein relate, for example, to embodiments of extractors. The methods can include treating a body lumen, such as a vessel, such as a neurovascular vessel. The methods can include expanding the extractor within a vessel to capture material, such as clot or emboli. The extractors can have several advantages over stent retrievers.

Figure 2:
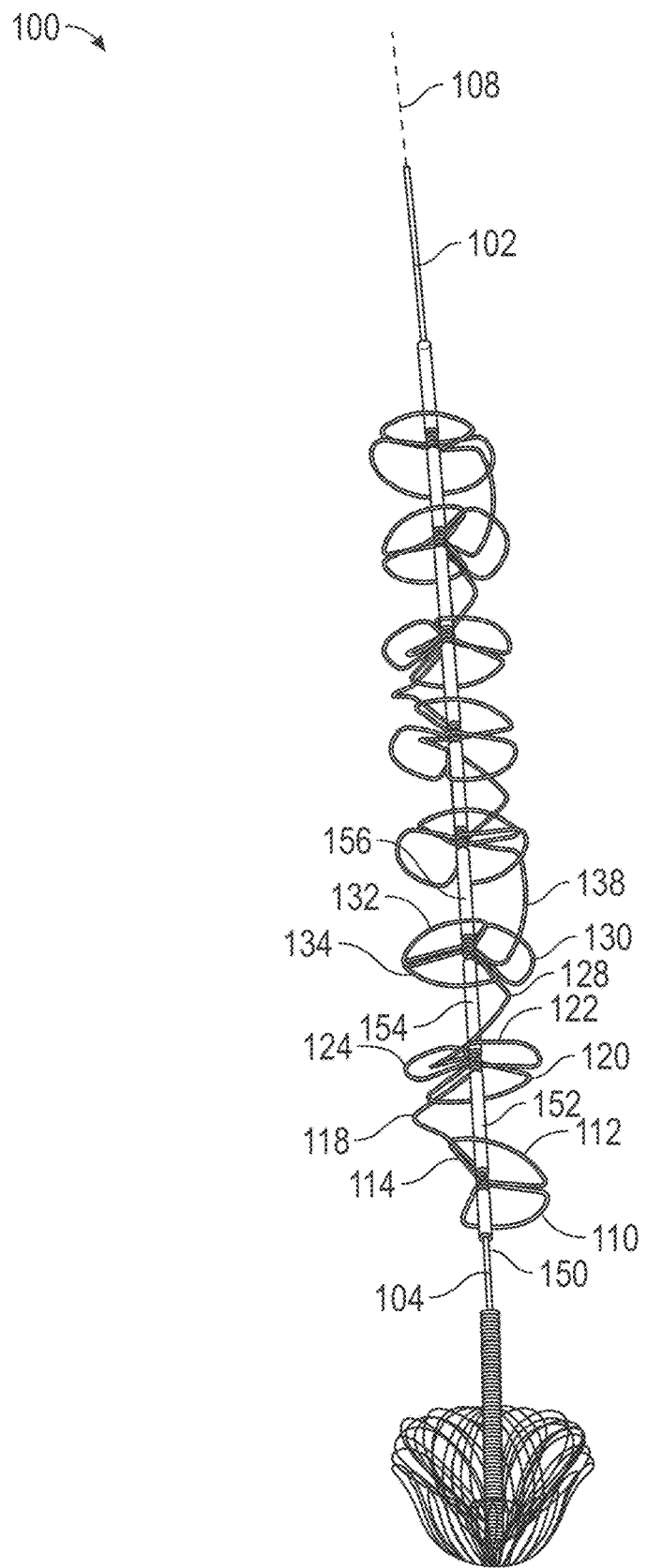
FIG. 2 is a side view of an embodiment of a three engagement panel extractor.
Figure 3:
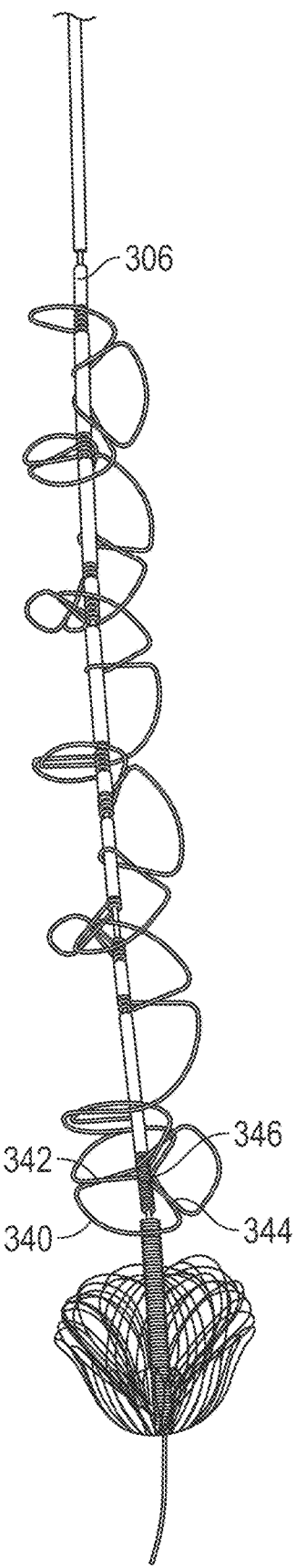
FIG. 3 is a side view of an embodiment of a helical engagement panel extractor.
Figure 4A:
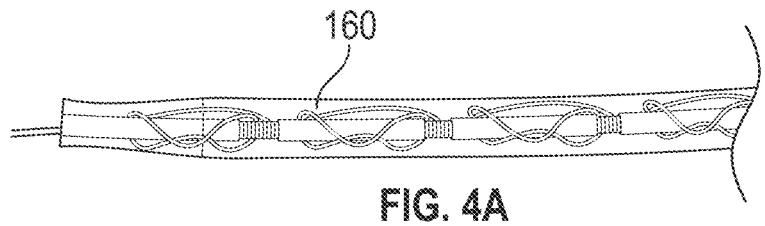
FIGS. 4A-4G are views of deployment of the first panel of the first embodiment of the three engagement panels extractor.
Figure 4B:
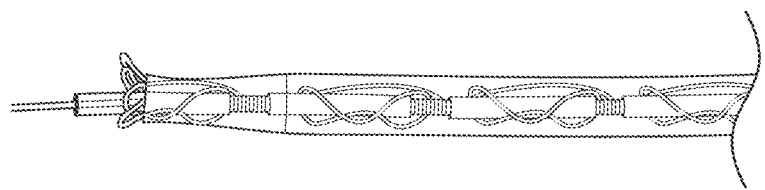
Figure 4C:
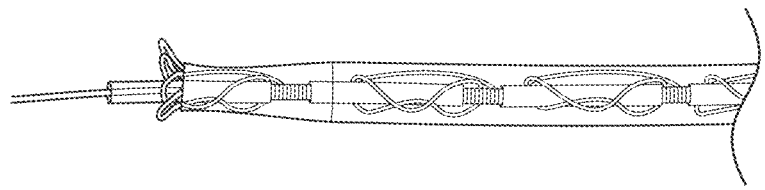
Figure 4D:
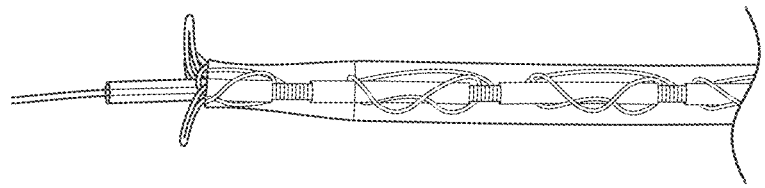
Figure 4E:
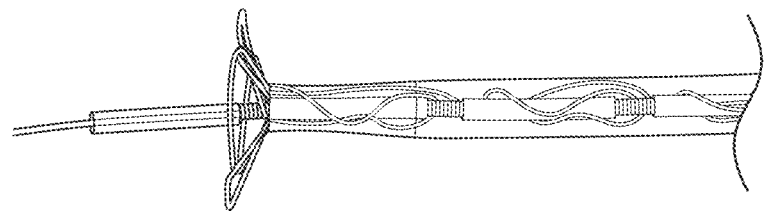
Figure 4F:
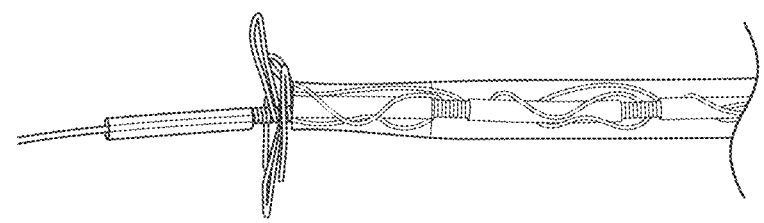
Figure 4G:
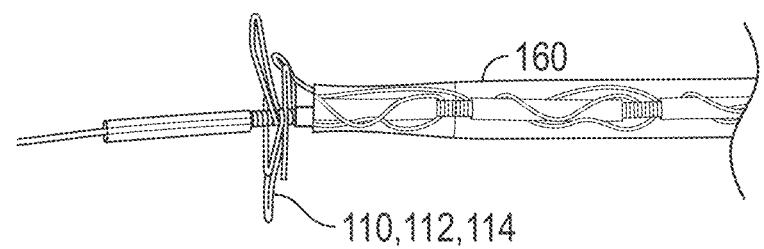

FIGS. 1-3 illustrate embodiments of an extractor 100. Other embodiments include extractor 200, the extractor 300, the extractor 400, and the extractor 500. The embodiments can include any feature described herein. The extractor 100 is configured for removal of clot material from a treatment site within a vessel. The extractor 100 can be particularly suited for neurovascular retrieval, wherein the vessels are fragile and delicate. The extractor 100 can be designed for the removal and retrieval of material by way of mechanical extraction within a lumen of a vessel.

The extractor 100 can include a proximal end 102 and a distal end 104. The extractor 100 can be a generally elongate member. The extractor 100 can include a length between the proximal end 102 and the distal end 104. In some embodiments, the proximal end 102 extends through the vasculature and is disposed outside of the body of the patient. The distal end 104 is configured to be advanced to a treatment site within a lumen of the patient. The extractor 100 can include one or more sections along the length of the extractor 100. The extractor 100 can include a distal member 180. The distal member 180 can include any feature described herein.

In some embodiments, a catheter shaft 106 is provided. The catheter shaft 106 can be advanced through the vasculature of the patient. The catheter shaft 106 can be a tubular shape with a lumen. The catheter shaft 106 can be a solid shaft. The catheter shaft 106 can be considered part of the extractor 100. The catheter shaft 106 can be considered separate from the extractor 100. The catheter shaft 106 can be made of, for example, metal such as stainless steel or nitinol, or another appropriate material. The distal end of the catheter shaft 106 can have a taper, such as a reduced outer diameter taper from proximal to distal, for example, to provide flexibility. The proximal end of the catheter shaft 106 can have a lubricious coating, or a PTFE jacket, or bare metal, as some examples. In some embodiments, the catheter shaft 106 is a core wire.

The extractor 100 can have a plurality of engagement panels 110, 112, 114, 120, 122, 124, 130, 132, 134. There can be a number of engagement panels at a single longitudinal location. There can be a number of engagement panels at a single location along the shaft 106. The engagement panels 110, 112, 114 are located at a first longitudinal location. The engagement panels 120, 122, 124 are located at a second longitudinal location spaced axially apart from the first longitudinal location. The engagement panels 130, 132, 134 are located at a third longitudinal location spaced axially apart from the first and second longitudinal locations. The first longitudinal location can be distal to the second longitudinal location. The second longitudinal location can be distal to the third longitudinal location. In other embodiments, the first longitudinal location can be proximal to the second longitudinal location. In other embodiments, the second longitudinal location can be proximal to the third longitudinal location. There can be any number of panels at a longitudinal location (e.g., one engagement panel, two engagement panels, three engagement panels, four engagement panels, five engagement panels, six engagement panels, seven engagement panels, eight engagement panels, nine engagement panels, ten engagement panels, or more or less or any range of two of the foregoing values). The longitudinal locations can be spaced apart at fixed regular intervals. The longitudinal locations can be spaced apart irregular intervals. In some embodiments, engagement panels located at the first longitudinal location comprise one engagement panel, two engagement panels, three engagement panels, four engagement panels, five engagement panels, six engagement panels, seven engagement panels, eight engagement panels, nine engagement panels, ten engagement panels, or more, or less or any range of two of the foregoing values. In some embodiments, engagement panels located at the second longitudinal location comprise one engagement panel, two engagement panels, three engagement panels, four engagement panels, five engagement panels, six engagement panels, seven engagement panels, eight engagement panels, nine engagement panels, ten engagement panels, or more or less, or any range of two of the foregoing values. In some embodiments, engagement panels located at the third longitudinal location comprise one engagement panel, two engagement panels, three engagement panels, four engagement panels, five engagement panels, six engagement panels, seven engagement panels, eight engagement panels, nine engagement panels, ten engagement panels, or more or less or any range of two of the foregoing values. In the illustrated embodiment, there are three engagement panels at each longitudinal location. It is contemplated that the extractor diameter can have any diameter combination thereof from the engagement panel at the first longitudinal location to the last engagement panel at the last longitudinal location. In some embodiments, the extractor 100 can be of the same diameter from the first longitudinal location to the last longitudinal location where engagement panels extend therefrom. In some embodiments, the engagement panels at the first longitudinal location have the same expanded diameter as engagement panels at the second longitudinal location. In some embodiments, the engagement panels at the second longitudinal location have the same expanded diameter as engagement panels at the third longitudinal location. In some embodiments, the extractor 100 can be various tapered geometries where the extractor diameter of the first longitudinal location is larger than the last longitudinal location. In some embodiments, the extractor 100 can be various tapered geometries where the extractor diameter can be tapered where the first longitudinal location is smaller than the last longitudinal location. In some embodiments, the extractor 100 can be various tapered geometries where the extractor diameter can be tapered the extractor middle members are larger than the first longitudinal location and the last longitudinal location. For example, the extractor diameter can be of the same diameter from the first longitudinal location to last longitudinal location end. For example, the extractor diameter can be 0.5 mm, 1 mm, 2 mm, 3 mm, 4 mm, 5 mm, 6 mm, 7 mm, 8 mm or higher or lower, or any range of two of the foregoing values. The extractor diameter can also differ from each longitudinal location. For example, the extractor diameter of the engagement panels 110, 112, 114 in the first longitudinal location can be 4 mm. The extractor diameter of the engagement panels 120, 122, 124 in the second longitudinal location can be 5 mm. The extractor diameter of the engagement panels 130, 132, 134 in the third longitudinal location can be 4 mm. The extractor diameter in the fourth longitudinal location can be 5 mm. In another embodiment, the extractor diameter of the engagement panels 110, 112, 114 in the first longitudinal location is larger than the extractor diameter of the engagement panels in the last longitudinal location at the distal end. For example, the engagement panels 110, 112, 114 in the first longitudinal location can be at 8 mm diameter and gradually transition to 7.5 mm, 7.0 mm, 6.5 mm, 6.0 mm, 5.5 mm, 5.0 mm, 4.5 mm, 4.0 mm, 3.5 mm, 3.0 mm, 2.5 mm, 2.0 mm and any diameter combination thereof at other longitudinal locations. In addition, the extractor diameter at the first longitudinal location can be smaller than the extractor diameter at the last longitudinal location. In some embodiments, the extractor 100 can have single layer of engagement panels at a longitudinal location (e.g., first longitudinal location, second longitudinal location, and/or third longitudinal location). In some embodiments, the extractor 100 can have double layers of engagement panels at a longitudinal location (e.g., first longitudinal location, second longitudinal location, and/or third longitudinal location). In some embodiments, the extractor can have three layers of engagement panels at a longitudinal location (e.g., first longitudinal location, second longitudinal location, and/or third longitudinal location). In some embodiments, the extractor 100 can have a plurality of layers of engagement panels. The engagement panels can extend along the circumference once. The engagement panels can extend along the circumference twice. The engagement panels can extend along the circumference three times. In some embodiments, the extractor 100 can have a combination of series of plurality of engagement panels such as single layer engagement panels at the first longitudinal location, double layers engagement panels at the second longitudinal location, single layer engagement panels at the third longitudinal location, and double layers of engagement panels at a fourth longitudinal location, for example. In some embodiments, the extractor 100 can have a series of double layers of engagement panels at the first longitudinal location, three layers of engagement panels at the second longitudinal location, and double layers of engagement panels at the third longitudinal location. In some embodiments, there can be any combinations thereof of layers of engagement panels.

In some embodiments, the extractor 100 can be adjusted or articulated at the proximal end using a control wire to either increase the diameter, distance, space, or opening between the engagement panels at the first longitudinal location and the engagement panels at the second longitudinal location or decrease the diameter, distance, space or opening between the engagement panels at the first longitudinal location and the engagement panels at the second longitudinal location. For example, the proximal end of the extractor 100 includes a control wire attached to the engagement panels. The control wire extends proximally and is attached to a control mechanism wherein the control wire can articulate to slidably move the eyelets of the engagement panels at the first longitudinal location and the second longitudinal location over the catheter shaft 106 or core wire to increase the diameter, distance, space, or opening between the engagement panels at the first longitudinal location and the second longitudinal location thereby creating a larger space or void for clot to reside into between the engagement panels at the first and second longitudinal locations. The control mechanism can also release to slidably allow the eyelets of the engagement panels at the first longitudinal location and the engagement panels at the second longitudinal location to shorten or move closer together reducing the distance, space, or opening between the engagement panels at the first and second longitudinal locations. The engagement panels at the first longitudinal location and the engagement panels at the second longitudinal location can be controlled to move relative to the catheter shaft 106 or core wire. The distance, space, or opening between the engagement panels at the first longitudinal location and the engagement panels at the second longitudinal location can be adjusted by a control mechanism.

The extractor 100 can have a plurality of connecting members 118, 128, 138. The connecting member 118 can connect the engagement panels 110, 112, 114 at the first longitudinal location and the engagement panels 120, 122, 124 at the second longitudinal location. The connecting member can be directed connected to one panel 110 at the first longitudinal location and one panel 120 at the second longitudinal location. The connecting member 128 can connect the engagement panels 120, 122, 124 at the second longitudinal location and the engagement panels 130, 132, 134 at a third longitudinal location. The connecting member 138 can connect the engagement panels 130, 132, 134 at a third longitudinal location and another set of engagement panels. The connecting members 118, 128, 138 can be helical. The connecting members 118, 128, 138 can be linear. The connecting members 118, 128, 138 can be curved. The connecting members can be coiled. The connecting members 118, 128, 138 can be radially offset or otherwise spaced apart from the longitudinal axis of the extractor 100 as shown. The connecting members 118, 128, 138 can be radially offset from the catheter shaft 106. The connecting members 118, 128, 138 can be inward from the outer circumference of the engagement panels. The connecting members 118, 128, 138 can be made of the same material as the engagement panels 110, 112, 114, 120, 122, 124, 130, 132, 134. The connecting members 118, 128, 138 can be made of a different material than the engagement panels 110, 112, 114, 120, 122, 124, 130, 132, 134. The connecting members 118, 128, 138 can be integrally formed with the engagement panels 110, 112, 114, 120, 122, 124, 130, 132, 134. The connecting members 118, 128, 138 can otherwise attached with the engagement panels 110, 112, 114, 120, 122, 124, 130, 132, 134, such as bonded together. The connecting members 118, 128, 138 can have the same flexibility than the engagement panels 110, 112, 114, 120, 122, 124, 130, 132, 134. The connecting members 118, 128, 138 can have more flexibility than the engagement panels 110, 112, 114, 120, 122, 124, 130, 132, 134. The connecting members 118, 128, 138 can have less flexibility than the engagement panels 110, 112, 114, 120, 122, 124, 130, 132, 134.

Figure 21:
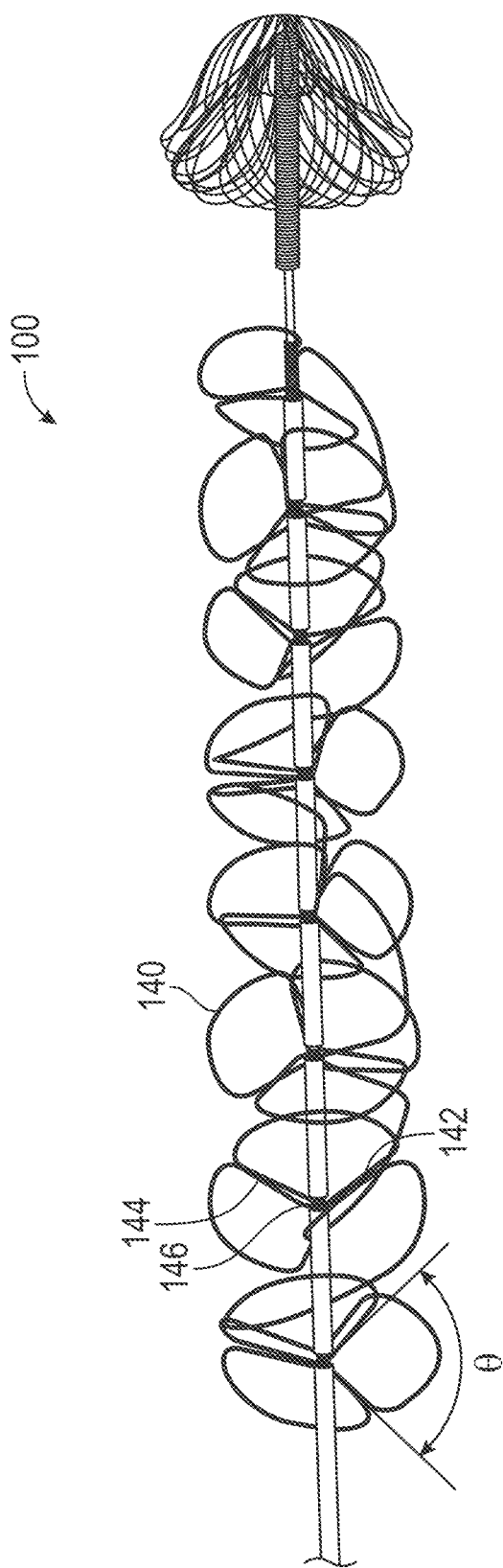
Figure 22:
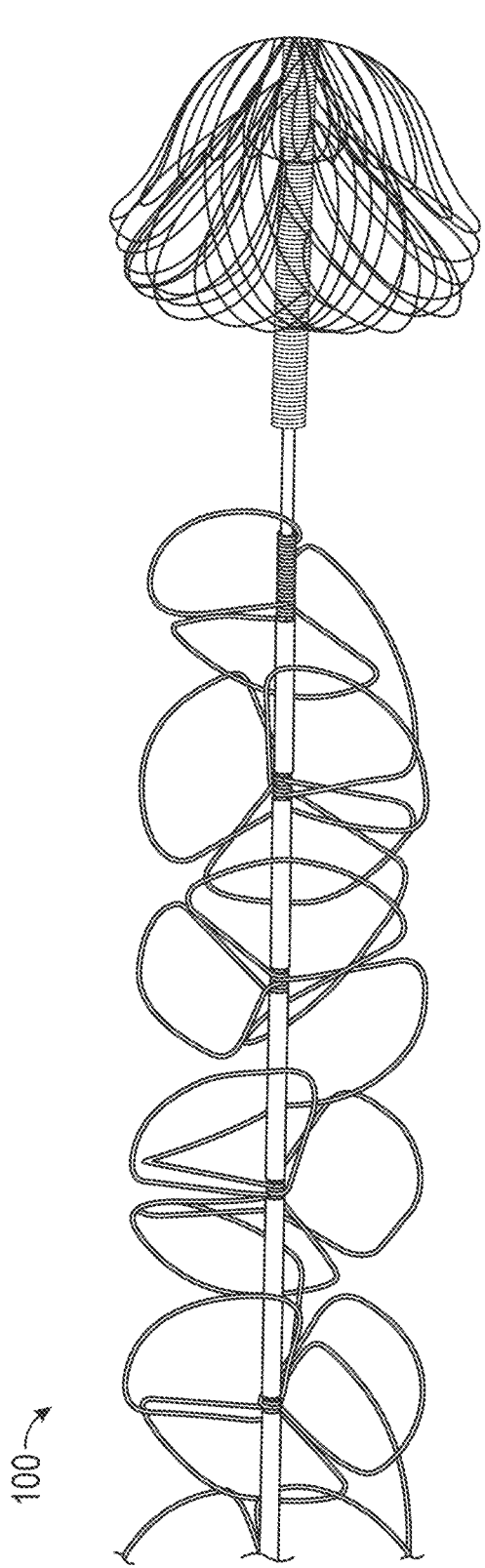
Figure 23:
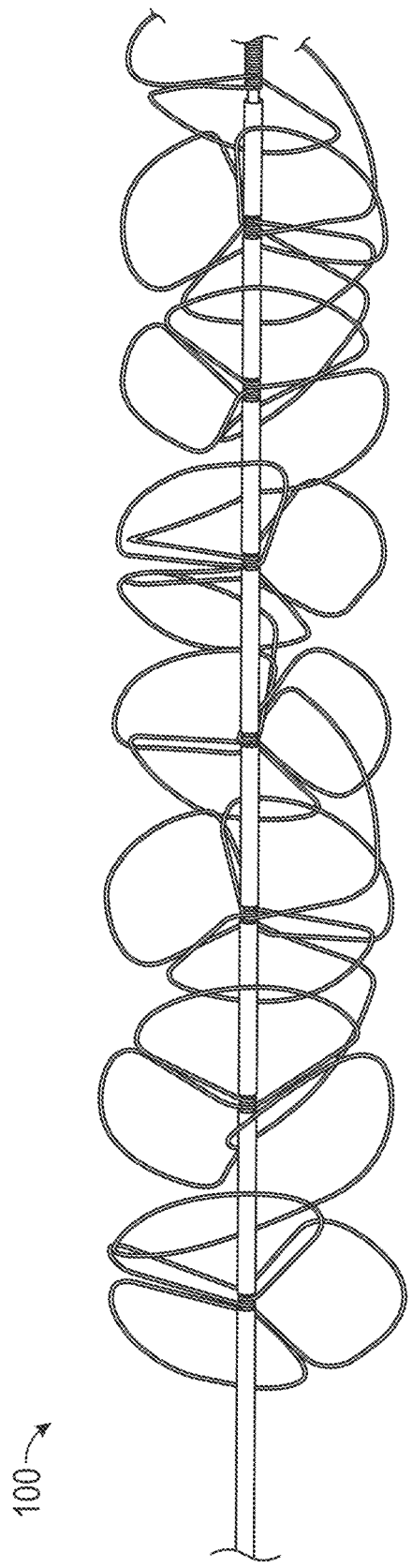
Figure 24:
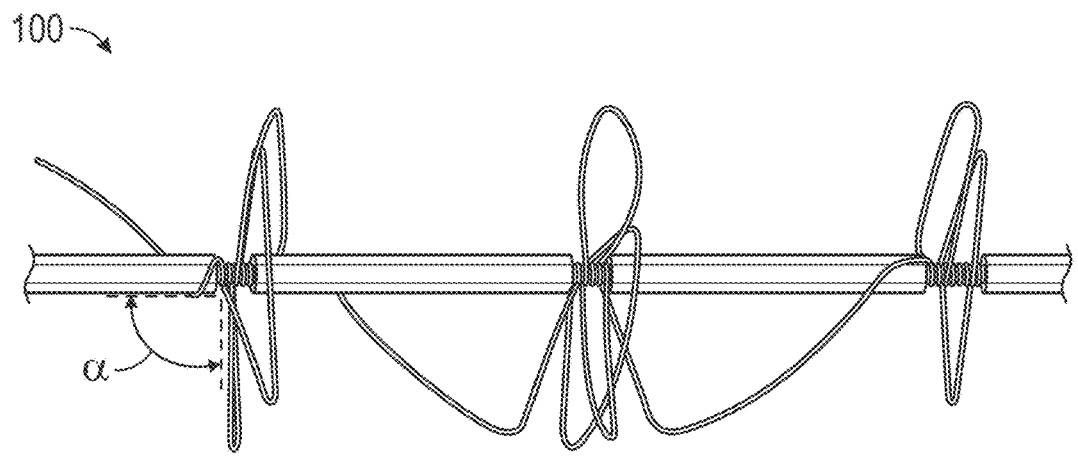
Figure 25:
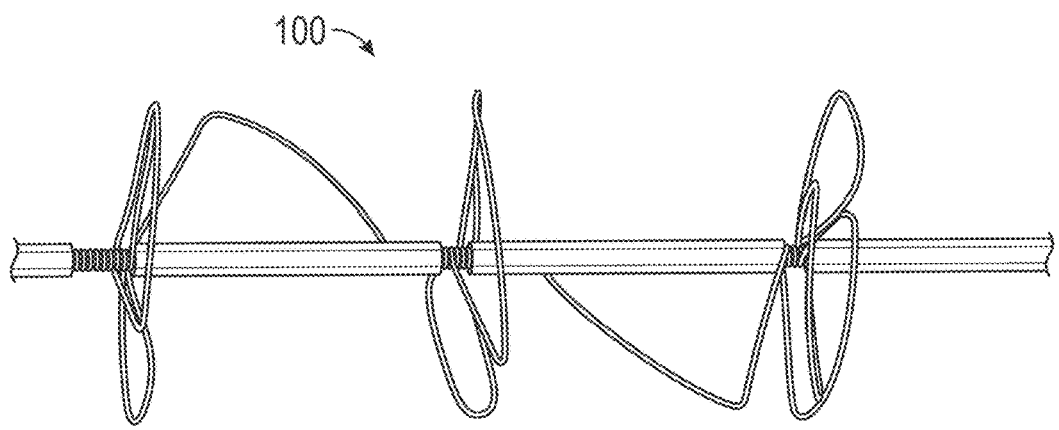
Figure 26:
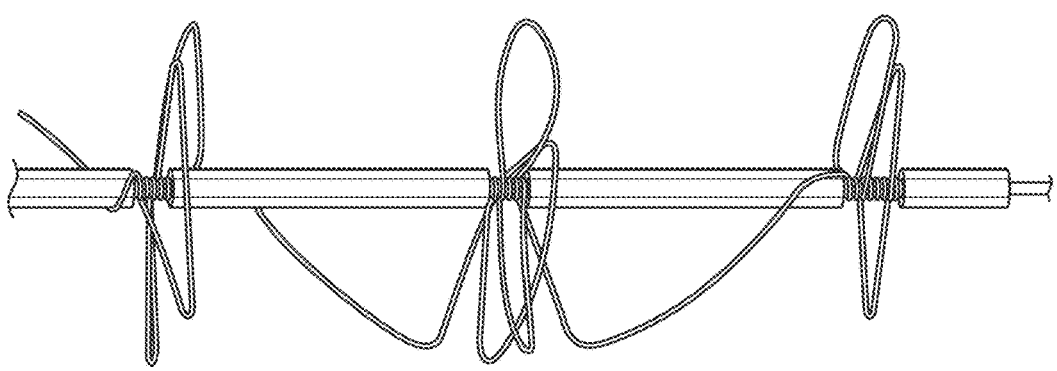
Figure 27:
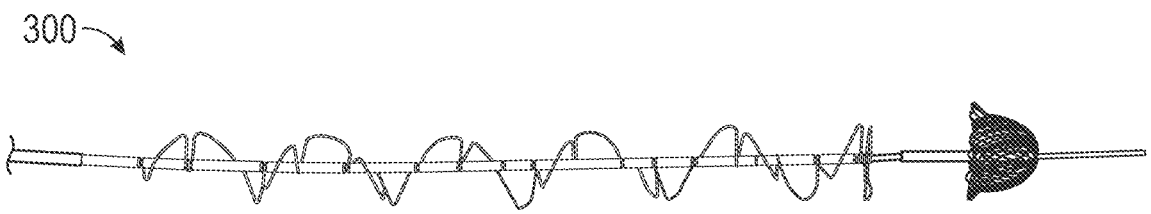
FIGS. 27-30 are views of the third embodiment of the helical engagement panel extractor.
Figure 28:
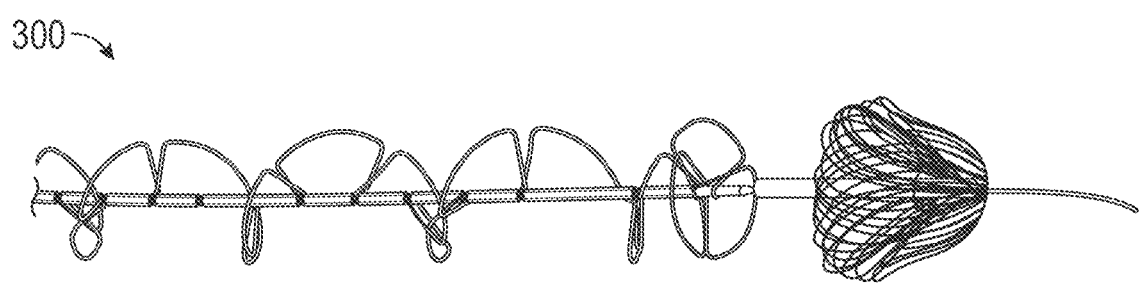
Figure 29:
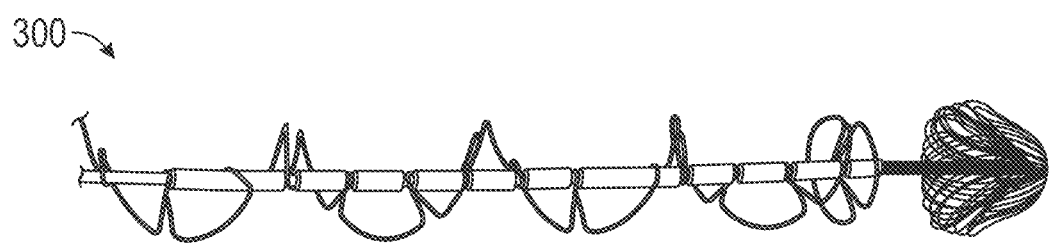
Figure 30:
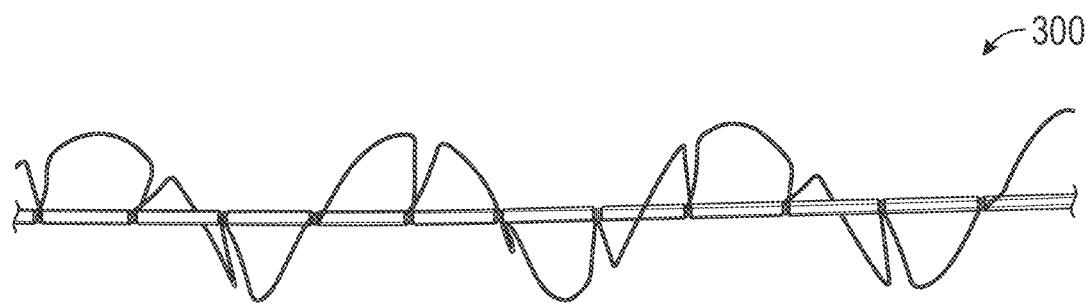

The engagement panels 110, 112, 114 can each form an arc 140 as shown in FIG. 21. The arc 140 can form a generally arcuate profile. The arc 140 can have round, circular, ellipse, or oval profile. The arc 140 can be configured to be atraumatic to the vessel wall. In some embodiments, the engagement panels 110, 112, 114 do not comprise barbs, or other sharp elements or vertices that are likely to pierce a luminal wall. In some embodiments, the engagement panels 110, 112, 114 form rounded corners. While the extractor 100 illustrated has three panels at a longitudinal location, other embodiments are contemplated. In some embodiments, the engagement panels located at a longitudinal location comprise one engagement panel, two engagement panels, three engagement panels, four engagement panels, five engagement panels, six engagement panels, seven engagement panels, eight engagement panels, nine engagement panels, ten engagement panels, or any range of two of the foregoing values. The engagement panels 110, 112, 114 at a single longitudinal location can form a circular profile. The engagement panels 110, 112, 114 at a single longitudinal location can extend around the circumference. Each engagement panel 110, 112, 114 can form a portion of a circle. Each arc 140 of the engagement panel 110, 112, 114 can form an segment of the circumference. Each arc 140 of the engagement panel 110, 112, 114 can include an approximately 120 degree arc. Each arc 140 of the engagement panel 110, 112, 114 can form an arc of, e.g. about 85 degrees, 90 degrees, 95 degrees, 105 degrees, 110 degrees, 111 degrees, 112 degrees, 113 degrees, 114 degrees, 115 degrees, 116 degrees, 117 degrees, 118 degrees, 119 degrees, 120 degrees, 125 degrees, 130 degrees, approximately 120 degrees, less than 120 degrees, greater than 110 degrees, more or less or any range of two of the foregoing values. Each arc 140 of the engagement panel 110, 112, 114 can form an arc that forms part of a circular, oval, or other arcuate profile. Each arc 140 of the engagement panels 110, 112, 114 can form the same arc. Each arc 140 of the engagement panels 110, 112, 114 can form the same degree of arc. Each arc 140 of the engagement panels 110, 112, 114 can form the same length of arc. Each arc 140 of the engagement panels 110, 112, 114 can form the arc with the same radius. Each arc 140 of the engagement panels 110, 112, 114 can form the arc with the same radius of curvature. Each arc 140 of the engagement panels 110, 112, 114 can be identical. Each arc 140 of the engagement panels 110, 112, 114 can be similar. Two or more arc 140 of the engagement panels 110, 112, 114 can be the same. Each arc 140 of the engagement panels 110, 112, 114 can form a different arc. Each arc 140 of the engagement panels 110, 112, 114 can form a different degree of arc. Each arc 140 of the engagement panels 110, 112, 114 can form a different length of arc. Each arc 140 of the engagement panels 110, 112, 114 can form the arc with a different radius. Each arc 140 of the engagement panels 110, 112, 114 can form the arc with a different radius of curvature. Each arc 140 of the engagement panels 110, 112, 114 can be different. Two or more engagement panels 110, 112, 114 can be different. Two or more arc 140 of the engagement panels 110, 112, 114 can have different diameters. Two or more arc 140 of the engagement panels 110, 112, 114 can have different arc angles.

Each engagement panels 110, 112, 114 can be formed by, or otherwise include one, or a plurality of legs, such as two legs 142, 144 shown in FIG. 21. The two legs 142, 144 connect to the arc 140 of engagement panel 110, 112, 114. The legs 142, 144 and the arc 140 can form rounded corners. The arc can form an atraumatic surface. The two legs 142, 144 can be radially outward from the longitudinal axis of the extractor 100. The two legs 142, 144 can be angled relative to each other. The two legs 142, 144 can be straight. The two legs 142, 144 can be linear. The two legs 142, 144 can have a constant angle therebetween. The two legs 142, 144 can connect to the ends of the arc 140. In some embodiments, the legs 142, 144 are integrally formed with the arc 140. In some embodiments, the legs 142, 144 are operably attached together with the arc 140. The legs 142, 144 and the arc 140 can be, made of the same material. The legs 142, 144 can be made of different material than the arc 140. The two legs 142, 144 can form a radius toward the arc 140. In some embodiments, legs 142, 144 of each engagement panel 110, 112, 114 can have any pattern. In some embodiments, legs 142, 144 of each engagement panel 110, 112, 114 can have a zig zag pattern. In some embodiments, legs 142, 144 of each engagement panel 110, 112, 114 can have a slight curve. In some embodiments, the legs 142, 144 and the arc 142 define the perimeter of a void or free space area that is devoid or substantially devoid of any material, thus advantageously minimizing the size/weight of the device. The legs 142, 144 and the arc 142 define a pore. Each engagement panel 110, 112, 114 comprises a pore.

In some embodiments, the engagement panels 110, 112, 114 of the first longitudinal location do not overlap. In some embodiments, the legs 142, 144 of the engagement panel 110 do not overlap with the legs 142, 144 of the engagement panels 112, 114. In some embodiments, the legs 142, 144 of the engagement panel 112 do not overlap with the legs 142, 144 of the engagement panels 110, 114. In some embodiments, the legs 142, 144 of the engagement panel 114 do not overlap with the legs 142, 144 of the engagement panels 110, 112. In some embodiments, the legs 142, 144 of the engagement panels 110, 112, 114 of the first longitudinal location do not touch. In some embodiments, the legs 142, 144 of the engagement panels 110, 112, 114 of the first longitudinal location are adjacent. In some embodiments, the legs 142, 144 of the engagement panels 110, 112, 114 of the first longitudinal location are spaced apart. In some embodiments, the legs 142, 144 of the engagement panels 110, 112, 114 of the first longitudinal location about each other. In some embodiments, the legs 142, 144 of the engagement panels 110, 112, 114 of the first longitudinal location are in contact along their length. In some embodiments, the legs 142, 144 of the engagement panels 110, 112, 114 of the first longitudinal location are in contact along a portion of the radius of the arc 140.

The engagement panels 110, 112, 114 can form an eyelet 146 as shown in FIG. 21. The engagement panels 110, 112, 114 are located at the first longitudinal location. The eyelet 146 can be located at the first longitudinal location. The engagement panels 110, 112, 114 can form a generally round eyelet 146. The engagement panels 110, 112, 114 can form a circular eyelet 146 at the single longitudinal location. Each engagement panel 110, 112, 114 can form a portion of the eyelet 146. In some embodiments, the legs 142, 144 of the engagement panels 110, 112, 114 form the eyelet 146. The legs 142, 144 of the engagement panels 110, 112, 114 can lie along the same plane. The legs 142, 144 of the engagement panels 110, 112, 114 can form a perimeter of the eyelet 146. The legs 142, 144 of the engagement panels 110, 112, 114 can be circumferentially spaced. The legs 142, 144 of the engagement panels 110, 112, 114 can have ends along the perimeter of the eyelet 146. In some embodiments, another portion of the engagement panels 110, 112, 114 forms the eyelet 146.

The eyelet 146 can accommodate the catheter shaft 106. The eyelet 146 can be wrapped around the outer diameter of the elongate member of the extractor. In some embodiments, the eyelet 146 is fixed to the catheter shaft 106. In some embodiments, the eyelet is moveable relative to the catheter shaft 106. The eyelet 146 of the engagement panels 110, 112, 114 is located at the first longitudinal location. The eyelet 146 of the engagement panels 120, 122, 124 is located at the second longitudinal location. The eyelet 146 of the engagement panels 130, 132, 134 is located at a third longitudinal location.

Figure 34:
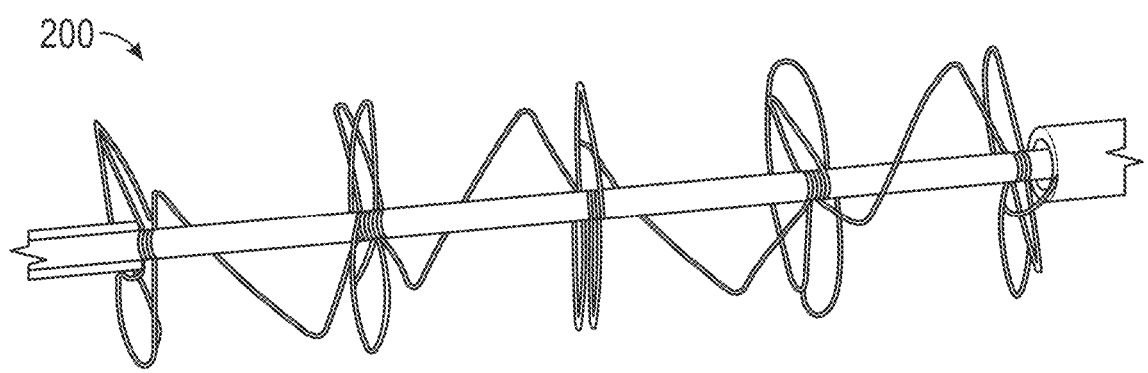
Figure 35:
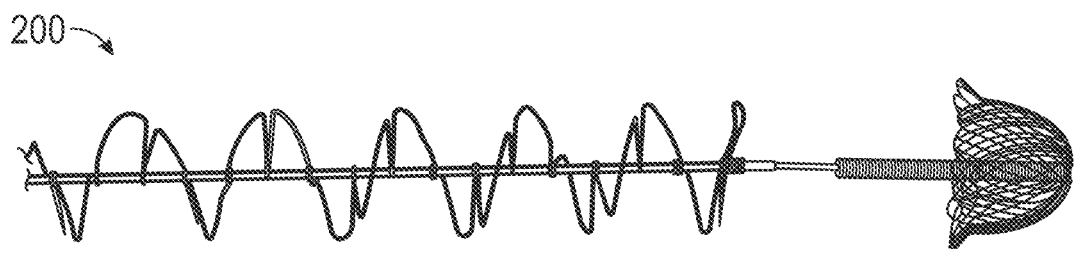
FIGS. 35-39 are views of the first embodiment of the helical engagement panel extractor with spacer in between the engagement panels and eyelets.
Figure 36:
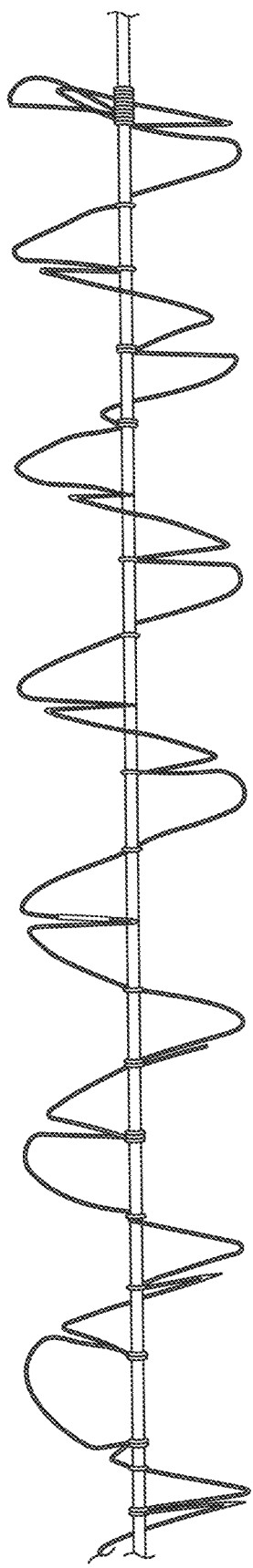
Figure 37:
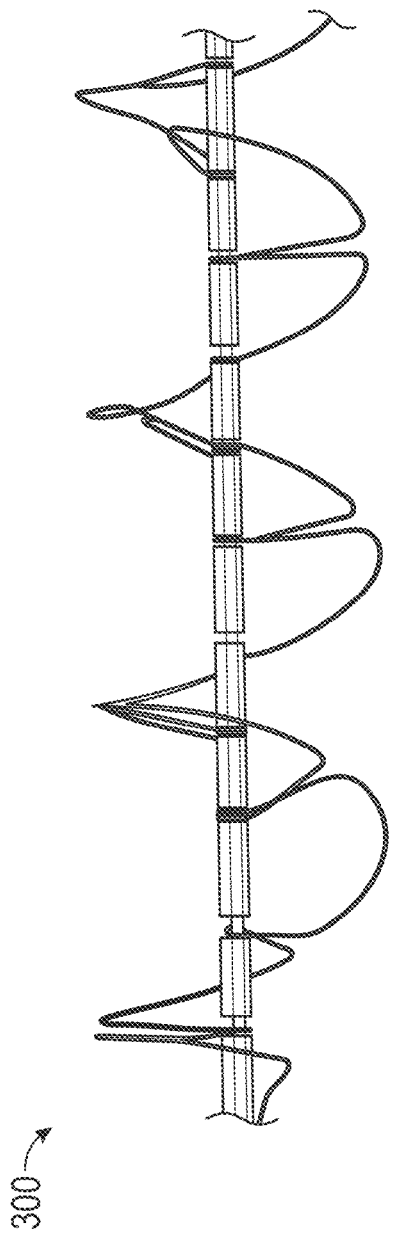
Figure 38:
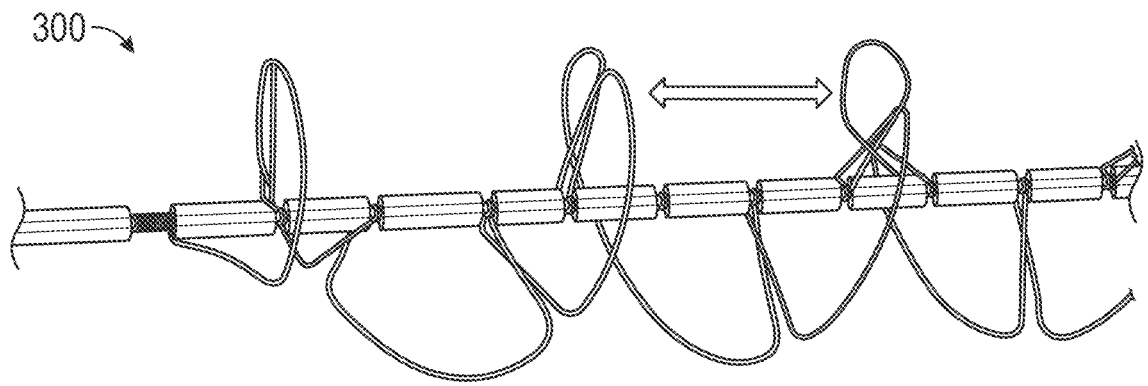
Figure 39:
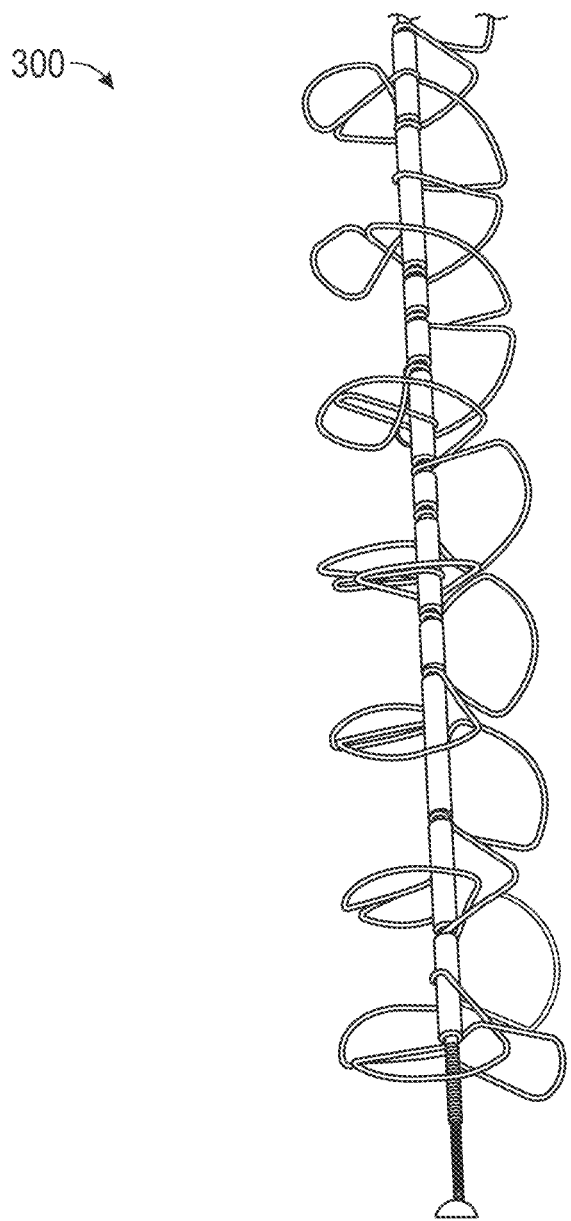

The extractor 100 can include a plurality of spacers 150, 152, 154, 156. The spacer 150 can be located between the distal end 104 and the engagement panels 110, 112, 114. The spacer 152 can be located between the engagement panels 110, 112, 114 and the engagement panels 120, 122, 124. The spacer 152 can be between the first longitudinal location and the second longitudinal location. The spacer 154 can be located between the engagement panels 120, 122, 124 and the engagement panels 130, 132, 134. The spacer 154 can be between the second longitudinal location and the third longitudinal location. In some embodiments, the spacer 156 can be located between the engagement panels 130, 132, 134 and another set of engagement panels. In some embodiments, the spacer 156 can be located between the engagement panels 130, 132, 134 and the proximal end 102. In some embodiments, engagement panels have space between them without spacers (FIG. 34). In some embodiments, engagement panels have space between them without a discrete structural feature. For example, the extractor or engager's engagement panels can couple directly to the catheter shaft or core wire. The Engagement panels at the first location is coupled to the catheter shaft or core wire. The engagement panels at the second panels is coupled at a distance away from the engagement panels at the first location. The engagement panels can be coupled to the catheter shaft or core wire either by laser, chemical or mechanical bond for example. In some embodiments, a spacer is interspersed in between some, or every adjacent set of engagement panels. The space can be located between the engagement panels 110, 112, 114 and the engagement panels 120, 122, 124. The space can be between the first longitudinal location and the second longitudinal location. The space can be located between the engagement panels 120, 122, 124 and the engagement panels 130, 132, 134. The spacer 154 can be between the second longitudinal location and the third longitudinal location. In some embodiments, engagement panels can be next to each other in series with no spacer, thereby minimal to no gap. The engagement panels 110, 112, 114 and the engagement panels 120, 122, 124 can be next to each other in in series with minimal to no gap. The first longitudinal location and the second longitudinal location can be next to each other. The engagement panels 120, 122, 124 and the engagement panels 130, 132, 134 can be next to each other in in series with minimal to no gap. The second longitudinal location and the third longitudinal location can be next to each other.

The spacers 150, 152, 154, 156 can include a lumen. The spacers 150, 152, 154, 156 can receive the catheter shaft 106 there through. The catheter shaft 106 can be a core wire or laser cut hypotube and any combination thereof. The connecting members 118, 128, 138 can be located within the lumen of the spacers 152, 154, 156. The connecting members 118, 128, 138 can be located outside of the spacers 152, 154, 156.

The extractor 100 can be used with a sheath 160. The sheath 160 can be an outer sheath. The sheath 160 can cover the extractor 100. The sheath 160 can cover the plurality of engagement panels 110, 112, 114, 120, 122, 124, 130, 132, 134, such that engagement panels are configured to move between radially expanded and radially compressed configurations. The sheath 160 can cover the shaft 106, or a portion thereof. The sheath 160 can cover additional components of the system, such as a filter.

The extractor 100 can be used with other components of a system. The extractor 100 can be used with a filter. The filter can be any filter. The filter can be any distal extraction member. The extractor 100 can be used with a collection chamber or collection bag. The extractor 100 can be used with a macerator tool. The extractor 100 can be used with an expanding filter. The extractor 100 can be used with an expanding guide catheter. The extractor 100 can be used with a suction catheter. The extractor 100 can be used with the catheter shaft 106.

In some embodiments, the extractor includes a distal member or distal plug 180. The distal member 180 functions to trap or capture loose emboli in transit or remove and capture soft emboli distal to the extractor. The distal member 180 is designed to have a low profile to be delivered through a small lumen. The distal member 180 is made of braided filaments, wires or woven. The braided wire or filaments can be a single or double layer. The braided wires or filaments can be metallic such as Nitinol, stainless steel, platinum iridium for example. The braided wires or filaments can also be polymeric materials such as polyethylene, PTFE, FEP for example. The braided wires can also include radiopaque metal such as tungsten or gold to aid with better visualization. The distal member 180 can form using laser stent cut hypotube. The distal member 180 can be formed in any geometrical configuration, including, but not limited to, circular, umbrella, ball, elliptical, and/or disc. The distal member 180 can be expandable. The distal member 180 can be compressible. The distal member 180 can conform to the vessel wall.

The extractor 100 can include the catheter shaft 106. The extractor 100 can have the plurality of engagement panels 110, 112, 114, 120, 122, 124, 130, 132, 134. The plurality of engagement panels 110, 112, 114, 120, 122, 124, 130, 132, 134 can be deployed. In some embodiments, the engagement panels are deployed by retracting a sheath 160. The sheath 160 will uncover engagement panels 110, 112, 114 at the first longitudinal location. The extractor 100 is fully functional to remove clot material with just the engagement panels 110, 112, 114 at the first longitudinal location. The sheath 160 will then uncover engagement panels 120, 122, 124 at the second longitudinal location, if needed. The extractor 100 is fully functional to remove clot material with just the engagement panels 110, 112, 114 at the first longitudinal location and engagement panels 120, 122, 124 at the second longitudinal location. The sheath 160 will then uncover engagement panels 130, 132, 134 at the third longitudinal location, if needed.

The extractor 100 consists of a series of engagement panels 110, 112, 114, 120, 122, 124, 130, 132, 134. The engagement panels 110, 112, 114, 120, 122, 124, 130, 132, 134 function to remove the clot away from the vessel wall. The engagement panels 110, 112, 114 at the first longitudinal location can form a generally circular profile similar to the circumference of the vessel wall. The engagement panels 110, 112, 114 at the first longitudinal location can sweep against the vessel wall with the arc 140. The engagement panels 110, 112, 114 at the first longitudinal location can include legs 142, 144 which support the arc 140 as the arc 140 removes the clot away from the vessel wall. The engagement panels 110, 112, 114 can be segmented to effectively oppose the vessel wall.

The engagement panels 110, 112, 114, 120, 122, 124, 130, 132, 134 can function to control, such as pinch the clot securely, in either or both axially and/or radially compressed directions. The engagement panels 110, 112, 114, 120, 122, 124, 130, 132, 134 can be used to pinch the clot during retrieving into a collection funnel or other device. The clot can be pinched between the engagement panels 110, 112, 114 at the first longitudinal location and the engagement panels 120, 122, 124 at the second longitudinal location. The clot can be pinched between the engagement panels 120, 122, 124 at the second longitudinal location and the engagement panels 130, 132, 134 at the third longitudinal location. For example, in some embodiments, the first longitudinal location engagement panels expand radially and outward to capture or pinch a portion of the clot either against the vessel wall and/or in between the open cavity. As the second longitudinal location engagement panels expand radially and outward, the engagement panels continue to capture or pinch a portion of the clot either against the vessel wall and/or in between the open cavity. The connect member, bridge extension 138 between the first longitudinal location and the second longitudinal location has tendency to pull the engagement panels of the first longitudinal location and the second longitudinal location together thereby creating a pinching effect and hold the clot better.

The engagement panels 110, 112, 114, 120, 122, 124, 130, 132, 134 are placed apart from each other creating a space or cavity for the clot or emboli to reside in. There is a space or cavity between the engagement panels 110, 112, 114 at the first longitudinal location and the engagement panels 120, 122, 124 at the second longitudinal location. There is a space between the first longitudinal location and the second longitudinal location for the clot or emboli. There is a space or cavity between the engagement panels 120, 122, 124 at the second longitudinal location and the engagement panels 130, 132, 134 at the third longitudinal location. There is a space between the second longitudinal location and the third longitudinal location for the clot or emboli.

The engagement panels 110, 112, 114, 120, 122, 124, 130, 132, 134 collapse, e.g., radially during delivery. The engagement panels 110, 112, 114, 120, 122, 124, 130, 132, 134 can be collapsed within the sheath 160. The engagement panels 110, 112, 114, 120, 122, 124, 130, 132, 134 can be folded inward. The engagement panels 110, 112, 114, 120, 122, 124, 130, 132, 134 can be folded against the catheter shaft 106.

The engagement panels 110, 112, 114, 120, 122, 124, 130, 132, 134 then expand or open at the treatment site in a manner that engage and pinch the clot securely for removal. The engagement panels 110, 112, 114, 120, 122, 124, 130, 132, 134 expand from the sheath 160. The legs 142, 144 bias each arc 140 radially outward toward the vessel wall. The legs 142, 144 provide support for the expanded engagement panel. The engagement panels 110, 112, 114, 120, 122, 124, 130, 132, 134 open at the treatment site. The engagement panels 110, 112, 114, 120, 122, 124, 130, 132, 134 capture the clot in the spaces between the first longitudinal location and the second longitudinal location. The engagement panels 110, 112, 114, 120, 122, 124, 130, 132, 134 capture the clot in the spaces between the second longitudinal location and the third longitudinal location. The engagement panels 110, 112, 114, 120, 122, 124, 130, 132, 134 can pull together along with the clot disposed in the spaces between the longitudinal locations. The engagement panels 110, 112, 114, 120, 122, 124, 130, 132, 134 can pull together along with the filter. The engagement panels 110, 112, 114, 120, 122, 124, 130, 132, 134 can pull together into a collection funnel, a guide catheter, or other device.

There are several potential advantages of the extractor 100. The engagement panels 110, 112, 114, 120, 122, 124, 130, 132, 134 open to deploy rather than radially expand like the stent retriever device. The engagement panels 110, 112, 114, 120, 122, 124, 130, 132, 134 open in some cases like petals of a flower. The engagement panels 110, 112, 114, 120, 122, 124, 130, 132, 134 pop outward once beyond the tip of the sheath 160. The engagement panels 110, 112, 114, 120, 122, 124, 130, 132, 134 radially expand without an axial movement, and unlike conventional expandable balloon or other retrieval members for example. The engagement panels 110, 112, 114, 120, 122, 124, 130, 132, 134 radially expand without axially shortening. The engagement panels 110, 112, 114, 120, 122, 124, 130, 132, 134 radially contract without axially lengthening. In contrast, conventional stent retriever devices can radially expand through a mesh-like structure. The stent retriever device can axially shorten as the device radially expands. When pulled, the stent retriever device can axially lengthen and pull away from the vessel wall.

The extractor 100 is functional when the engagement panels 110, 112, 114, 120, 122, 124, 130, 132, 134 open. The extractor 100 is functional when the engagement panels 110, 112, 114 at the first longitudinal location open. The extractor 100 is functional when the engagement panels 110, 112, 114 at the first longitudinal location and the engagement panels 120, 122, 124 at the second longitudinal location open. The extractor 100 is functional when the engagement panels 110, 112, 114 at the first longitudinal location, the engagement panels 120, 122, 124 at the second longitudinal location, and the engagement panels 130, 132, 134 at the third longitudinal location open. The extractor 100 is functional when one or more engagement panels 110, 112, 114 open. The extractor 100 is functional when partially deployed. The extractor 100 is functional to engage a clot once the engagement panels 110, 112, 114 are opened. The functional length of the extractor 100 is adjustable. The complete length of the extractor 100 is not required to be open to be functional, depending on the size of the clot and the desired clinical result. A partial, and less than full length of the extractor 100 can be opened, such as unsheathed in some cases, for the extractor 100 to be able to engage and remove the clot. The length of the extractor can range from, for example, 0.1 cm to 30 cm. In some embodiments, preferably, the extractor length is about 5 cm. In some embodiments, the extractor length is about 6 cm. In some embodiments, the extractor length is about 4 cm, or ranges including any two values as disclosed herein. The number of extractor engagement panels can range from, for example, one engagement panel to 150 engagement panels.

In contrast, conventional stent retriever devices generally must be fully deployed to be functional. The entire length of the stent retriever device must be opened from the catheter. The functional length of the stent retriever device is typically not adjustable.

The sheath 160 can unsheath the extractor 100 partially, such as half-way or even less in some cases, to expose some engagement panels while retaining some engagement panels inside the sheath 160. The engagement panels 110, 112, 114 at the first longitudinal location and the engagement panels 120, 122, 124 at the second longitudinal location can be opened (e.g., radially expanded), while the engagement panels 130, 132, 134 at the third longitudinal location can remain within the sheath 160. The engagement panels 110, 112, 114 at the first longitudinal location and the engagement panels 120, 122, 124 at the second longitudinal location can function to engage the clot. The engagement panels 110, 112, 114 at the first longitudinal location and the engagement panels 120, 122, 124 at the second longitudinal location can function to control, e.g., pinch the clot between the first longitudinal location and the second longitudinal location. The sheath 160 can unsheath the remaining engagement panels if needed for example. The sheath 160 can unsheath the engagement panels 130, 132, 134 at the third longitudinal location.

As the engagement panels 110, 112, 114, 120, 122, 124, 130, 132, 134 pull back, e.g., proximally within the body lumen to remove the clot obstruction, the engagement panels can be more resistant to compression or bending upon interacting with a clot obstruction. The engagement panels 110, 112, 114, 120, 122, 124, 130, 132, 134 can include legs 142, 144 which support the arc 140. The legs 142, 144 resist compression of the arc 140 of the engagement panels 110, 112, 114, 120, 122, 124, 130, 132, 134. The arc 140 of the engagement panels 110, 112, 114, 120, 122, 124, 130, 132, 134 can advantageously remain open even when the arc encounters a tough resistance such as an organized clot obstruction. The legs 142, 144 provide structural support to prevent the arc 140 from sliding past the clot without engaging the clot. The legs 142, 144 provide structural support to remove tough clots. The legs 142, 144 provide structural support to remove clots wedged against the vessel wall due to blow flow or pressure. In some embodiment, the legs of the engagement panels are longitudinally aligned. In some embodiments, the legs of the engagement panels can be offset from each other from, for example, about 1 to 179 degrees. For example, in some embodiments, the legs of the engagement panels are offset by 45 degrees. In some embodiment, the legs are offset by 90 degrees. In some embodiment, the legs of each engagement panel are offset from relative to the next engagement panel. As compared to conventional stent retriever devices, the stent retriever device will compress, and slide pass the clot against the vessel wall when encounter a tough resistance such as an organized clot obstruction particularly when the clot obstruction is further wedged due to blood flow or pressure.

The engagement panels 110, 112, 114, 120, 122, 124, 130, 132, 134 also can be configured to function independently. Each engagement panels 110, 112, 114, 120, 122, 124, 130, 132, 134 comprises the arc 140 and legs 142, 144 which are independent from the other engagement panels. There are multiple positions where the clot can engage and be captured with respect to the engagement panels during the retrieval. As the clot is trapped in the spaces between the engagement panels, the engagement panels 110, 112, 114 at the first longitudinal location and the engagement panels 120, 122, 124 at the second longitudinal location have a pinching effect to ensure the clot does not move relative to the extractor while in transit. The longitudinal separation between the engagement panels 110, 112, 114 at the first longitudinal location and the engagement panels 120, 122, 124 at the second longitudinal location creates a cavity or space for the clot to reside. As the clot is trapped in the spaces between the engagement panels, the engagement panels 120, 122, 124 at the second longitudinal location and the engagement panels 130, 132, 134 at the third longitudinal location have a pinching effect to ensure the clot does not move while in transit. The longitudinal separation between the engagement panels 120, 122, 124 at the second longitudinal location and the engagement panels 130, 132, 134 at the third longitudinal location creates a cavity or space for the clot to reside. There are multiple longitudinal separations between the engagement panels for the clot to reside.

The extractor 100 can include the plurality of spacers 150, 152, 154, 156. The spacer 150 can be located between the distal end 104 and the engagement panels 110, 112, 114. The spacer 150 can keep the engagement panels 110, 112, 114 apart from the filter. The spacer 152 can be located between the engagement panels 110, 112, 114 and the engagement panels 120, 122, 124. The spacer 152 can keep the engagement panels 110, 112, 114 apart from the engagement panels 120, 122, 124. The spacer 154 can be located between the engagement panels 120, 122, 124 and the engagement panels 130, 132, 134. The spacer 154 can keep the engagement panels 120, 122, 124 apart from the engagement panels 130, 132, 134. In some embodiments, the spacer 156 can be located between the engagement panels 130, 132, 134 and another set of engagement panels or the proximal end 102. The spacers 150, 152, 154, 156 keep the engagement panels apart. The spacers 150, 152, 154, 156 distance the sets of engagement panels from each other in a longitudinal direction. The spacer can be made of, for example, polymeric materials such as Pebax, Polyester, polyethylene, polypropylene, Polyurethane, silicone, or any combination of these materials. In some embodiments, the spacer can be made of metallic materials such as stainless steel, platinum, gold, silver, nitinol, or any combination of these materials. The spacer can be integrated into the extractor and the material can be, e.g., nitinol. The spacer 150, 152, 154, 156 can provide a pinching force. The spacer 150, 152, 154, 156 can provide a spring force. The spacer 150, 152, 154, 156 can provide a resistive force. The spacer 150, 152, 154, 156 can provide a compressive force. The spacer 150, 152, 154, 156 can bias the engagement panels toward each other. The spacer 150, 152, 154, 156 can function as a spring. The spacer 150, 152, 154, 156 can be passive. The engagement panels 110, 112, 114 can be biased toward the engagement panels 120, 122, 124 by the spacer 152. The engagement panel 120, 122, 124 can be biased toward the engagement panels 130, 132, 134 by the spacer 154. The spacers 150, 152, 154, 156 are not actuated in some cases. The spacers 150, 152, 154, 156 are not actively pulled toward each other in some cases. Rather, the spacers 150, 152, 154, 156 are passively actuated in some cases. The engagement panels 110, 112, 114 and the engagement panels 120, 122, 124 can be inherently biased toward each other. The engagement panels 120, 122, 124 and the engagement panels 130, 132, 134 can be inherently biased toward each other. The spacer 150, 152, 154, 156 can help to keep the engagement panels 110, 112, 114, 120, 122, 124, 130, 132, 134 open. The spacer 150, 152, 154, 156 can allow movement of the engagement panels 110, 112, 114, 120, 122, 124, 130, 132, 134. The spacer 150, 152, 154, 156 create a certain amount of biasing force. The spacers 150, 152, 154, 156 can be connected to eyelets of the engagement panels 110, 112, 114, 120, 122, 124, 130, 132, 134. The spacer 150, 152, 154, 156 can abut the eyelets.

The spacers 150, 152, 154, 156 can provide a force to separate the engagement panels from each other. The spacers 150, 152, 154, 156 can provide a separation force. The spacers 150, 152, 154, 156 provide a resistive force to keep the engagement panels separated. The force can range from, for example, 0.01 grams to 50 grams. The spacers 150, 152, 154, 156 can bias the engagement panels away from each other. The spacers 150, 152, 154, 156 can bias the engagement panels toward each other. The spacers 150, 152, 154, 156 can comprise a coiled wire. The spacers 150, 152, 154, 156 can comprise a tubular member. The spacers 150, 152, 154, 156 can comprise a polymer material such as Pebax, Polyester, polyethylene, polypropylene, Polyurethane, silicone or any combination of these materials. The spacers 150, 152, 154, 156 can comprise a shape memory material. The spacers 150, 152, 154, 156 can comprise a spring. The spacers 150, 152, 154, 156 can comprise a metal such as stainless steel, platinum, gold, silver, nitinol or any combination of these materials. The spacers 150, 152, 154, 156 can exert a force on adjacent engagement panels. The spacers 150, 152, 154, 156 can exert a force on engagement panels and an adjacent structure.

In some embodiments, the first longitudinal location has one engagement panel 110. The engagement panel 110 can form a generally circular profile, or a portion thereof. The engagement panel 110 can form the arc 140. The engagement panel 110 can include an approximately 360 degree arc. The engagement panel 110 can form a complete circle. In some embodiment, the eyelet 146 is located at the center of the one engagement panel configuration.

In some embodiments, the first longitudinal location has two engagement panels 110, 112. Each engagement panels 110, 112 can be considered a section or loop. Each engagement panel 110, 112 can include an arc 140 which forms a portion of a circle or other arcuate geometry. Each engagement panel 110, 112 can include the arc 140 of approximately 180 degrees or more or less. Each engagement panel 110, 112 can include the arc 140 that is semi-circular. In some embodiment, the engagement panel 110, 112 does not form a complete circular shape such as a semi-circular shape, three-quarter of a circular shape, a partial of a circular shape, or any partial circular shape less than 360 degrees. In some embodiments, the partial circular shape is offset from one engagement panel to the next. In some embodiments, the engagement panel 110, 112 form a complete circular shape. In some embodiments, the eyelet 146 is located at the center of the multi, e.g., two engagement panel configuration.

In some embodiment, the first longitudinal location has three engagement panels 110, 112, 114. Each engagement panels 110, 112, 114 can be considered a section or loop. Each engagement panel 110, 112, 114 can include an arc 140 which forms a portion of a circle. Each engagement panel 110, 112, 114 can include the arc 140 of approximately 120 degree. In some embodiments, the three engagement panels arc does not form a complete circular shape. In some embodiments, the three engagement panels arc form a partial circular shape such as three-quarter shape, semi-circular shape, or any partial circular shape less than 360 degrees. The engagement panels 110, 112, 114 have three sections or loops at a single longitudinal location. In some embodiment, the eyelet 146 is located at the center of the three engagement panel configuration.

In some embodiments, the first longitudinal location has four engagement panels. Each engagement panel can include an arc which forms a portion of a circle. Each engagement panel can include the arc of approximately 90 degree. In some embodiments, the four engagement panels arc does not form a complete circular shape. In some embodiments, the three engagement panels arc form a partial circular shape such as three-quarter shape, semi-circular shape, or any partial circular shape less than 360 degrees. In some embodiments, the eyelet 146 is located at the center of the four engagement panel configuration. In some embodiments, the first longitudinal location has five engagement panels. Each engagement panel can include the arc of approximately 72 degrees. In some embodiments, the eyelet 146 is located at the center of the five engagement panel configuration. In some embodiments, the first longitudinal location has six engagement panels. Each engagement panel can include the arc of approximately 60 degrees. In some embodiments, the eyelet 146 is located at the center of the six engagement panel configuration.

The eyelet 146 can be formed at the center of the engagement panels. The eyelet 146 can be formed at the center of the engagement panels 110, 112, 114. In some embodiment, the multiple engagement panel configuration generally surrounds the eyelet 146. In some embodiment, the engagement panels 110, 112, 114 is continuously connecting over the catheter shaft 106 in a spiral configuration. Each engagement panels 110, 112, 114 can include an additional arc that forms the eyelet 146. Each engagement panels 110, 112, 114 can form a portion of the eyelet 146. At the center of the engagement panels 110, 112, 114 is the eyelet 146. The eyelet 146 can be a shaped set circular eyelet. The eyelet 146 can be multiple coils members.

The engagement panels 110, 112, 114 can be made from one continuous wire. The engagement panels 110, 112, 114 can be made from individual wire members for each engagement panel. The individual wire members can be coupled to form the engagement panels 110, 112, 114 at the first longitudinal location. The engagement panels 110, 112, 114 can include additional segments that form the eyelet. The engagement panels 110, 112, 114 can include coils that reinforce the eyelet.

The spacers 150, 152, 154, 156 can help to maintain the separation between the engagement panels 110, 112, 114, 120, 122, 124, 130, 132, 134. When the clot is ready to be retrieved, the extractor 100 can be pulled. This pulling tension creates a pinching effect upon contacting the clot. In some embodiment, the spacers 150, 152, 154, 156 can be integrated onto the extractor 100. Each spacer 150, 152, 154, 156 can be formed with a member that is coiled along the length of extractor and connecting the eyelets 146. Each spacer 150, 152, 154, 156 can be integrally formed with the engagement panels 110, 112, 114, 120, 122, 124, 130, 132, 134. Each spacer 150, 152, 154, 156 can be integrally formed with the eyelets 146.

In some embodiment, the spacers 150, 152, 154, 156 can be separately formed from the engagement panels 110, 112, 114, 120, 122, 124, 130, 132, 134. Each spacer 150, 152, 154, 156 can be a tubular member disposed along the length of the extractor 100. Each spacer 150, 152, 154, 156 can be formed with a member that is coiled. Each spacer 150, 152, 154, 156 can be separately formed from the engagement panels 110, 112, 114, 120, 122, 124, 130, 132, 134. Each spacer 150, 152, 154, 156 can be separately formed from the eyelets 146. In some embodiment, the engagement panels couple to the catheter shaft without the spacer. In some embodiment, the engagement panels couple to the catheter shaft without a space therebetween. In some embodiment, the engagement panels couple to the catheter shaft in series, adjacent to one another.

The engagement panels 110, 112, 114, 120, 122, 124, 130, 132, 134 can be at various angles relative to a center axis 108. The center axis 108 can extend along the length of the catheter shaft 106. The engagement panels 110, 112, 114 can be at a first angle relative to the center axis 108. The first angle can range from 45 degrees to 135 degrees relative to the center axis 108. The engagement panels 120, 122, 124 can be at a second angle relative to the center axis 108. The second angle can range from 45 degrees to 135 degrees relative to the center axis 108. The engagement panels 130, 132, 134 can be at a third angle relative to the center axis 108. The third angle can range from 45 degrees to 135 degrees relative to the center axis 108. The first angle and the second angle can be the same angle. The first angle and the second angle can be different angles. The first angle, the second angle, and the third angle can be the same angle. The first angle, the second angle, and the third angle can be different angles. The extractor 100 can include a plurality of engagement panels 110, 112, 114, 120, 122, 124, 130, 132, 134.

The engagement panels 110, 112, 114, 120, 122, 124, 130, 132, 134 can angle in the same direction distally. The engagement panels 110, 112, 114, 120, 122, 124, 130, 132, 134 can angle in the same direction proximally. The engagement panels 110, 112, 114 and the engagement panels 120, 122, 124 can angle in the same direction. The engagement panels 110, 112, 114 and the engagement panels 120, 122, 124 can angle in different direction. The engagement panels 110, 112, 114 and the engagement panels 120, 122, 124 can angle in alternate manner. The engagement panels 120, 122, 124 and the engagement panels 130, 132, 134 can angle in alternate manner. The engagement panels 110, 112, 114, 120, 122, 124, 130, 132, 134 can angle in alternate manner for each engagement panels at a longitudinal location such that one engagement panels at the first longitudinal location can angle toward distally and the adjacent engagement panels at the second longitudinal location angle toward proximally.

The engagement panels 110, 112, 114 can have a diameter. The diameter of the engagement panels 110, 112, 114 can be, e.g., about 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, or more or less, between 2 and 8 mm, or any range of the foregoing values. The engagement panels 120, 122, 124 can have a diameter. The diameter of the engagement panels 120, 122, 124 can be, e.g. about 2 mm, 2.5 mm, 3 mm, 3.5 mm, 4 mm, 4.5 mm, 5 mm, 5.5 mm, 6 mm, 6.5 mm, 7 mm, 7.5 mm, 8 mm, or more or less, between 2 and 8 mm, or any range of the foregoing values. The diameter of the engagement panels 110, 112, 114, and the diameter of the engagement panels 120, 122, 124 can be the same. The diameter of the engagement panels 110, 112, 114, and the diameter of the engagement panels 120, 122, 124 can be different. The diameter of the engagement panels can be different or alternating diameter between the engagement panels.

In some embodiments, the diameter of the engagement panels 110, 112, 114 and the diameter of the engagement panels 120, 122, 124 are about 4 mm. In some embodiments, the diameter of the engagement panels 110, 112, 114, the diameter of the engagement panels 120, 122, 124, the diameter of the engagement panels 130, 132, 134 are about 4 mm. In some embodiments, the diameter of the engagement panels 110, 112, 114 and the diameter of the engagement panels 120, 122, 124 are about 5 mm. In some embodiments, the diameter of the engagement panels 110, 112, 114, the diameter of the engagement panels 120, 122, 124, the diameter of the engagement panels 130, 132, 134 are about 5 mm. In some embodiments, the diameter of the engagement panels 110, 112, 114 and the diameter of the engagement panels 120, 122, 124 are about 6 mm. In some embodiments, the diameter of the engagement panels 110, 112, 114, the diameter of the engagement panels 120, 122, 124, the diameter of the engagement panels 130, 132, 134 are about 6 mm. In some embodiments, the diameter of the engagement panels 110, 112, 114, the diameter of the engagement panels 120, 122, 124, the diameter of the engagement panels 130, 132, 134 have an alternating diameter of about 4 mm and about 6 mm along the length of the extractor 100. In some embodiments, the diameter of the engagement panels 110, 112, 114, the diameter of the engagement panels 120, 122, 124, the diameter of the engagement panels 130, 132, 134 have an alternating diameter of about 4 mm and about 5 mm along the length of the extractor 100. In some embodiments, the diameter of the engagement panels 110, 112, 114, the diameter of the engagement panels 120, 122, 124, the diameter of the engagement panels 130, 132, 134 have an alternating diameter of about 3 mm and about 4 mm along the length of the extractor 100.

In some embodiments, the spacers 150, 152, 154, 156 can be loosely fit. The spacers 150, 152, 154, 156 can be movable along the catheter shaft 106. The spacers 150, 152, 154, 156 can be moveable relative to the eyelets 146. The spacers 150, 152, 154, 156 can be movable relative to the engagement panels 110, 112, 114, 120, 122, 124, 130, 132, 134. The spacers 150, 152, 154, 156 can create tension between the engagement panels 110, 112, 114, 120, 122, 124, 130, 132, 134. In some embodiments, the spacers 150, 152, 154, 156 can be fixed to remove the tension between the engagement panels 110, 112, 114, 120, 122, 124, 130, 132, 134.

FIGS. 1-3 illustrate the extractor 100, the spacers 150, 152, 154, 156, and the collection funnel. The extractor 100 can be made of a wire member. The extractor 100 can be formed in a helix-like shape. The extractor 100 can be formed with a series of round eyelets 146. The extractor 100 can be formed with a series of legs 142, 144. The extractor 100 can be formed with a series of arcs 140. The extractor 100 can be formed with connecting members 118, 128, 138. The extractor 100 can be formed with one continuous wire member defining all, or a subset of the engagement members, including legs, arcs, and/or spacers. The extractor 100 can be formed with one or more wires.

The eyelet 146 connects to the legs 142, 144. The leg 142 extend outward where the leg 142 is connected to the arc 140. The arc 140 is connected to the next leg 144 where the leg 144 is connected to the next eyelet 146. The continuation of the series of eyelets 146, legs 142, 144, and arcs 140 form the extractor 100. Each eyelet 146 can be independent of other eyelets. Each eyelet 146 can be connected together. The legs 142, 144 and the arc 140 aid in applying tension when the eyelets 146 are spaced apart. In the unconstrained position, the eyelets 146 are positioned adjacent to each other. The eyelets 146 are separated by the spacer 150, 152, 154, 156 to keep the eyelets 146 apart. In some embodiment, the spacer 150, 152, 154, 156 can be integrated as part of the extractor 100.

The wire member of the extractor 100 can be made of metallic material. The wire member of the extractor 100 can be made, for example, of a shape memory material such as Nitinol. The wire member of the extractor 100 can have a diameter of, e.g. about 0.0005", 0.001", 0.0015", 0.002", 0.0025", 0.003", 0.0035", 0.004", 0.0045", 0.005", or more or less, from 0.0005" to 0.005", or any range of two of the foregoing values.

The filter can be positioned at the distal end of the catheter shaft 106. The filter can be made, in some cases, of dual nitinol braid layer. The filter can attach to the distal end of the catheter shaft 106. The extractor 100 can be proximal to the filter. The spacers 150, 152, 154, 156 can be positioned between the eyelets 146 to keep the eyelets 146 apart and to create a space to capture the clot.

The extractor 100 can be made of a wire member that is formed with a series of round eyelets 146, spacers 150, 152, 154, 156 formed as coils, the legs 142, 144 and the arcs 140. The eyelet 146 connects to the leg 142 that extends outward where the leg 142 is connected to the arc 140. The arc 140 is connected to the next leg 144 where it is connected to the next eyelet 146. The continuation of the series of the eyelets 146, the legs 142, 144 and the arc 140 form the extractor 100. The legs 142, 144 and the arc 140 aid in applying tension when the eyelets 146 are spaced apart. In the unconstrained position, the eyelets 146 are positioned adjacent to each other. The eyelets 146 are separated by the spacer 150, 152, 154, 156 to keep the eyelets 146 apart. The spacer 150, 152, 154, 156 is positioned between the eyelets 146 to keep the eyelets 146 apart and to create a space opening to capture the clot. In some embodiment, the spacer 150, 152, 154, 156 is made of coil. The spacer 150, 152, 154, 156 formed from the coil can be part of the extractor 100. The spacer 150, 152, 154, 156 formed from the coil can be separate from the extractor 100. The spacer 150, 152, 154, 156 formed from the coil can be close pitch or loose pitch which can be spring-like.

The extractor 100 can be made of a wire member that is formed in a helix-like shaped with series of round eyelets 146, the legs 142, 144, and the arcs 140. The helix-like shaped can be a single helix. In some embodiments, the helix can be a double helix. In some embodiments, the helix can be a triple helix or more. The eyelet 146 connects to the leg 142 that extends outward where the leg 142 is connected to the arc 140. The other end of the arc 140 is connected to the next leg 144 that is connected to the next eyelet 146. Continuation of the series of eyelets 146, the legs 142, 144 and the arcs form the extractor 100. Each eyelet 146 can be independent of the other eyelet 146 or connected to the adjacent eyelet 146. In some embodiments, the eyelets 146, the legs 142, 144 and the arcs 140 are connected by a single wire. The legs 142, 144 and the arcs 140 can apply tension when the eyelets 146 are spaced apart. In the unconstrained position, the eyelets 146 are position adjacent to each other. The eyelets 146 are separated by the spacer 150, 152, 154, 156 to keep the eyelets 146 apart. In some embodiment, the spacer 150, 152, 154, 156 can be integrated with the extractor. The wire member can be made of, e.g., one or more metallic materials such as nitinol. The wire member diameter can range from, e.g., 0.0005" to 0.005". The extractor 100 can be compressed in the delivery configuration to the intended treatment site through a sheath or a catheter. The extractor 100 is expanded as it is unsheathed. The extractor length can be unsheathed as needed for use as the entire length of the extractor 100 does not need to be open for the extractor 100 to be functional. In some embodiment, a filter can be used and is positioned distal to the extractor and aids in capturing fragmented clot or emboli during the removal of the extractors. The filter can be compressed during delivery and expand when unsheathed. The filter aids in capturing potential fragmented clot or emboli when retrieving the clot or emboli. In some embodiment, there is a collection funnel used to capture the extractor 100 and the filter with clot. The collection funnel can be positioned proximal to the extractor 100.

To use the extractor 100, a guidewire can be used to access the treatment area. A guide catheter with balloon tip can be placed in the carotid artery. The sheath 160 can be introduced through the guide catheter to the treatment site. The extractor 100, the filter and the collection funnel can introduced over the guidewire to the treatment site via the sheath 160. The sheath 160 is then unsheathed to deploy the filter and the extractor 100 and the collection funnel. The sheath 160, the extractor 100 and the filter then withdraw into the collection funnel. Once inside the collection funnel, the entire system is withdrawn into the guide catheter. In some embodiment, a collection funnel is introduced and position near the treatment site via the balloon catheter. The sheath 160 is introduced via the collection funnel to the treatment site. The extractor 100 and the filter are introduced through the sheath 106 to the treatment site. The sheath 160 is then retracted to deploy the extractor 100 and the filter. The sheath 160, the extractor 100 and the filter withdraw into the collection funnel. The entire assembly is then withdrawn into the guide catheter from the vascular system.

FIG. 4A through 4G represents the extractor deployment. The extractor 100 is first inside the sheath 160 in FIG. 4A. Then, the sheath 160 is unsheathed (e.g., moved in a direction longitudinally along the extractor) to fully deploy the engagement panels 110, 112, 114 of the extractor 100 in FIG. 4G. The extractor 100 has three engagement panels 110, 112, 114. The engagement panels 110, 112, 114 are at the first longitudinal location. The engagement panels 110, 112, 114 can deploy together. The engagement panels 110, 112, 114 can deploy simultaneously. The engagement panels 110, 112, 114 can deploy as the sheath 160 moves past the first longitudinal location. The engagement panels 110, 112, 114 open like a flower. The arcs 140 of the engagement panels 110, 112, 114 deploy first as the sheath 160 moves. The legs 142, 144 gradually deploy as the sheath 160 moves. The legs 142, 144 fully deploy thereby expanding the arcs 140. The engagement panels 110, 112, 114 open to the expanded diameter when the legs 142, 144 are unsheathed. The engagement panels 110, 112, 114 are fully deployed. The engagement panels 110, 112, 114 can function to engage a clot.

Figure 5A:
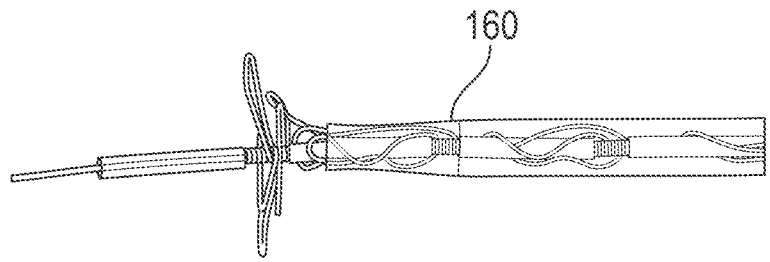
FIGS. 5A-5G are views of deployment of the second panel of the first embodiment of the three engagement panels extractor.
Figure 5B:
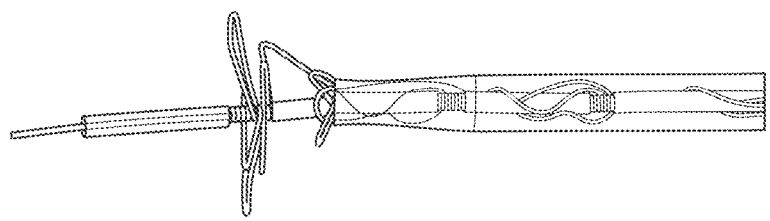
Figure 5C:
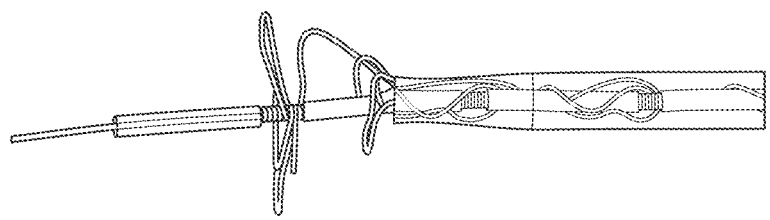
Figure 5D:
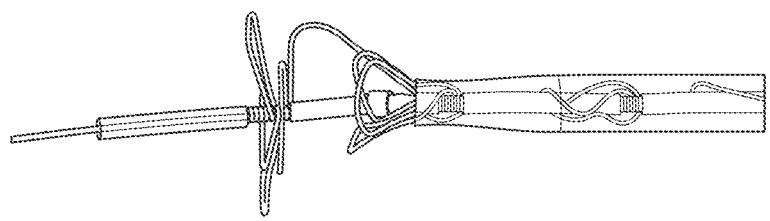
Figure 5E:
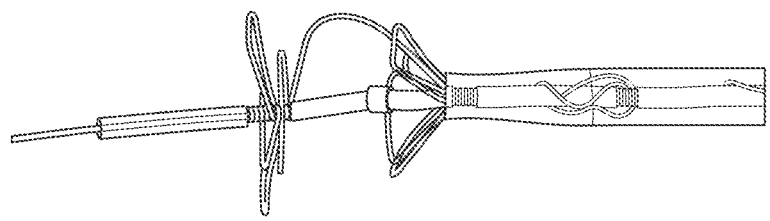
Figure 5F:
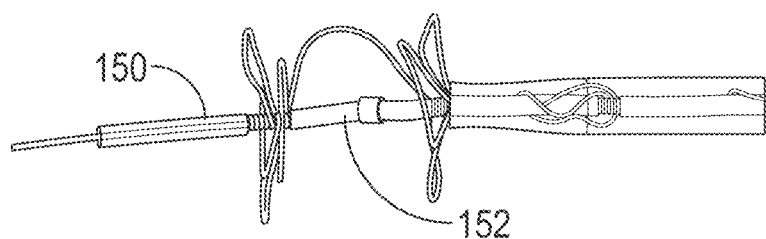
Figure 5G:
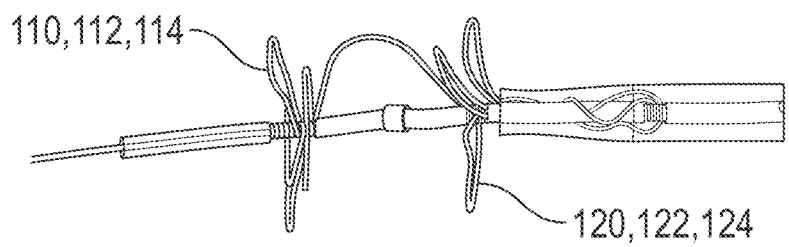

FIG. 5A though 5G represents the deployment of the engagement panels 120, 122, 124 of the extractor 100. The engagement panels 110, 112, 114 are fully deployed. The engagement panels 120, 122, 124 of the extractor 100 are first inside the sheath 160 in FIG. 5A. Then, the sheath 160 is unsheathed to fully deploy the engagement panels 120, 122, 124 of the extractor 100 in FIG. 5G. The extractor 100 has three engagement panels 120, 122, 124. The engagement panels 120, 122, 124 are at the second longitudinal location. The engagement panels 120, 122, 124 can deploy together. The engagement panels 120, 122, 124 can deploy simultaneously. The engagement panels 120, 122, 124 can deploy as the sheath 160 moves past the second longitudinal location. The engagement panels 120, 122, 124 open like a flower. The arcs 140 of the engagement panels 120, 122, 124 deploy first as the sheath 160 moves. The legs 142, 144 gradually deploy as the sheath 160 moves. The legs 142, 144 fully deploy thereby expanding the arcs 140. The engagement panels 120, 122, 124 open to the expanded diameter when the legs 142, 144 are unsheathed. The engagement panels 120, 122, 124 are fully deployed. The engagement panels 120, 122, 124 can function to engage a clot. The engagement panels 110, 112, 114 and the engagement panels 120, 122, 124 can function to pinch a clot therebetween.

FIG. 6A through 6G represents the extractor deployment of an extractor 200. The extractor 200 can have any of the features described herein. The extractor 200 can have a plurality of engagement panels 210, 212, 214, 216, 220, 222, 224, 226, 230, 232, 234, 236. The engagement panels 210, 212, 214, 216 are located at a first longitudinal location. The engagement panels 220, 222, 224, 226 are located at a second longitudinal location. The engagement panels 230, 232, 234, 236 are located at a third longitudinal location. The first longitudinal location can be distal to the second longitudinal location. The second longitudinal location can be distal to the third longitudinal location. In the illustrated embodiment, there are four engagement panels at each longitudinal location. The engagement panels 210, 212, 214, 216 can form a generally round profile. The engagement panels 210, 212, 214, 216 at a single longitudinal location can form a circular profile. Each engagement panel 210, 212, 214, 216 can form a portion of a circle. Each engagement panel 210, 212, 214, 216 can form an arc 240. Each engagement panel 210, 212, 214, 216 can include an approximately 90 degree arc. Each engagement panel 210, 212, 214, 216 can form an arc of, e.g. about 75 degrees, 80 degrees, 81 degrees, 82 degrees, 83 degrees, 84 degrees, 85 degrees, 86 degrees, 87 degrees, 88 degrees, 90 degrees, less than 90 degrees, greater than 80 degrees, or any range of two of the foregoing values. Each engagement panel 210, 212, 214, 216 can form an arc that forms part of a circular profile. Each engagement panel 210, 212, 214, 216 can form the same arc. Each engagement panel 210, 212, 214, 216 can form a different arc. The two legs 242, 244 connect to an arc 240 of engagement panel 210, 212, 214, 216. The two legs 242, 244 can be linear. The two legs 242, 244 can have a constant angle therebetween. The two legs 242, 244 can connect to the ends of the arc 240.

Figure 6A:
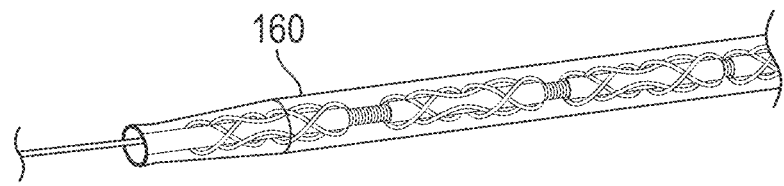
FIGS. 6A-6G are views of deployment of the first panel of a second embodiment of the four engagement panels extractor.
Figure 6B:
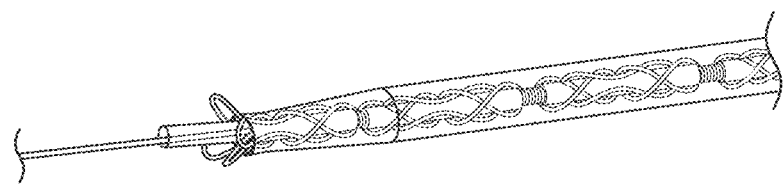
Figure 6C:
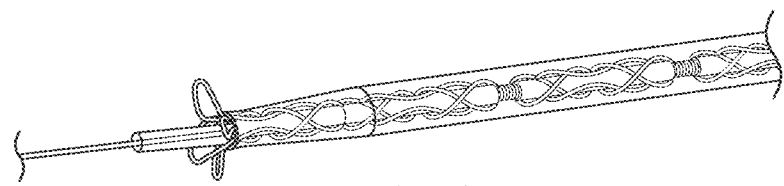
Figure 6D:
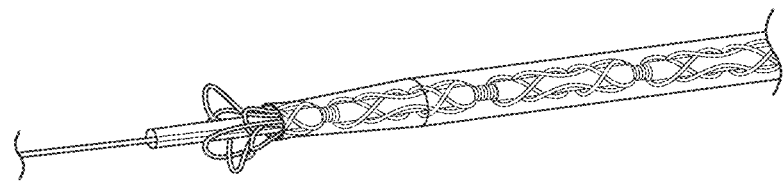
Figure 6E:
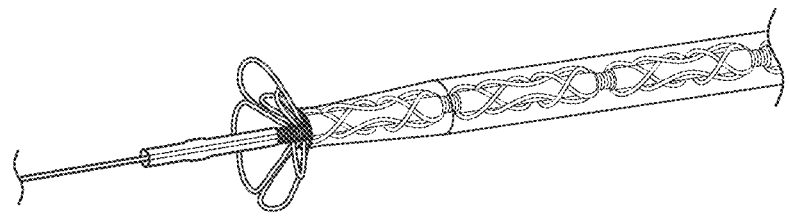
Figure 6F:
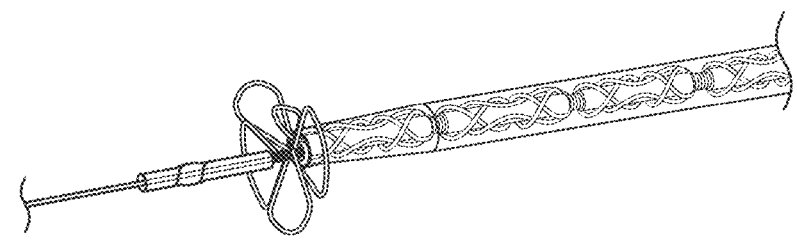
Figure 6G:
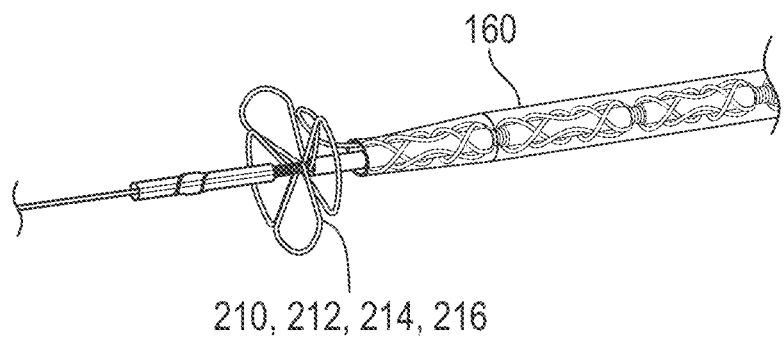

The extractor 200 is first inside the sheath 160 in FIG. 6A. Then, the sheath 160 is unsheathed to fully deploy the engagement panels 210, 212, 214, 216 of the extractor 200 in FIG. 6G. The extractor 200 has three engagement panels 210, 212, 214, 216. The engagement panels 210, 212, 214, 216 are at the first longitudinal location. The engagement panels 210, 212, 214, 216 can deploy together. The engagement panels 210, 212, 214, 216 can deploy simultaneously. The engagement panels 210, 212, 214, 216 can deploy as the sheath 160 moves past the first longitudinal location. The engagement panels 210, 212, 214, 216 open like a flower. The arcs 240 of the engagement panels 210, 212, 214, 216 deploy first as the sheath 160 moves. The legs 242, 244 gradually deploy as the sheath 160 moves. The legs 242, 244 fully deploy thereby expanding the arcs 240. The engagement panels 210, 212, 214, 216 open to the expanded diameter when the legs 242, 244 are unsheathed. The engagement panels 210, 212, 214, 216 are fully deployed. The engagement panels 210, 212, 214, 216 can function to engage a clot. In some embodiments, the extractor 200 can include a distal member 280. The distal member 280 can include any feature described herein. In some embodiments, the distal member 280 can deploy before the engagement panels 210, 212, 214, 216.

Figure 7A:
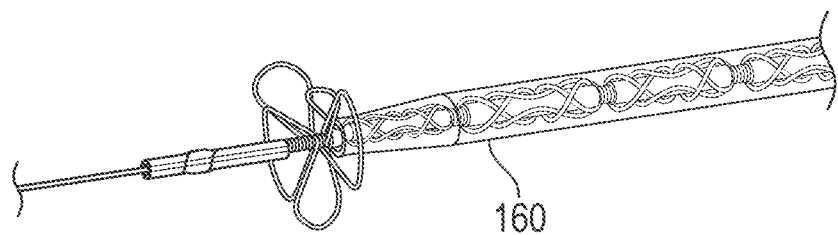
FIGS. 7A-7G are views of deployment of the second panel of an extractor the second embodiment of the four engagement panels extractor.
Figure 7B:
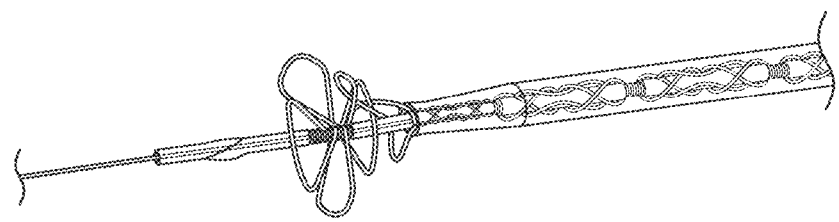
Figure 7C:
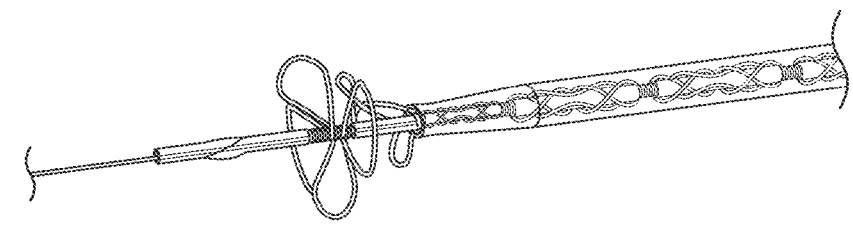
Figure 7D:
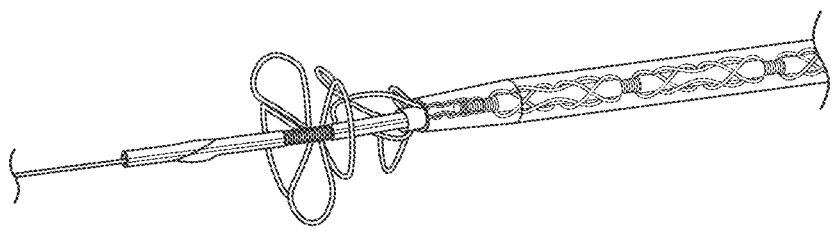
Figure 7E:
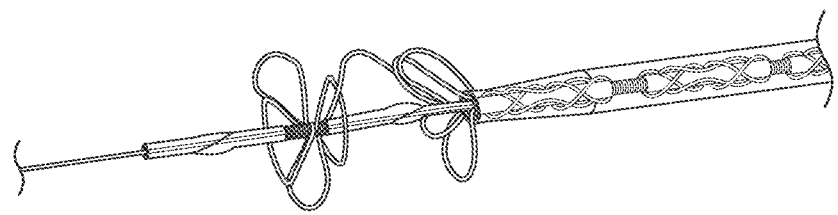
Figure 7F:
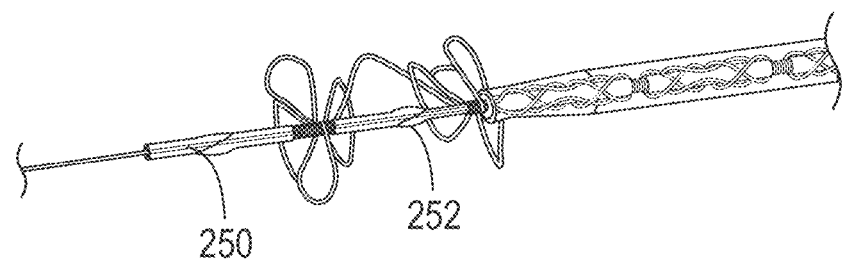
Figure 7G:
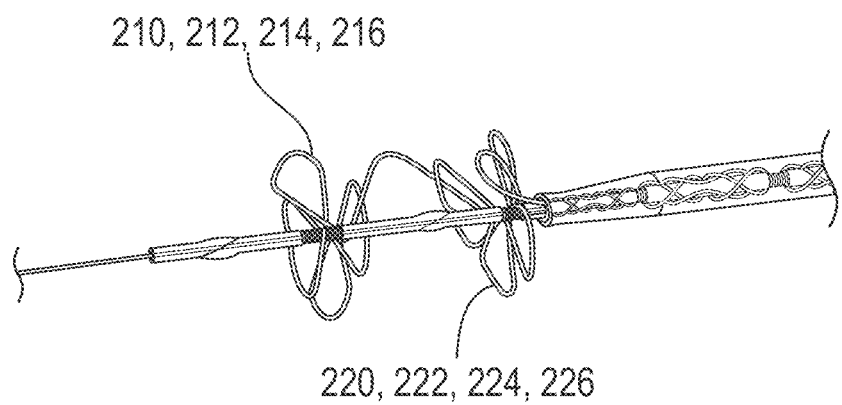

FIG. 7A though 7G represents the deployment of the engagement panels 220, 222, 224, 226 of the extractor 200. The engagement panels 210, 212, 214, 216 are fully deployed. The engagement panels 220, 222, 224, 226 of the extractor 200 are first inside the sheath 160 in FIG. 7A. Then, the sheath 160 is unsheathed to fully deploy the engagement panels 220, 222, 224, 226 of the extractor 200 in FIG. 7G. The extractor 200 has three engagement panels 220, 222, 224, 226. The engagement panels 220, 222, 224, 226 are at the second longitudinal location. The engagement panels 220, 222, 224, 226 can deploy together. The engagement panels 220, 222, 224, 226 can deploy simultaneously. The engagement panels 220, 222, 224, 226 can deploy as the sheath 160 moves past the second longitudinal location. The engagement panels 220, 222, 224, 226 open like a flower. The arcs 240 of the engagement panels 220, 222, 224, 226 deploy first as the sheath 160 moves. The legs 242, 244 gradually deploy as the sheath 160 moves. The legs 242, 244 fully deploy thereby expanding the arcs 240. The engagement panels 220, 222, 224, 226 open to the expanded diameter when the legs 242, 244 are unsheathed. The engagement panels 220, 222, 224, 226 are fully deployed. The engagement panels 220, 222, 224, 226 can function to engage a clot. The engagement panels 210, 212, 214, 216 and the engagement panels 220, 222, 224, 226 can function to pinch a clot therebetween.

Figure 8A:
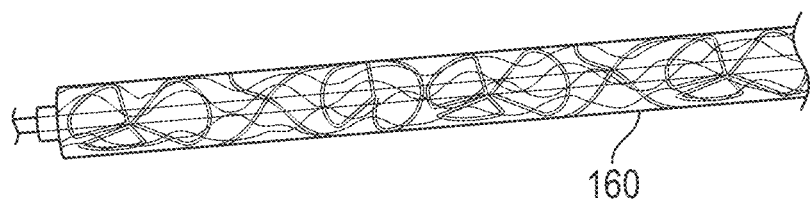
FIGS. 8A-8G are views of further detailed deployment of the first panel of the first embodiment of the extractor.
Figure 8B:
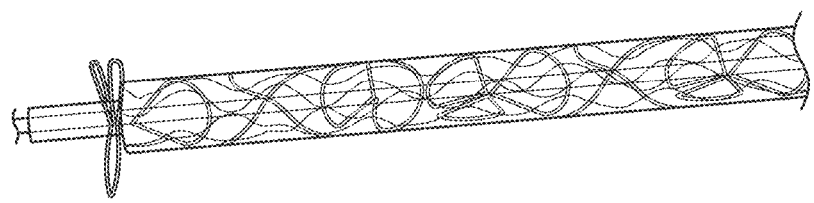
Figure 8C:
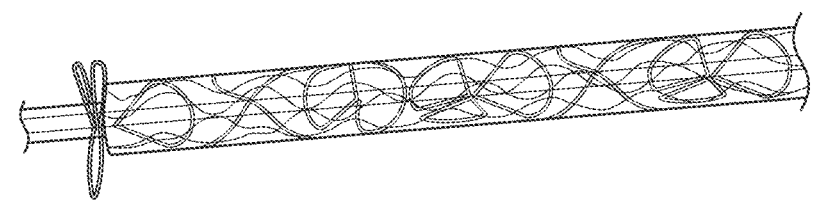
Figure 8D:
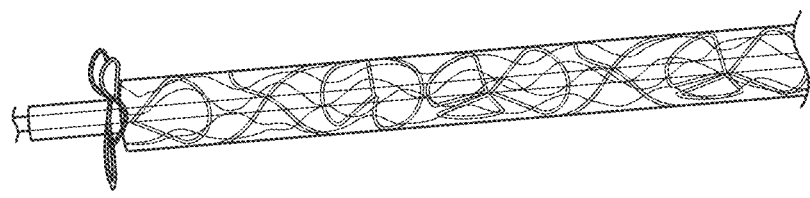
Figure 8E:
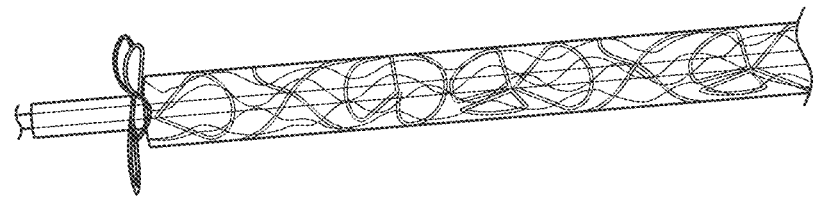
Figure 8F:
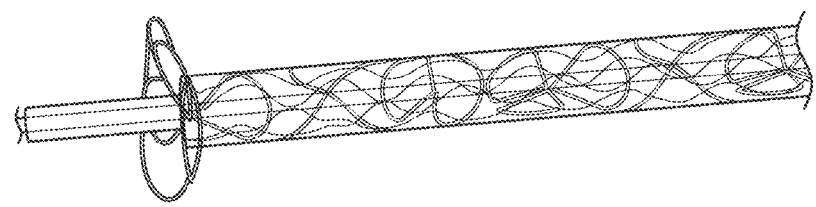
Figure 8G:
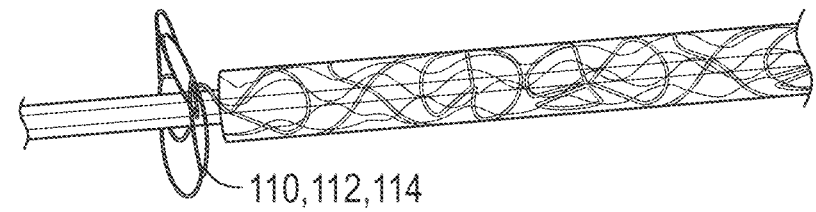
Figure 9A:
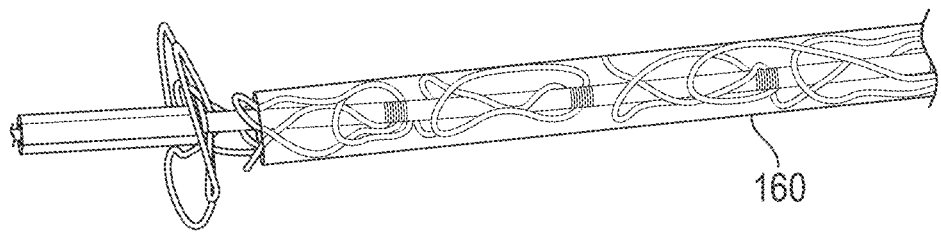
FIGS. 9A-9H are views of further detailed deployment of the second panel of the first embodiment of the extractor.
Figure 9B:
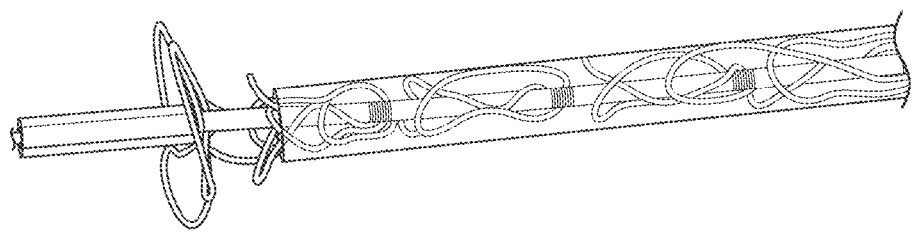
Figure 9C:
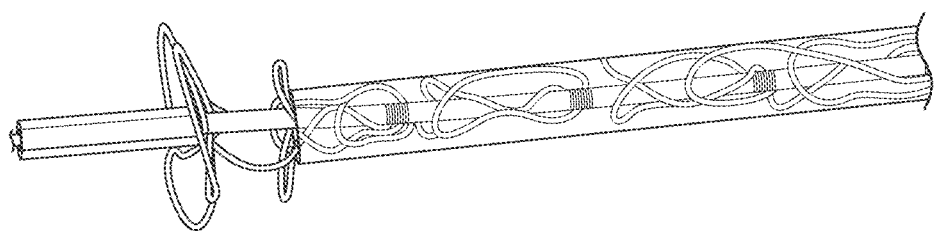
Figure 9D:
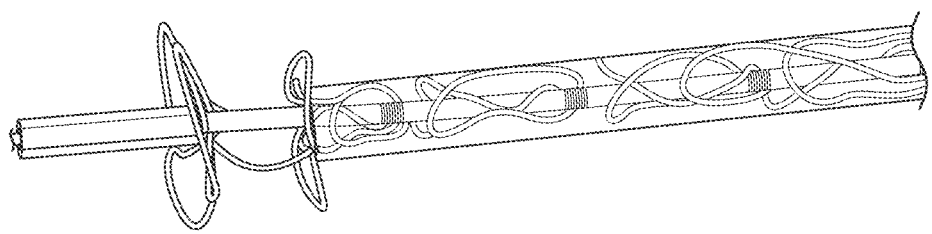
Figure 9E:
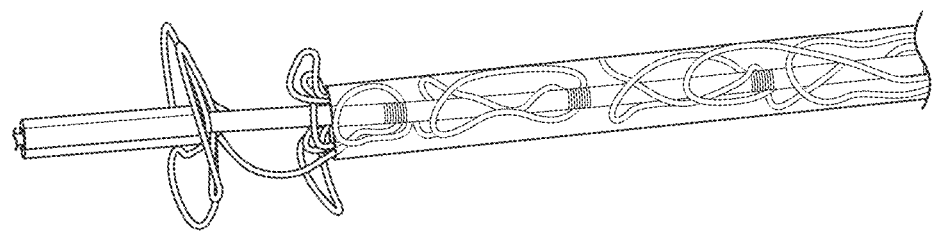
Figure 9F:
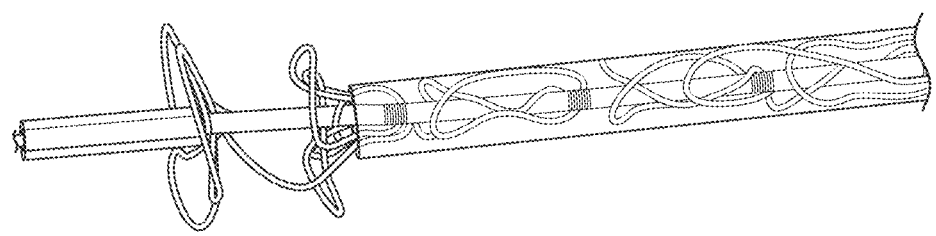
Figure 9G:
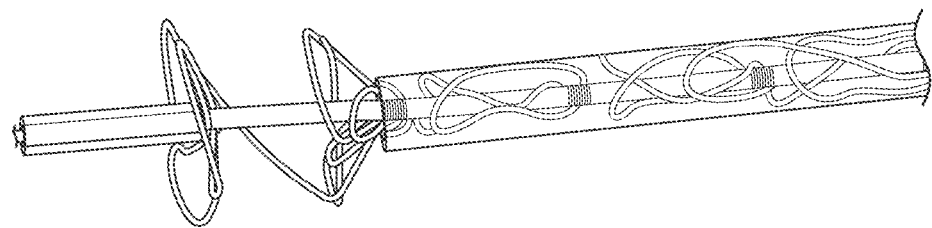
Figure 9H:
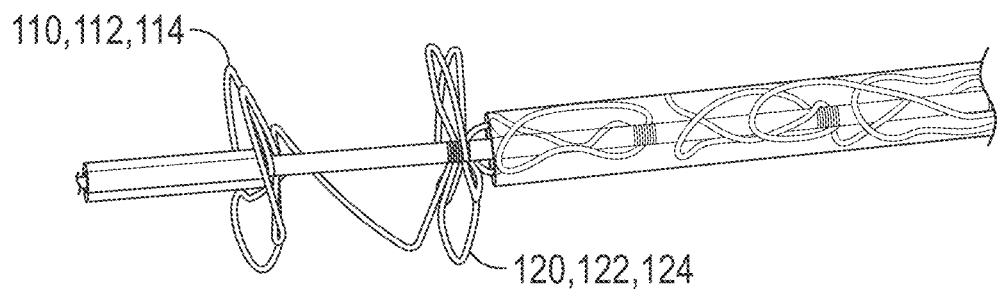

FIG. 8A through 8G represents the extractor deployment where the extractor 100 is first inside the sheath in FIG. 8A, then the sheath 106 is unsheathed to fully deploy the engagement panels 110, 112, 114 in FIG. 8G. FIG. 9A though 9H represents the deployment of the engagement panels 120, 132, 134 of the extractor 100. The engagement panels 110, 112, 114 are fully deployed. The engagement panels 120, 122, 124 of the extractor 100 are first inside the sheath 160 in FIG. 9A. Then, the sheath 160 is unsheathed to fully deploy the engagement panels 120, 122, 124 of the extractor 100 in FIG. 9H. The extractor 100 has three engagement panels 120, 122, 124. The engagement panels 120, 122, 124 are at the second longitudinal location. The engagement panels 120, 122, 124 can deploy together. The engagement panels 120, 122, 124 can deploy such that a portion of the engagement panels 120, 122, 124 is proximal to the distal end of the sheath 160 in FIG. 9E. The engagement panels 120, 122, 124 can wrap around the distal end during deployment. The engagement panels 120, 122, 124 can extend proximally during deployment. The engagement panels 120, 122, 124 can be distal to the distal end of the sheath 160 when fully deployed. The initial expanded portion of the engagement panels revert proximally when the engagement panels first deploy.

Figure 10:
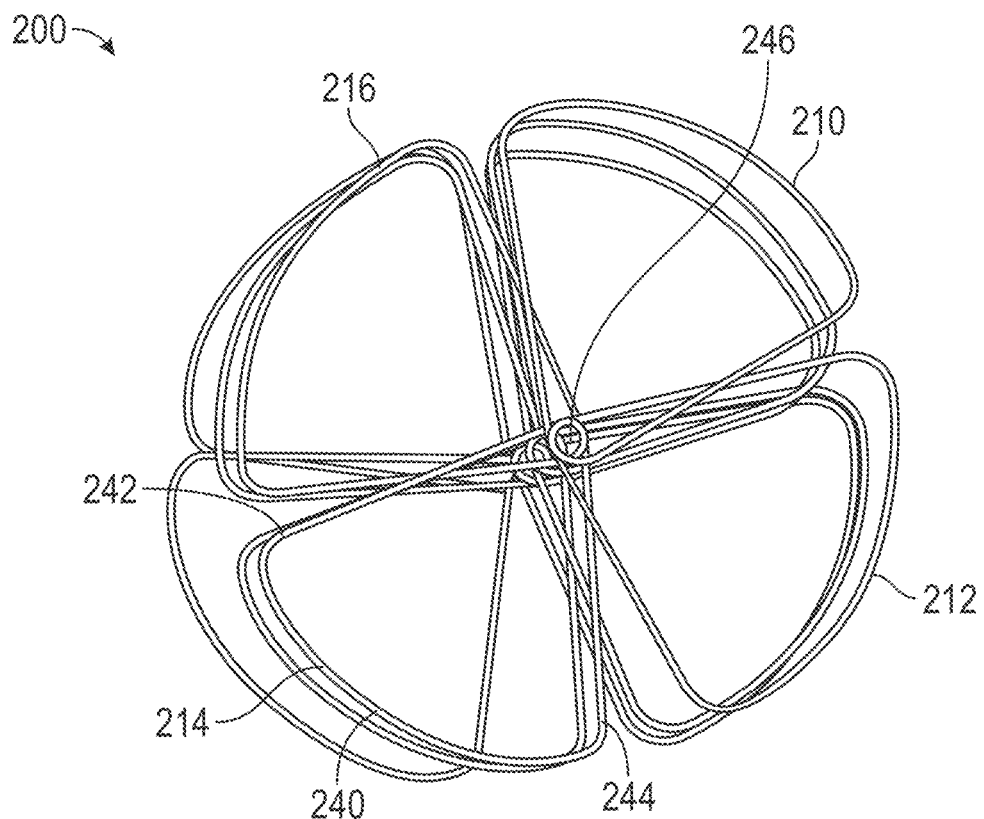
FIG. 10 is a top view of the second embodiment of the four engagement panels extractor.
Figure 11:
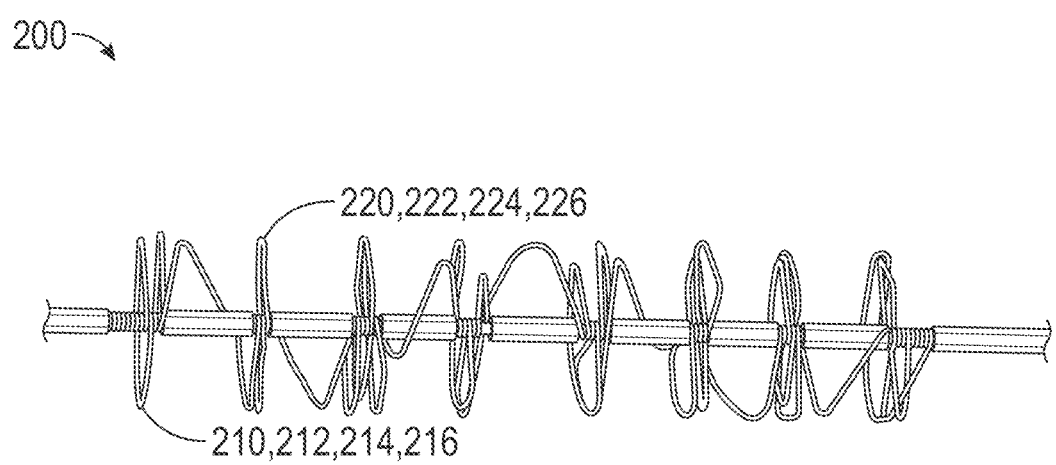
FIGS. 11-14 are side views of the second embodiment of the four engagement panels extractor.
Figure 12:
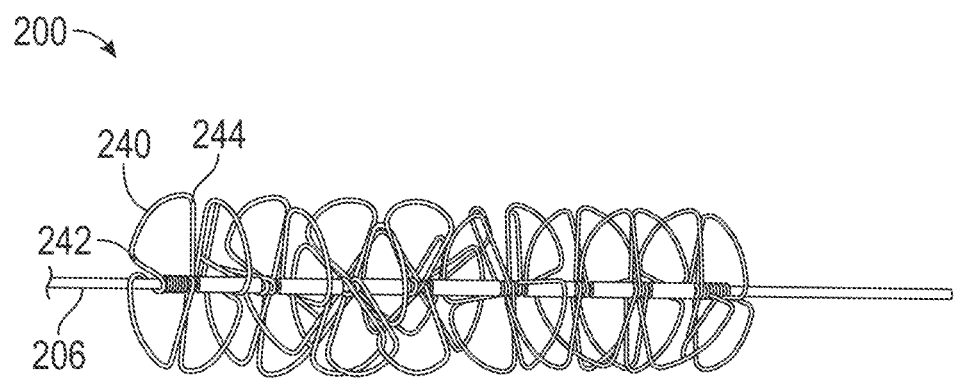
Figure 13:
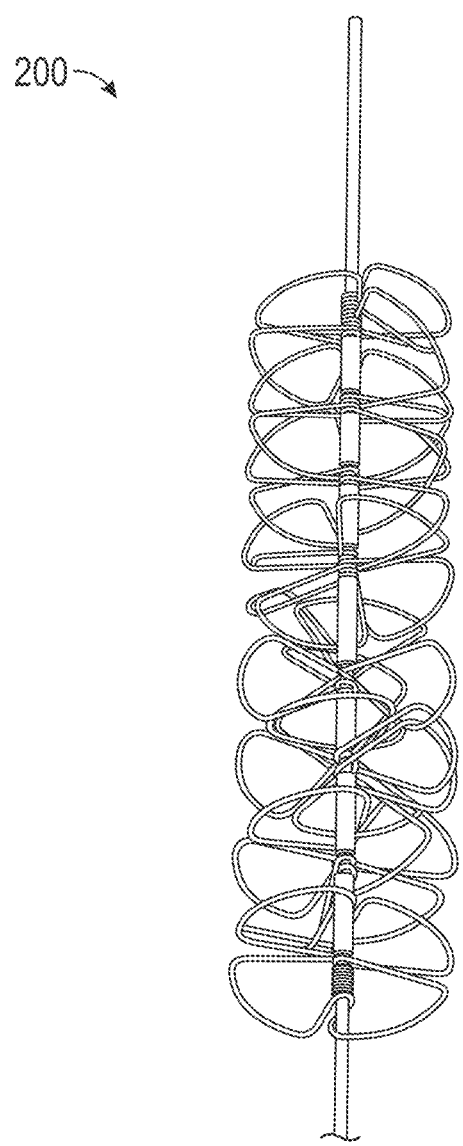
Figure 14:
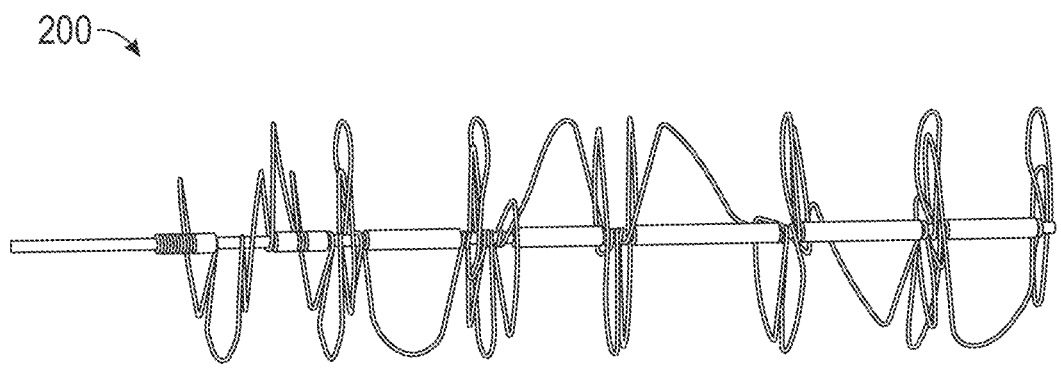

FIG. 10 represents a top view of the extractor 200. FIGS. 11-14 represent side views of the extractor 200. The engagement panels 210, 212, 214, 216 can be configured to be approximately 90 degrees to the catheter shaft 206.

The engagement panels 210, 212, 214, 216, 220, 222, 224, 226, 230, 232, 234, 236 can be at various angles relative to a center axis 208. The center axis 208 can extend along the length of the catheter shaft 206. The engagement panels 210, 212, 214, 216 can be at a first angle relative to the center axis 208. The first angle can range from, e.g., 30 degrees to 150 degrees relative to the center axis 208. The engagement panels 220, 222, 224, 226 can be at a second angle relative to the center axis 208. The second angle can range from, e.g., 30 degrees to 150 degrees relative to the center axis 208. The engagement panels 230, 232, 234, 236 can be at a third angle relative to the center axis 208. The third angle can range from 30 degrees to 150 degrees relative to the center axis 208. The first angle and the second angle can be the same angle. The first angle and the second angle can be different angles. The first angle, the second angle, and the third angle can be the same angle. The first angle, the second angle, and the third angle can be different angles.

The engagement panels 210, 212, 214, 216, 220, 222, 224, 226, 230, 232, 234, 236 can angle in the same direction distally. The engagement panels 1 210, 212, 214, 216, 220, 222, 224, 226, 230, 232, 234, 236 can angle in the same direction proximally. The engagement panels 210, 212, 214, 216 and the engagement panels 220, 222, 224, 226 can angle in the same direction. The engagement panels 210, 212, 214, 216 and the engagement panels 220, 222, 224, 226 can angle in different direction. The engagement panels 210, 212, 214, 216 and the engagement panels 220, 222, 224, 226 can angle in a different, e.g., alternate manner. The engagement panels 220, 222, 224, 226 and the engagement panels 230, 232, 234, 236 can angle in alternate manner. The engagement panels 210, 212, 214, 216, 220, 222, 224, 226, 230, 232, 234, 236 can angle in an alternate manner for each engagement panels at a longitudinal location such that one engagement panels at the first longitudinal location can angle toward distally and the adjacent engagement panels at the second longitudinal location angle toward proximally. In some embodiments, the engagement panels 210, 212, 214, 216 and the engagement panels 220, 222, 224, 226 can angle in the same direction. In some embodiments, the engagement panels 210, 212, 214, 216 and the engagement panels 220, 222, 224, 226 can alternate pointing distally or proximally and vice versa. Each engagement panels 210, 212, 214, 216 can angle in the same direction or alternate direction, e.g., facing distally or proximally or any combination thereof. When the engagement panel first exposes or exit the microcatheter, the first portion of the panel revert back proximally behind the tip of the sheath. Then the latter portion of the engagement panel expand or flare outward. The reverting back of the panel tip will grab and pull the clot away from the vessel wall.

In some embodiments, the diameter of the engagement panels 110, 112, 114, 120, 122, 124, 130, 132, 134 can be adjusted to a larger or smaller diameter depending on the vessel diameter as needed. The arcs 140 can expand to be against the vessel wall. The engagement panels 110, 112, 114, 120, 122, 124, 130, 132, 134 can partially flare outward to contact the vessel wall. The engagement panels 110, 112, 114, 120, 122, 124, 130, 132, 134 can fully flare outward to contact the vessel wall. The engagement panels 110, 112, 114, 120, 122, 124, 130, 132, 134 can function when the legs 142, 144 are partially expanded. The engagement panels 110, 112, 114, 120, 122, 124, 130, 132, 134 can function when the legs 142, 144 when the legs are straight. The engagement panels 110, 112, 114, 120, 122, 124, 130, 132, 134 can function when the legs 142, 144 are perpendicular to the catheter shaft 106. The engagement panels 110, 112, 114, 120, 122, 124, 130, 132, 134 can function when the legs 142, 144 are angled to the catheter shaft 106.

Figure 15:
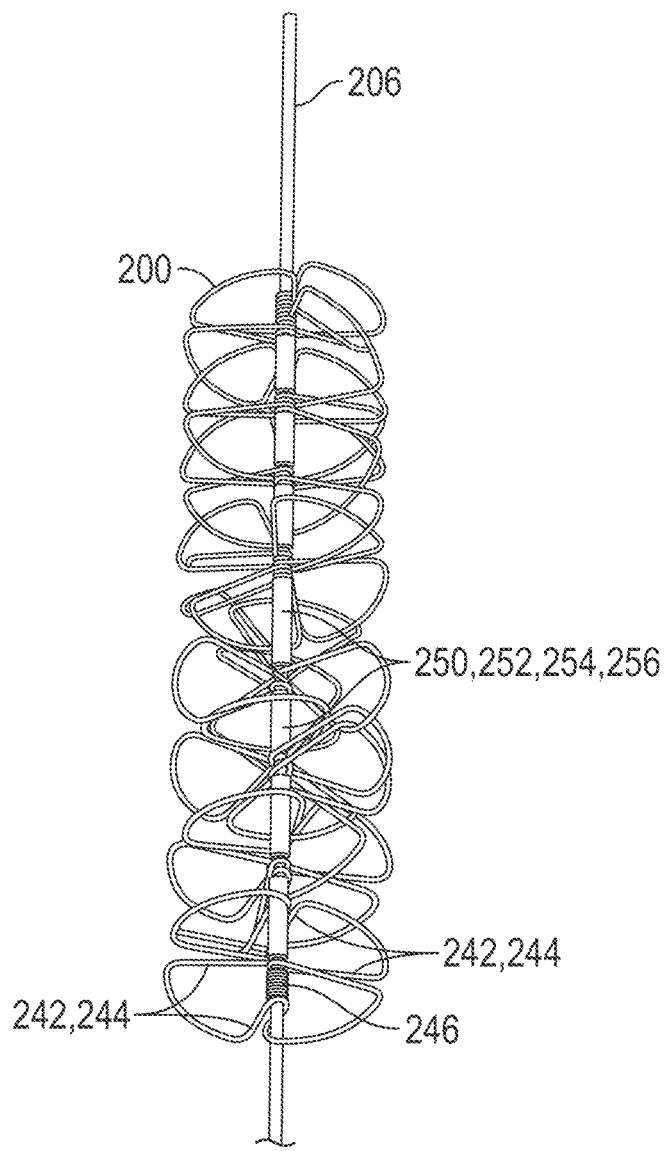
FIG. 15 is another view of the second embodiment of the extractor.

FIG. 15 is another view of the extractor 200. The extractor 200 can include the legs 242, 244. The extractor 200 can include the eyelets 246. The extractor 200 can include the spacers 250, 252, 254, 256. The extractor 200 can include the catheter shaft 206. The extractor 200 can include any of the features described herein.

Figure 16:
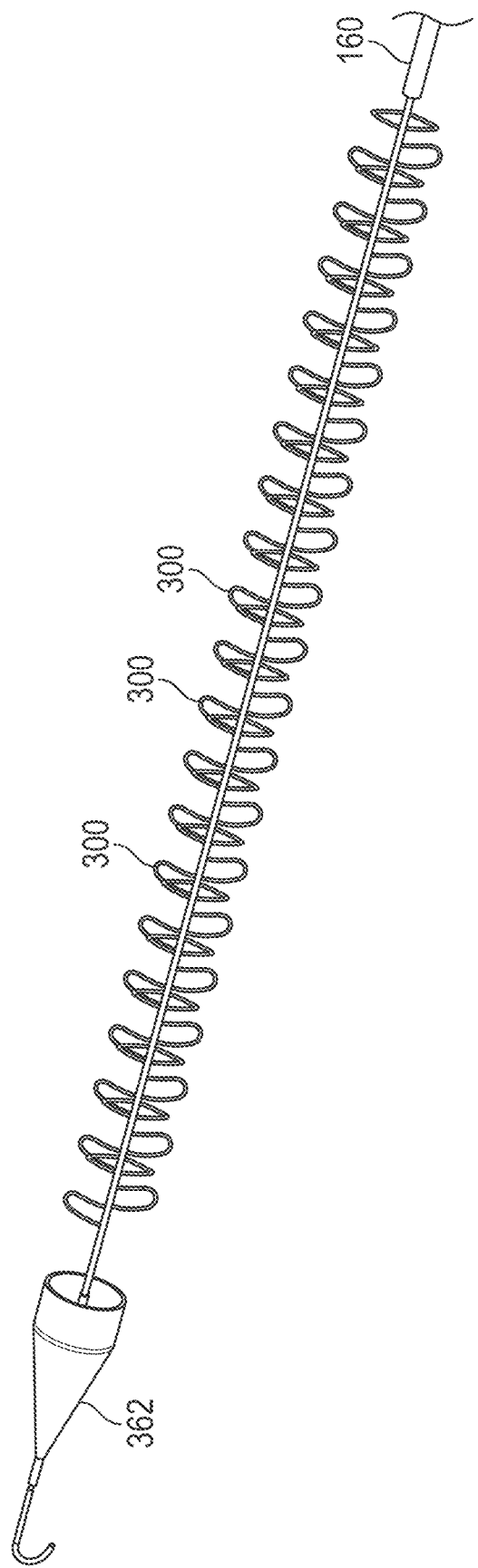
FIGS. 16-18 are views of the third embodiment of the helical engagement panel extractor.
Figure 17:
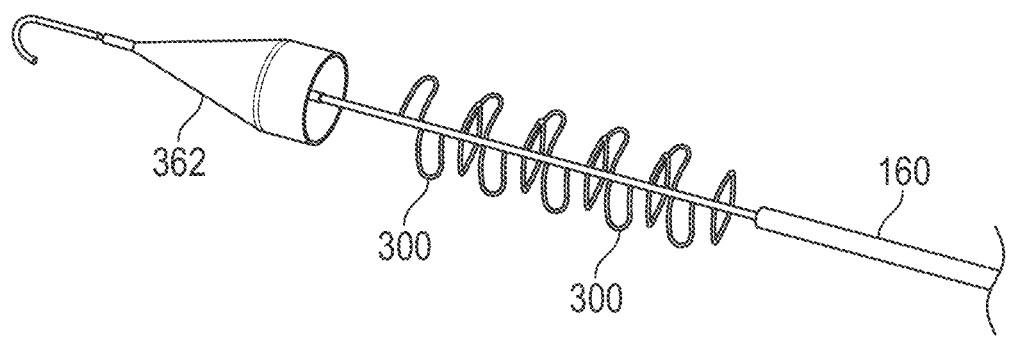
Figure 18:
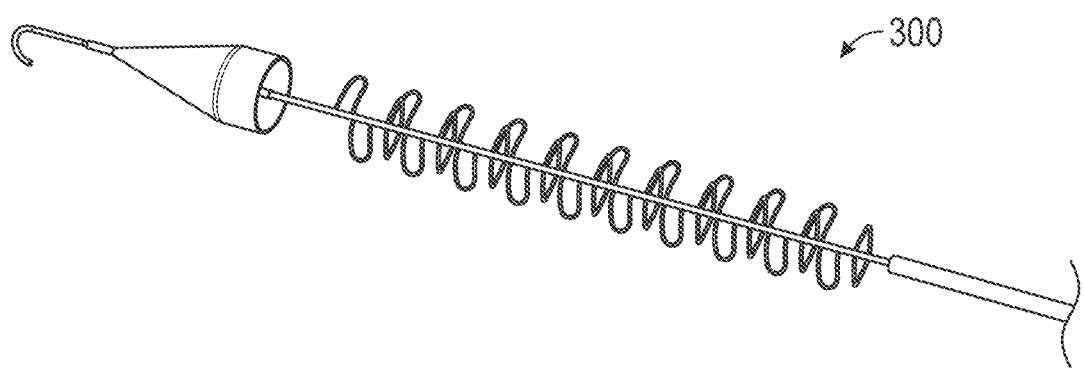

FIG. 16 is a view of an extractor 300. The extractor 300 can have any of the features described herein. The engagement panels 310, 320, 330 can be arranged in a helical configuration. FIG. 17 is a view of the extractor 300. The engagement panels 310, 320, 330 can be partially deploy distal to the sheath 160. FIG. 18 is a view of the extractor 300 and sheath 160. The extractor 300 can include a distal member 380. The distal member 380 can include any feature described herein.

Figure 19:
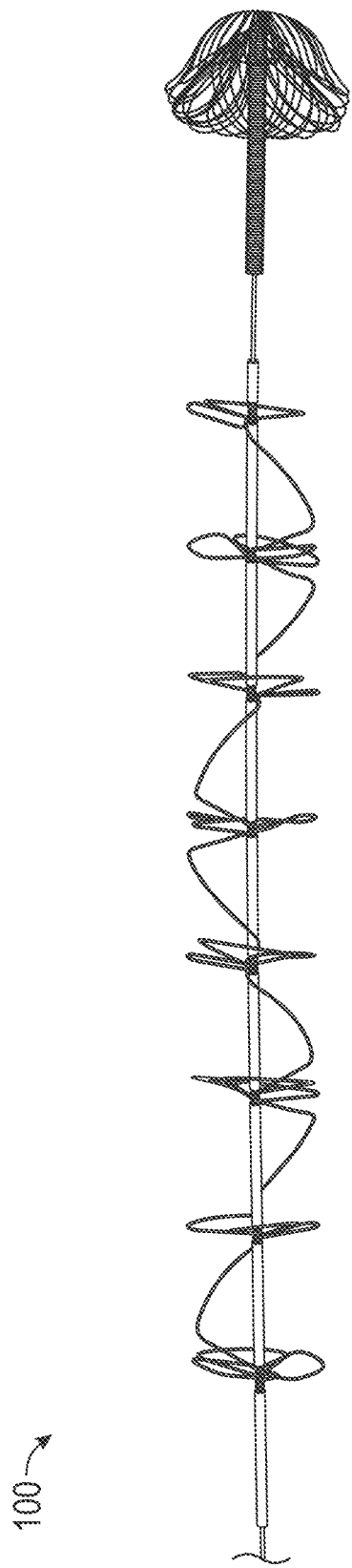
FIGS. 19-26 are views of the first embodiment of the three engagement panels extractor.

FIG. 19 is a view of the extractor 100. The engagement panels 110, 112, 114, 120, 122, 124, 130, 132, 134 can expand or open from the right to left. The engagement panels 110, 112, 114, 120, 122, 124, 130, 132, 134 can open upward. The engagement panels 110, 112, 114, 120, 122, 124, 130, 132, 134 can create a scraping effect. The engagement panels 110, 112, 114, 120, 122, 124, 130, 132, 134 can create a pinching effect.

Figure 20:
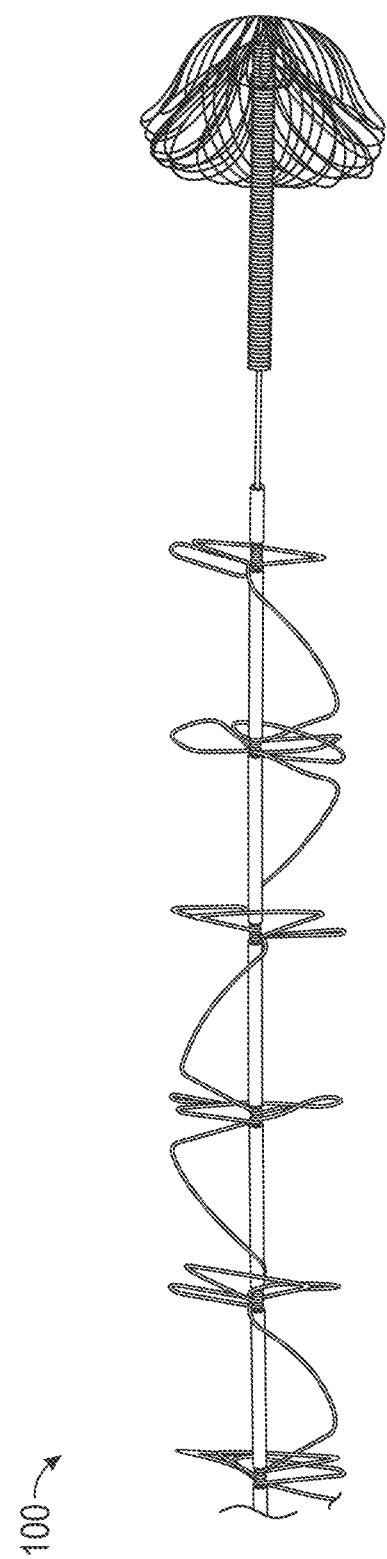

FIG. 20 is another view of the extractor 100.

FIG. 21 is a view of the extractor 100. The engagement panels 110, 112, 114 can each form an angle theta relative to the central axis 108. The engagement panels 110, 112, 114 can each form an angle theta of approximately 120 degrees.

FIGS. 22-26 are views of the extractor 100. The engagement panels 110, 112, 114 can each form an angle alpha relative to the central axis 108. The engagement panels 110, 112, 114 can each form an angle alpha approximately 90 degrees.

FIGS. 27-30 are views of the extractor 300.

Figure 31:
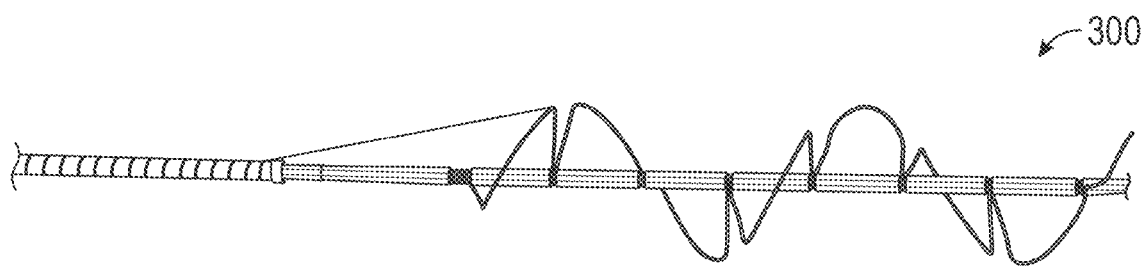
FIG. 31 is a view of the third embodiment of the helical engagement panels extractor.
Figure 32:
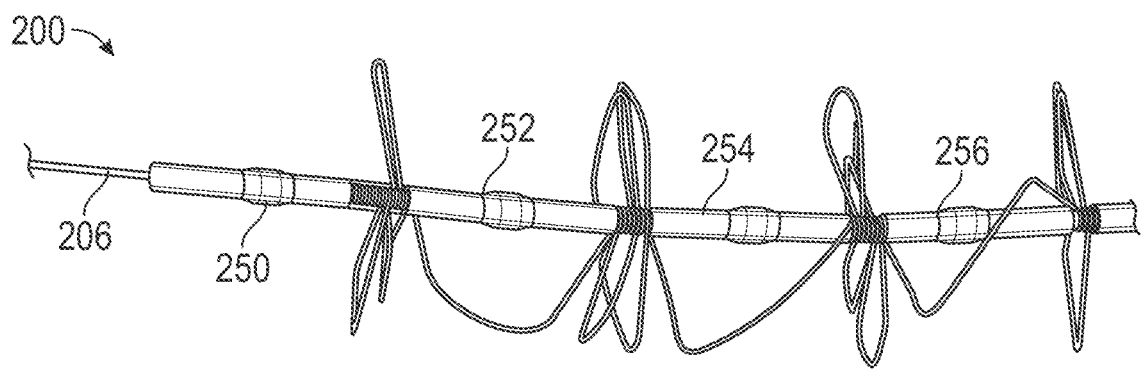
FIGS. 32-34 are views of the second embodiment of the three engagement panels extractor deployed.
Figure 33:
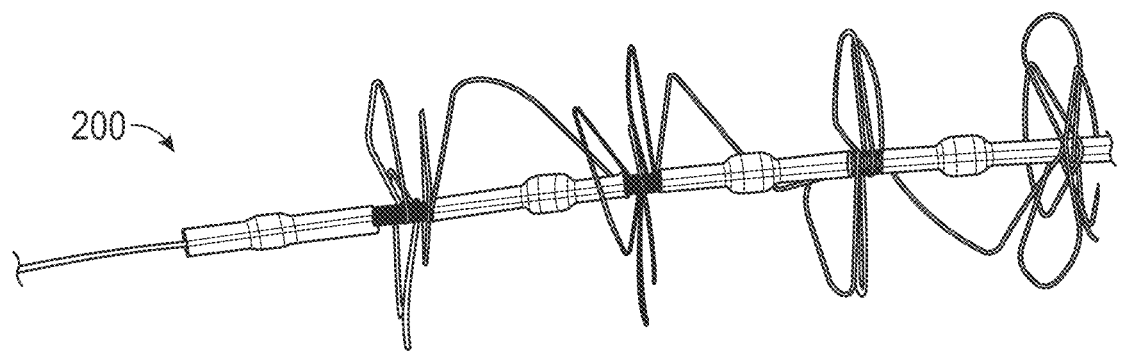

FIG. 31 is a view of the extractor 300.

FIG. 32-35 are views showing the extractor 200. FIGS. 36-39 show the extractor with the engagement panels in a helical shape.

Figure 42:
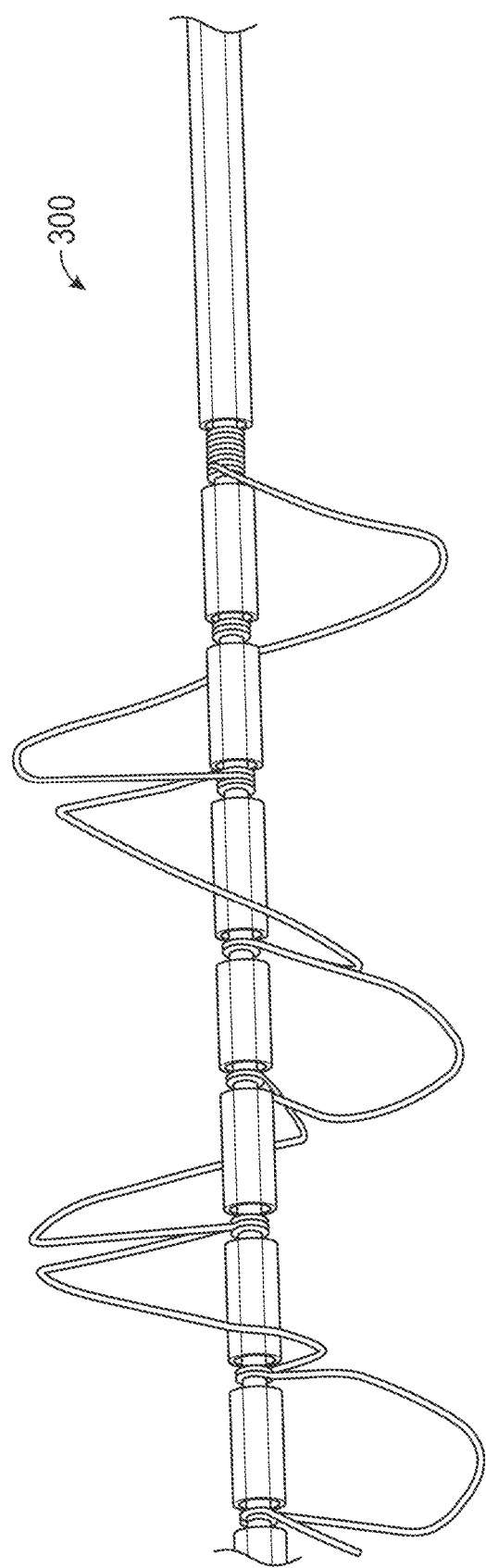

FIGS. 40-42 are views of the third embodiment of the extractor 300. The engagement panels can be arranged in a helical configuration.

FIGS. 43-44 are views of the second embodiment of the extractor 200. The extractor 200 can have four engagement panels per longitudinal location.

Figure 45:
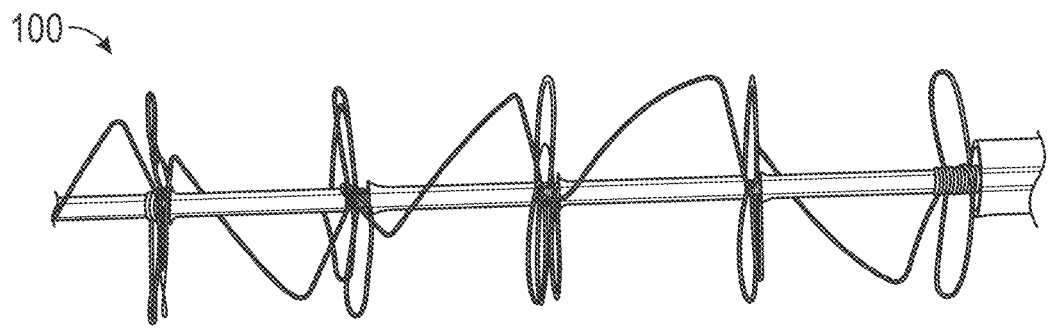
FIGS. 45-47 are view of the first embodiment of the three engagement panel extractor fixed on the catheter shaft.
Figure 46:
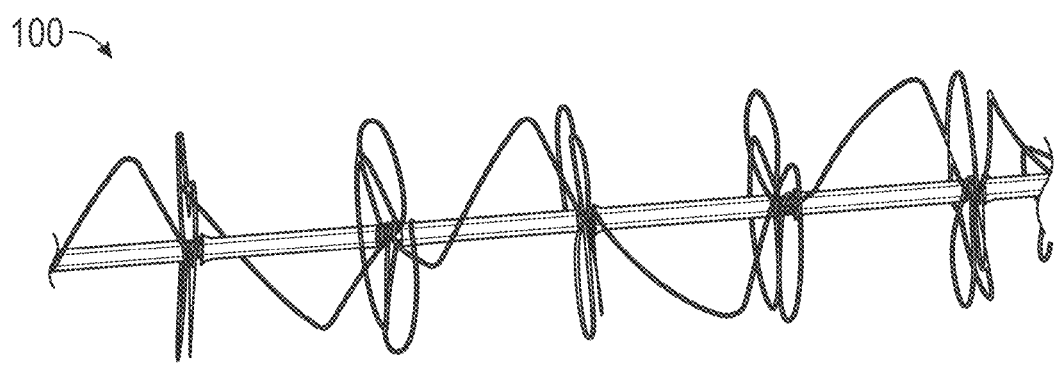
Figure 47:
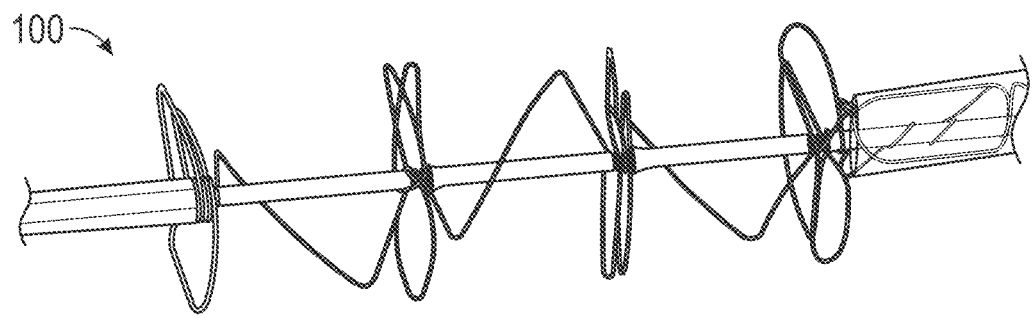
Figure 50:
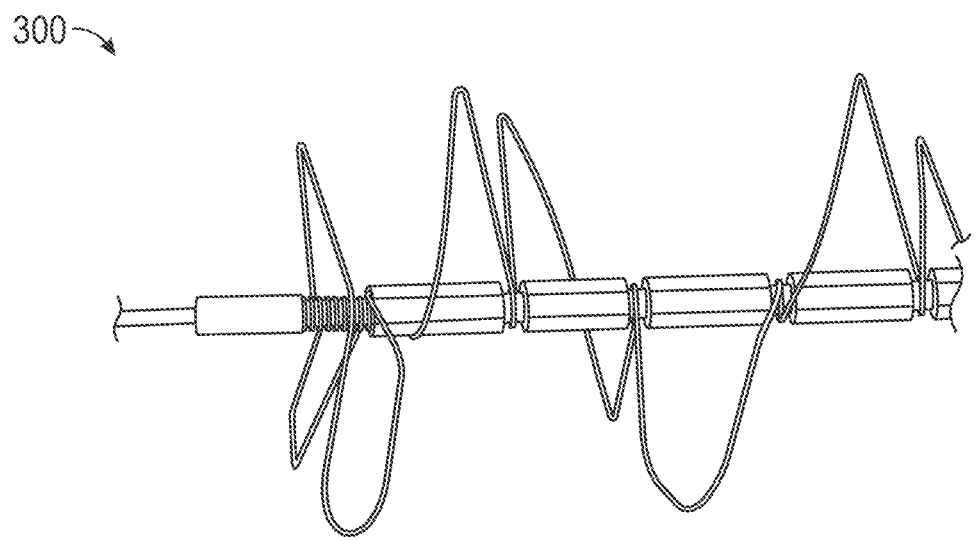
Figure 51:
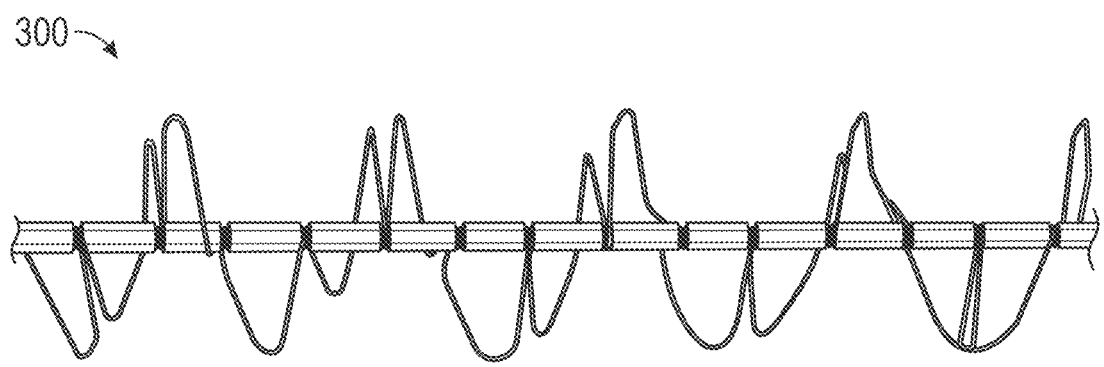
Figure 52:
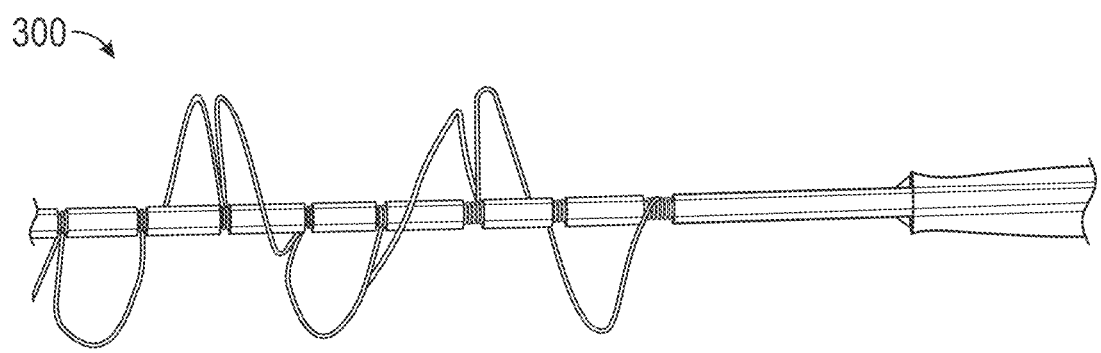
Figure 53:
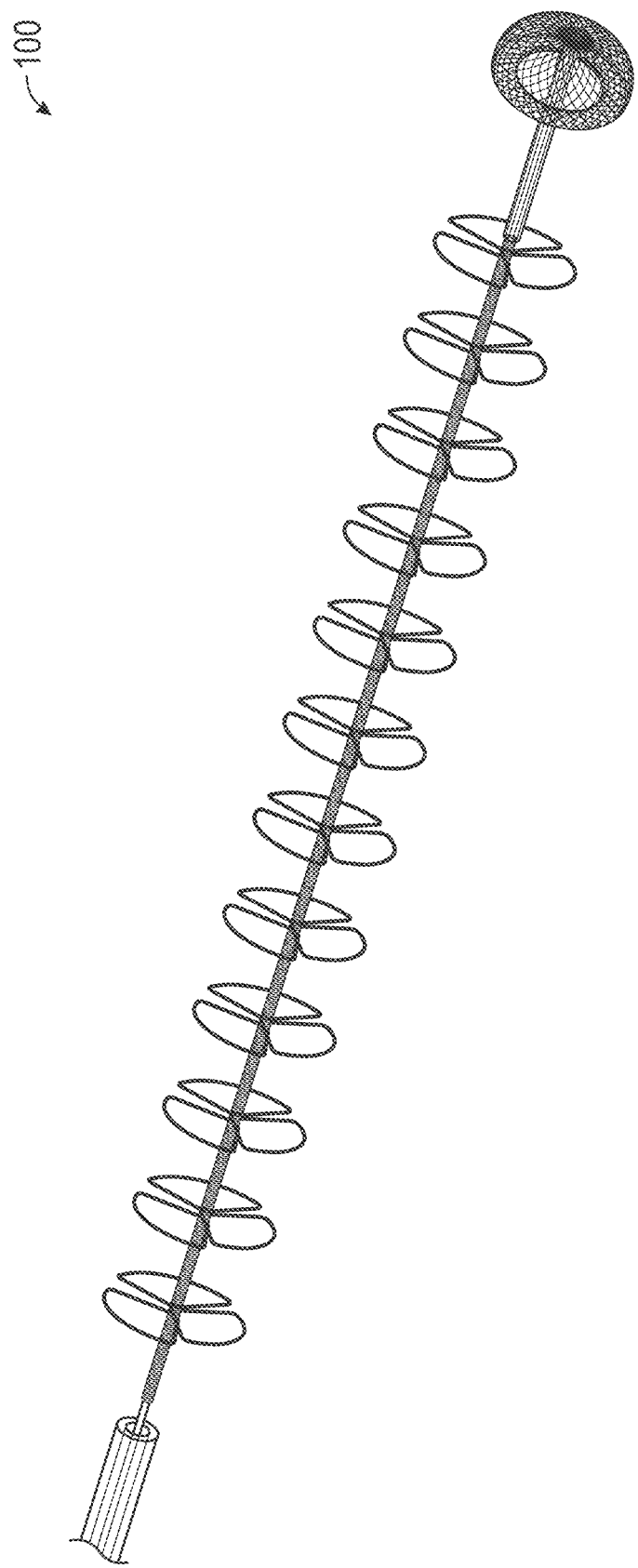
FIG. 53 is view of a three engagement panels extractor system.

FIGS. 45-47 are views of the first embodiment of the extractor 100. The extractor 100 can have three engagement panels per longitudinal location. The engagement panels can be3 coupled to the catheter shaft.

FIGS. 48-52 are views of the third embodiment of the extractor 300. The engagement panels can be a helix engagement panel.

Figure 54:
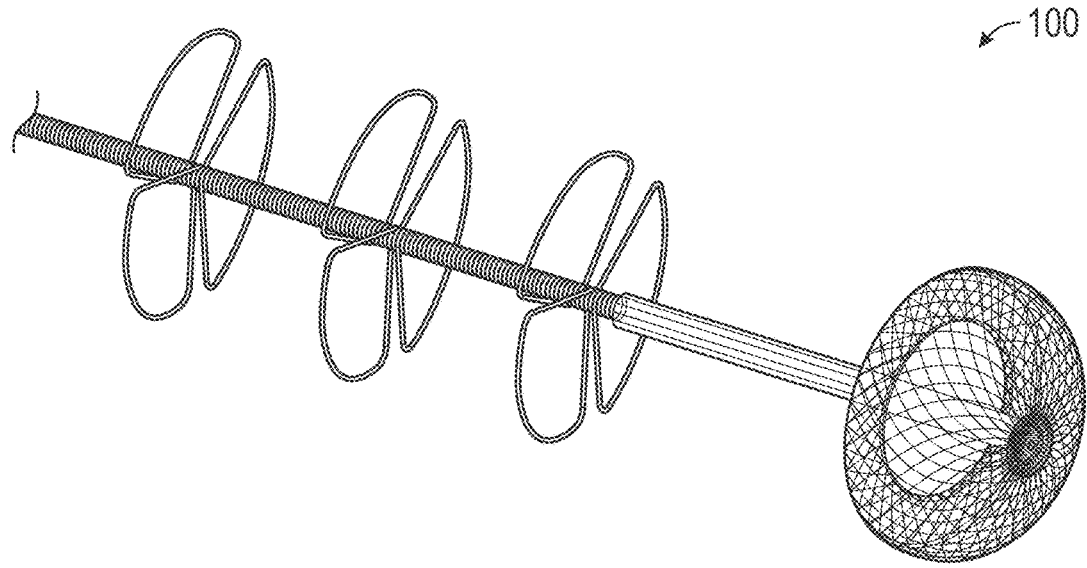
FIG. 54 is view of a three engagement panels extractor system with integral coil spacer.
Figure 55:
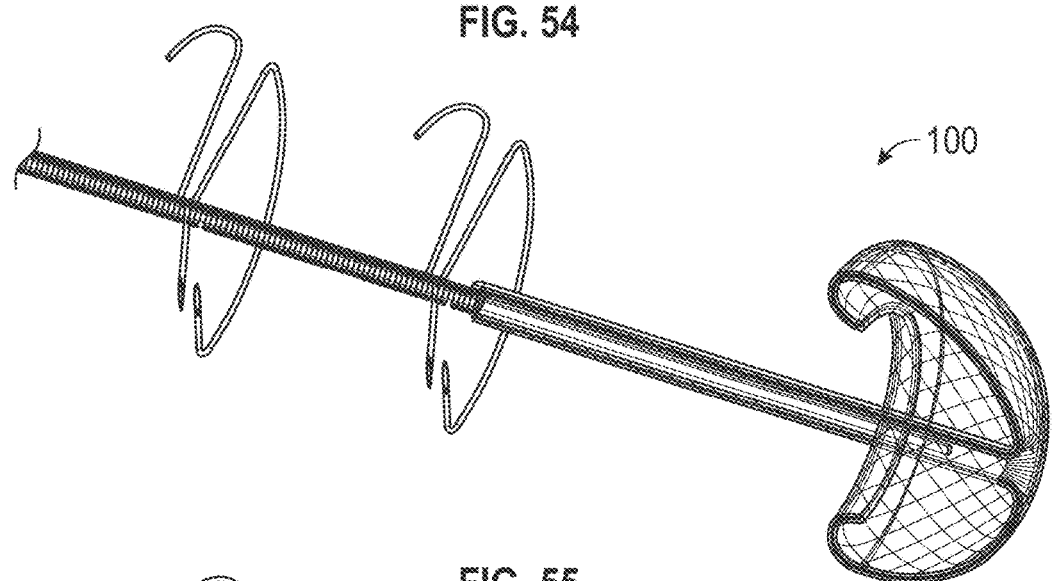
FIG. 55 is view showing a panel and coil spacer.
Figure 56:
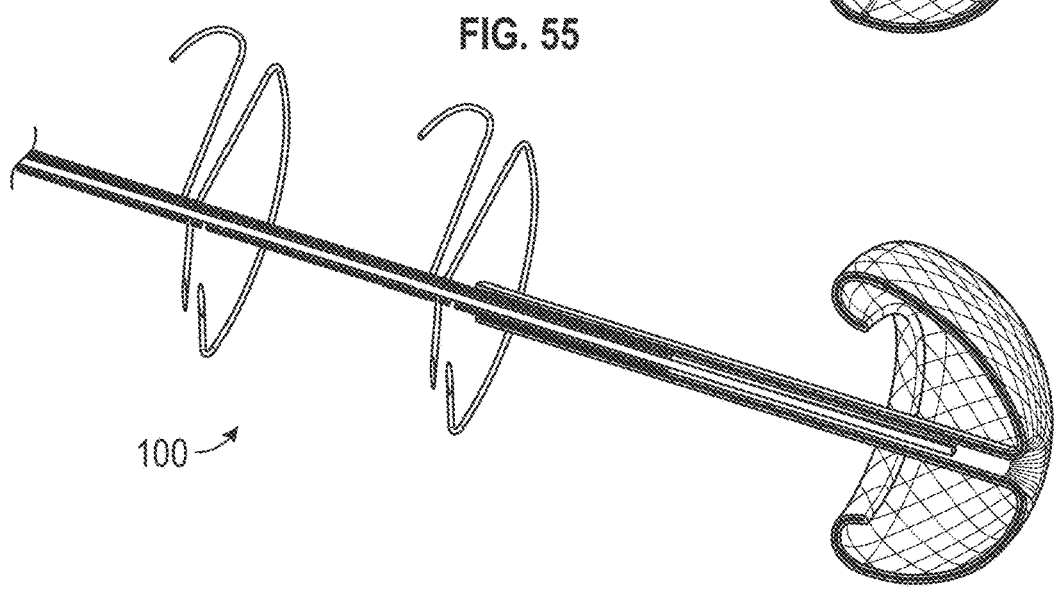
FIG. 56 is another view showing the engagement panel.
Figure 57:
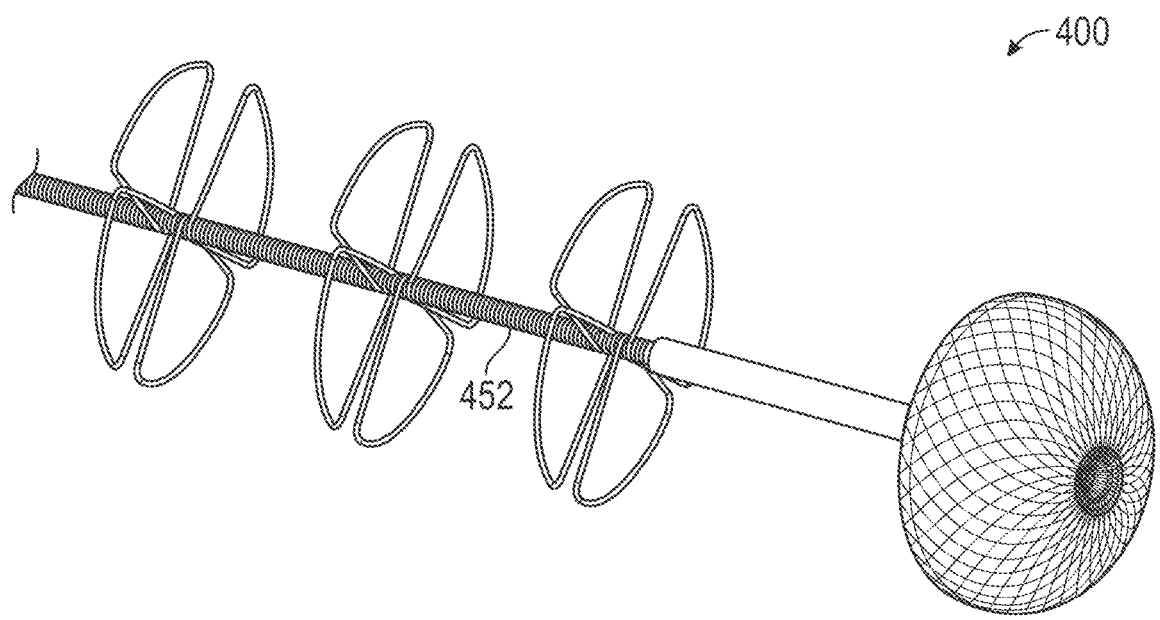
FIG. 57 is view of a four engagement panels extractor system with coil spacer of a fourth embodiment.
Figure 58:
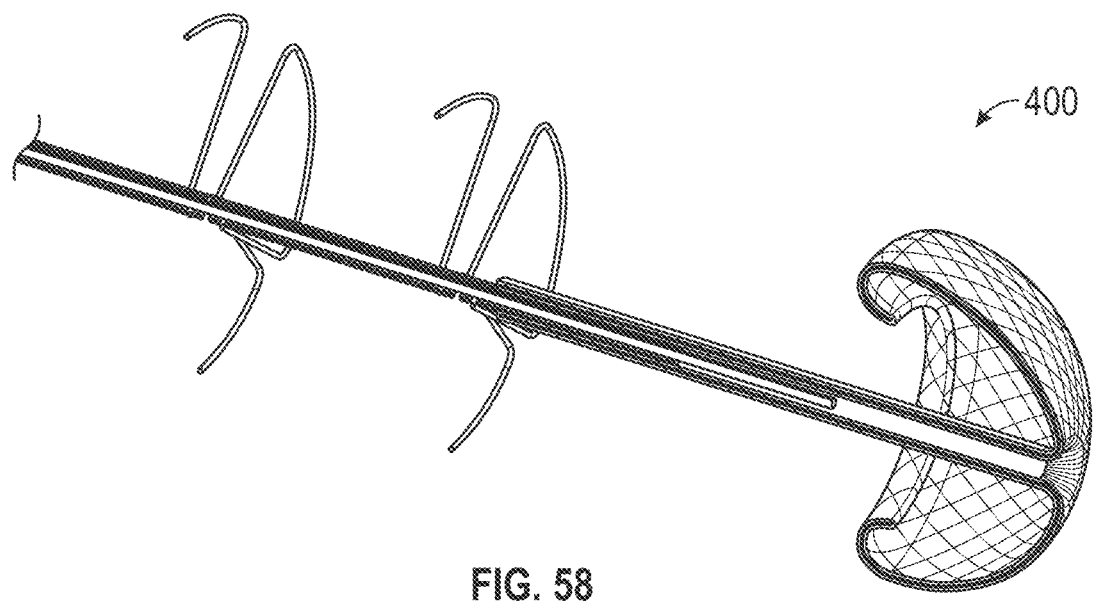
FIG. 58 is view showing a panel of a four engagement panels extractor system of the fourth embodiment.
Figure 59:
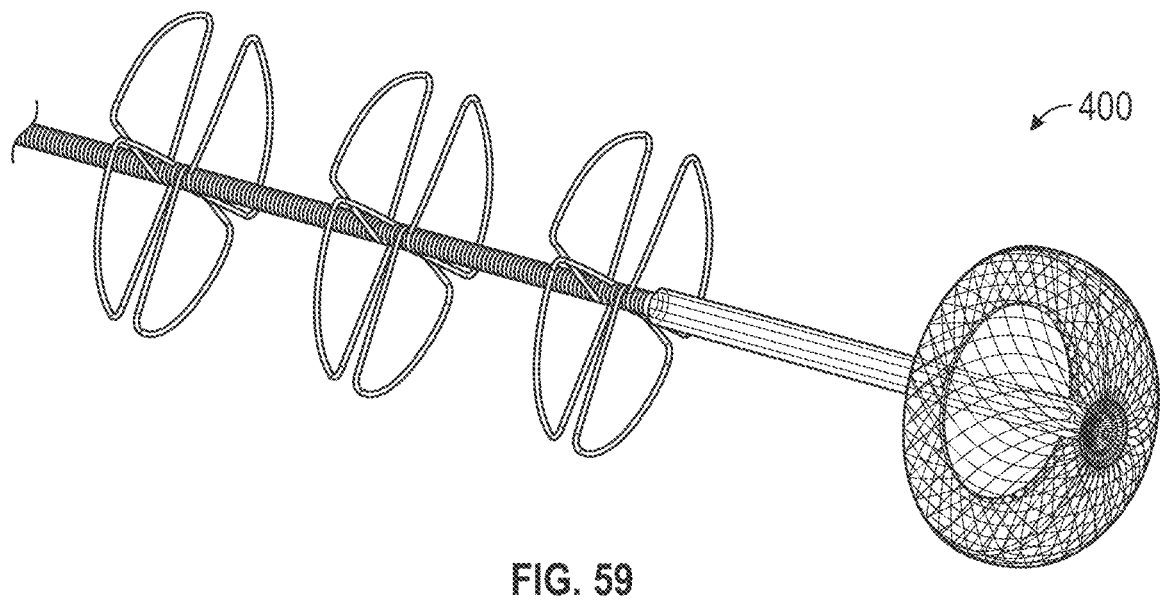
FIG. 59 is view of a four engagement panels extractor system with integral coil spacer of the fourth embodiment.
Figure 60:
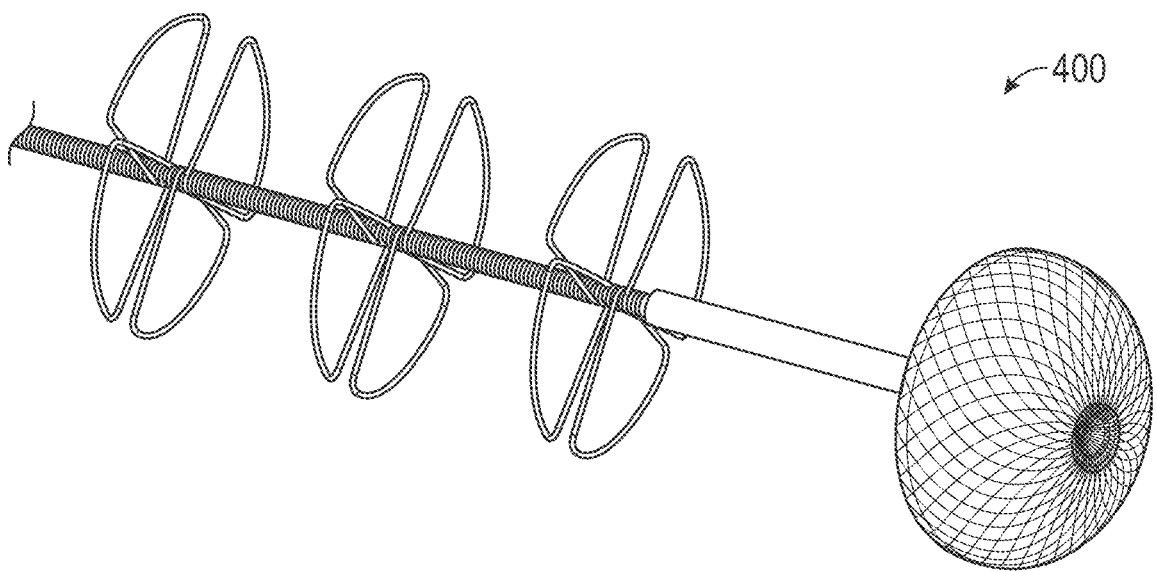
FIG. 60 is view of another four engagement panels extractor system with integral coil spacer of the fourth embodiment

FIGS. 53-56 are views of a system. The system can include a cover sheath to load the extractor. The system can include a distal filter. The system can include any of the extractors described herein, with the extractor 100 illustrated. The system can include any of the engagement panels described herein. The system can include any of the spacers described herein. The system can include a core wire. FIG. 54 is an enlarged view of the extractor. FIG. 55 is a cross-sectional view. FIG. 56 is a cross-sectional view.

FIGS. 57-64 are views of a fourth embodiment of the extractor 400. The extractor 400 can have any of the features described herein. The extractor 400 can have a plurality of engagement panels 410, 412, 414, 416, 420, 422, 424, 426, 430, 432, 434, 436. The engagement panels 410, 412, 414, 416 are located at a first longitudinal location. The engagement panels 420, 422, 424, 426 are located at a second longitudinal location. The engagement panels 430, 432, 434, 436 are located at a third longitudinal location. In the illustrated embodiment, there are four engagement panels at each longitudinal location. The engagement panels 410, 412, 414, 416 at a single longitudinal location can form a circular profile. The extractor 400 can include a plurality of spacers 450, 452, 454, 456. The spacer 450 can be located between a distal end and the engagement panels 410, 412, 414, 416. The spacer 452 can be located between the engagement panels 410, 412, 414, 416, and the engagement panels 420, 422, 424, 426. The spacer 452 can be between the first longitudinal location and the second longitudinal location. The spacer 454 can be located between the engagement panels 420, 422, 424, 426, and the engagement panels 430, 432, 434, 436. The spacer 454 can be between the second longitudinal location and the third longitudinal location. In some embodiments, the spacer 456 can be located between the engagement panels 430, 432, 434, 436 and another set of engagement panels. In some embodiments, the spacer 456 can be located between the engagement panels 430, 432, 434, 436 and a proximal end.

Figure 61:
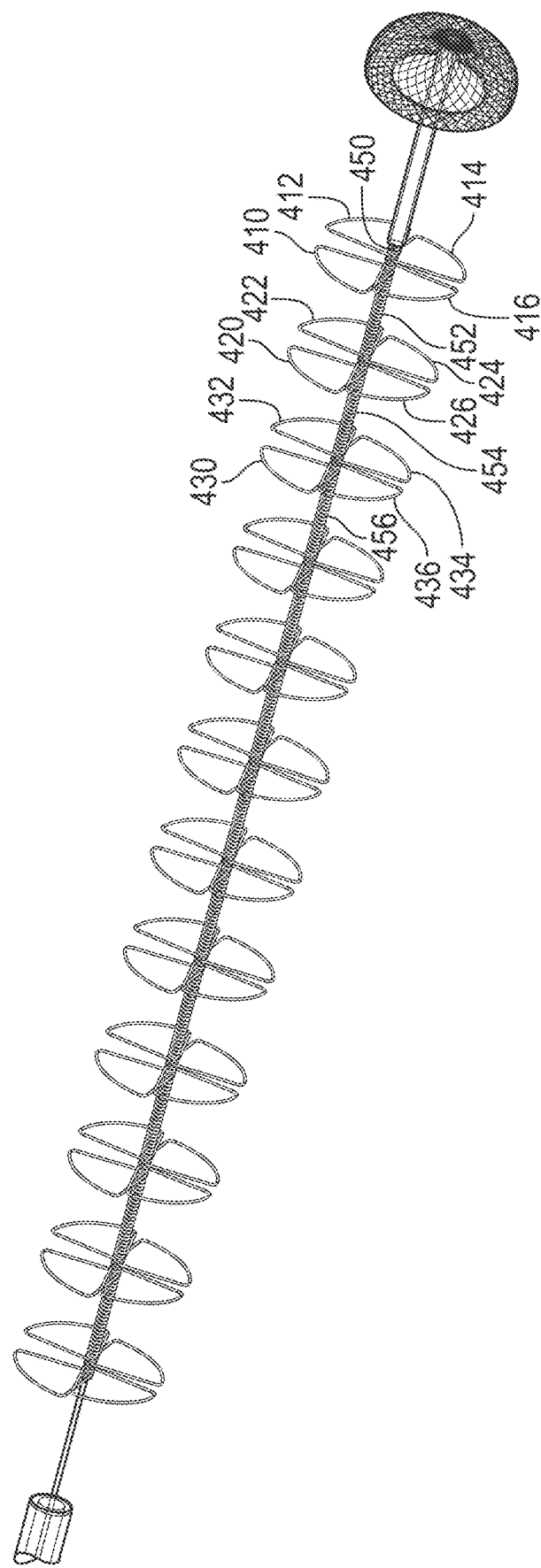
FIG. 61 is view of the four engagement panels extractor system of the fourth embodiment.
Figure 62:
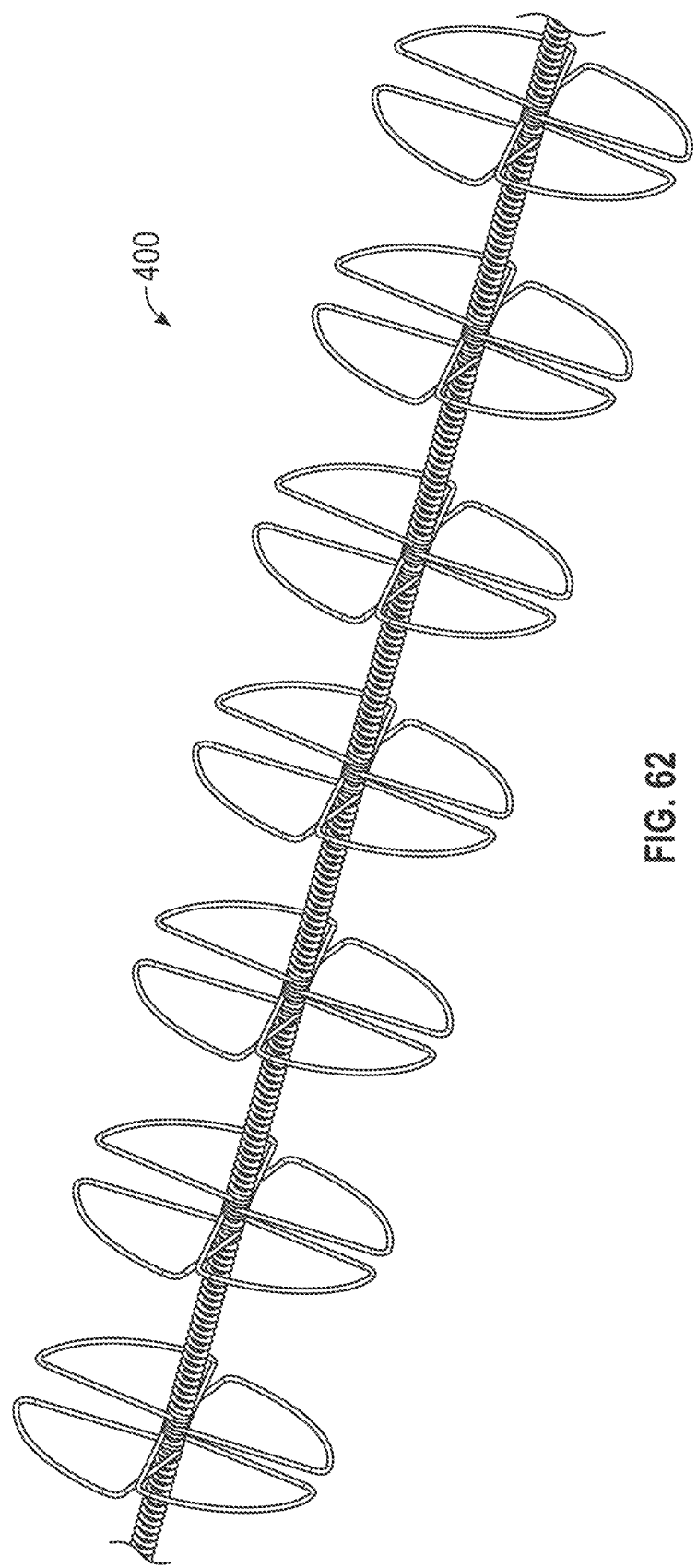
FIG. 62 is view of the four engagement panels extractor system with coil spacer of the fourth embodiment.
Figure 63:
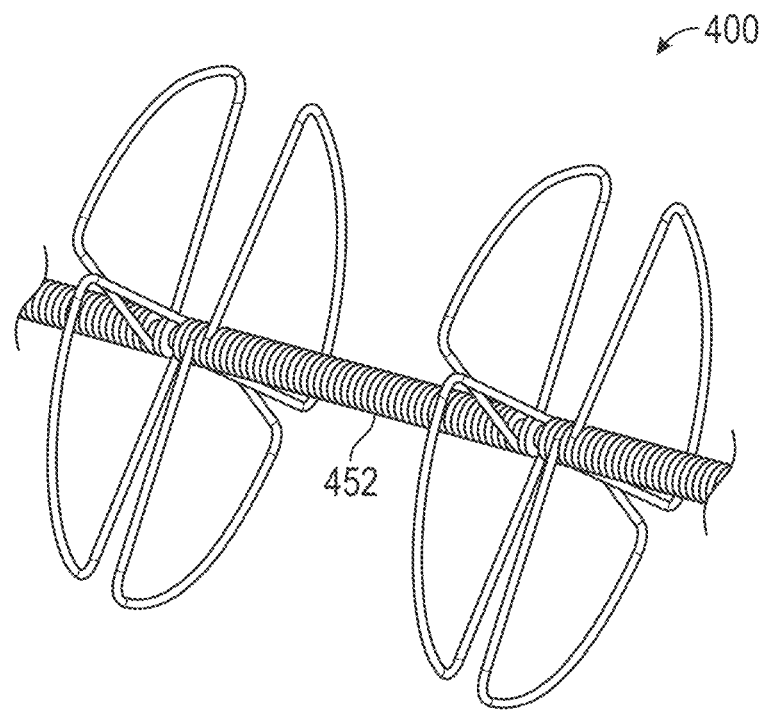
FIG. 63 is another view of the four engagement panels with closed gap coil spacer of the fourth embodiment.
Figure 64:
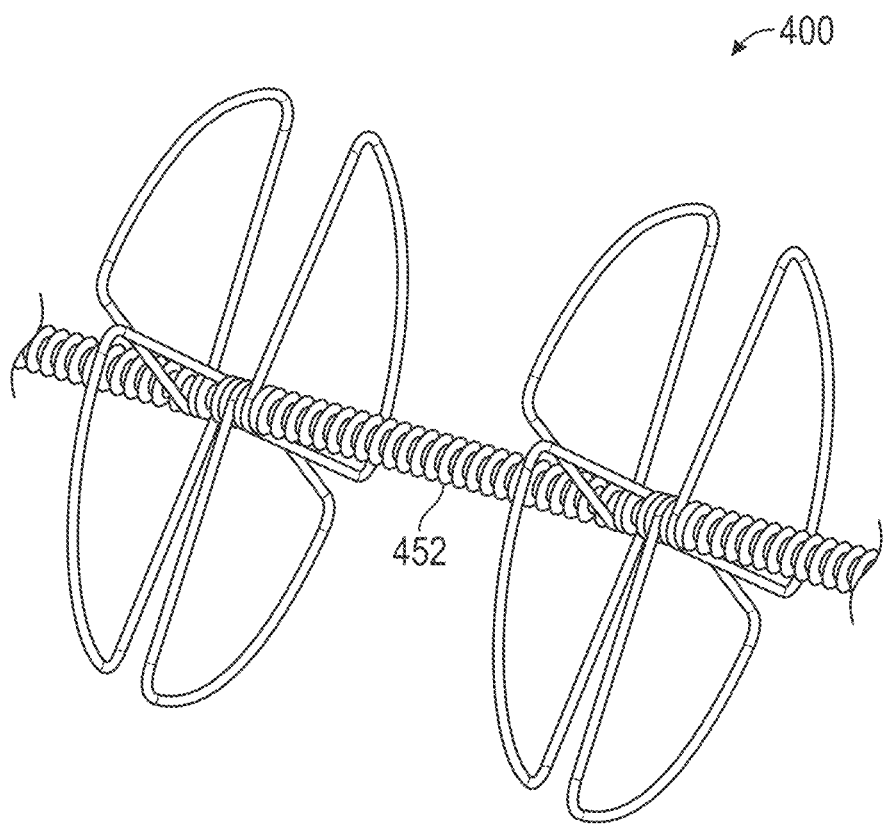
FIG. 64 is another view of the four engagement panels with open gap coil spacer of the fourth embodiment.

The spacers 450, 452, 454, 456 can be formed from a coil. The coil of the spacer can be integral with the engagement panels. The coil of the spacer can be unitarily formed with the engagement panels. The coil of the spacer can be separate from the with the engagement panels. In some embodiments, the spacer can be formed from a hypo tube. FIG. 61 is a cross-sectional view. FIGS. 62-67 are additional views. The spacer 450, 452, 454, 456 can have a close gap. The spacer 450, 452, 454, 456 can be a tight coil. The spacer 450, 452, 454, 456 can have a loose gap. The spacer 450, 452, 454, 456 can be a looser coil or spring.

Figure 65:
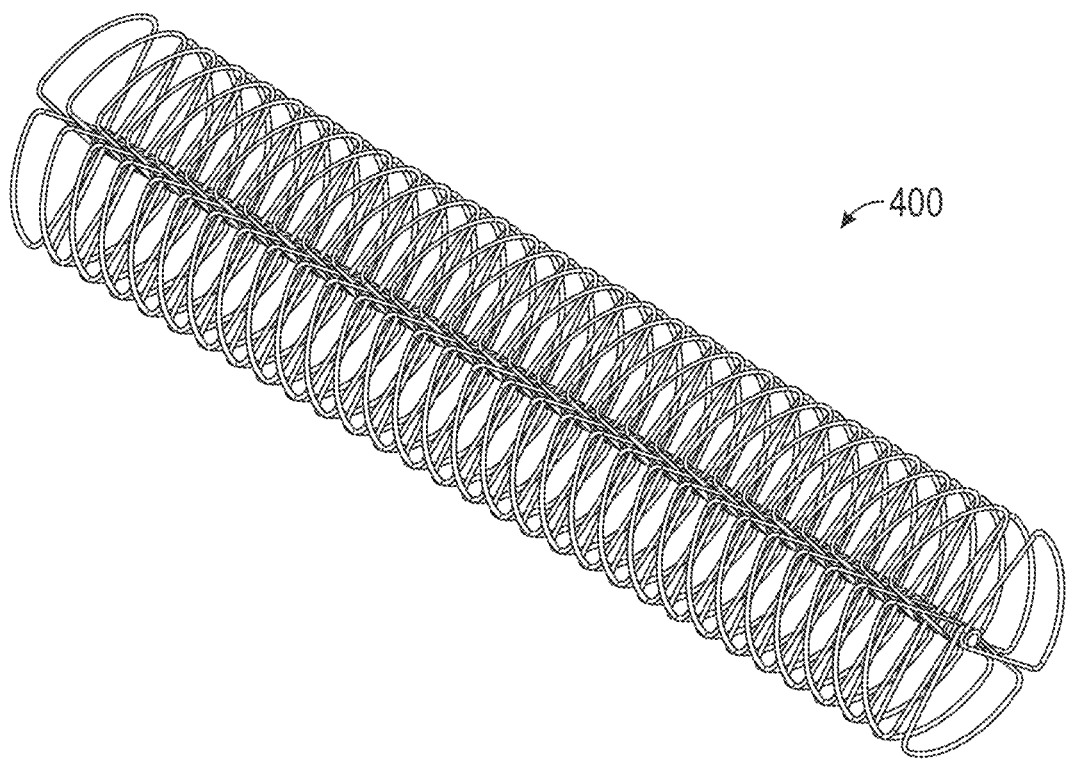
FIG. 65 is view of the four engagement panels extractor without spacer. The extractor engagement panels are in an unconstrained or unstretched position of the fourth embodiment.
Figure 66:
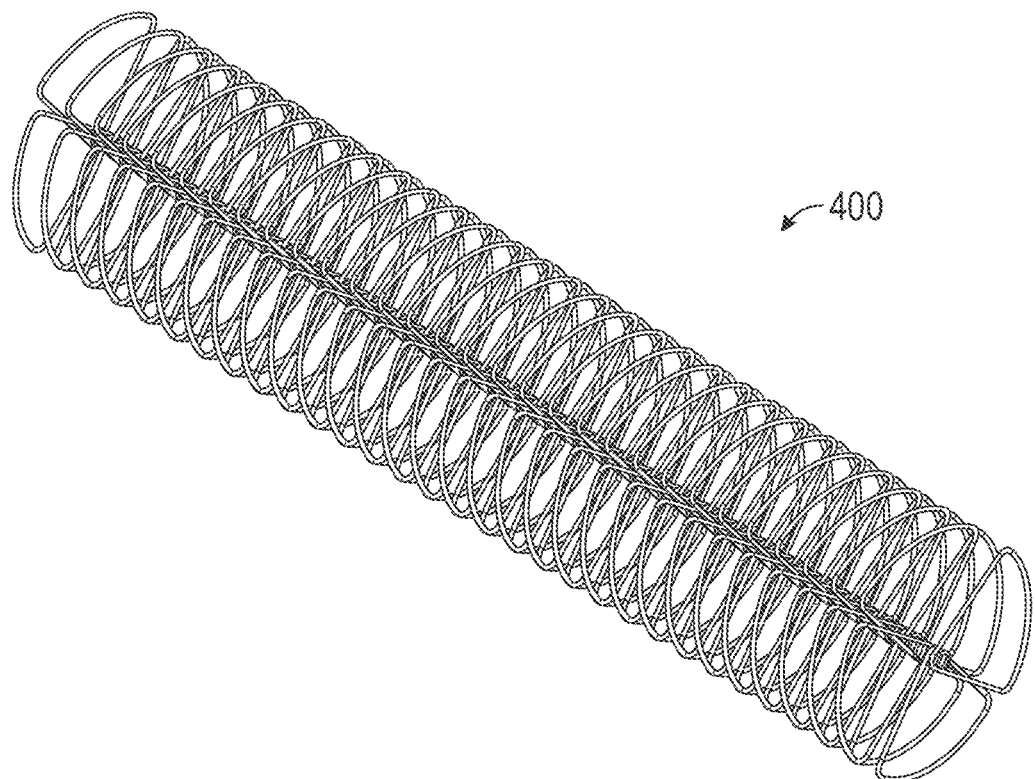
FIG. 66 is another view of the four engagement panels extractor with spacer and is in an unconstrained unstretched position of the fourth embodiment.

FIGS. 65-66 are views of the extractor 400. The extractor can be biased to for the engagement panels to move toward each other. The biased for the engagement panels to move towards each other have a compressive force thereby a pinch force where it can pinch a clot during clot capture.

The extractors 100, 200, 300 describe herein can include engagement panels. The engagement panels can form a diameter. The diameter can be formed from engagement panels at a single longitudinal location. The engagement panels can have a single diameter. The single diameter can be 3 mm, 4 mm, 5 mm, or more. The engagement panels can have multiple diameters. The diameters can be, e.g., 4 mm at a longitudinal location, 5 mm at the next longitudinal location, 4 mm at the next longitudinal location, and 5 mm at the next longitudinal location. The diameter formed from engagement panels can alternate in different sizes along the extractor 100.

The engagement panels can form a round perimeter. The engagement panels can form a elliptical perimeter. The engagement panels can form an oblong perimeter. The engagement panels can form an angle relative to catheter shaft. The angle can be, e.g. about 1 degree, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, range from 1 degrees to 360 degrees, or any range of two of the foregoing values.

The engagement panels can have equal longitudinal spacing. The engagement panels can have unequal longitudinal spacing. The spacing between adjacent engagement panels can be, e.g. about 1 mm, 2 mm, 3 mm, 4 mm, 5 mm, 6 mm, 7 mm, 8 mm, 9 mm, 10 mm, 15 mm, range from 2 mm to 15 mm, or any range of two of the foregoing values. The engagement panels can have a custom distance between adjacent engagement panels. The spacing between adjacent engagement panels can be 3 mm, then the spacing between adjacent engagement panels can be 4 mm, and then spacing between adjacent engagement panels can be 5 mm.

In some embodiments, the engagement panels can have one leg. In some embodiments, the engagement panels can have two legs. In some embodiments, the engagement panels can have three legs. In some embodiments, the engagement panels can be connected. The extractor can include connecting members. There can be connection between engagement panels. There can be no connection between engagement panels. In some embodiments, the engagement panels can be formed of a single wire. In some embodiments, the engagement panels can be formed of multiple wires.

Figure 67:
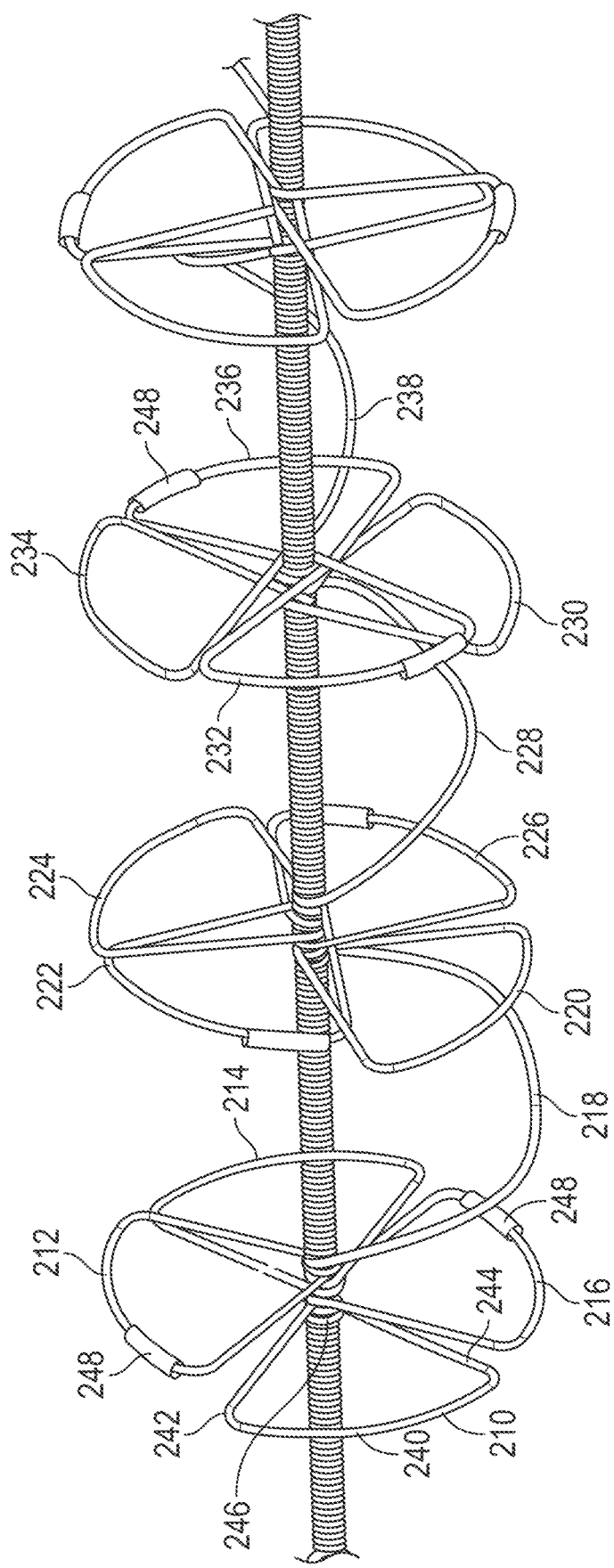
FIG. 67 is another view of the extractor of the second embodiment.
Figure 68:
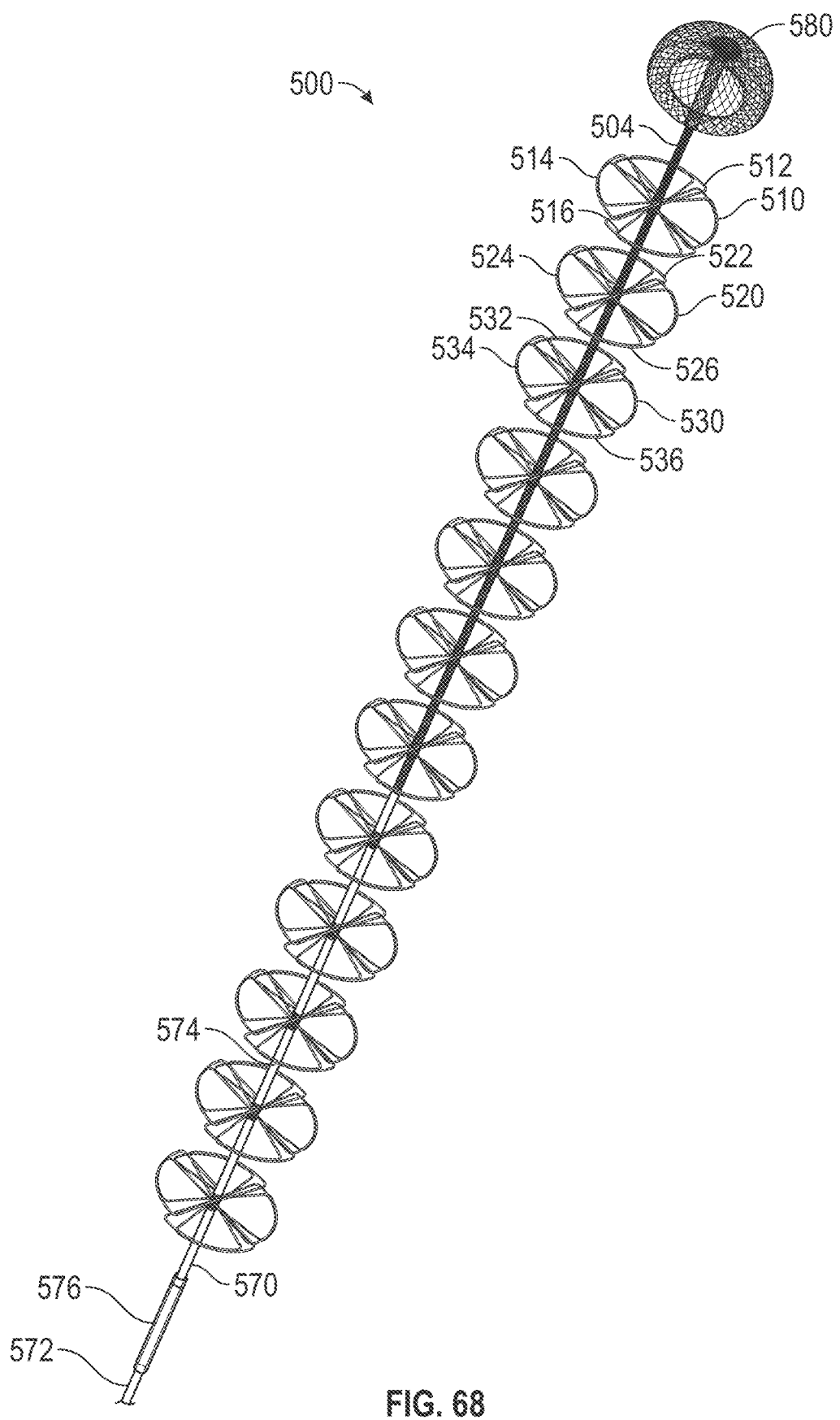
FIG. 68 is a view of an extractor with double four engagement panels with a proximal core wire, sleeve connector and distal core wire of a fifth embodiment.

FIG. 67 is another view of the extractor 200. The extractor 200 can include any feature of the extractor 100 described herein. Each engagement panels 210, 212, 214, 216 can be formed by two legs 242, 244 shown in FIG. 67. The two legs 242, 244 connect to the arc 240 of engagement panel 210, 212, 214, 216. The two legs 242, 244 can be radially outward from the longitudinal axis of the extractor 200. The two legs 242, 244 can be angled relative to each other. The two legs 242, 244 can be straight. The two legs 242, 244 can have a constant angle therebetween. The two legs 242, 244 can connect to the ends of an arc 240. The extractor 200 can include the eyelet 246. The eyelet can form a lumen. The extractor can include the connecting member, extension or bridge 218. The engagement panels 210, 212, 214, 216 can be at the first longitudinal location. The engagement panels 220, 222, 224, 226 can be at the second longitudinal location. The engagement panels 230, 232, 234, 236 can be at the third longitudinal location. The engagement panels 210, 212, 214, 216 can be continuous with no loop ends. The engagement panels 220, 222, 224, 226 can be continuous with no loop ends. The engagement panels 230, 232, 234, 236 can be continuous with no loop ends. In some embodiments, the engagement panels 220, 222, 224, 226, 230, 232, 234, 236 can be continuous with no loop ends. In some embodiments, all the engagement panels of the extractor is one single unit with no loop ends. The arc 240 of each engagement panel 210, 212, 214, 216, 220, 222, 224, 226, 230, 232, 234, 236 can be configured to be in contact with the vessel wall preferably. The arc 240 of each engagement panel 210, 212, 214, 216, 220, 222, 224, 226, 230, 232, 234, 236 can also be configured to be near the vessel wall without contact with the vessel wall. The arc 240 of each engagement panel 210, 212, 214, 216, 220, 222, 224, 226, 230, 232, 234, 236 can form a smooth, atraumatic edge.

In some embodiments, the eyelet 246 can allow the engagement panels 210, 212, 214, 216 at the first longitudinal location to move longitudinally. In some embodiments, the eyelet 246 can allow the engagement panels 220, 222, 224, 226 at the second longitudinal location to move longitudinally. In some embodiments, the eyelet 246 can allow the engagement panels 230, 232, 234, 236 at the third longitudinal location to move longitudinally.

The extractor 200 can have a plurality of connecting members 218, 228, 238. The connecting member 218 can connect the engagement panels 210, 212, 214, 216 at the first longitudinal location and the engagement panels 220, 222, 224, 226 at the second longitudinal location. The connecting member 228 can connect the engagement panels 220, 222, 224, 226 at the second longitudinal location and the engagement panels 230, 232, 234, 236 at the third longitudinal location. The connecting member 338 can connect the engagement panels 230, 232, 234, 236 at the third longitudinal location and another set of engagement panels. The connecting members 218, 228, 238 and the engagement panels 210, 212, 214, 216, 220, 222, 224, 226, 230, 232, 234, 236 can be continuous and integrally formed. The connecting members 218, 228, 238 can be formed of the same material as the engagement panels 210, 212, 214, 216, 220, 222, 224, 226, 230, 232, 234, 236. The connecting members 218, 228, 238 can be separately formed from the engagement panel 210, 212, 214, 216, 220, 222, 224, 226, 230, 232, 234, 236. The connecting members 218, 228, 238 can be formed of a different material as the engagement panels 210, 212, 214, 216, 220, 222, 224, 226, 230, 232, 234, 236.

The extractor 200 can include one or more radiopaque markers 248. The radiopaque marker 248 can be located on the arc 240. The first longitudinal location can include one or more radiopaque markers 248. Two arcs 240 at the first longitudinal location can include radiopaque markers 248. Two diametrically opposed arcs 240 at the first longitudinal location can include radiopaque markers 248. The second longitudinal location can include one or more radiopaque markers 248. The third longitudinal location can include one or more radiopaque markers 248. Other configuration and location are contemplated.

FIG. 68-73 are views of an extractor 500. The extractor 500 can include any feature described herein. The extractor 500 can include double layers engagement panels. The extractor 500 can include radiopaque markers. The extractor 500 can include a distal end 504. The extractor 500 can include a catheter shaft 506. The extractor 500 can have a plurality of engagement panels 510, 512, 514, 516, 520, 522, 524, 526, 530, 532, 534, 536. The engagement panels 510, 512, 514, 516 are located at a first longitudinal location. The engagement panels 520, 522, 524, 526 are located at a second longitudinal location. The engagement panels 530, 532, 534, 536 are located at a third longitudinal location. In some embodiments, the extractor 500 can include four engagement panels at each longitudinal location. The extractor 500 can include a distal member 580. The distal member 580 can include any feature described herein.

The extractor 500 can include a core wire 570. The core wire 570 can be made of one, two, three or more components. The core wire 570 can include a proximal core wire 572. The proximal core wire 572 can comprise stainless steel, nitinol, laser cut tube, polymers, and/or combinations thereof. The core wire 570 can include a distal core wire 574. The distal core wire 574 can comprise stainless steel, nitinol, laser cut tube, polymers, and/or combinations thereof. The extractor 500 can include a sleeve connector 576. The sleeve connector 576 can comprise stainless steel, nitinol, laser cut tube, polymers, and/or combinations thereof. The sleeve can be of radiopaque material for better visualization.

Figure 69:
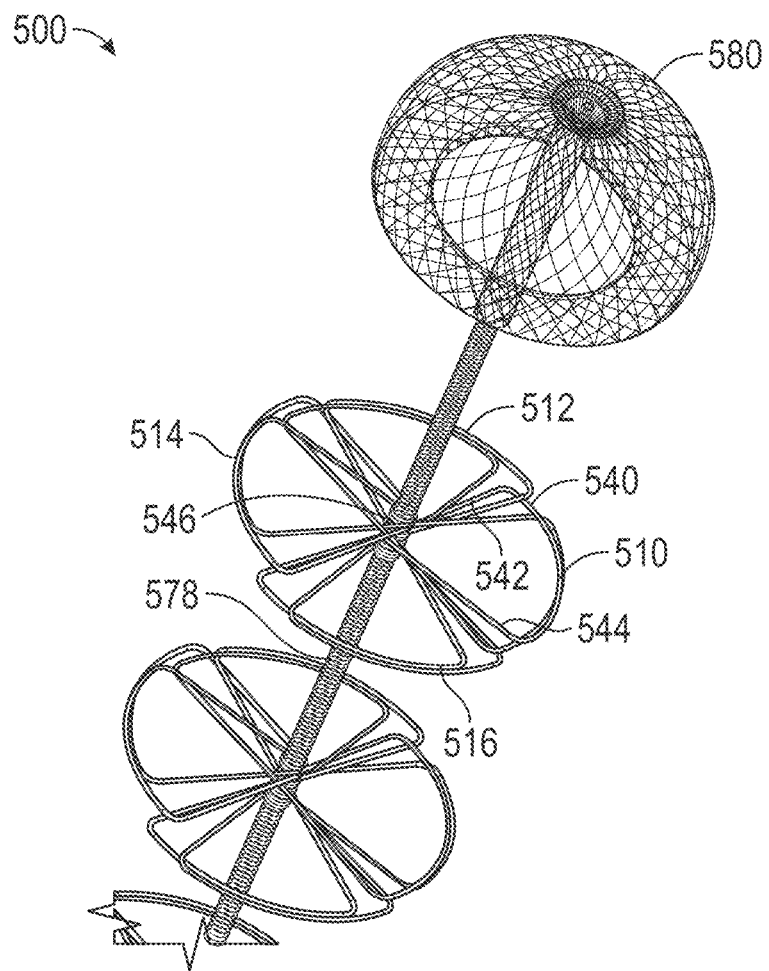
FIG. 69 is a view of the double four engagement panels of the fifth embodiment.
Figure 70:
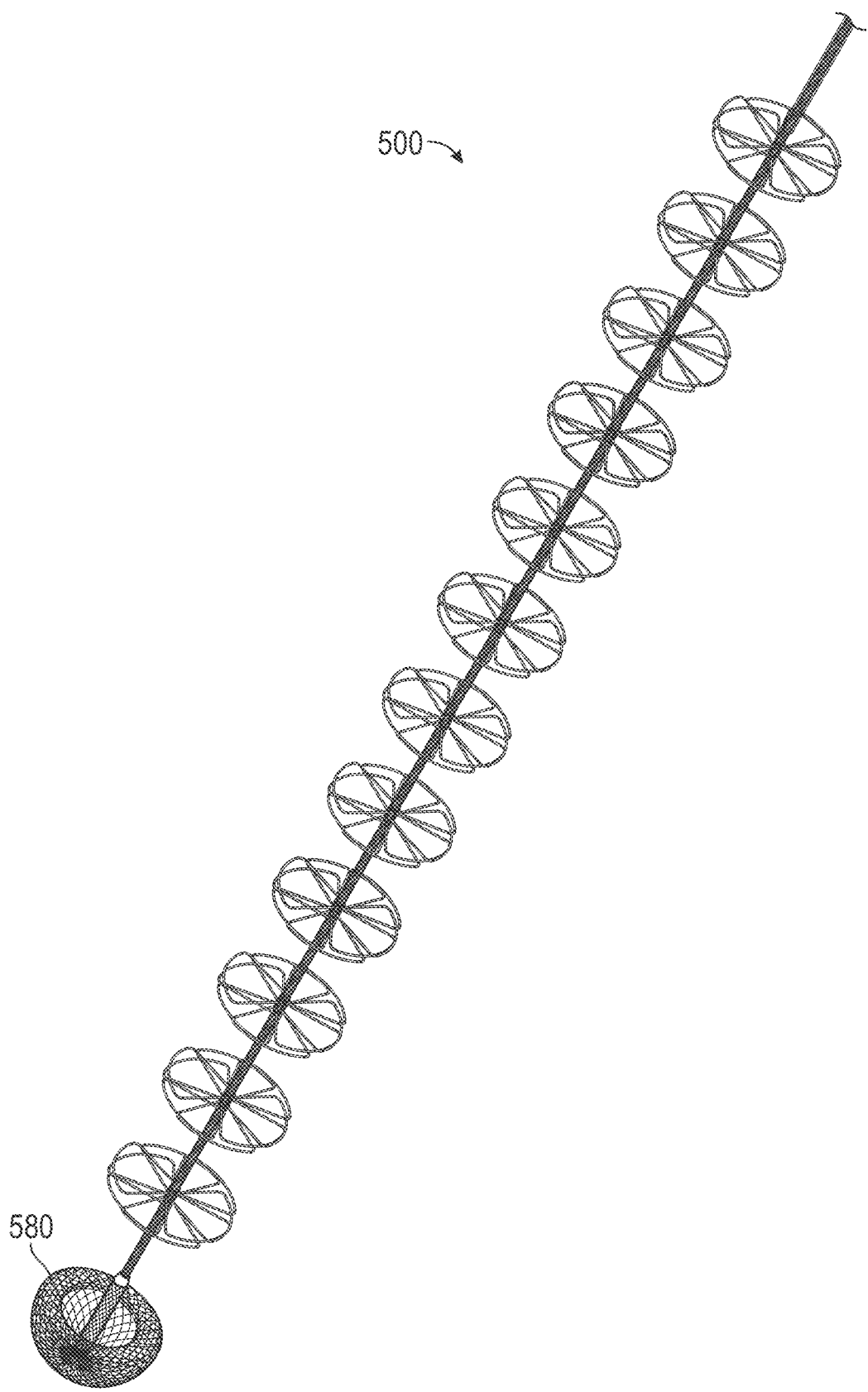
FIG. 70 is another view of the double four engagement panels of the fifth embodiment.
Figure 71:
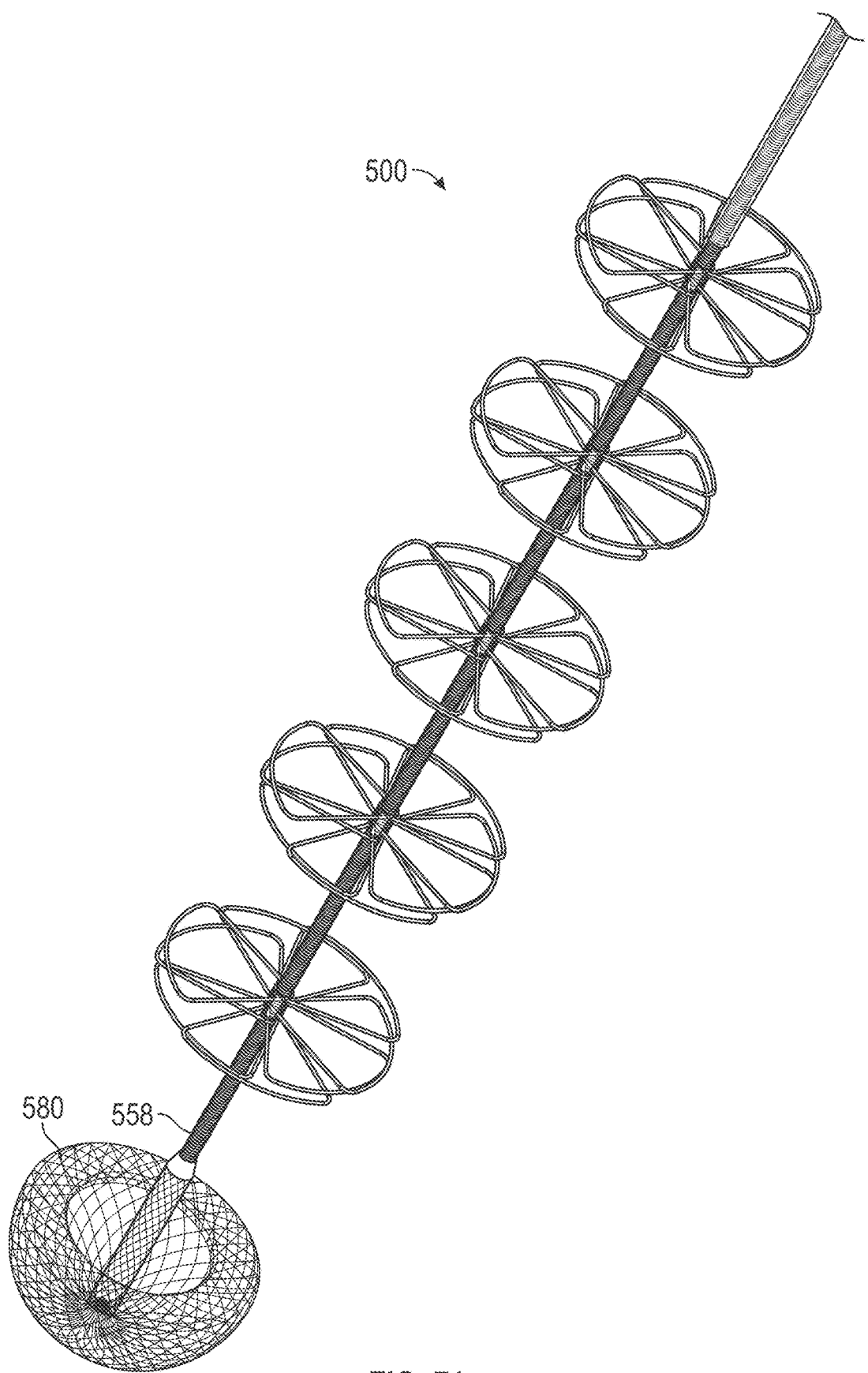
FIG. 71 is another view of the double four engagement panels where the panels can be 1, 2, 3 or more layers of nitinol, Stainless steel or shape memory polymers of the fifth embodiment.

FIG. 69 illustrates the engagement panels. The extractor 500 can include double layer engagement panels. Each engagement panel 510, 512, 514, 516 can be formed from two layers. The two layers can be aligned. The two layers can be offset. The first layer can form one substantially complete circumference. The second layer can form one substantially complete circumference.

Each engagement panels 510, 512, 514, 516 can be formed by two legs 542, 544. The two legs 542, 544 connect to the arc 540 of engagement panel 510, 512, 514, 516. The two legs 542, 544 can be radially outward. The two legs 542, 544 can be angled relative to each other. The two legs 542, 544 can connect to the ends of the arc 540. The two legs 542, 544 of the first layer can be offset from the two legs 542, 544 of the second layer. The arc 540 of the first layer can be offset from the arc 540 of the second layer. The layers can be circumferentially offset. The layers can be twisted relative to a eyelet 546. The layers can be offset by a small degree. The layers can partially overlap. The two legs 542, 544 of the first layer can be aligned with the two legs 542,

544 of the second layer. The arc 540 of the first layer can be aligned with the arc 540 of the second layer. The layers can be longitudinally aligned. The layers can abut. The layers can overlap. The layers can be stacked. The layers can completely align. The first layer can be distal to the second layer.

The extractor 500 can include a coil 578. The coil 578 can form a lumen for the core wire 570. The coil 578 can function as a connecting member. The coil 578 can function as a spacer. The coil 578 can connect the engagement panels 510, 512, 514, 516 at the first longitudinal location and the engagement panels 520, 522, 524, 526 at the second longitudinal location. The coil 578 can connect the engagement panels 520, 522, 524, 526 at the second longitudinal location and the engagement panels 530, 532, 534, 536 at a third longitudinal location. The coil 578 can connect the engagement panels 530, 532, 534, 536 at a third longitudinal location and another set of engagement panels. The coil 578 and the engagement panels 510, 512, 514, 516, 520, 522, 524, 526, 530, 532, 534, 536 can be continuous. The coil 578 and the engagement panels 510, 512, 514, 516, 520, 522, 524, 526, 530, 532, 534, 536 can be integrally formed. The coil 578 and the engagement panels 510, 512, 514, 516, 520, 522, 524, 526, 530, 532, 534, 536 can be separately formed and connected together. The coil 578 can include a radiopaque marker. The coil 578 can include a radiopaque material. The coil 578 is substantially inside an outer member 568. The outer member 568 can be made of polymeric materials such as polyethylene, PTFE, FEP, polyurethane, nylon, PEBAX for example. The outer member 568 can be made of metallic materials. The coil 578 can include a distal marker 558 shown in FIG. 71.

The engagement panels 510, 512, 514, 516, 520, 522, 524, 526, 530, 532, 534, 536 can be made of 1, 2, 3 or more layers. The engagement panels 510, 512, 514, 516, 520, 522, 524, 526, 530, 532, 534, 536 can be made of nitinol, stainless steel, shape memory polymers and/or combinations thereof.

Figure 72:
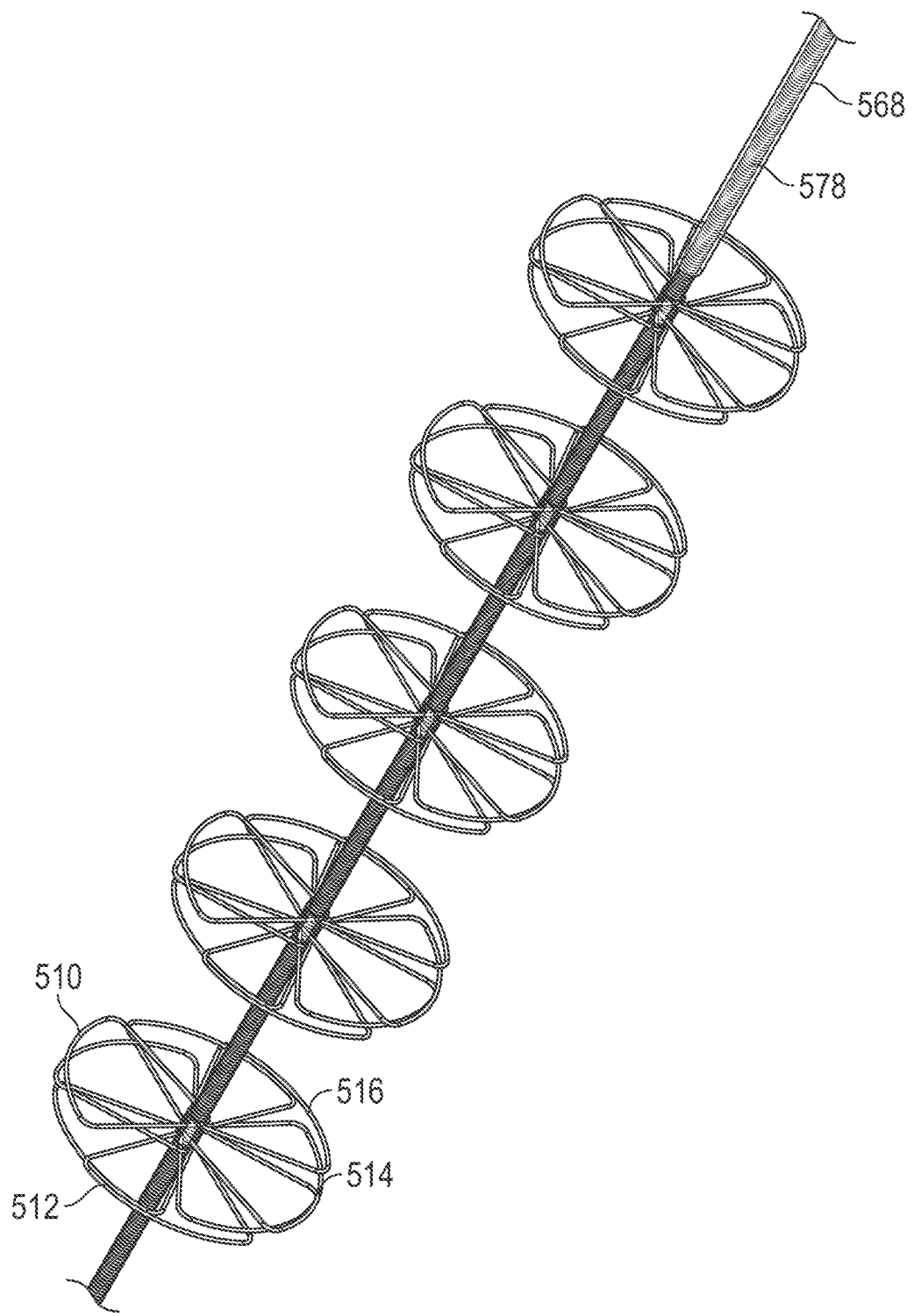
FIG. 72 is another view of the double four engagement panels with support coils and PTFE jacket of the fifth embodiment.

FIG. 72 illustrates the extractor 500 with a triple layer engagement panel. The two legs 542, 544 of the first layer can be offset from the two legs 542, 544 of the second layer. The two legs 542, 544 of the second layer can be offset from the two legs 542, 544 of the third layer. The arc 540 of the first layer can be offset from the arc 540 of the second layer. The arc 540 of the second layer can be offset from the arc 540 of the third layer. The layers can be circumferentially offset. The layers can be offset by a small degree. The layers can be offset by a large degree. The layers can at least partially overlap. The two legs 542, 544 of the first layer can be aligned with the two legs 542, 544 of the second layer and the two legs 542, 544 of the third layer. The arc 540 of the first layer can be aligned with the arc 540 of the second layer and the arc 540 of the third layers. The plurality of layers can be longitudinally aligned. The plurality of layers can abut. The plurality of layers can overlap. The plurality of layers can be stacked. The plurality of layers can completely align. The first layer can be distal to the second layer. The second layer can be distal to the third layer. The coil 578 can function as a support coil. The coil 578 can include a jacket 568. The jacket 568 can comprise PTFE.

Figure 73:
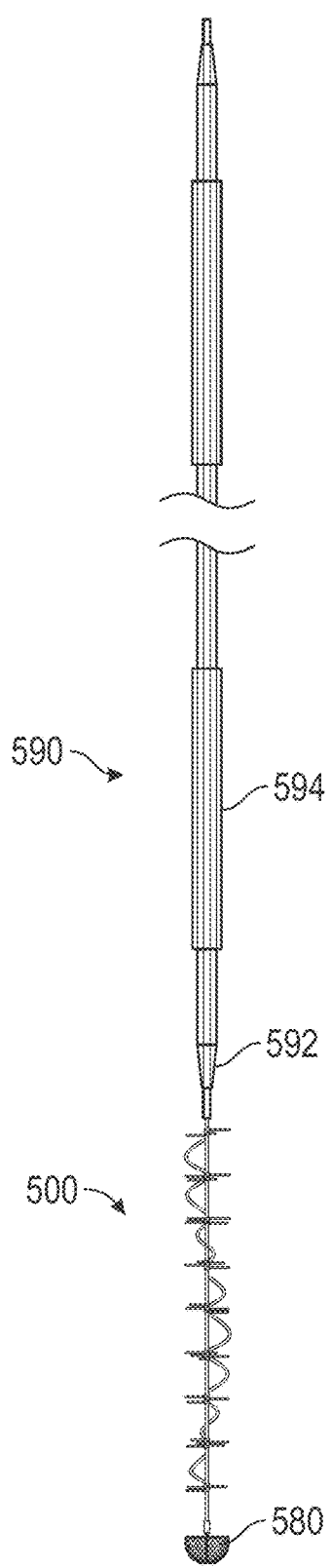
FIG. 73 is a view of the loading tube assembly used to load the extractor into the delivery catheter. The loading tube assembly can also be a sheath or a tubular member.
Figure 74:
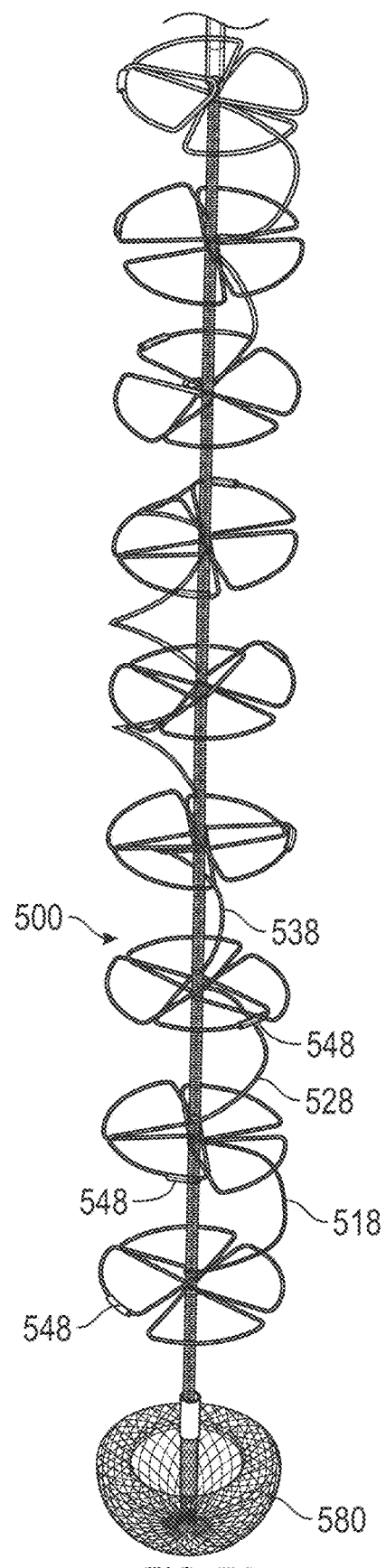
FIG. 74 is a view of the single four engagement panels of the fifth embodiment.
Figure 75:
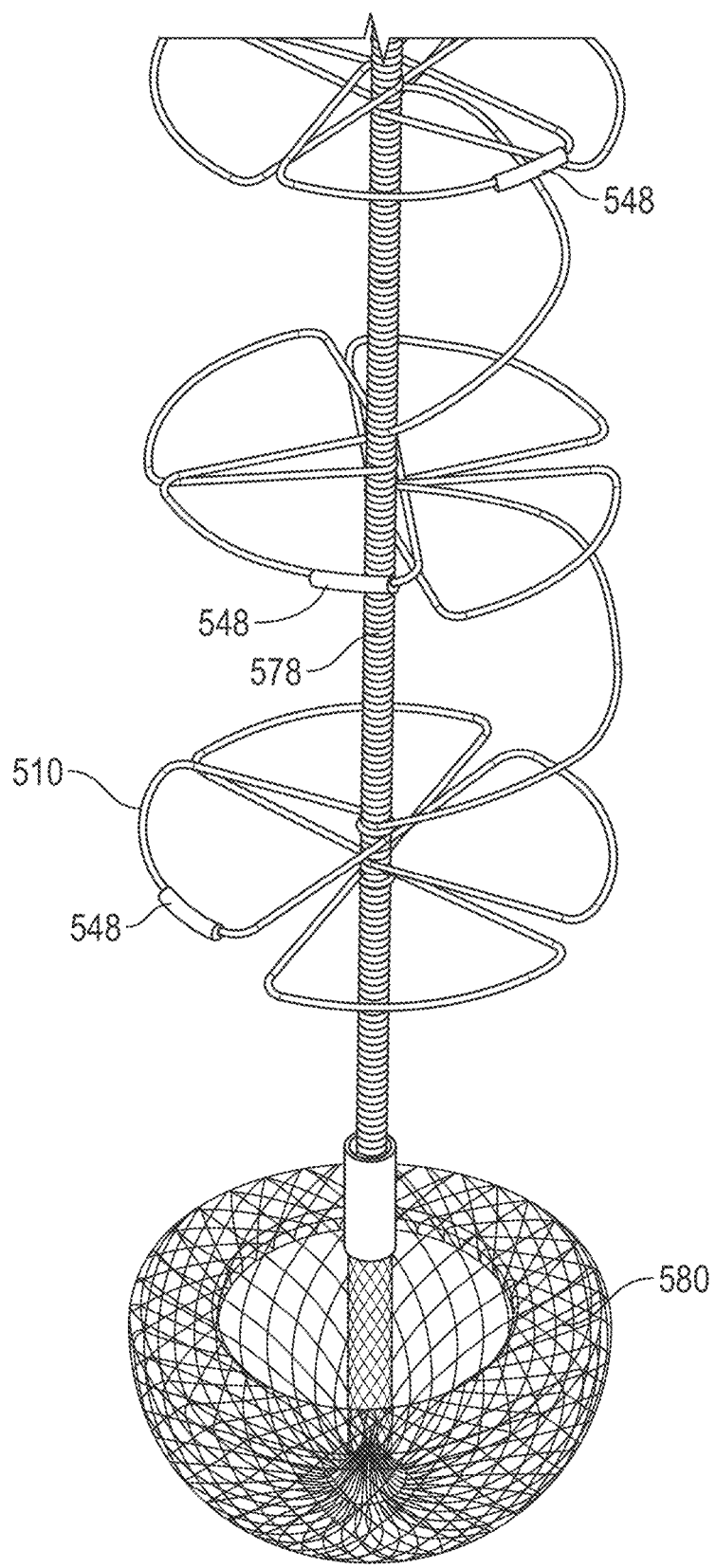
FIG. 75 is a view of the single four engagement panels with marker bands that can be made of platinum/iridium tube or coils. The engagement panels can be made of solid elastic nitinol wire or DFT wire (drawn filled tubing) Nitinol with platinum core of the fifth embodiment.
Figure 76A:
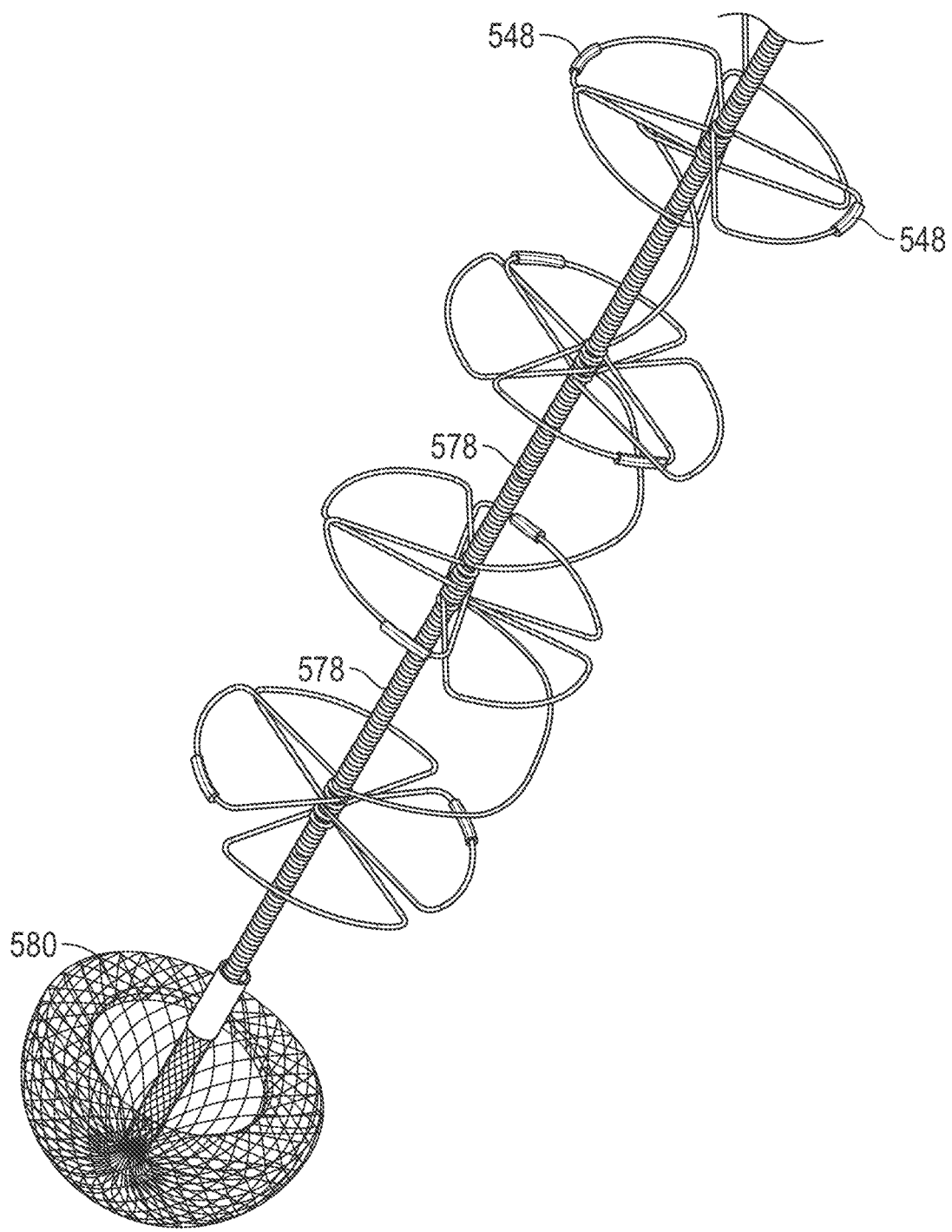
FIGS. 76A-76B are views of the single four engagement panels with platinum coils and radiopaque markers of the fifth embodiment.
Figure 76B:
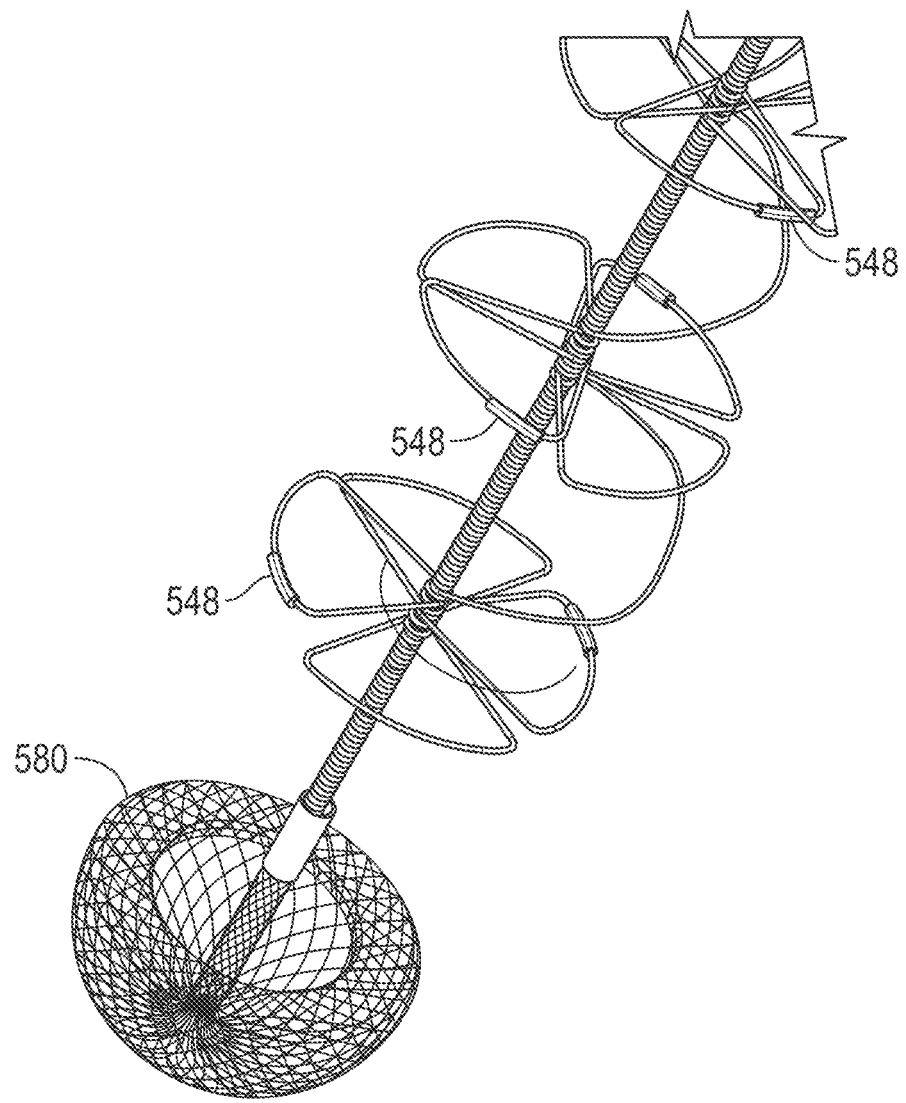
Figure 77:
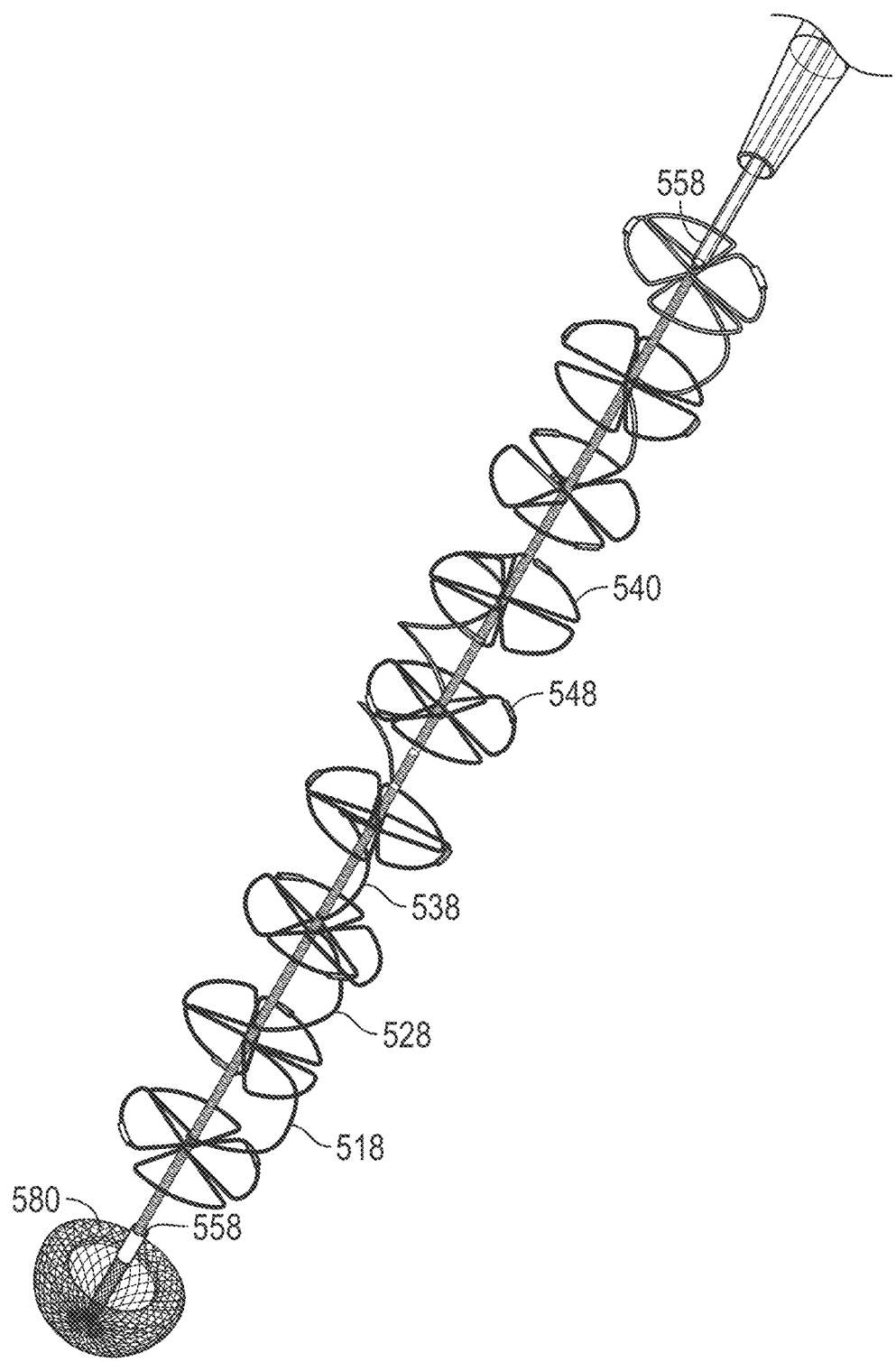
FIG. 77 is another view of the single four engagement panels with marker bands showing at both ends of the fifth embodiment.
Figure 78A:
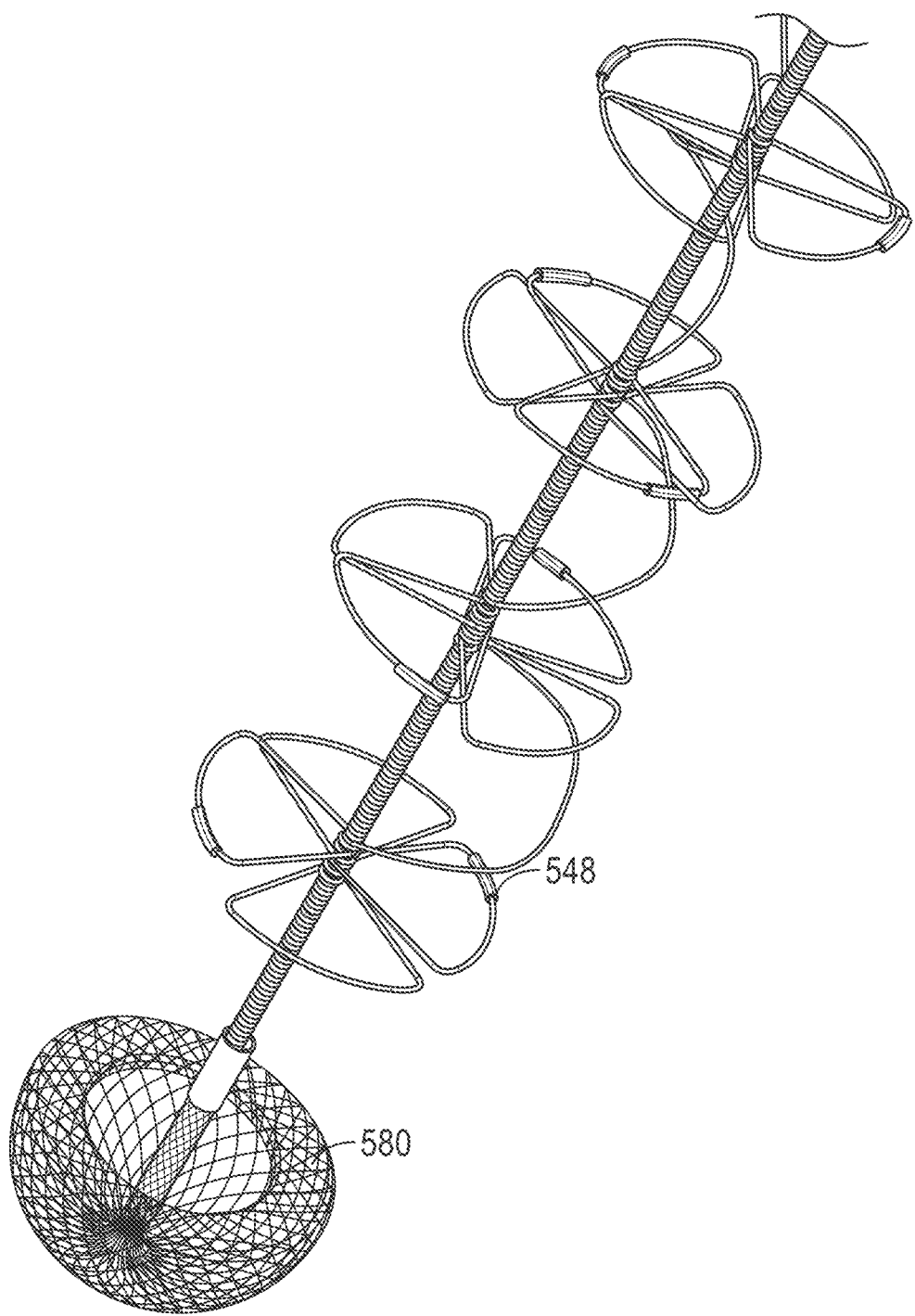
FIG. 78A is a view of the single four engagement panels of the fifth embodiment.
Figure 78B:
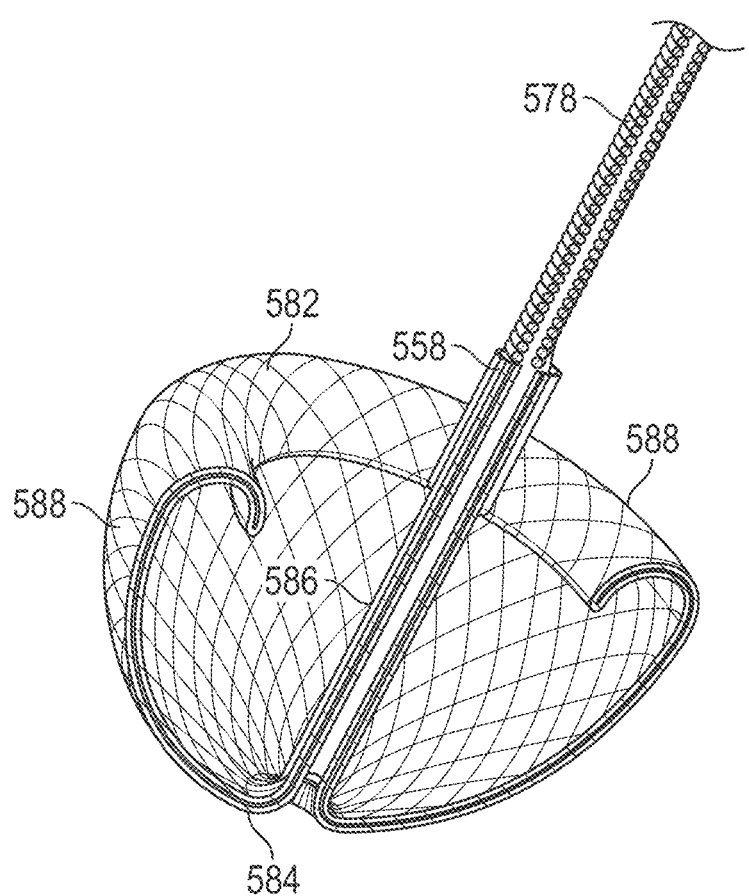
FIG. 78B is a view of a distal member.
Figure 79:
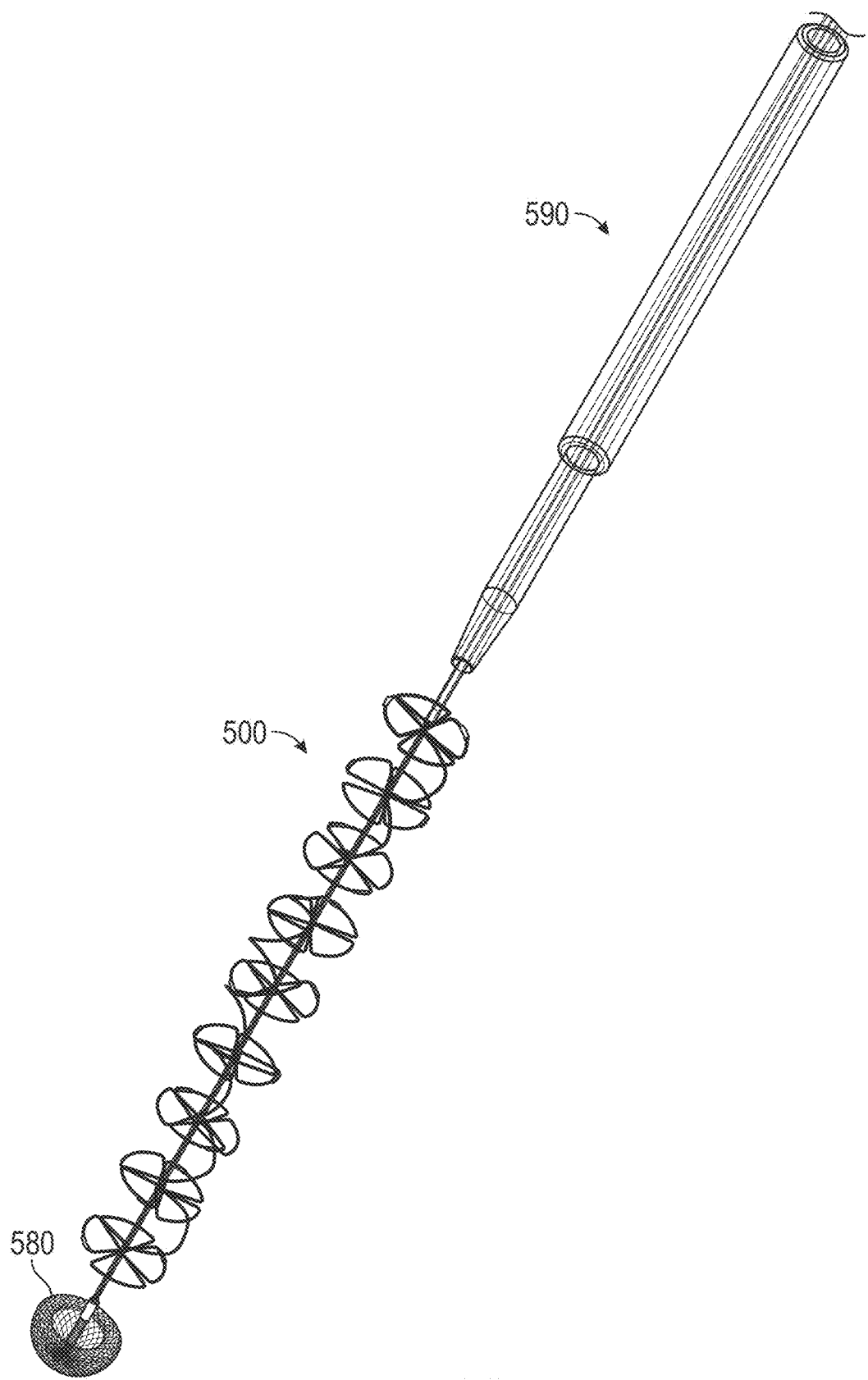
FIG. 79 is a view of the extractor in the expanded configuration and loading tube assembly. The loading tube assembly can also be a tubular member or a sheath.

FIG. 73 illustrates the loading tube assembly 590. The loading tube assembly 590 can include a taper end 592 for engagement with the microcatheter. The loading assembly 590 can include a larger section 594 to minimize slippage during device insertion. The loading tube aids to introduce the device into the microcatheter or delivery catheter and advance within the microcatheter or delivery catheter to the treatment site. The loading tube can be made of polymeric materials such as Polyethylene, PTFE, FEP, Nylon, Polyurethane, PEBAX or PET for example. The loading tube assembly can also be a tubular member or a sheath.

FIG. 74-79 are view of the extractor 500 with single layer engagement panels. The extractor 500 can include radiopaque markers on the engagement panels. The extractor 500 can include one or more radiopaque markers 548. The radiopaque marker 548 can be located on the arc 540. The first longitudinal location can include one or more radiopaque markers 548. One arc 540 can include radiopaque markers 548 at the first longitudinal location. The second longitudinal location can include one or more radiopaque markers 548. The third longitudinal location can include one or more radiopaque markers 548. Other configuration are contemplated. The coil segment in between the engagement panels can be radiopaque. For example, the coil segment between the first longitudinal location and the second longitudinal location is made of platinum/iridium or tungsten. The radiopaque markers 548 can be marker bands. The radiopaque markers 548 can be made of platinum and/or iridium. The radiopaque markers 548 can be made of tubes or coils. The extractor 500 can also connecting members, extension or bridge 518, 528, 538. The engagement panels 510, 512, 514, 516, 520, 522, 524, 526, 530, 532, 534, 536 can be made of solid super elastic nitinol wire. The engagement panels 510, 512, 514, 516, 520, 522, 524, 526, 530, 532, 534, 536 can be made of DFT (drawing filled tubing) nitinol with a platinum core.

The engagement panels 510, 512, 514, 516, 520, 522, 524, 526, 530, 532, 534, 536 can be formed from a single layer. The two legs 542, 544 of the engagement panel 510 can be angled from the two legs 542, 544 of the engagement panel 512. The two legs 542, 544 of the engagement panel 510 can be separated from the two legs 542, 544 of the engagement panel 512. The arcs 540 of the engagement panels 510, 512, 514, 516, 520 can form an incomplete circle. The arcs 540 of the engagement panels 510, 512, 514, 516, 520 can form segments of a circle. There can be one radiopaque marker 548 on the engagement panels 510, 520, 530. The extractor 500 can include platinum coils along the core wire 570. The extractor 500 can include one or more additional bands 558. There can be a band 558 at the distal end. There can be a band 548 at or near the proximal end. There can be a band 558 at any location along the length. There can be a band 558 at both ends. The coil 578 can include platinum coils. There can be one, two, or more radiopaque marker 558 at a longitudinal location.

The extractor 500 can have a plurality of connecting members 518, 528, 538. The connecting member 518 can connect the engagement panels 510, 512, 514, 516 at the first longitudinal location and the engagement panels 520, 522, 524, 526 at the second longitudinal location. The connecting member 528 can connect the engagement panels 520, 522, 524, 526 at the second longitudinal location and the engagement panels 530, 532, 534, 536 at the third longitudinal location. The connecting member 538 can connect the engagement panels 530, 532, 534, 536 at the third longitudinal location and another set of engagement panels. The connecting members 518, 528, 538 can be curved.

The distal member 580 can be made from a single layer nitinol braid. The distal member 580 can be made from a double layer nitinol braid. The distal member 580 can be made from closed end single layer nitinol braid. The distal member 580 can be made from closed end double layer nitinol braid. The distal member 580 can be straightened in a loaded configuration. In some embodiments, the distal member 580 can be straightened distally. In some embodiments, the distal member 580 can invert during deployment. In some embodiments, the distal member 580 can invert to sweep the vessel wall. The distal member 580 can fold proximally when unsheathed.

In some embodiments, the distal member 580 can include a proximal end 582. The proximal end 582 can be cupped. The proximal end 582 can be folded distally. The proximal end 582 can be folded inward. The proximal end 582 can function as a funnel into the distal member 580. The distal member 580 can collect material within the distal member. In some embodiments, the distal member 580 can include a distal end 584. The distal end 584 can be a floating end. The distal end 584 of the distal member 580 can form the distal end of the device. The distal member 580 can include a tubular portion 586. The tubular portion 586 can extend along a longitudinal or central axis. The tubular portion 586 can extend to the distal end 584. The distal member 580 can include an expanded portion 588. The expanded portion 588 flares outward from the tubular portion 586. The expanded portion 588 encircles the tubular portion 586. The space between the tubular portion 586 and the expanded portion 588 allows for the collection of material. The space between the tubular portion 586 and the expanded portion 588 is enclosed.

In some embodiments, the distal member 580 can be coupled to the core wire 570. In some embodiments, the distal member 580 can be coupled to the coil 578. In some embodiments, the distal member 580 can be coupled to distal marker 558. The distal marker 558 can be coupled to the tubular portion 586 of the distal member 580. The distal marker 558 can be laser welded to the distal member 580. The distal marker 558 can be bonded with an adhesive to the distal member 580. The distal marker 558 can be crimped or swaged or press fit to the distal member 580.

The loading tube assembly 590 can compress the extractor 500. The loading tube assembly 590 can compress the engagement panels. The loading tube assembly 590 can compress the distal member 580. The distal member can straighten in the loading tube assembly 580.

Figure 80A:
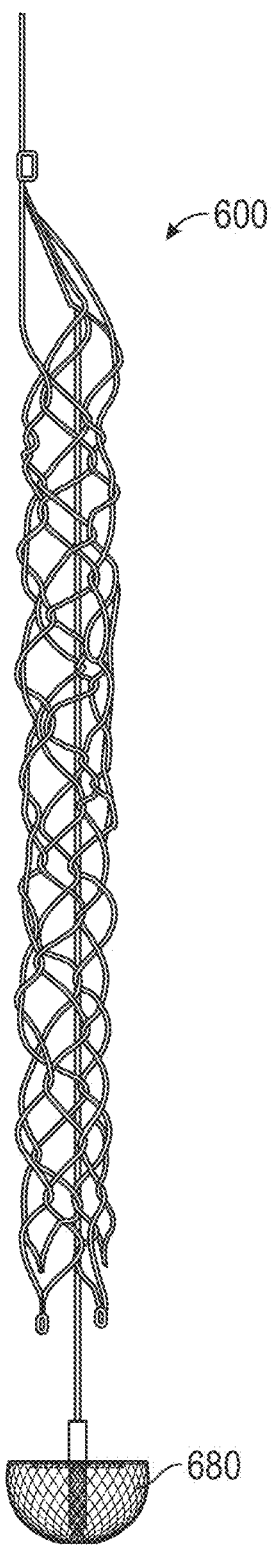
FIGS. 80A-80B are views of a stent retriever assembly.
Figure 80B:
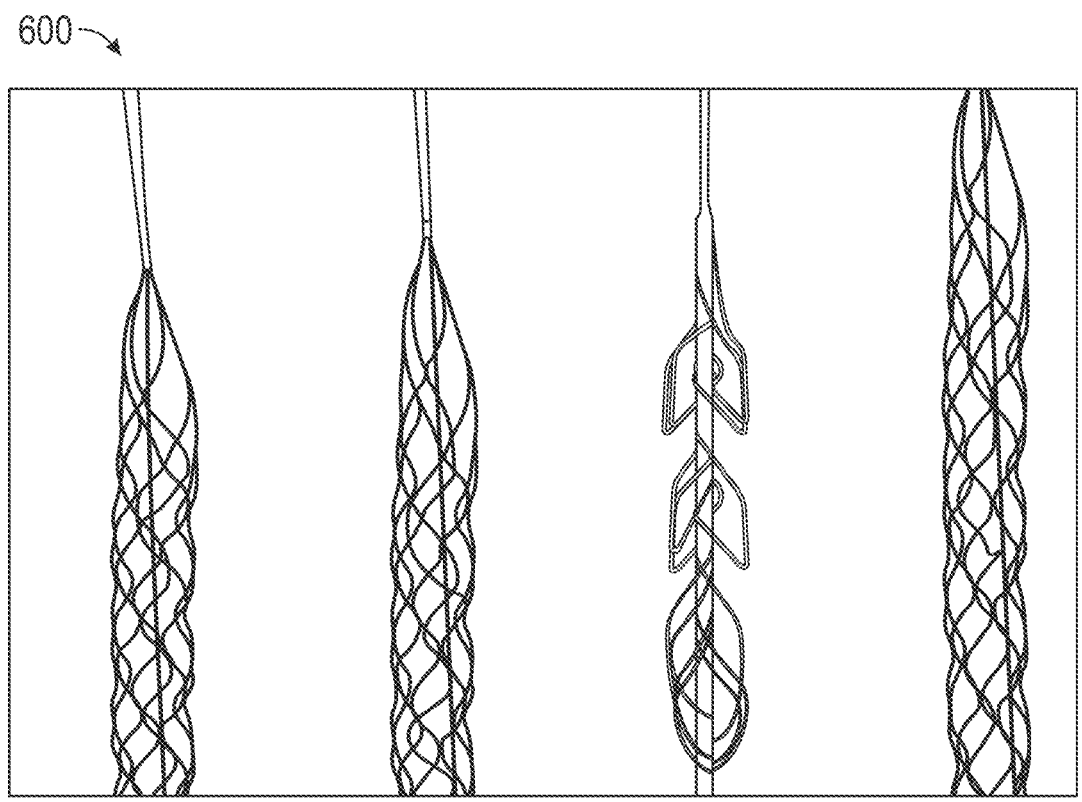

FIGS. 80A-80B are views of examples of a stent retriever 600. The stent retriever 600 can be laser cut. The stent retriever 600 can be self-expandable. The stent retriever 600 can be any shape including the shapes shown. The extractors 100, 200, 300, 400, 500 can be used in combination with the stent retriever 600. The stent retriever 600 can include a distal member 680. The distal member 680 can include any feature described herein. The distal member 680 can capture debris.

Figure 81A:
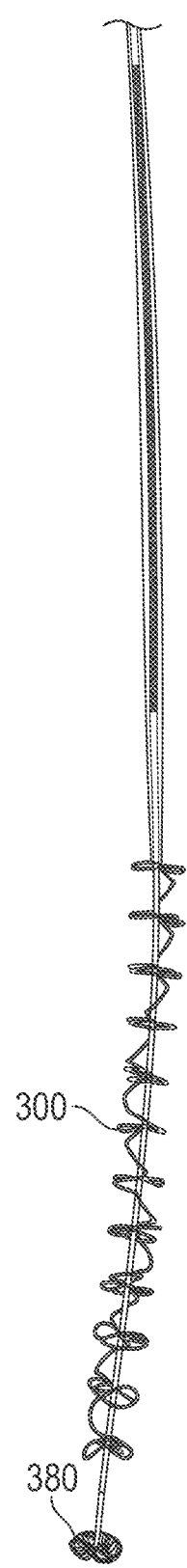
FIGS. 81A-C are views of the extractor and a proximal funnel assembly.
Figure 81B:
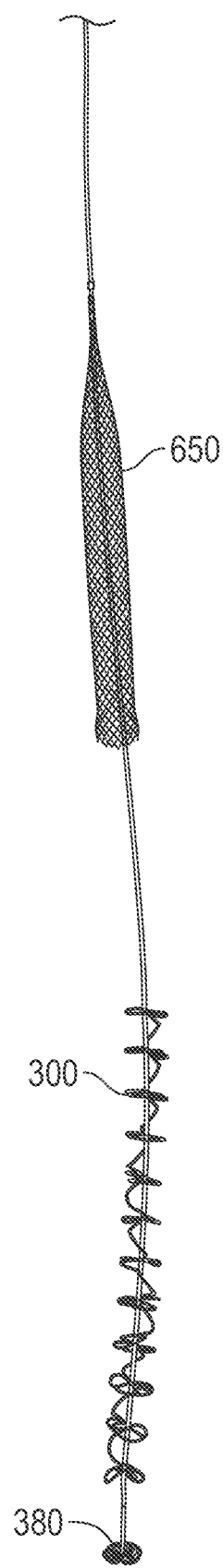
Figure 81C:
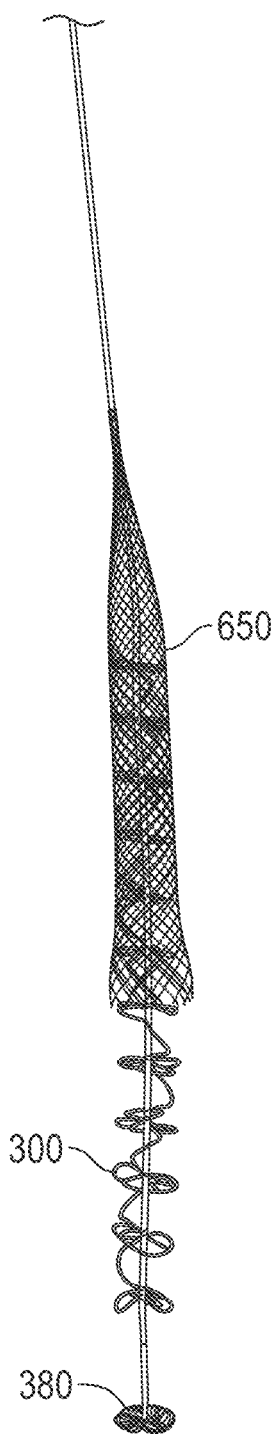

FIGS. 81A-81C are views of the extractor 300 and proximal funnel or collection bag 650. The extractor 300 can include the distal member 380. The extractor 100, 200, 300, 400, 500 can be used in combination with the proximal funnel or collection bag 650. The proximal funnel or collection bag 650 can be built-in. The proximal funnel or collection bag 650 can be proximal to the extractor 100, 200, 300, 400, 500. FIG. 81A illustrates the funnel loaded configuration. FIG. 81B illustrates the funnel deployed configuration. There can be a proximal stopper and a distal stopper. FIG. 81C illustrates the extractor 300 retracted into the proximal funnel or collection bag 650.

Figure 82A:
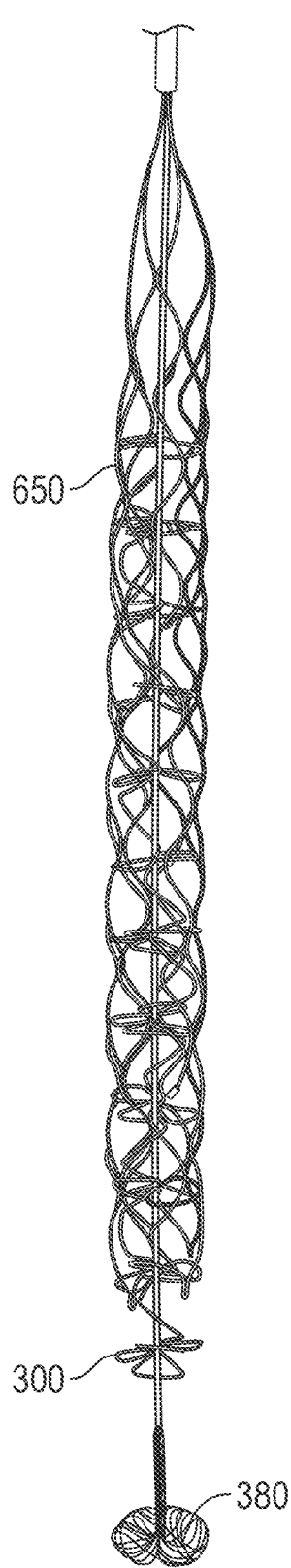
FIGS. 82A-82B are views of the extractor that is within the stent retriever assembly.
Figure 82B:
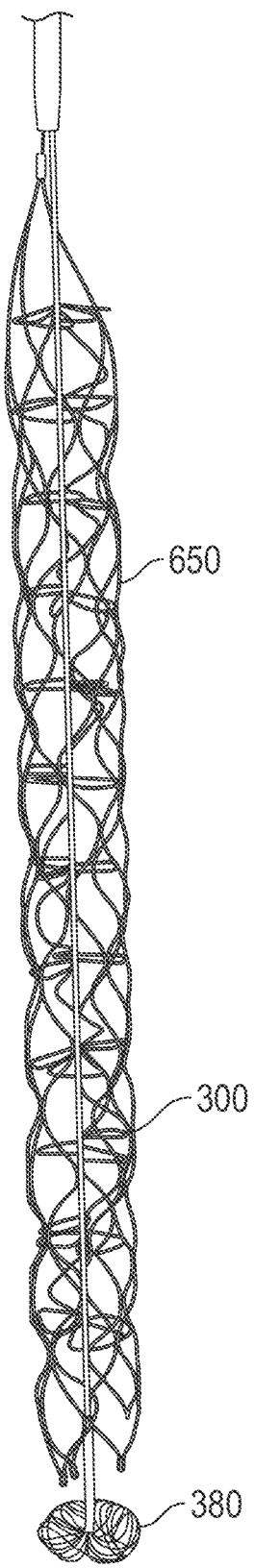

FIGS. 82A-82B are views of the extractor 300 and a stent retriever 600. The extractor 300 can be positioned distal to the stent retriever 600 to enable better clot removal. The extractor 300 can be positioned outside the stent retriever 650. The extractor 300 can be positioned within the stent retriever 650. The extractor 300 can include the distal member 380.

Figure 83A:
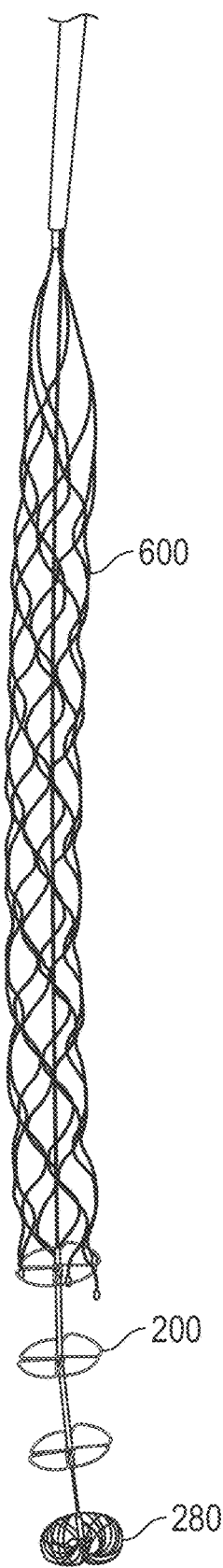
FIGS. 83A-83C are views of the extractor that can be distal to and/or within the stent retriever.
Figure 83B:
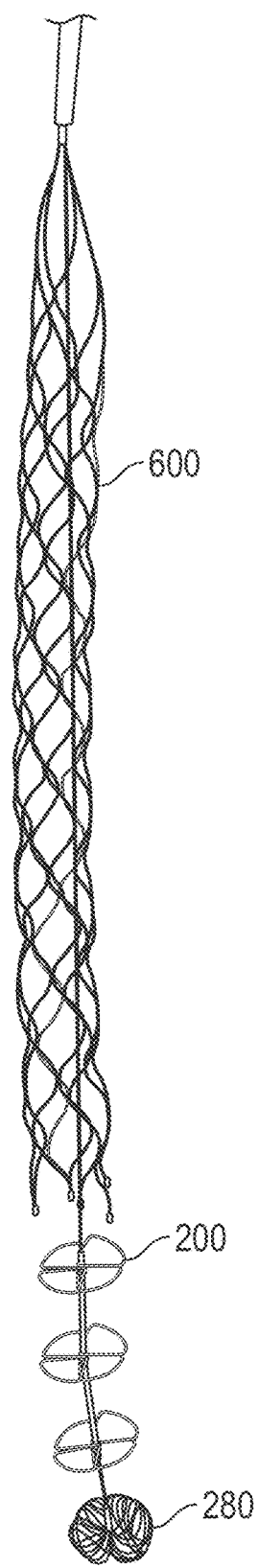
Figure 83C:
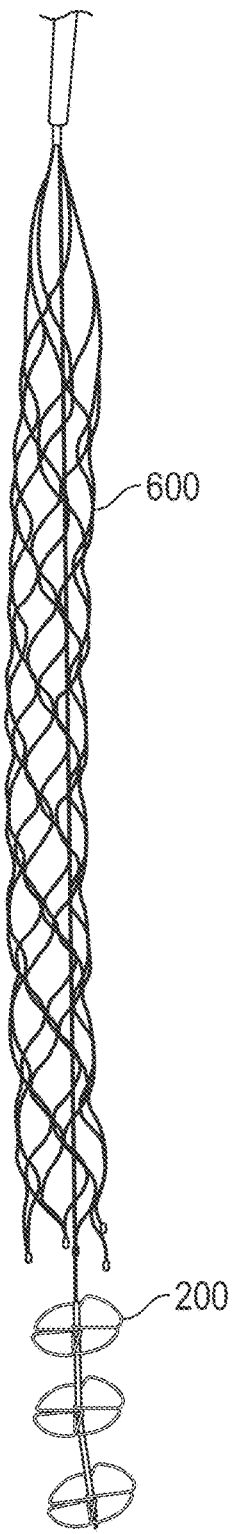
Figure 84A:
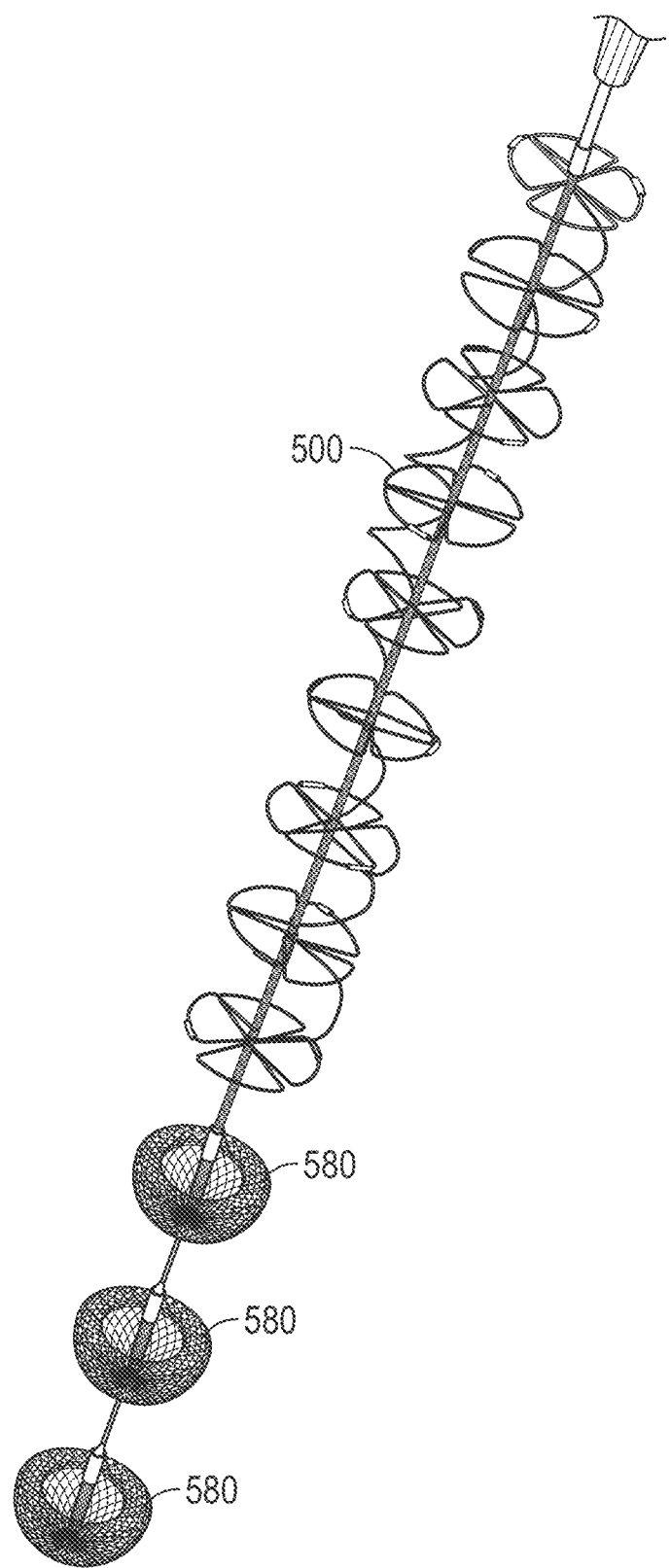
FIGS. 84A-84D are views of the single four engagement panels with multiple distal members. The distal member can be positioned at any location along the extractor to collect loose clot, soft clot, or in transit clot.
Figure 84B:
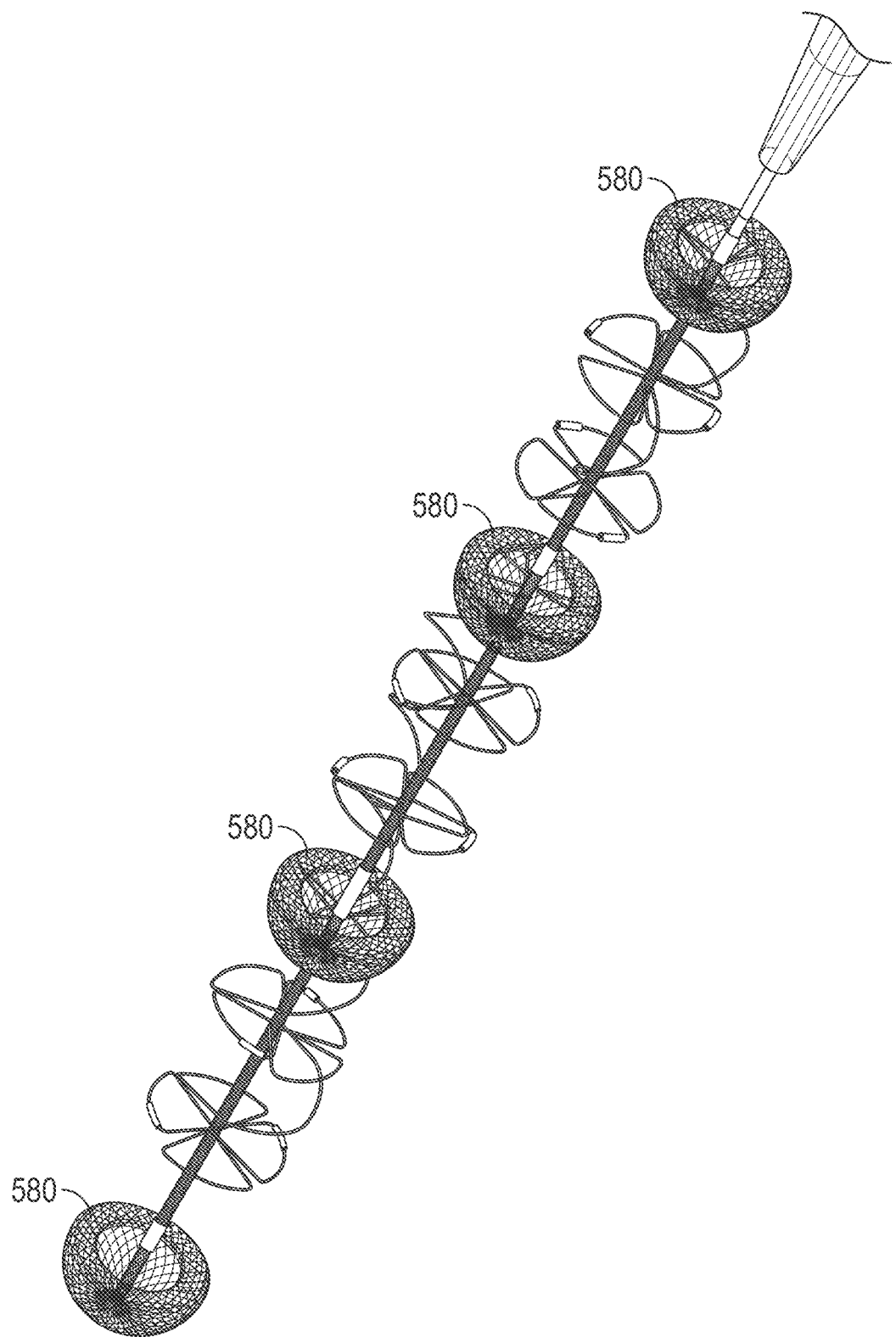
Figure 84C:
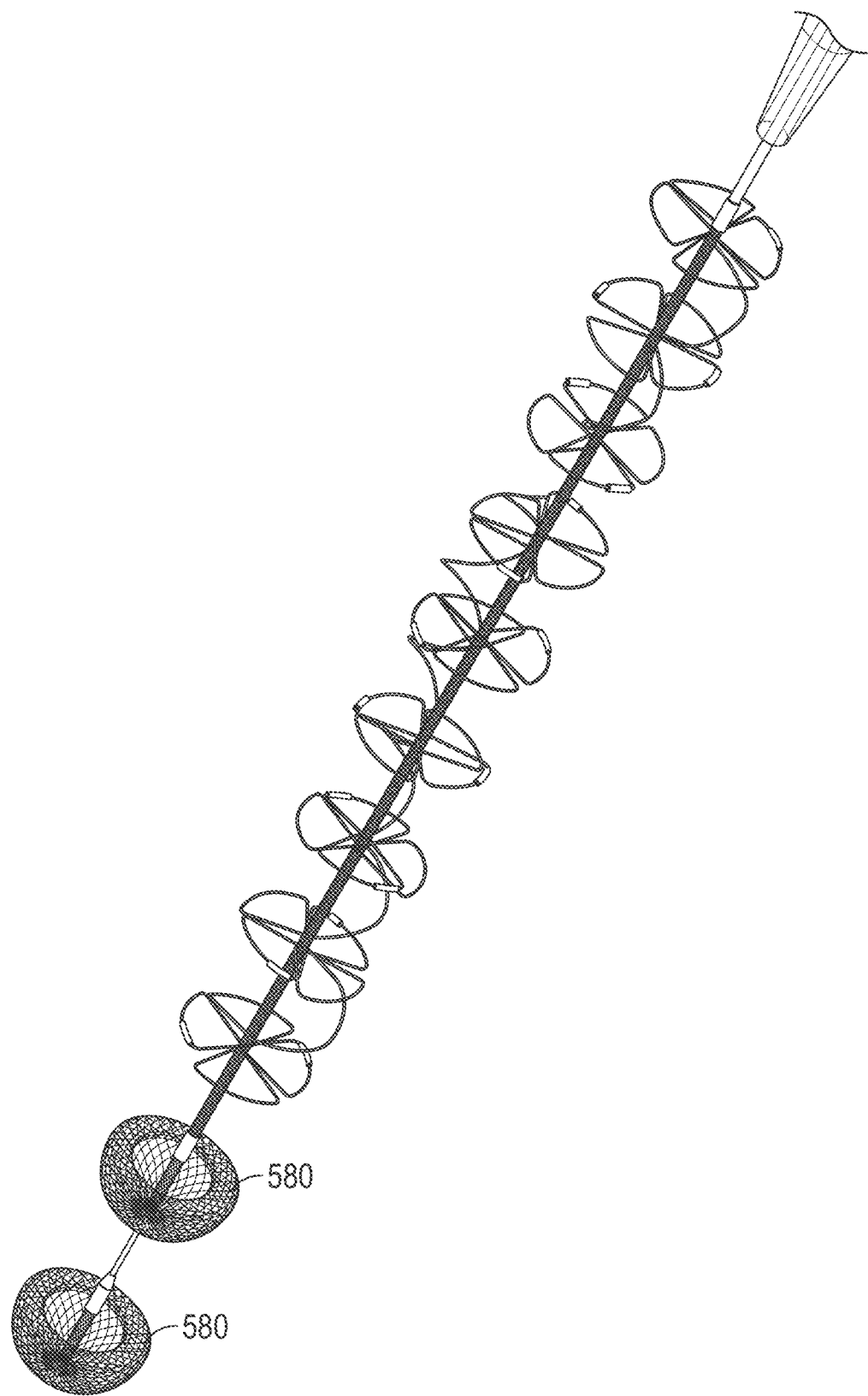
Figure 84D:
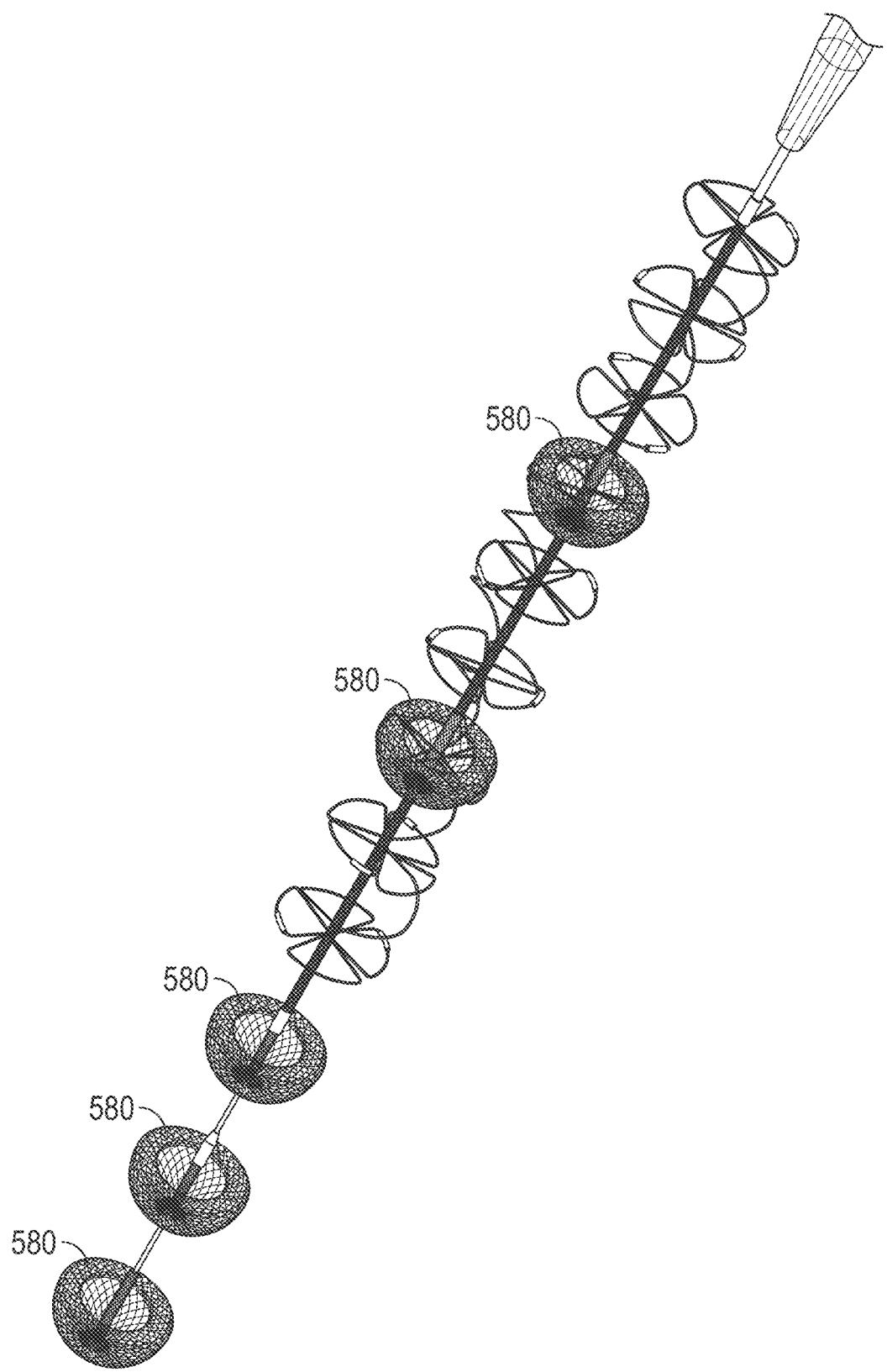

FIGS. 83A-83C views of the extractor 200 stent retriever 600. The extractor 200 can include the distal member 280.

FIGS. 84A-84D are views of the extractor 500. The extractor 500, or any embodiment disclosed herein, can include one or more distal members. FIGS. 84A-84D are views of multiple distal members 580. The distal member 580 can be positioned at any location along the extractor 500. The distal member can collect loose clot, soft clot, or in transit clot. The figures illustrates that the distal end of the device can include one, two, three, four, five, six, or more distal members 580. The distal members 580 can function as end caps. The distal members 580 can be located at various positions of the extractor 500. In some embodiments, the distal member 580 can be located distal to the first longitudinal location. Two or more distal members 580 can be located distal to the first longitudinal location. The engagement panel 510, 512, 514, 516 can be located at the first longitudinal location. The engagement panel 520, 522, 524, 526 can be located at the second longitudinal location. The engagement panel 530, 532, 534, 536 can be located at the second longitudinal location. In some embodiments, one or more distal members 580 can be located between the first longitudinal location and the second longitudinal location. In some embodiments, no distal members 580 are located between the first longitudinal location and the second longitudinal location. In some embodiments, one or more distal members 580 can be located between the second longitudinal location and the third longitudinal location. In some embodiments, no distal members 580 are located between the second longitudinal location and the third longitudinal location. In some embodiments, one or more distal members 580 can be located proximal to the third longitudinal location. In some embodiments, no distal members 580 are located proximal to the third longitudinal location. In some embodiments, one or more distal members 580 are regularly spaced. In some embodiments, one or more distal members 580 are irregularly spaced. In some embodiments, the engagement panel 510, 512, 514, 516 and the engagement panel 520, 522, 524, 526 are between adjacent distal members 580.

Figure 85A:
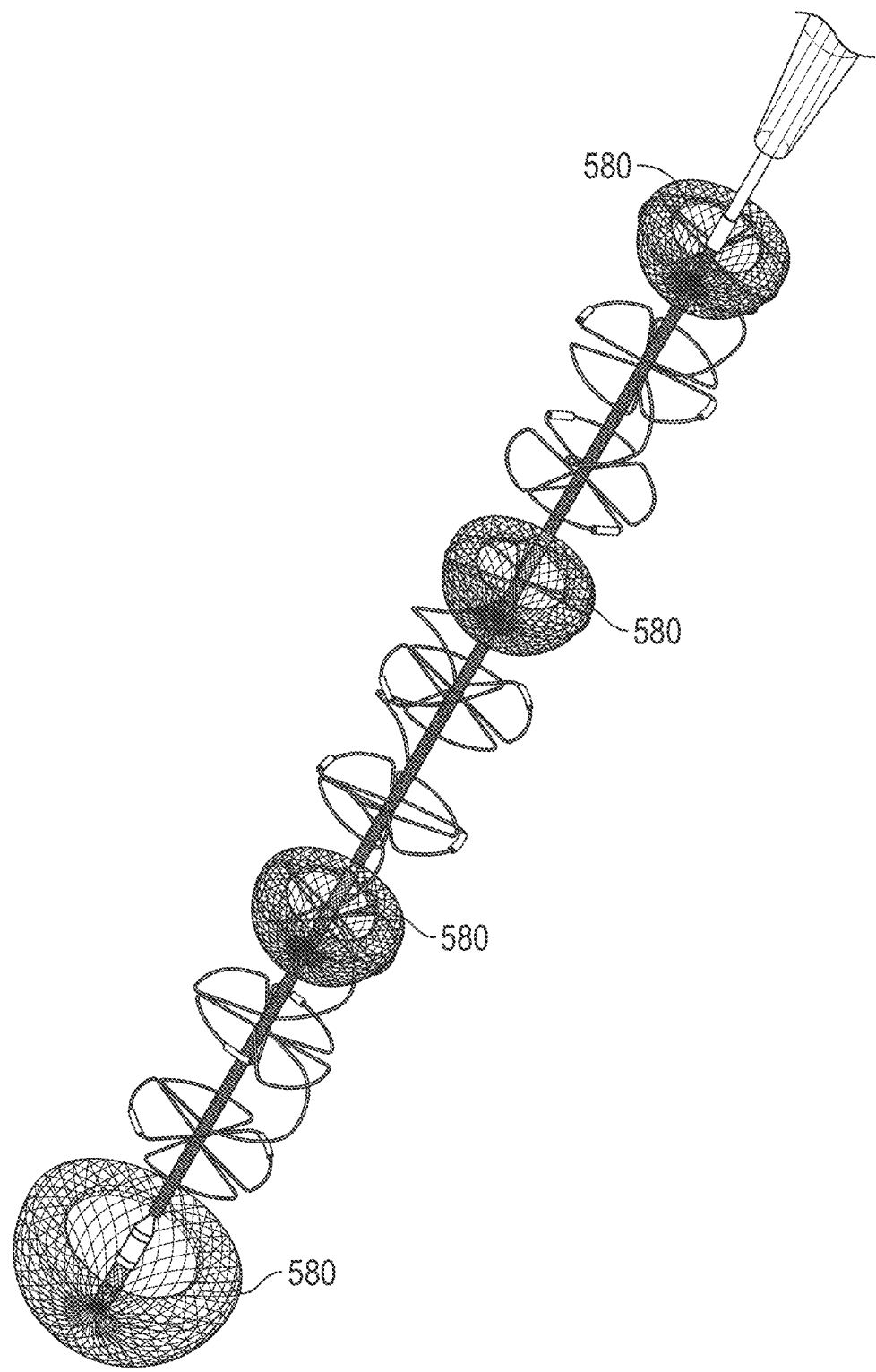
FIGS. 85A-85B are views of the single four engagement panels showing a single distal member configuration and a multiple distal members configuration.
Figure 85B:
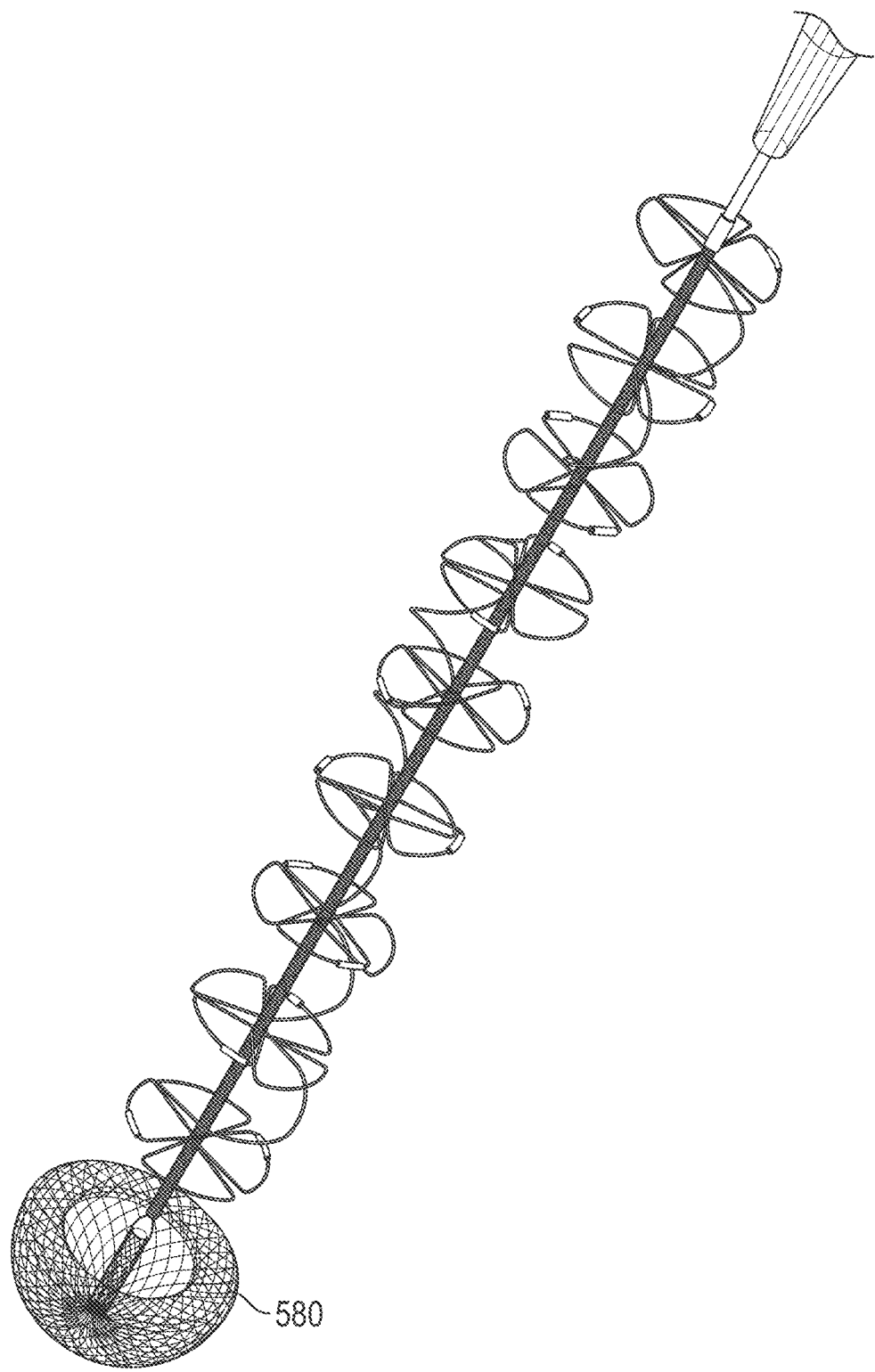

FIGS. 85A-85B are views of the extractor 500. The extractor 500 can include a single distal member configuration. The extractor 500 can include a multiple distal members configuration. In some embodiments, the distal member 580 can have the same diameter as the engagement panel 510, 512, 514, 516. In some embodiments, the distal member 580 can have the same diameter as the engagement panel 520, 522, 524, 526. In some embodiments, the distal member 580 can have the same diameter as the engagement panel 530, 532, 534, 536. In some embodiments, the distal member 580 can have the same diameter as the engagement panels with the largest diameter. In some embodiments, the distal member 580 can have the same diameter as the engagement panels with the smallest diameter. In some embodiments, the distal member 580 can have a different diameter than the engagement panels. In some embodiments, the distal member 580 can have a smaller diameter as the engagement panel 510, 512, 514, 516. In some embodiments, the distal member 580 can have a smaller diameter as the engagement panel 520, 522, 524, 526. In some embodiments, the distal member 580 can have a smaller diameter as the engagement panel 530, 532, 534, 536. In some embodiments, the distal member 580 can have a smaller diameter than the smallest diameter engagement panels. In some embodiments, the distal member 580 can have a larger diameter as the engagement panel 510, 512, 514, 516. In some embodiments, the distal member 580 can have a larger diameter as the engagement panel 520, 522, 524, 526. In some embodiments, the distal member 580 can have a larger diameter as the engagement panel 530, 532, 534, 536. In some embodiments, the distal member 580 can have a larger diameter than the largest diameter engagement panels. In some embodiments, two or more distal members 580 have the same diameter. In some embodiments, two or more distal members 580 have different diameters. In some embodiments, the distal member 580 with the larger diameter is distal to the distal member with the smaller diameter.

Figure 86A:
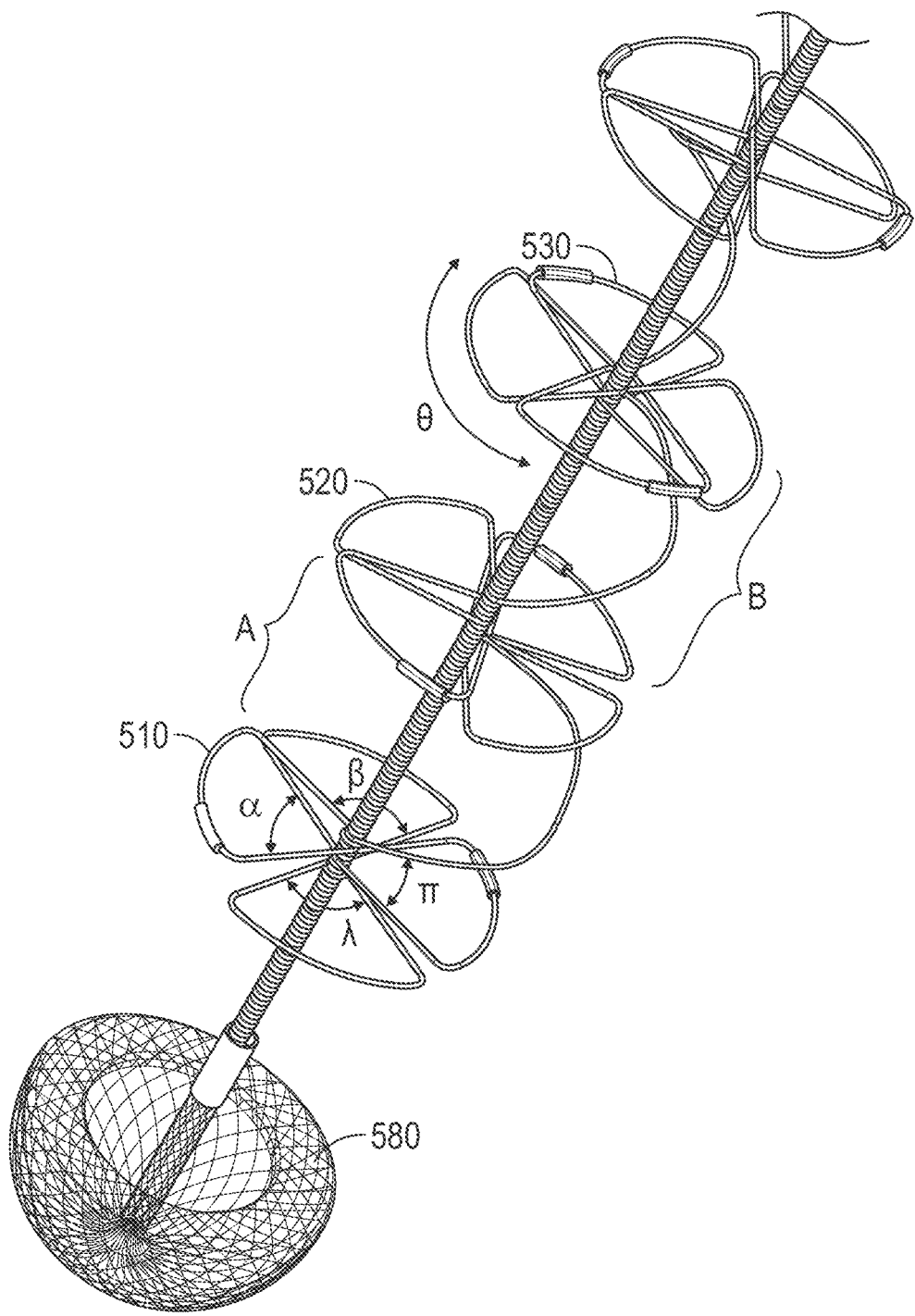
FIGS. 86A-86B are views of the single four engagement panels of the fifth embodiment. The panels can have angles alpha, beta, pi, lamda. The panels can have arcs theta.
Figure 86B:
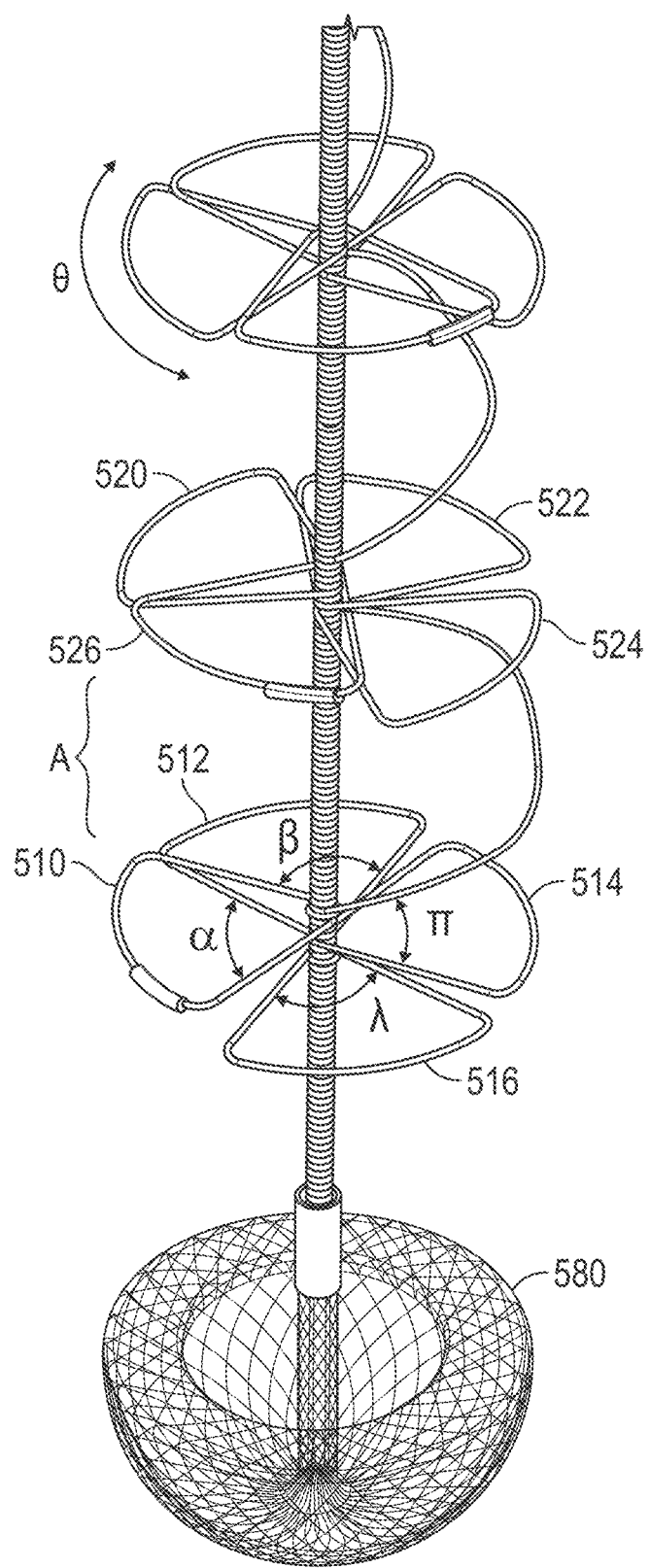

FIGS. 86A-86B are views of the extractor 500. The engagement panels 510, 512, 514, 516 can have two or more different angles alpha, beta, pi, lambda. The engagement panels 510, 512, 514, 516 can have one or more same angles alpha, beta, pi, lambda. The engagement panels 510, 512, 514, 516 can have two more different arcs 540 theta. The engagement panels 510, 512, 514, 516 can have one or more of the same arcs 540 theta. Two, three, or four of the engagement panels 510, 512, 514, 516 at the first longitudinal location have the same angle. Two, three, or four of the engagement panels 510, 512, 514, 516 at the first longitudinal location have the same arc. Two, three, or four of the engagement panels 510, 512, 514, 516 at the first longitudinal location have different angles. Two, three, or four of the engagement panels 510, 512, 514, 516 at the first longitudinal location have different arcs 540.

The engagement panels 510, 512, 514, 516 at the first longitudinal location A and the engagement panels 520, 522, 524, 526 at the second longitudinal location B can be different. The engagement panels 510, 512, 514, 516 at the first longitudinal location A and the engagement panels 520, 522, 524, 526 at the second longitudinal location B can be the same. The engagement panels 520, 522, 524, 526 at the second longitudinal location B and the engagement panels 530, 532, 534, 536 at the third longitudinal location C can be different. The engagement panels 520, 522, 524, 526 at the second longitudinal location B and the engagement panels 530, 532, 534, 536 at the third longitudinal location C can be the same. The engagement panels 510, 512, 514, 516 at the first longitudinal location A and the engagement panels 530, 532, 534, 536 at the third longitudinal location C can be different. The engagement panels 510, 512, 514, 516 at the first longitudinal location A and the engagement panels 530, 532, 534, 536 at the third longitudinal location C can be the same.

Figure 87A:
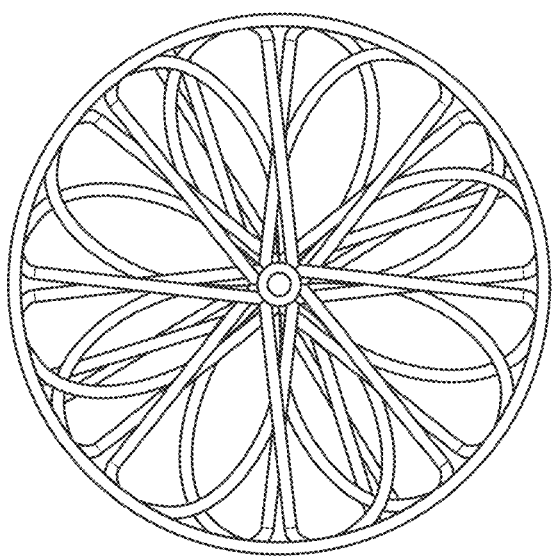
FIGS. 87A-87C are view of the extractor showing the engagement panels and connecting members.
Figure 87B:
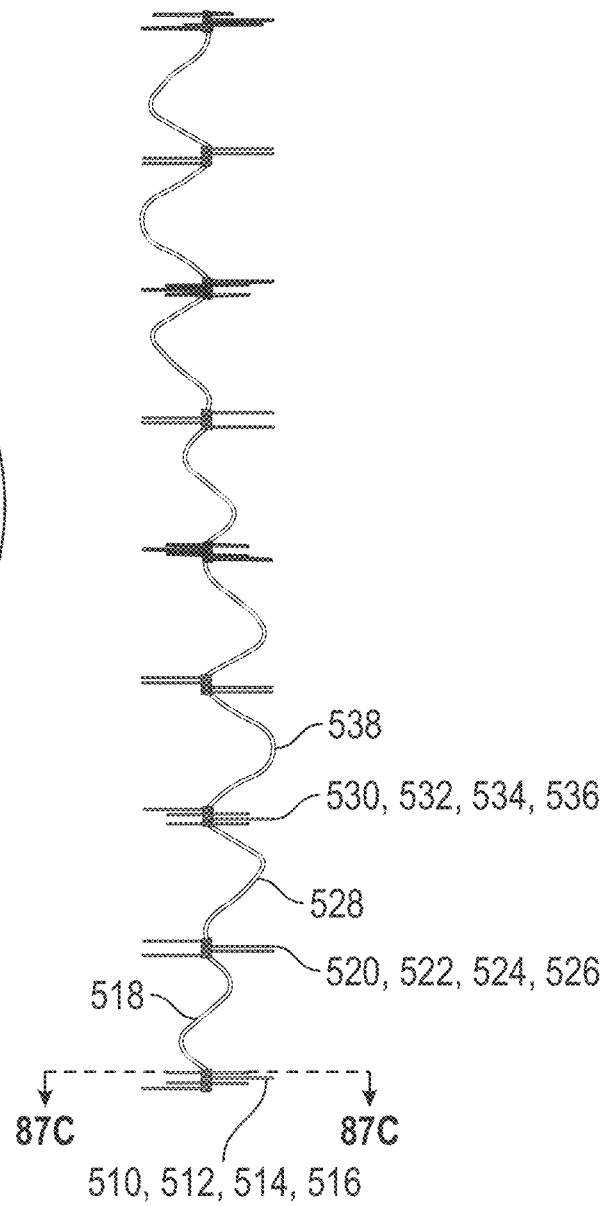
Figure 87C:
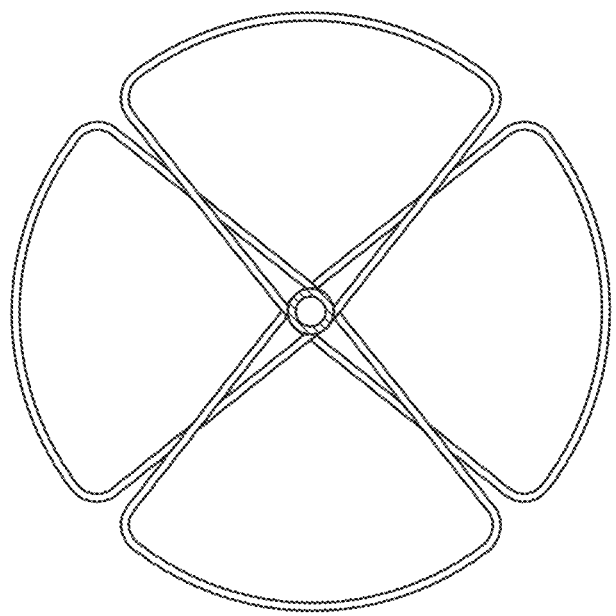

FIGS. 87A-87C are view of the extractor 500. FIG. 87B is a side view of the extractor showing the engagement panels 510, 512, 514, 516, 520, 522, 524, 526, 530, 532, 534, 536 and the connecting members 518, 528, 538. The engagement panels are stacked and next to each other.

Figure 88A:
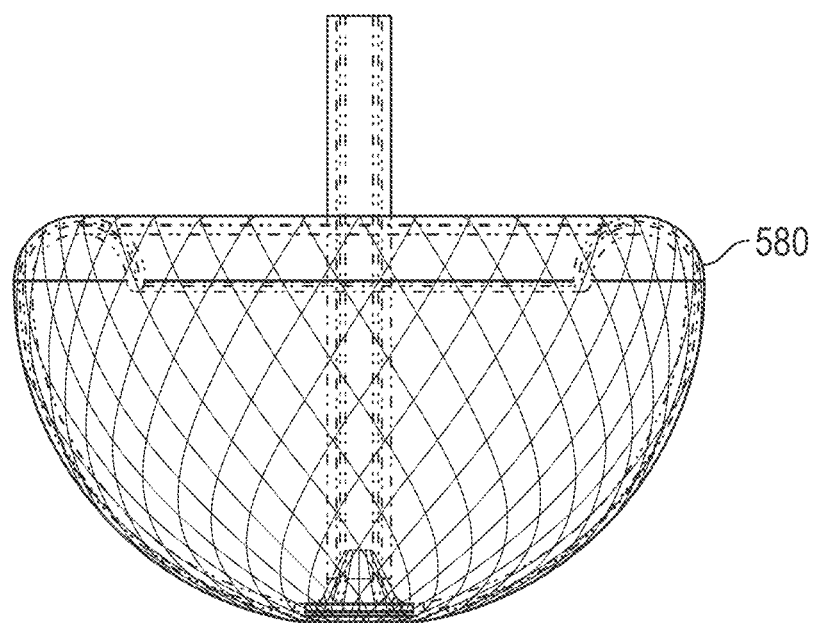
FIGS. 88A-88B are view of the distal member.
Figure 88B:
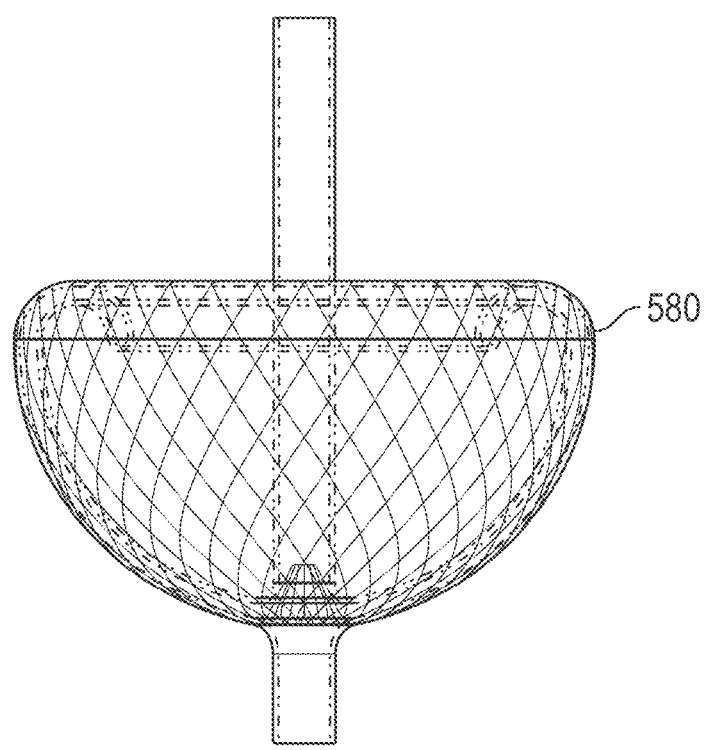

FIGS. 88A-88B are view of the distal member. FIG. 88A illustrates a distal member 580 with a double layer construction. FIG. 88B illustrates a distal member with a single layer construction.

Figure 89A:
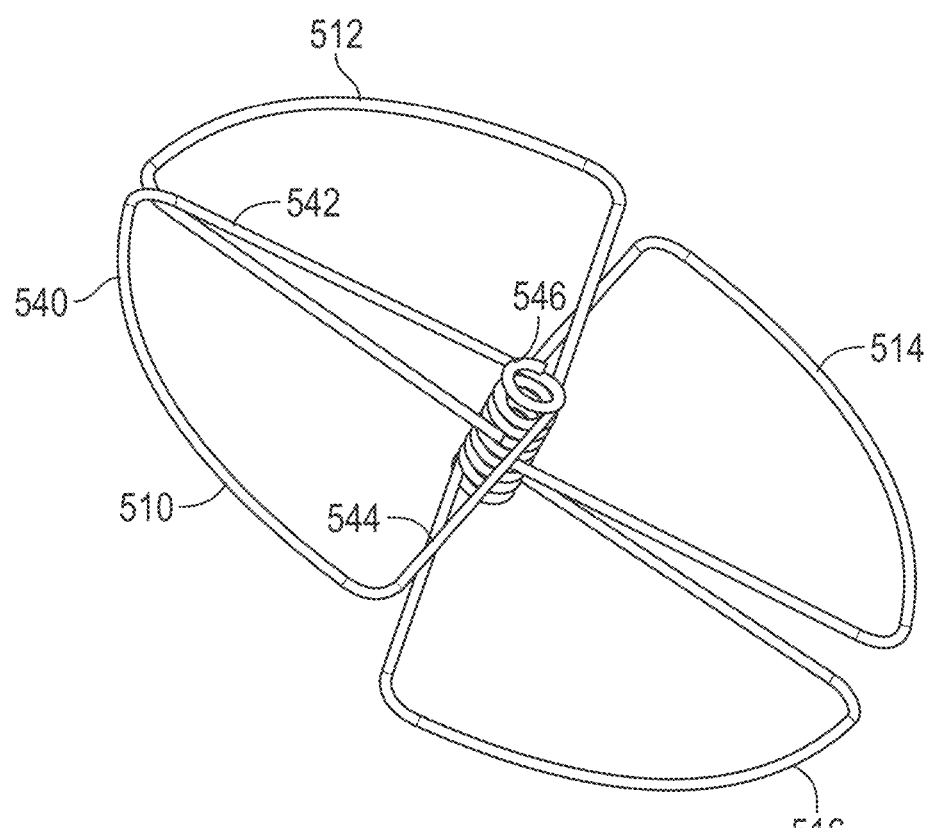
FIGS. 89A-89C are views of the single four engagement panels of the fifth embodiment.
Figure 89B:
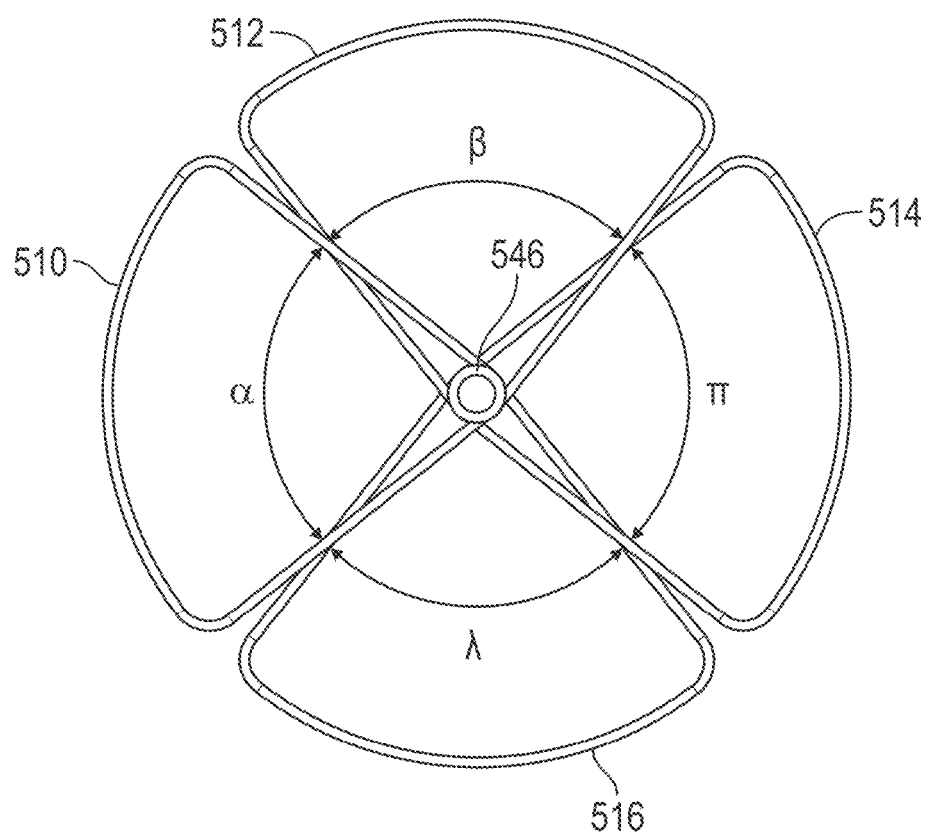
Figure 89C:
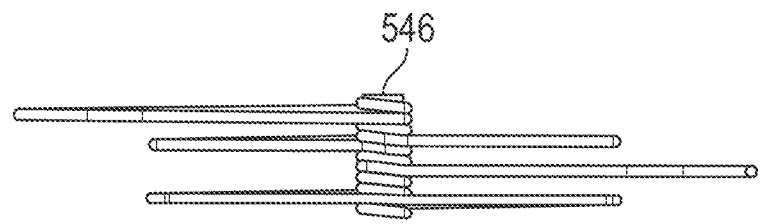

FIGS. 89A-89C illustrate a single layer engagement panel of the extractor 500. FIG. 89A is a perspective view. FIG. 89B is a front view. FIG. 89C is a side view. Each engagement panel 510, 512, 514, 516 forms a portion of the eyelet 546. The elongate member forms a portion of the eyelet 546, the leg 542 of the engagement panel 510, the arc 540 of the engagement panel 510, and the leg 544 of the engagement panel 510. Then the elongate member forms a portion of the eyelet 546, the leg 542 of the engagement panel 512, the arc 540 of the engagement panel 512, and the leg 544 of the engagement panel 512. Then the elongate member forms a portion of the eyelet 546, the leg 542 of the engagement panel 514, the arc 540 of the engagement panel 514, and the leg 544 of the engagement panel 514. Then the elongate member forms a portion of the eyelet 546, the leg 542 of the engagement panel 516, the arc 540 of the engagement panel 516, and the leg 544 of the engagement panel 516. The elongate member can be continuous. Each engagement panel 510, 512, 514, 516 can form an angle with the legs 542, 544. The angles alpha, beta, pi, lambda can be the same. The angles alpha, beta, pi, lambda can be different. In some embodiments, the legs 542, 544 can cross. In some embodiments, the legs 542, 544 can stack. In some embodiments, the legs 542, 544 can be longitudinally offset. There can be one or more portions of the eyelet 546 between adjacent engagement panel 510, 512, 514, 516. The engagement panel 510, 512, 514, 516 can be spaced apart along the length of the eyelet. The elongate wire member of the extractor can have a diameter of, e.g. about 0.0005", 0.001", 0.0015", 0.002", 0.0025", 0.003", 0.0035", 0.004", 0.0045", 0.005", or more or less, from 0.0005" to 0.005", or any range of two of the foregoing values. The arc length of each panel can be of any size such that the total arc length of all panels will substantially form a 360 degrees circle. For example, a four engagement panels will have 90 degrees arc length for each panel. For example, a three engagement panels will have a 120 degree arc length for each panel. The total arc length for all engagement panels at each longitudinal location will form a 360 degrees circle. In some embodiments, the total arc length is less than 360 degrees. The eyelet diameter can have different luminal diameters. The luminal diameter can be 0.005", 0.010", 0.014", 0.017", 0.024", 0.027", 0.035", 0.040", 0.050" for example. The luminal diameter can range from 0.005" to 0.050". The angles alpha, beta, pi, lambda can have the same or different angles such that in total all angles alpha, beta, pi, lambda will be 360 degrees. For example, angles alpha, beta, pi, lambda can be 90 degrees each in some embodiment. The angles can be different for example, alpha and pi angles are 80 degrees and beta and lambda are 100 degrees. The angles can vary in some embodiments. Similarly, a three engagement panels will have similar angles configuration where the total angle of all three panels will be 360 degrees. The length of the eyelet can range from 0.1 cm to 100 cm. The distance between the engagement panels can range from 1 mm to 30 mm. The diameter of the engagement panels can range from 1 mm to 40 mm. In some embodiments with multiple engagement panels layer, the offset layers can range from 1 degree to 180 degrees. The engagement panels at each longitudinal location can be tightly packed where each panel is next to each other. In some embodiment, the engagement panels at each longitudinal location can be loosely packed where there is gap between the panels. In some embodiment, the entire length of the extractor engagement panels and eyelets are loosely packed where there is gap in between. In some embodiment, the entire length of the extractor engagement panels and eyelets are tightly packed where there are no gap in between. In some embodiment, the entire length of the extractor engagement panels and eyelets has certain portion that is tightly packed where there are no gaps and has certain portion that is loosely packed where there are gaps in between the engagement panels and eyelets.

The extractor, or a portion thereof, can be manufactured from a single elongate member, such as a wire. The engagement panels 510, 512, 514, 516 and the eyelet 546 at the longitudinal location can be manufactured from a single elongate member. The single elongate member can form a portion of the eyelet 546. The portion of the eyelet can be a complete circle, or a portion of a circle such as, e.g. about 45 degrees, 60 degrees, 75 degrees, 90 degrees, 105 degrees, 120 degrees, 135 degrees, 150 degrees, 165 degrees, 180 degrees, 195 degrees, 210 degrees, 225 degrees, 240 degrees, 255 degrees, 270 degrees, 285 degrees, 300 degrees, 360 degrees, more or less, or any range of two of the foregoing values. The single elongate member can extend to form the leg, the arc, and the leg of the first engagement panel 510. There is a gap in the eyelet 546 between the legs 542, 544 of the engagement panel 510, 512, 514, 516. Each leg 542, 544 begins and ends at the eyelet 546. However, the single wire forms the arc 540 between the legs 542, 544 and not a portion of the eyelet. The single elongate member can extend from the leg 544 to form another portion of the eyelet. The single elongate member can extend to form the leg 542, the arc 540, and the leg 544 of the second engagement panel 512. The engagement panel are offset longitudinally by the diameter of the single elongate member. The engagement panel are offset longitudinally by a portion of the eyelet 546. The single elongate member continues to form a plurality of panels and a plurality of sections of the eyelet 546. The engagement panels 510, 512, 514, 516 at the longitudinal location are offset around the circumference of the eyelet 546. The engagement panels 510, 512, 514, 516 and the eyelet 546 at the longitudinal location are spaced to form a circumferential engagement surface with the arcs 540. The arcs 540 form nearly an entire circumference. The engagement panels 510, 512, 514, 516 are stacked. The first engagement panel 510 is distal to the second engagement panel 512. The second engagement panel 512 is distal to the third engagement panel 514. The third engagement panel 514 is distal to the fourth engagement panel 516. The eyelet 546 is formed by a plurality of partial coils. While four engagement panels are shown, the same method can be used to form any number of panels at the first longitudinal location (e.g., one, two, three, four, five, six, seven, eight, nine, ten, or any range of two of the foregoing values. While the panels at the first longitudinal location are shown, the process can be repeated to form additional arrays at the second longitudinal location and third longitudinal location. The elongate member can form the coil 578 between the eyelets 546.

Figure 90A:
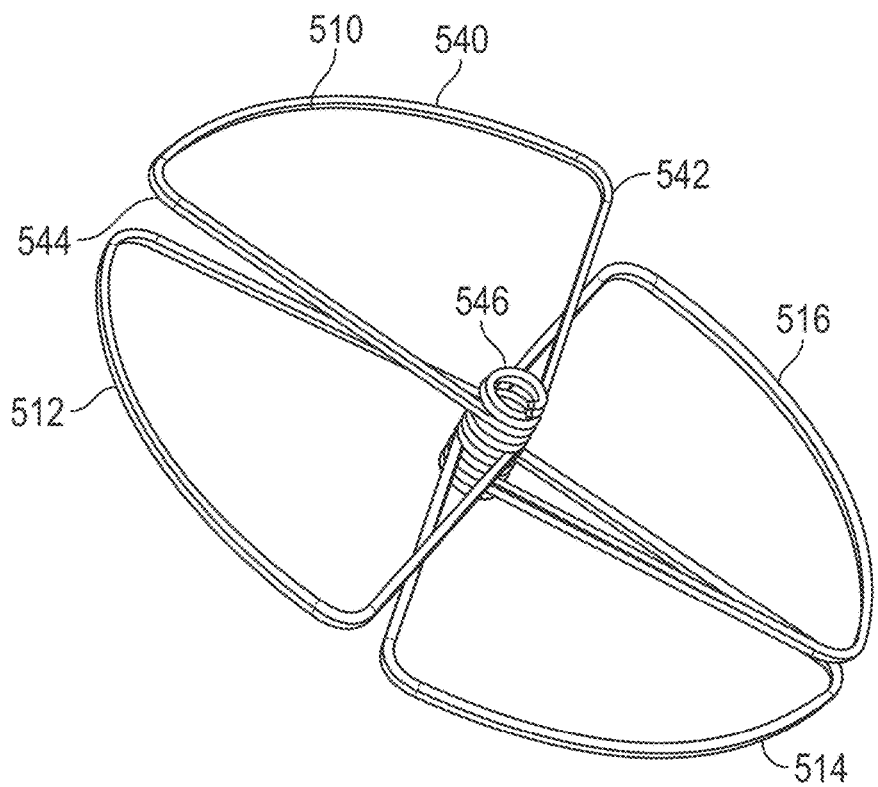
FIGS. 90A-90C are views of the double four engagement panels of the fifth embodiment.
Figure 90B:
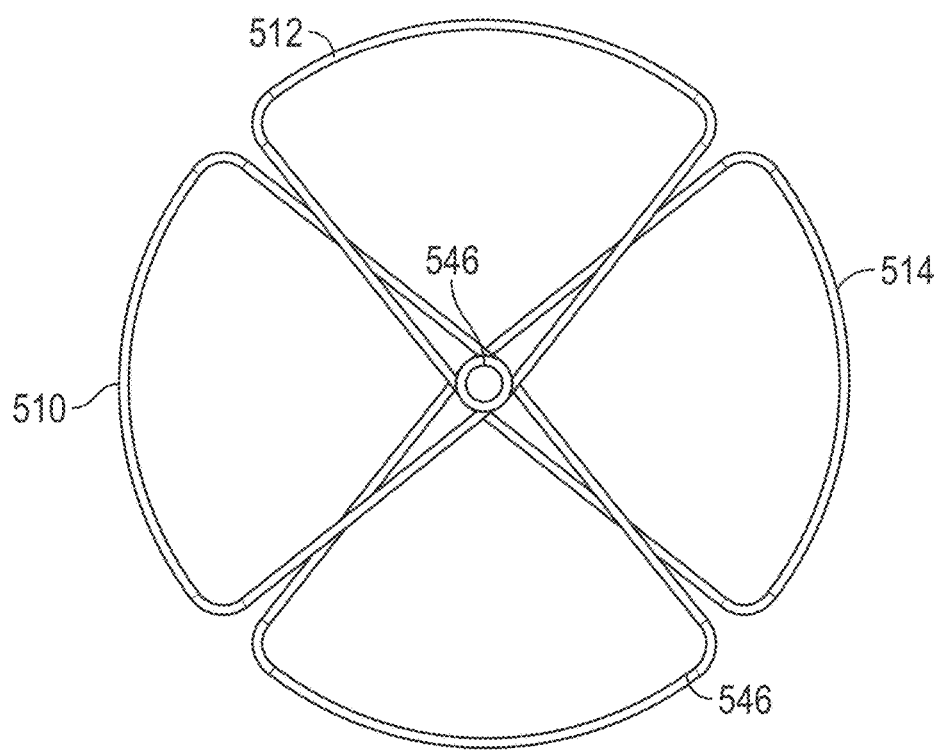
Figure 90C:
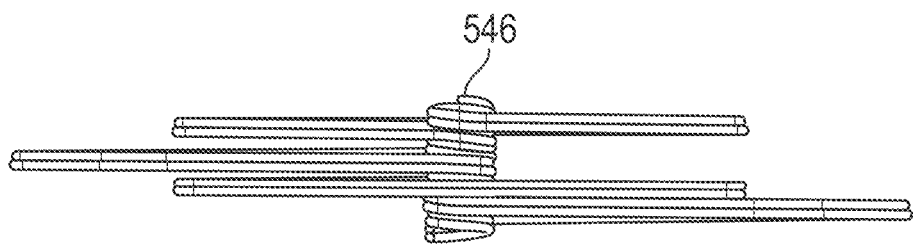

FIGS. 90A-90C illustrate a double layer engagement panel of the extractor 500. FIG. 90A is a perspective view. FIG. 90B is a front view. FIG. 90C is a side view. The first layer and the second layer can be stacked. The first layer and the second layer can follow the same path. The first layer and the second layer are aligned when viewed from the front in FIG. 90B. In some embodiments, the first layer and the second layer are offset. The two layers can be separated and/or offset from each other. The offset angle can be 5 degrees, 10 degrees, 15 degrees, 20 degrees, 25 degrees, 35 degrees. The offset angle can range from 5 degrees up to 175 degrees.

The extractor, or a portion thereof, can be manufactured from a two or more elongate members, such as a double wire as shown in FIG. 90A or a triple wire. The double wire can be side-by-side as shown. The double wire can be offset. Each elongate member can form a layer. The double layers can extend or wrap together as illustrated in FIGS. 90A-90C. The double layers can be offset as illustrated in FIG. 69. The engagement panels and the eyelet at the longitudinal location can be manufactured from double elongate members. The double elongate members can form a portion of the eyelet 546. The portion of the eyelet 546 can be a complete circle, or a portion of a circle such as, e.g. about 45 degrees, 60 degrees, 75 degrees, 90 degrees, 105 degrees, 120 degrees, 135 degrees, 150 degrees, 165 degrees, 180 degrees, 195 degrees, 210 degrees, 225 degrees, 240 degrees, 255 degrees, 270 degrees, 285 degrees, 300 degrees, 360 degrees, more or less, or any range of two of the foregoing values. The double elongate members can extend to form the leg 542, the arc 540, and the leg 544 of the first engagement panel 510. The double elongate members can be a mirror image. The double elongate members can be stacked directly on top of each other. The double elongate members can be axially aligned. The double elongate members can be offset. The double elongate members can be twisted about the eyelet 546. There is a gap in the eyelet 546 between the legs 542, 544 of the engagement panel 510. This gap can be the diameter of the double elongate members. Each leg 542, 544 begins and ends at the eyelet 546. Each leg 542, 544 of the double elongate members can begin at the same location. Each leg of the double elongate members can begin at a different location. However, the double elongate members forms the arc 540 between the legs 542, 544 and not a portion of the eyelet 546. The double elongate members can extend to form another portion of the eyelet 546. The double elongate members can extend to form the leg 542, the arc 540, and the leg 544 of the second engagement panel 512. The engagement panel are offset longitudinally by the diameter of the double elongate members. The engagement panel are offset longitudinally by a portion of the eyelet 546. The double elongate members continues to form a plurality of panels 510, 512, 514, 516 and a plurality of sections of the eyelet 546. The eyelet 546 can be thicker for the double elongate members than the single elongate member. The engagement panel can be thicker for the double elongate members than the single elongate member. In some embodiments, the double elongate members can form panels of different panel size. The smaller panel can be halved the size of the larger panel. The smaller panel can be a third the size of the larger panel.

Figure 91A:
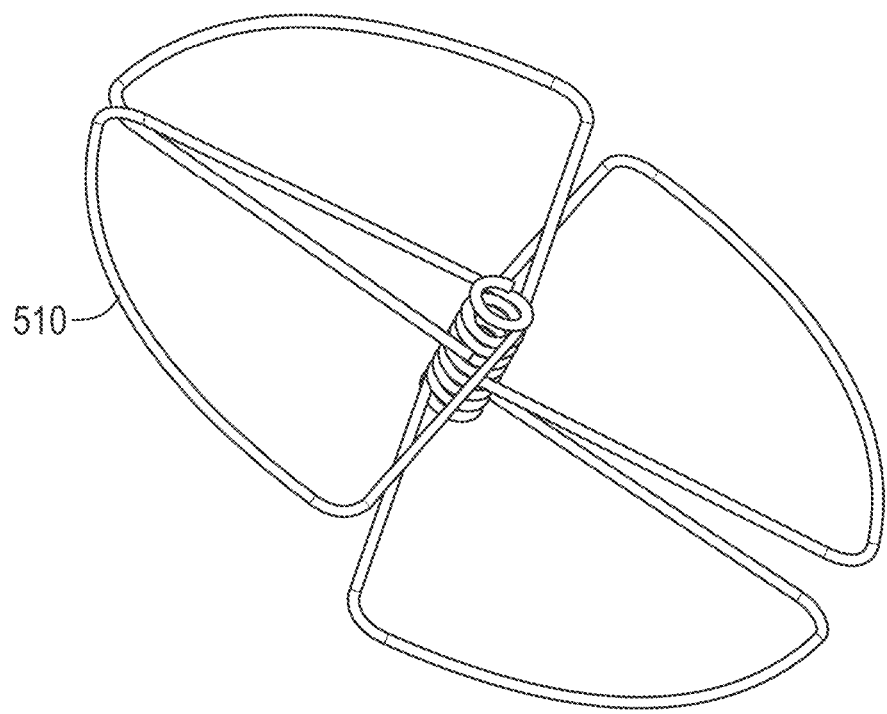
FIGS. 91A-91C are additional views of the single four engagement panels of the fifth embodiment.
Figure 91B:
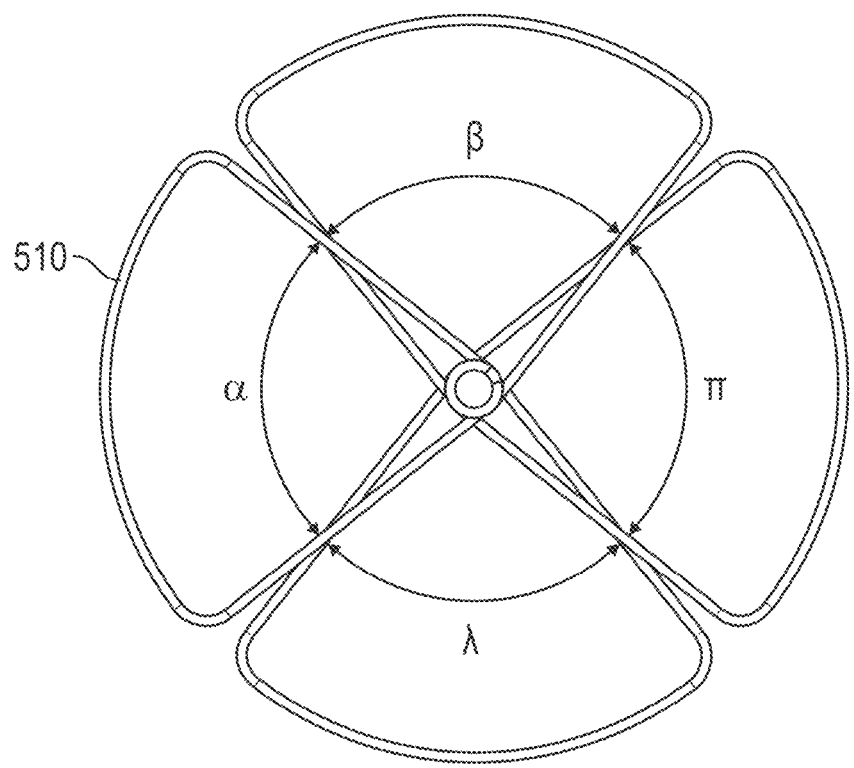
Figure 91C:
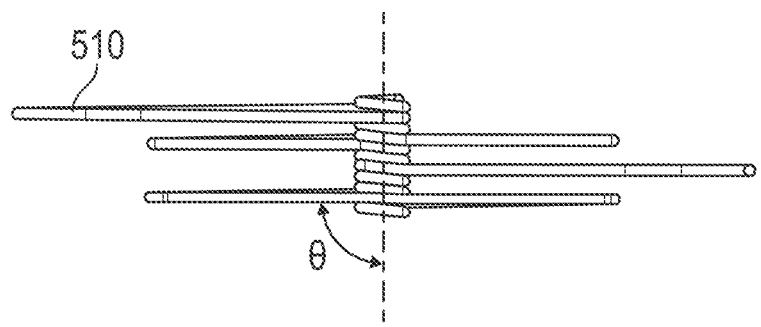

FIGS. 91A-91C are additional view of the extractor 500. Relatively to the core wire, the angle theta (FIG. 91C) can range from 1 degree to 89 degrees.

Figure 92A:
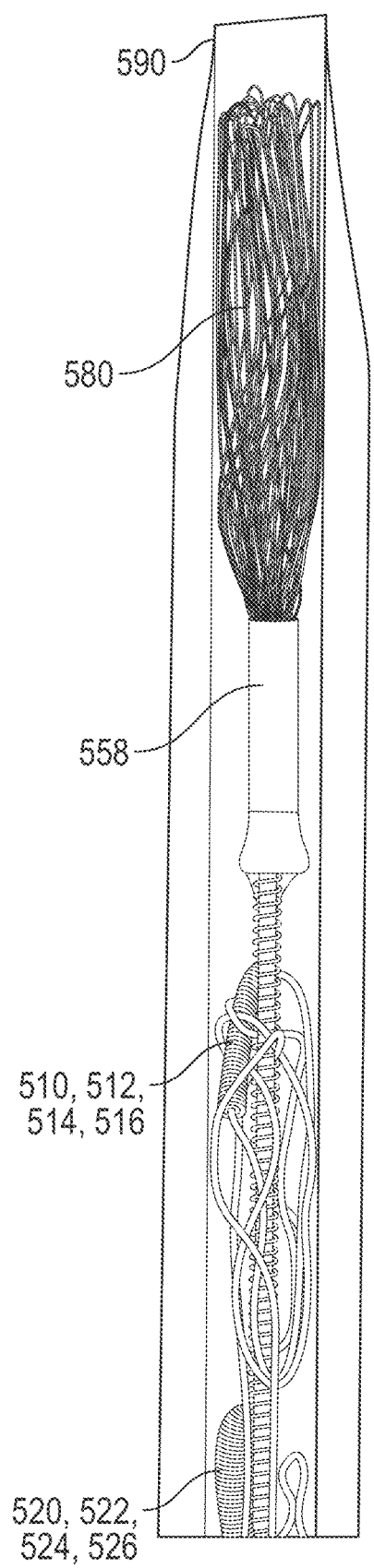
FIGS. 92A-92H are views of the distal member and the loading tube assembly.
Figure 92B:
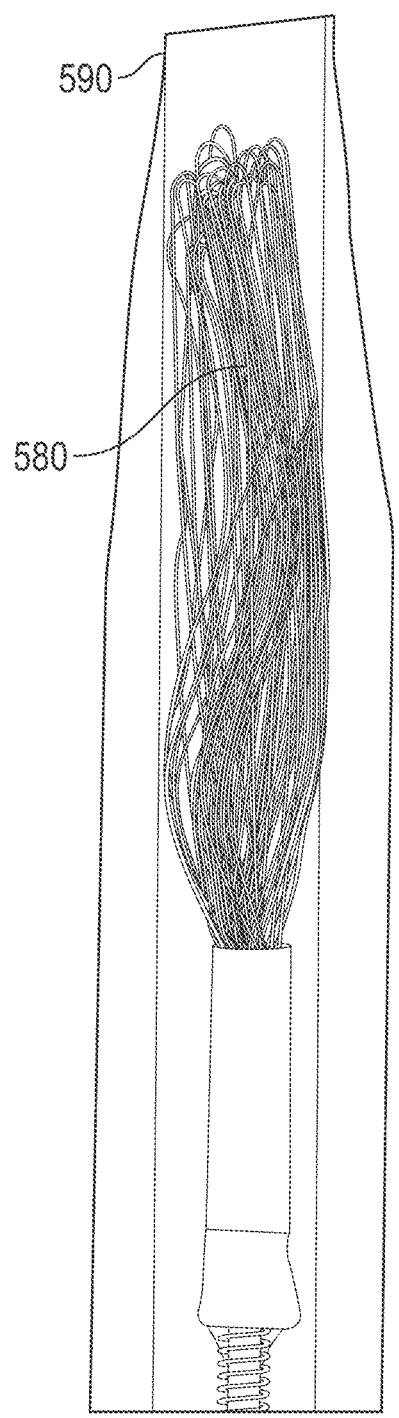

FIGS. 92A-92H are views of the distal member 580 and the loading tube assembly 590. FIGS. 92A and 92B indicates the distal member 580 is constrained in the loading tube assembly 590. The distal member 580 is designed to have a low profile for delivery. The distal member 580 can be made of braided or woven material. The distal member 580 can be made of wires or filaments. The distal member 580 can have a single or double layer. The distal member 580 can comprise a metal such as Nitinol, stainless steel, platinum, iridium, or combinations thereof. The distal member 580 can comprise polymeric materials such as polyethylene, PTFE, FEP, or combinations thereof. The distal member 580 can comprise a shape memory material such as a shape memory metal or polymer. In the constrained position, the distal member 580 is elongated to maintain a low profile.

The distal member 580 can include a radiopaque material such as tungsten or gold to aid with visualization. The distal member 580 can include a radiopaque marker. The distal marker 558 can be coupled to the distal member 580. The distal marker 558 can comprise platinum and/or iridium. The distal marker 558 can provide visualization of the distal member. The distal marker 558 can facilitate securing the distal member 580 to the distal end of the catheter shaft 506 or core wire 570. As described herein, proximal to the distal member 580 are the engagement panels 510, 512, 514, 516 at the first longitudinal location, the engagement panels 520, 522, 524, 526 at the second longitudinal location, and the engagement panels 530, 532, 534, 536 at the third longitudinal location. The engagement panels 510, 512, 514, 516, 520, 522, 524, 526, 530, 532, 534, 536 are constrained within the loading tube assembly 590. FIG. 92A shows the proximal engagement panels and the distal member 580 in a loaded configuration. FIG. 92B is a close up view.

Figure 92C:
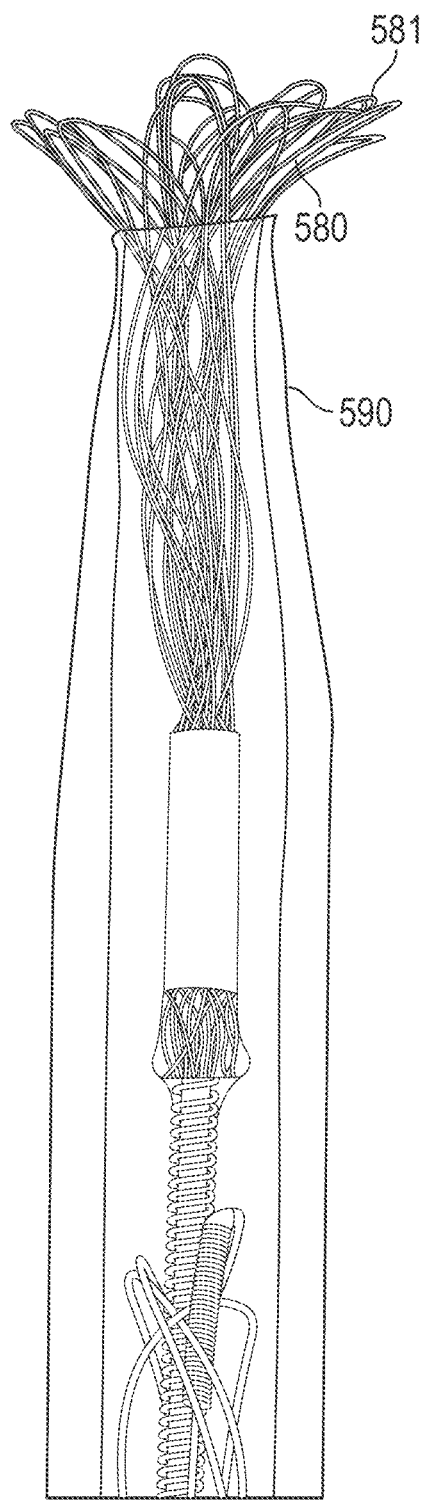

FIG. 92C indicates the distal portion of the distal member 598 is in the initial deployed position as the loading tube assembly 590 is retracted. The loading tube assembly 590 can be retracted by being pulled proximally. As the loading tube assembly 590 is retracted proximally, the leading edge 581 of distal member 580 begins to open upward. The distal portion of the distal member 580 extends beyond the end of the loading tube assembly 590. The distal portion of the distal member 580 extends distally. The distal portion of the distal member 580 flares outward from the loading tube assembly 590. The majority of the distal member 580 remains constrained in the loading tube assembly 590. FIG. 92C shows retracting the loading tube assembly 590 to deploy the distal member 580.

Figure 92E:
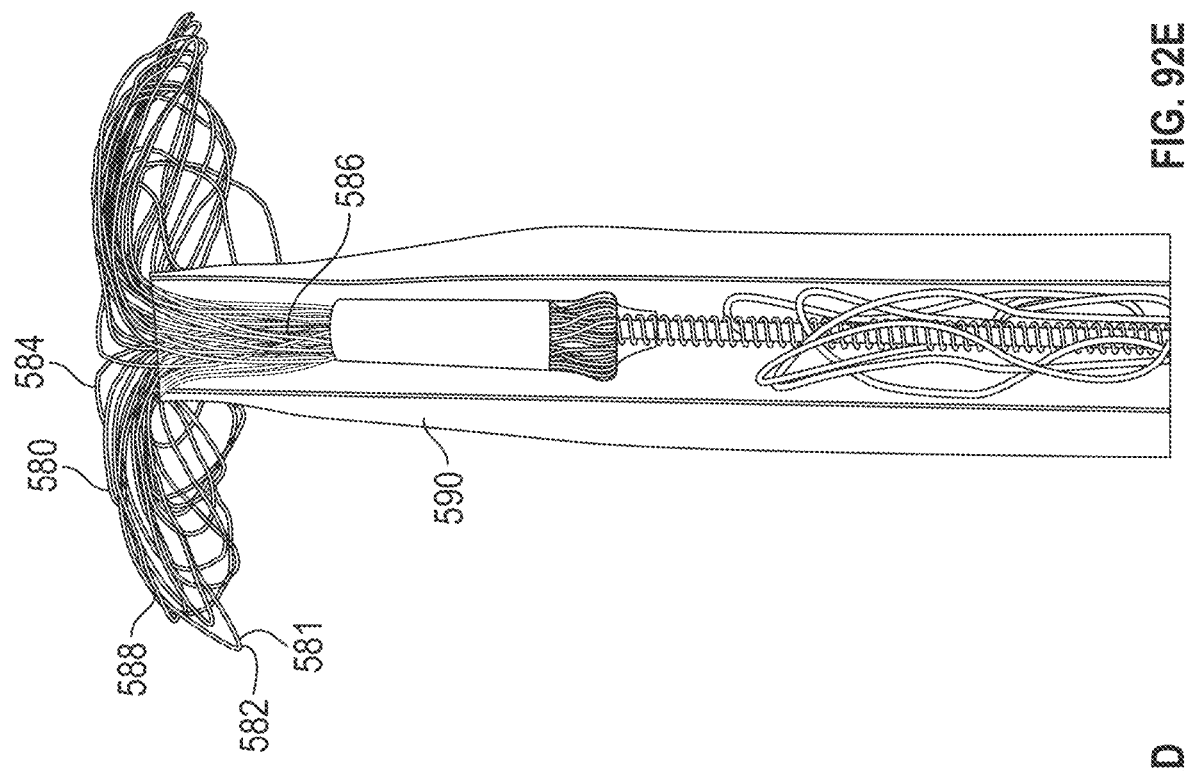
Figure 92D:
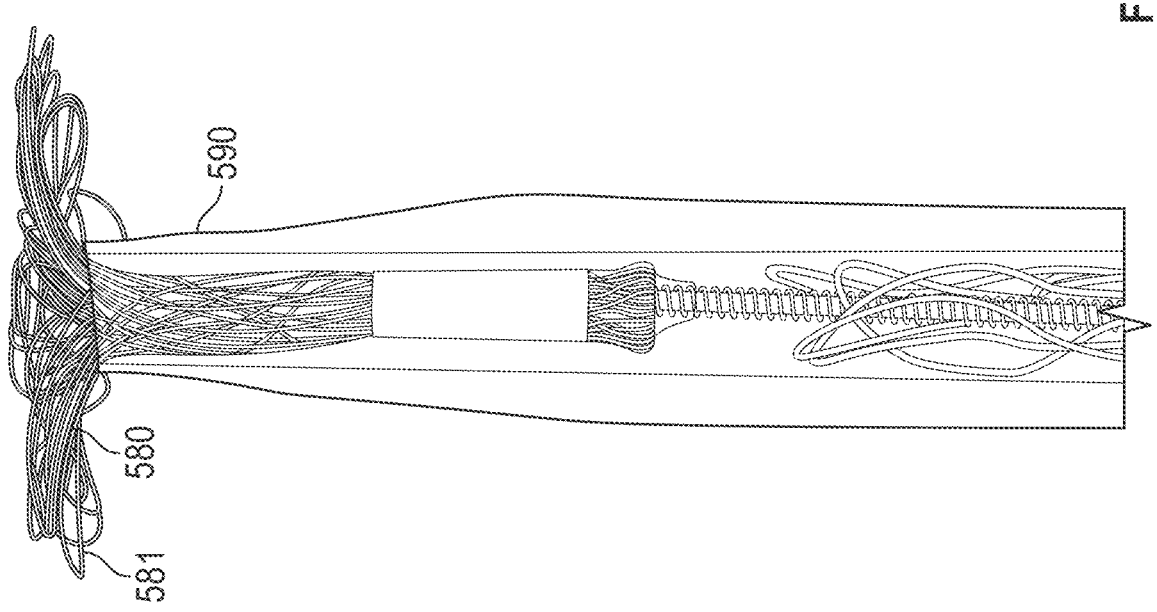

FIG. 92D is a view of the distal member 580. The distal member 580 can have a partially deployed position at approximately half-way. The distal member 580 can open upward. As the loading tube assembly 590 retracts, the distal member 580 curls. As the loading tube assembly 590 retracts, the distal member 580 moves in the proximal direction as shown in FIG. 92D. The leading edge 581 of the distal member 580 forms a cup or lip. The curling or moving proximally enable the distal member 580 to collect and capture more efficiently. In some embodiments, the leading edge 581 can form a pronounced curl wherein the edge turns back. In some embodiments, the leading edge 581 does not form a pronounced curl. The leading edge 581 can form any straight or curved edge in the fully deployed configuration. FIG. 92D shows a view when continuing to deploy the distal member 580.

FIG. 92E is a view of a position of the distal member 580 when being deployed. In some embodiments, the front edge 581 is proximal or behind the distal end of the loading tube assembly 590. The leading edge 581 can form the proximal end 582 of the distal member 580 when the distal member 580 is being deployed. The proximal end 582 can function as a funnel into the distal member 580. The distal member 580 can include a distal end 584 when the distal member 580 is being deployed. The distal end 584 can be a floating end. The distal member 580 can include a tubular portion 586. The tubular portion 586 can extend along a longitudinal or central axis of the loading tube assembly 580. The distal member 580 can include an expanded portion 588. The expanded portion 588 flares outward from the tubular portion 586 toward the proximal end 582.

Figure 92F:
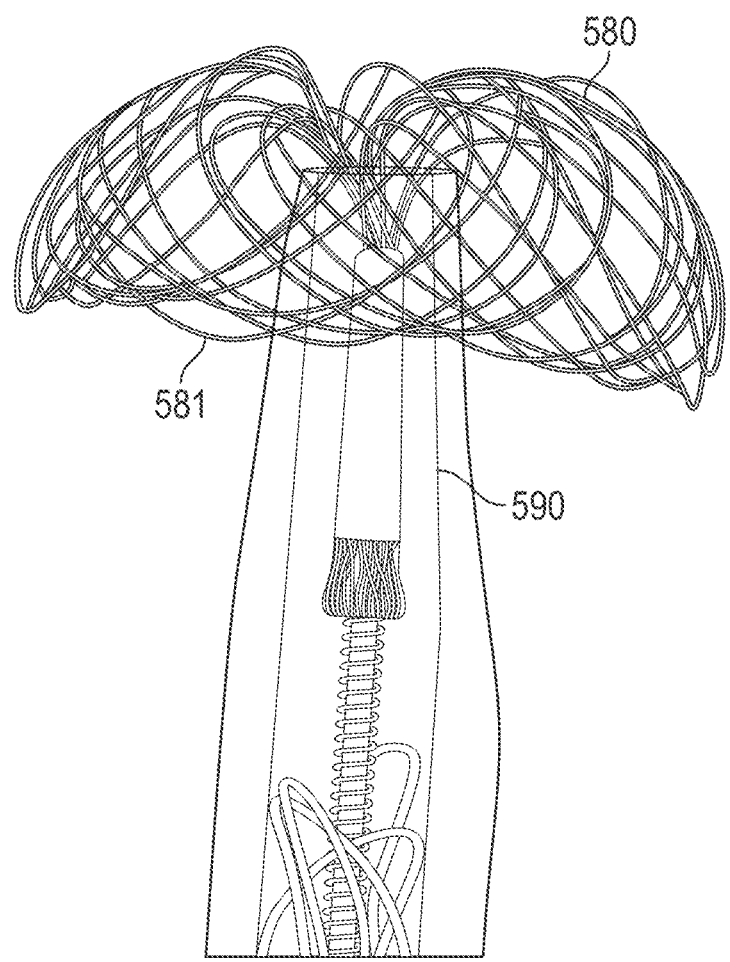
Figure 92G:
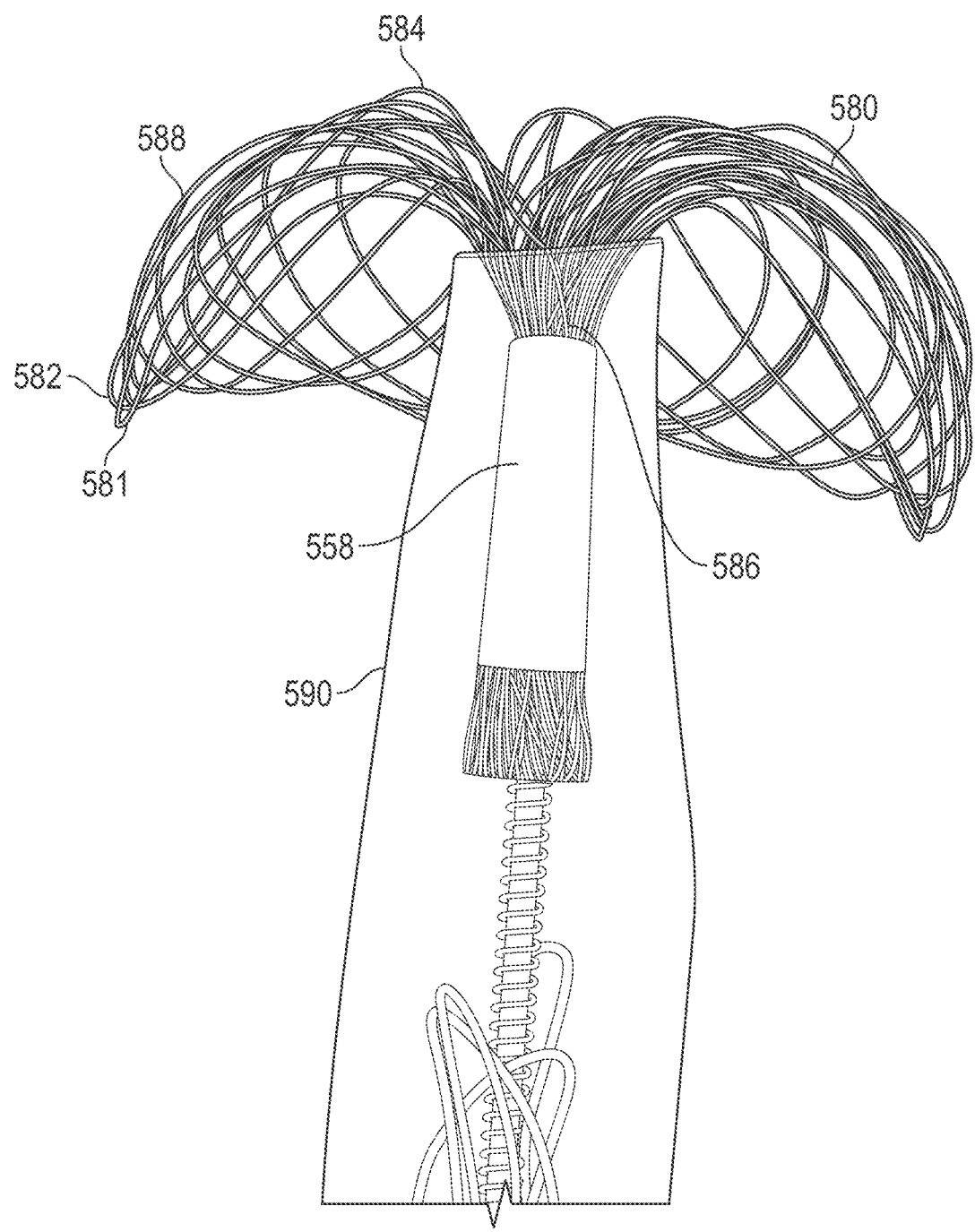

FIGS. 92F and 92G show the distal member 580 is completely expanded. In some embodiments, when the loading tube assembly 590 is retracted to the distal marker 558, the distal member 580 is fully deployed. The front edge 581 of the distal member 580 is proximal to the loading tube assembly 590. The expanded portion 588 surrounds the tubular portion 586 along a portion of the length of the tubular portion 586. The expanded portion 588 surrounds the distal marker 558 along a portion of the length of the distal marker 558. The space between the tubular portion 586 and the expanded portion 588 allows for the collection of material. In some embodiments, the distal member 580 is porous. The distal member 580 can allow blood to flow through the distal member 580. The distal member 580 can be configured to trap or capture loose emboli in transit or remove and capture soft emboli. The distal member 580 can capture material distal to the engagement panels 510, 512, 514, 516, 520, 522, 524, 526, 530, 532, 534, 536.

The distal member 580 can be made of braided material. The distal member 580 can also be made metals such as nitinol, stainless steel, platinum, tungsten, gold, and combinations thereof. The distal member 580 can be made of polymeric filaments such as Polyethylene, PET, nylon, FEP, PTFE, polyurethane, or combinations thereof. The distal member 580 can comprise wire or filaments having a diameter or cross-section between 0.0005" and 0.010", such as, e.g. about 0.0005", 0.001", 0.0015", 0.002", 0.0025", 0.003", 0.0035", 0.004", 0.0045", 0.005", 0.0055", 0.006", 0.0065", 0.007", 0.0075" 0.008", 0.0085", 0.009", 0.0095", 0.01", or any range of two of the foregoing values.

The distal member 580 can include a number of filaments or wire that range from, e.g. about 1 to 144 wires, such as 5 to 20, 10 to 50, 20 to 70, 30 to 100, 50 to 100, 60 to 120, or any range of two of the foregoing values. The distal member 580 can have an expanded diameter that can range from 1 mm to 40 mm, such as 1 mm, 5 mm, 10 mm, 15 mm, 20 mm, 25 mm, 30 mm, 35 mm, 40 mm, or any range of two of the foregoing values. The distal member 580 can have a pore size that can range from, e.g. about 25 microns to 2000 microns, such as 25 microns, 50 microns, 75 microns, 100 microns, 150 microns, 200 microns, 250 microns, 375 microns, 500 microns, 750 microns, 1000 microns, 1250 microns, 1500 microns, 2000 microns, or any range of two of the foregoing values.

Figure 92H:
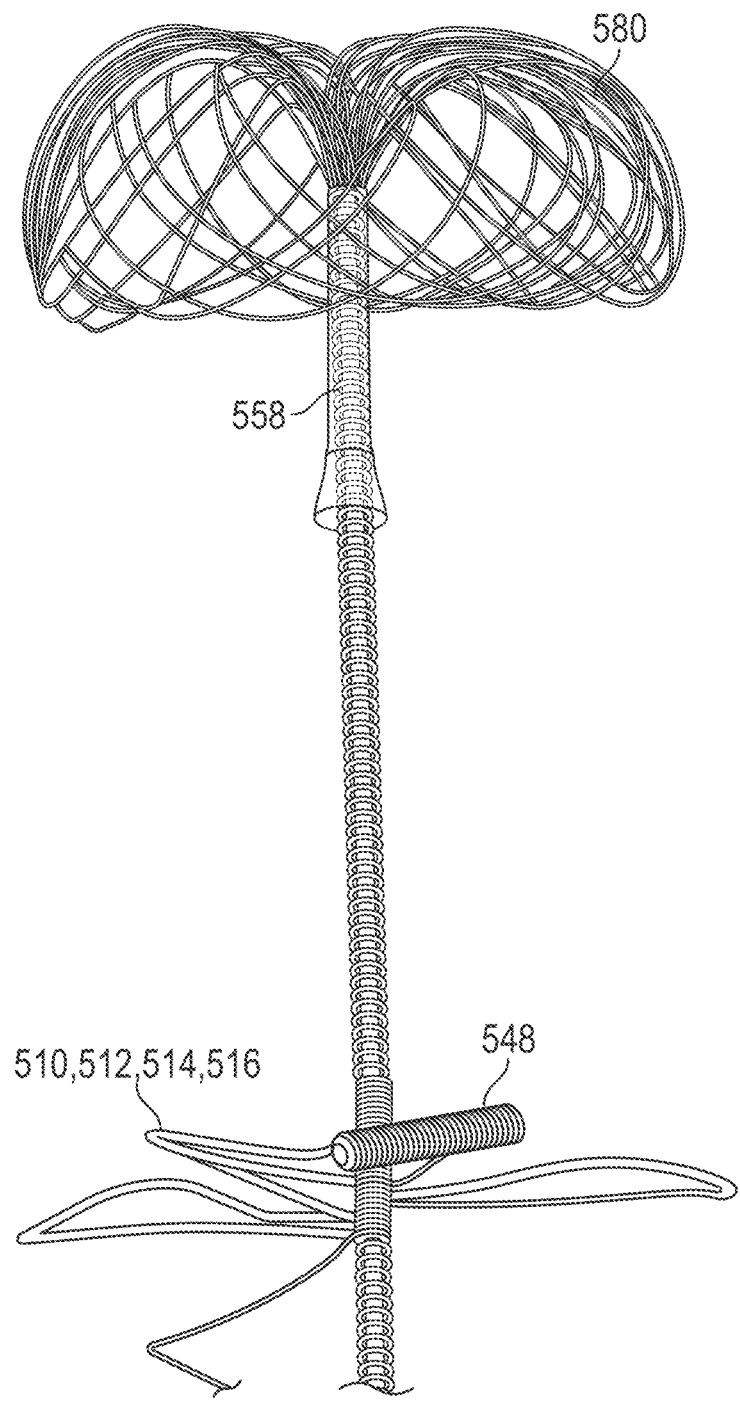

FIG. 92H shows the distal marker 558. The distal marker 558 can include a platinum/iridium tube. The distal marker 558 can function as a radiopaque marker. FIG. 92H shows the fully deployed position with the distal member 580 and the deployed engagement panels 510, 512, 514, 516. The extractor 500 can include one or more radiopaque markers 548. The radiopaque marker 548 can be located on the arc 540 of one of the engagement panels 510, 512, 514, 516. The first longitudinal location can include one or more radiopaque markers 548. The radiopaque marker 548 can include a platinum/iridium coil.

There are several advantages of the extractors described herein. The extractor can include the eyelet with a lumen to receive a catheter shaft or core wire. Each engagement panel can include the eyelet, or a portion thereof. The engagement panels at the first longitudinal location can form the first eyelet. The engagement panels at the second longitudinal location can form the second eyelet. The engagement panels at the third longitudinal location can form the third eyelet. In some embodiments, the eyelet can allow movement along the catheter shaft or core wire. In some embodiments, the eyelet can allow the engagement panel to move relative to the catheter shaft or core wire. In some embodiments, the eyelet can allow the engagement panels to move together to pinch material between two engagement panels. In some embodiments, the eyelet can allow the engagement panels to move apart to accept material between two engagement panels. In some embodiments, the eyelet can allow the space between two engagement panels to lengthen and/or shorten. In some embodiments, the eyelet can allow the engagement panels to move longitudinally along the catheter shaft or core wire. In some embodiments, the engagement panel are not fixed to a longitudinal location along the catheter shaft or core wire. In some embodiments, the extractor can include an eyelet with a lumen to receive a catheter shaft or core wire. In some embodiments, the extractor is distinguished from devices without an eyelet.

Figure 93A:
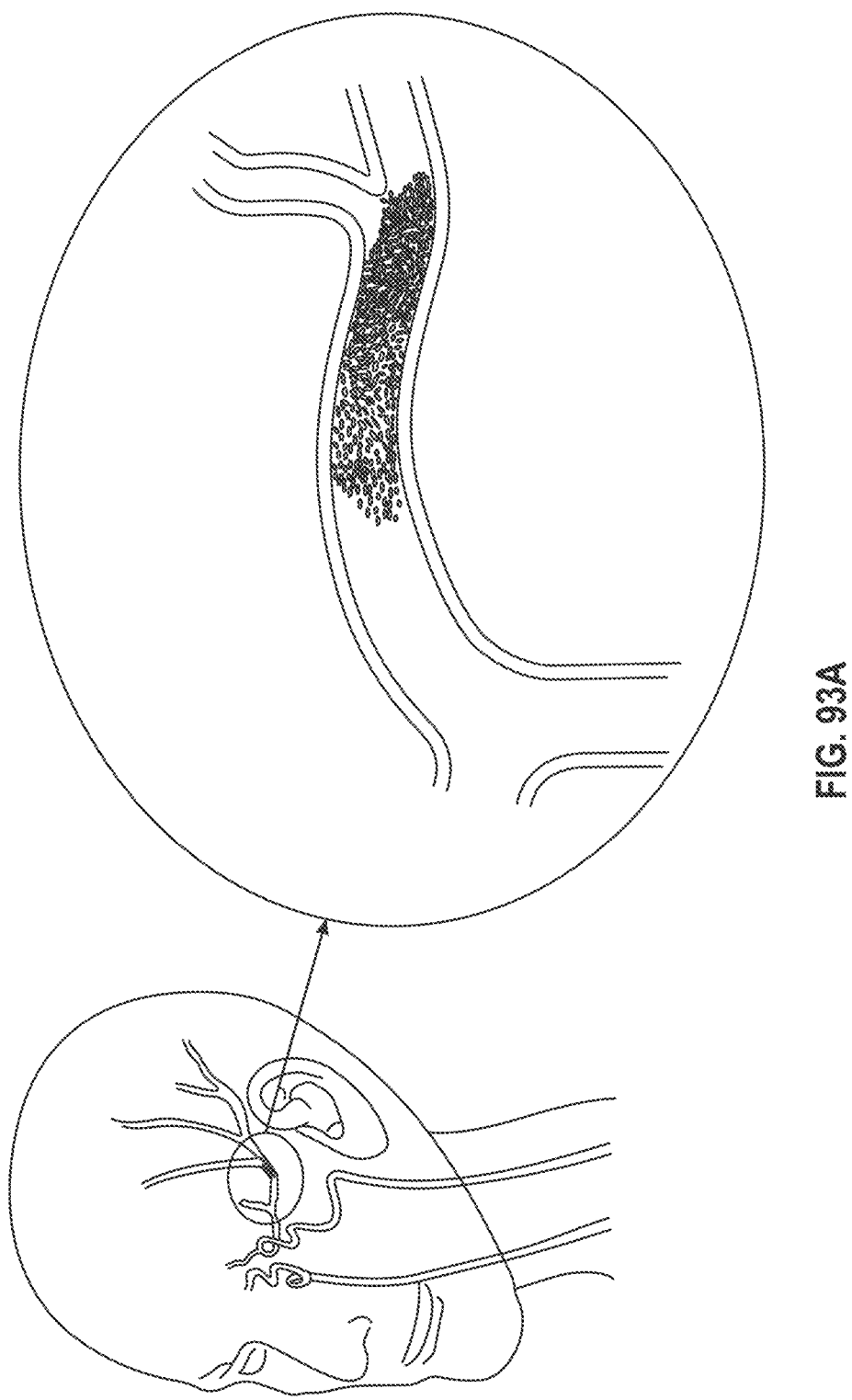
FIGS. 93A-93F are views of methods of use.
Figure 93B:
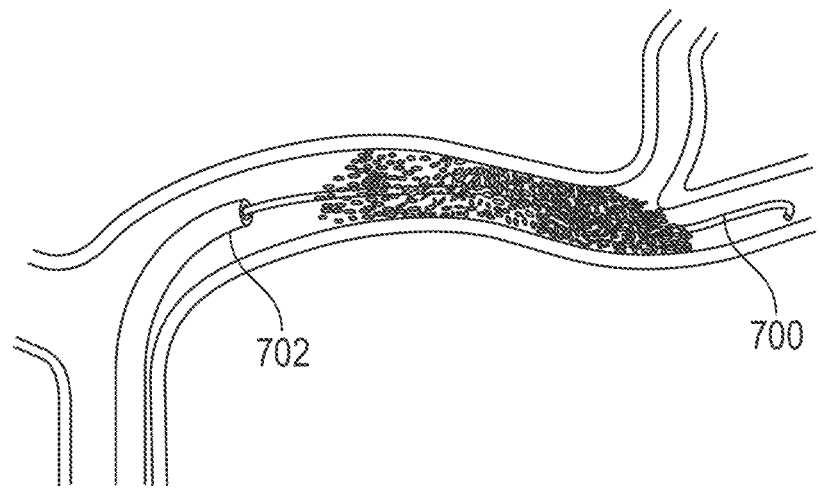
Figure 93C:
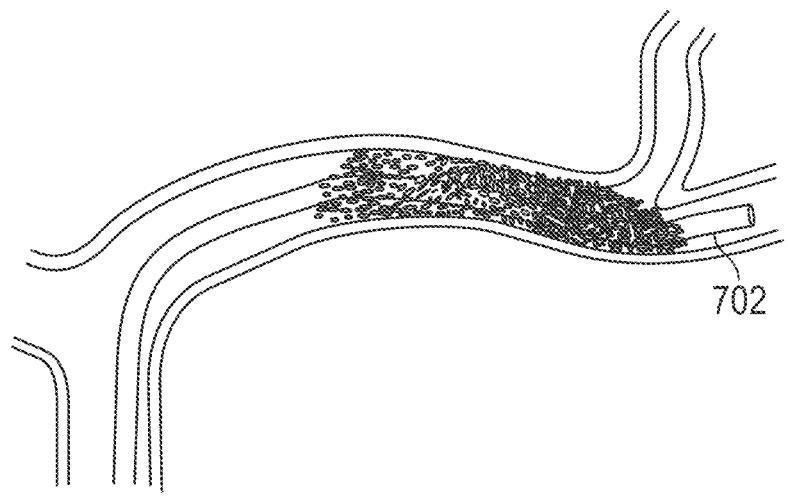

FIGS. 93A-93F are views of methods of use of some embodiments of extraction systems as described elsewhere herein, such as, for example, the extraction system of FIG. 92A-92H. FIG. 93A illustrates a blood clot within a blood vessel. In the illustrated embodiment, the clot blockage is located within the middle cerebral artery. FIG. 93B illustrates a guidewire 700 with its distal end passed entirely through the clot. The guidewire 700 can be used with any system described herein. The method can include a microcatheter 702 to be passed along the guidewire 700. The microcatheter 702 can be positioned proximal to the clot as shown in FIG. 93B. The microcatheter 702 can be any microcatheter system used to deliver the extractors described herein. In some embodiments, the standard Seldinger technique is used to access an access vessel, e.g., the femoral artery and to introduce a preliminary guidewire. The preliminary guidewire can be, e.g., a 0.035" guidewire. In some embodiments, a balloon guide catheter is advanced over the preliminary guidewire to the carotid artery. In some embodiments, the guidewire 700 is exchange for the preliminary guidewire. In some embodiments, the guidewire 700 is an 0.018" guidewire. In some embodiments, an 0.018" guidewire (e.g., a first, smaller diameter guidewire) is exchanged for an 0.035" guidewire (e.g., a second, larger diameter guidewire). The microcatheter 702 is introduced over the guidewire 700 through the balloon guide catheter to the occlusion treatment area. The guidewire 700 then advances through the clot and is positioned distal to the clot. The microcatheter 702 is then advanced through the clot and positioned distal to the clot. FIG. 93C illustrates the microcatheter 702 passed through the clot. The guidewire 700 can be removed.

Figure 93D:
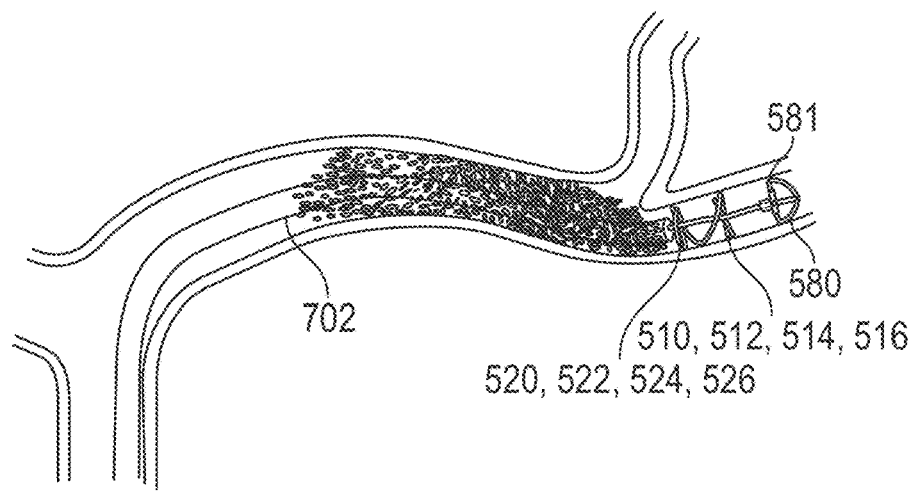
Figure 93E:
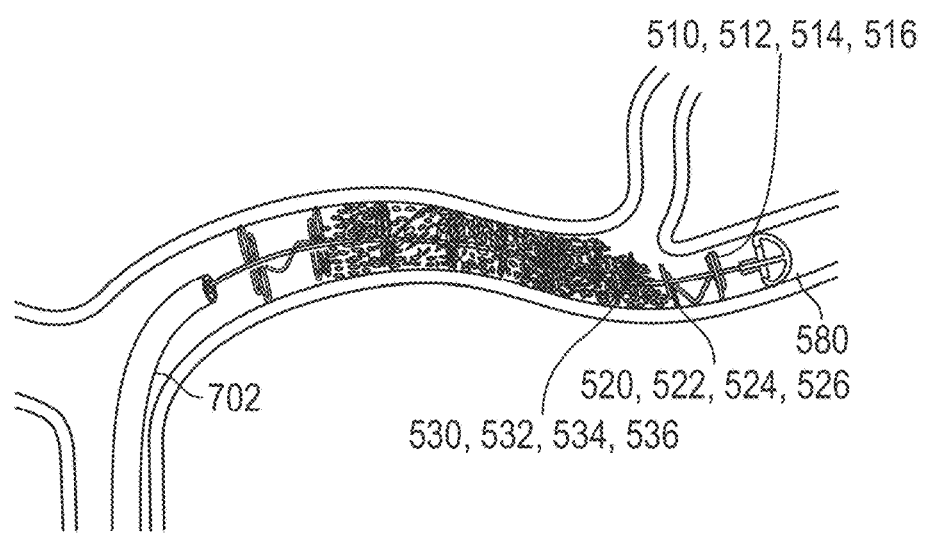

FIG. 93D illustrates the extractor 500 at least partially deployed. The distal member 580 including leading edge 581 can be deployed distal to the clot blockage. The extractor 500 is at least partially deployed. The engagement panels 510, 512, 514, 516 at the first longitudinal location can be deployed. The engagement panels 520, 522, 524, 526 at the second longitudinal location can be deployed. The engagement panels at the third longitudinal location can be constrained within the microcatheter 700. In some embodiments, the extractor 500 can be pre-loaded in the loading tube assembly 590. The loading tube assembly 590 can be introduced into the microcatheter 702. The extractor 500 can continue to be inserted into the microcatheter 702. The loading tube assembly 590 can be removed. The extractor 500 can be advanced under fluoroscopy to the distal tip of the microcatheter 702. The microcatheter 702 can be retracted to deploy at least a portion of the extractor 500 distal to the clot as shown in FIG. 93D. The microcatheter 702 can be retracted to deploy at least a portion of the extractor 500 within to the clot as shown in FIG. 93E. The microcatheter 702 can be retracted to deploy at least a portion of the extractor 500 proximal to the clot as shown in FIG. 93E. In some methods, one or more arrays of engagement panels are distal to the clot. In some methods, one or more arrays of engagement panels are within the clot. In some methods, one or more arrays of engagement panels are proximal to the clot.

The engagement panels can be folded within the loading tube assembly 590. The engagement panels can be folded distally such that the arcs of the engagement panels at the first longitudinal location are distal to the respective eyelet. The engagement panels can be laid down such that the arcs of the engagement panels are toward the distal member 580. The extractor 500 can be constrained within the loading tube assembly 590 with the engagement panels at the first, second, and third longitudinal location folded distally. The extractor 500 can be inserted into the microcatheter 702 with the engagement panels at the first, second, and third longitudinal location folded distally. The extractor 500 can be advanced until the distal member 580 is near the distal tip of the microcatheter 702.

The microcatheter can be retracted and the distal member 580 can expand. As the microcatheter 702 is retracted proximally, the leading edge 581 of distal member 580 begins to open. The distal portion of the distal member 580 extends beyond the distal end of the microcatheter 702. The distal portion of the distal member 580 flares outward from the microcatheter 702. As the microcatheter 702 retracts, the distal member 580 curls. As the microcatheter 702 retracts, the distal member 580 moves in the proximal direction. The curling or moving proximally enable the distal member 580 to collect and capture more efficiently. FIG. 93D is a view of a position of the distal member 580 when being deployed from the microcatheter 702.

As the microcatheter 702 is retracted proximally, the engagement panels at the first longitudinal location deploy. The engagement panels at the first longitudinal location can deploy at approximately the same time from the distal end of the microcatheter 702, for instance if there is little or no gap in the eyelet. The engagement panels at the first longitudinal location can deploy sequentially or independently from the distal end of the microcatheter 702, for instance if there is a gap in the eyelet.

In some embodiments, the engagement panels at the first longitudinal location are in a first, constrained position within the microcatheter 702. The arcs of the engagement panels are distal to the eyelet at the first longitudinal location. The legs of the engagement panels are distal to the eyelet at the first longitudinal location. The engagement panels at the first longitudinal location can be folded downward toward the catheter shaft or core wire. The engagement panels at the first, second, and third longitudinal location can be similarly folded.

As the microcatheter 702 is retracted proximally, the engagement panels revert proximally. The engagement panels move outward until the engagement panels are relatively aligned with the respective eyelet. In some embodiments, the arcs of the engagement panels can be substantially perpendicular to the catheter shaft or core wire. The engagement panels moved in an arc from the constrained state toward the inner wall of the vessel. The engagement panels can expand to the diameter of the vessel. The engagement panels can expand to any size vessel up to the maximum diameter wherein the engagement panels are perpendicular to the eyelet.

Figure 93F:
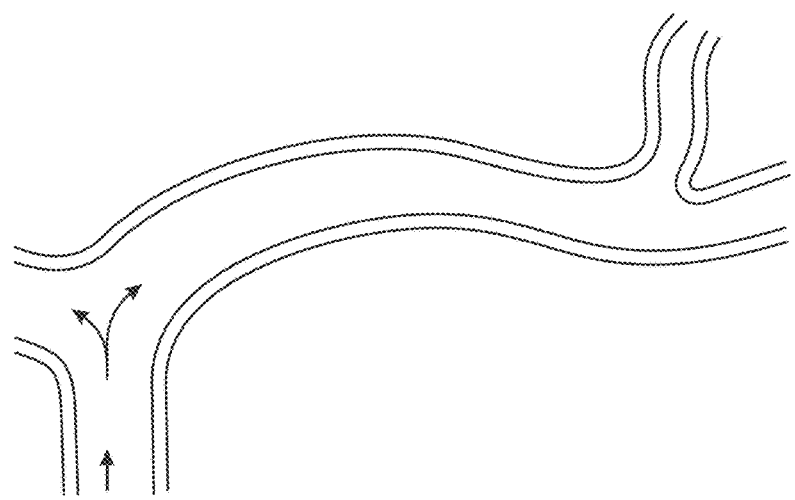

Once the extractor 500 is deployed, the extractor 500 and the microcatheter 702 are withdrawn into the balloon guide catheter to remove the system from the vascular system. Aspiration can be used to assist when retracting the extractor 500 and the microcatheter 702. FIG. 93E illustrates the distal member 580 and the extractor 500 when completely deployed. FIG. 93F illustrates the microcatheter 702 and the extractor 500 when completely removed with the clot.

Figure 94A:
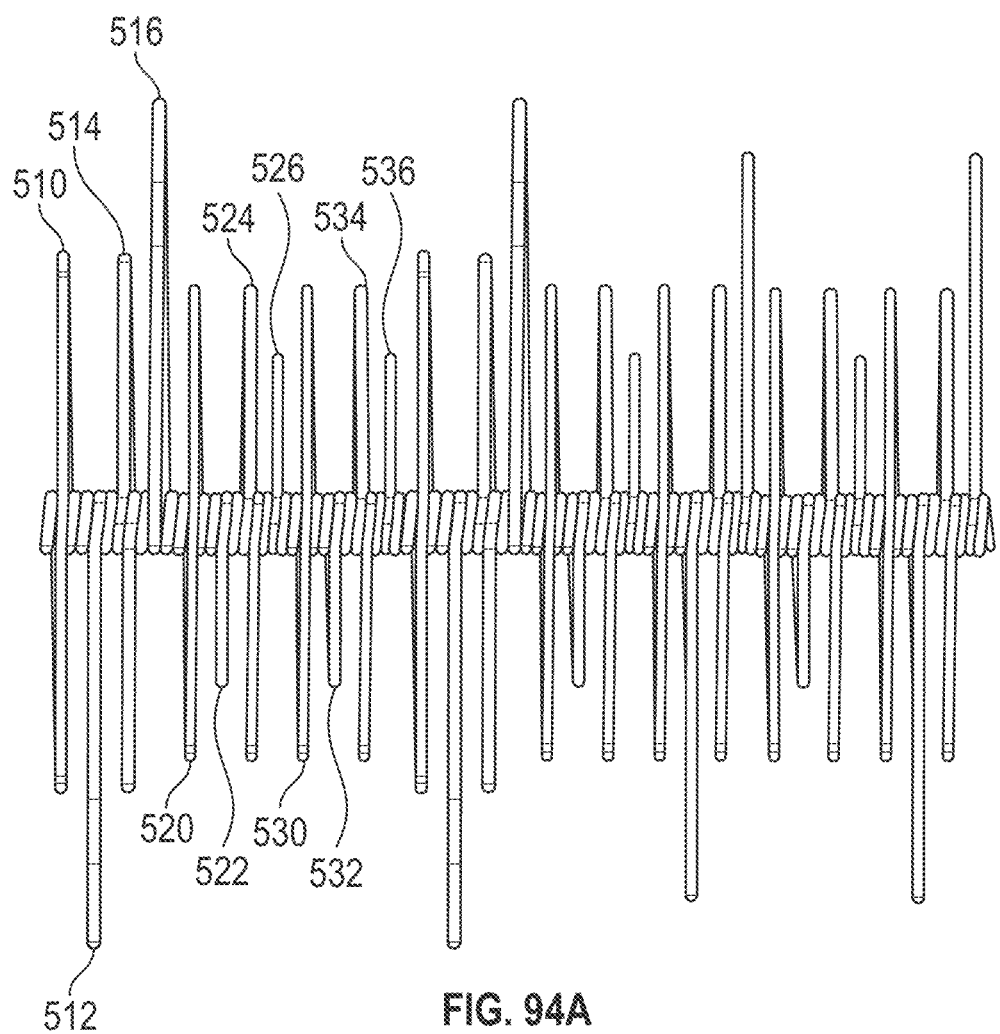
FIGS. 94A-94B are views of engagement panels.
Figure 94B:
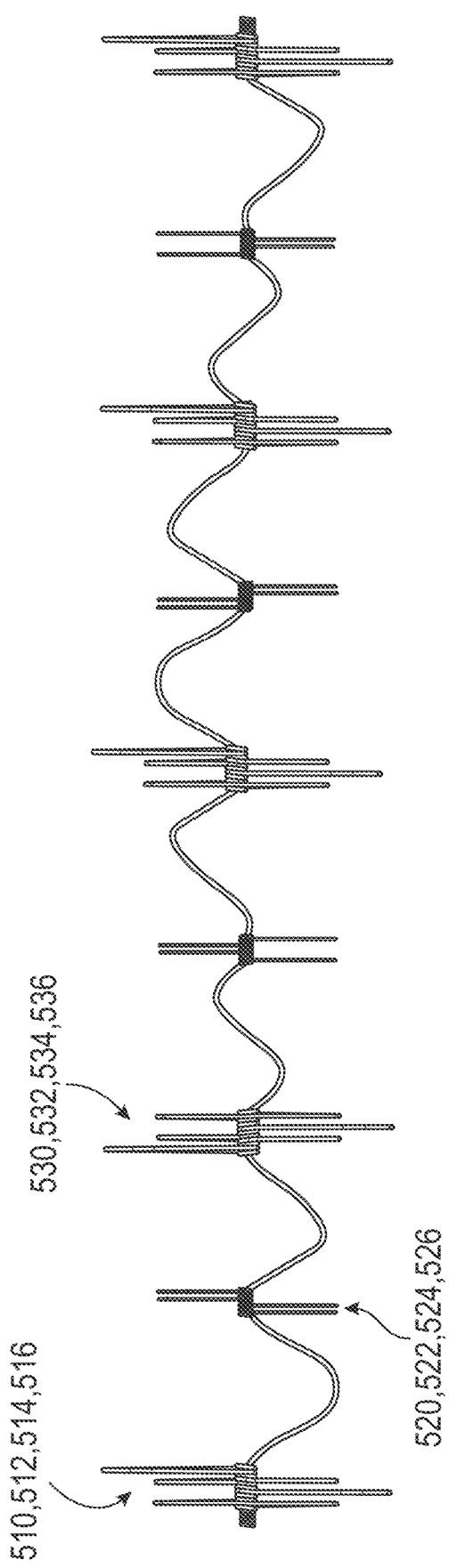

FIGS. 94A-94B illustrate a side views of a single layer engagement panels of the extractor 500. The engagement panels can have a different diameter at each location. Each engagement panel 510, 512, 514, 516 at the first longitudinal location forms a portion of a first diameter. The engagement panels at the first longitudinal location form the first diameter. The total arc length of the engagement panel 510, 512, 514, 516 at the first longitudinal location can substantially form a 360 degrees circle. The total arc length of the engagement panel 510, 512, 514, 516 at the first longitudinal location can be less than a 360 degrees circle. Each engagement panel 520, 522, 524, 526 at the second longitudinal location forms a portion of a second diameter. The engagement panels at the second longitudinal location form the second diameter. The total arc length of the engagement panel 520, 522, 524, 526 at the second longitudinal location can substantially form a 360 degrees circle. The total arc length of the engagement panel 520, 522, 524, 526 at the second longitudinal location can be less than a 360 degrees circle. Each engagement panel 530, 532, 534, 536 at the third longitudinal location forms a portion of a third diameter. The engagement panels at the third longitudinal location form the third diameter. The total arc length of the engagement panel 530, 532, 534, 536 at the third longitudinal location can substantially form a 360 degrees circle. The total arc length of the engagement panel 530, 532, 534, 536 at the third longitudinal location can be less than a 360 degrees circle. The extractor 500 can have engagement panels at a fourth longitudinal location. The extractor 500 can have engagement panels at a fifth longitudinal location. The extractor 500 can have engagement panels at a sixth longitudinal location. The extractor 500 can have engagement panels at a seventh longitudinal location. The extractor 500 can have engagement panels at a eighth longitudinal location. The extractor 500 can have engagement panels at any number of longitudinal locations such as one, two, three, four, five, six, seven, eight, nine, ten, eleven, twelve, thirteen, fourteen, fifteen, sixteen, seventeen, eighteen, nineteen, twenty, or any range of two of the foregoing values.

The first diameter can be greater than the second diameter. The first diameter can be less than the second diameter. The first diameter can be the same as the second diameter. The first diameter can be different from the second diameter. The first diameter can be greater than the third diameter. The first diameter can be less than the third diameter. The first diameter can be the same as the third diameter. The first diameter can be different from the third diameter. The second diameter can be greater than the third diameter. The second diameter can be less than the third diameter. The second diameter can be the same as the third diameter. The second diameter can be different from the third diameter.

The extractor 500 can have engagement panels that have diameters which form a repeating pattern. The extractor 500 can have engagement panels that have diameters which form a random pattern. The extractor 500 can have engagement panels that are symmetric. The extractor 500 can have engagement panels that are asymmetric. The extractor 500 can have engagement panels that have one diameter, two diameters, three diameter, four diameter, five diameter, six diameters, or any range of two of the foregoing values.

The elongate member can form the engagement panels. Each engagement panel 510, 512, 514, 516 at the first longitudinal location forms a portion of the eyelet 546. Each engagement panel 520, 522, 524, 526 at the second longitudinal location forms a portion of the eyelet 546. Each engagement panel 5530, 532, 534, 536 at the third longitudinal location forms a portion of the eyelet 546. The coil 578 can extend between the eyelets 546. The elongate member can form the eyelets 546. The elongate member can form the coil 578. The engagement panels can be spaced apart by the coil 578. The length of coil 578 between the eyelets 546 can be the same length. The length of coil 578 between the eyelets 546 can be different lengths. The distance between the engagement panels can be 1 mm, 5 mm, 10 mm, 15 mm, 20 mm, 25 mm, 30 mm, 35 mm, 40 mm, 45 mm, 50 mm, 55 mm, or any range of two of the foregoing values. The engagement panels at each longitudinal location can be spaced close to each other, such as a gap of 1 mm, 2 mm, 3 mm, 4 mm, 5 mm, 6 mm, 7 mm, 8 mm, 9 mm, 10 mm, or any range of two of the foregoing values. The engagement panels at each longitudinal location can be spaced farther apart from each other, such as a gap of 20 mm, 30 mm, 40 mm, 50 mm, or any range of two of the foregoing values. The length of the eyelet can be 1 mm, 5 mm, 10 mm, 15 mm, 20 mm, 25 mm, 30 mm, 35 mm, 40 mm, 45 mm, 50 mm, 55 mm, or any range of two of the foregoing values. The extractor 500 can be manufactured from a single elongate member. The eyelet 546 can be located in the center of the first diameter. The eyelet 546 can be located offset from the center of the first diameter. The eyelet 546 can be located in the center of the second diameter. The eyelet 546 can be located offset from the center of the second diameter. The eyelet 546 can be located in the center of the third diameter. The eyelet 546 can be located offset from the center of the third diameter.

The luminal diameter of the vessel can be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or any range of two of the foregoing values. The first diameter of the engagement panel 510, 512, 514, 516 at the first longitudinal location can be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or any range of two of the foregoing values. The second diameter of the engagement panel 520, 522, 524, 526 at the second longitudinal location can be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or any range of two of the foregoing values. The third diameter of the engagement panel 530, 532, 534, 536 at the third longitudinal location can be 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, 16 mm, 17 mm, 18 mm, 19 mm, 20 mm, 21 mm, 22 mm, 23 mm, 24 mm, 25 mm, 26 mm, 27 mm, 28 mm, 29 mm, 30 mm, 31 mm, 32 mm, 33 mm, 34 mm, 35 mm, 36 mm, 37 mm, 38 mm, 39 mm, 40 mm, or any range of two of the foregoing values.

The extractor can include the coil. The coil can be in the space between two engagement panels. The coil and the engagement panels can be continuously formed. The coil and the engagement panels can be unitary or integrally formed. The coil and the engagement panels can be formed of the same material. The coil and the engagement panels can be connected. The coil and the engagement panels can be formed of different materials. The coil can be more flexible than the engagement panels. The engagement panels can be more flexible than the coil. In some embodiments, the coil allows flexible spacing of the engagement panels. In some embodiments, the coil allows the space between two engagement panels to lengthen and/or shorten. In some embodiments, the coil allows the extractor to bend within the vasculature. In some embodiments, the coil allows the extractor to follow the tortuous path of a vessel. In some embodiments, the coil is freely bendable. In some embodiments, the coil has column strength to allow pushability of the extractor.

The extractor can include the connecting member. The connecting member can be in the space between two engagement panels. The connecting member and the engagement panels can be continuously formed. The connecting member and the engagement panels can be unitary or integrally formed. The connecting member and the engagement panels can be formed of the same material. The connecting member and the engagement panels at two longitudinal locations can be connected. The connecting member and the engagement panels can be formed of different materials. The connecting member can be more flexible than the engagement panels. The engagement panels can be more flexible than the connecting member. The connecting member can be helical. The connecting member can be spaced inward from the circumference of the engagement panels. The connecting member can be sized not to make contact with the vessel wall. In some embodiments, the connecting member allows flexible spacing of the engagement panels. In some embodiments, the connecting member allows the space between two engagement panels to lengthen and/or shorten. In some embodiments, the connecting member acts as a biasing member to maintain a space between two engagement panels. In some embodiments, the connecting member acts as a biasing member to maintain a space between the first longitudinal location and the second longitudinal location. In some embodiments, the connecting member acts as a biasing member to maintain a space between the second longitudinal location and the third longitudinal location.

In some embodiments, the extractor can be formed from a single wire. In some embodiments, the extractor is not formed with multi-loop ends. The engagement panels can have no discrete ends. In some embodiments, the single wire can form the connecting members. In some embodiments, the single wire can form the coil. In some embodiments, the single wire can form the engagement panels. The single wire can form the coil near the distal end. The single wire can form the engagement panels at the first longitudinal location. The single wire can form the coil between the engagement panels at the first longitudinal location and the engagement panels at the second longitudinal location. The single wire can form the engagement panels at the second longitudinal location. The single wire can form the coil between the engagement panels at the second longitudinal location and the engagement panels at the third longitudinal location. The single wire can form the engagement panels at the third longitudinal location. The single wire can form the coil near the proximal end. In some embodiments, the extractor is distinguished from devices with multi-loop ends. In some embodiments, the extractor has one single wire where each engagement panel has no discrete ends.

The engagement panel include the arc. The arc can be supported by legs. The legs can extend radially outward from the eyelet. The arc of the engagement panel is in relatively complete contact with vessel wall. In some embodiments, the arcs of the engagement panel at the first longitudinal location form a nearly complete circle. In some embodiments, the arcs of the engagement panel at the first longitudinal location contact more than 80% of the circumference of the vessel wall, more than 85% of the circumference of the vessel wall, more than 90% of the circumference of the vessel wall, more than 95% of the circumference of the vessel wall, nearly all of the circumference of the vessel wall, more or less, or any range of two of the forgoing values. In some embodiments, the arcs of the engagement panel at the second longitudinal location form a nearly complete circle. In some embodiments, the arcs of the engagement panel at the third longitudinal location form a nearly complete circle. The engagement panels each have a partial circumferential arc that together have more vessel wall contact. In some embodiments, the engagement panels arc is relatively complete contact with vessels. In some embodiments, the engagement panel circumferential arc has more vessel wall contact.

The engagement panel has minimal surface contact with the vessel wall along the length of the extractor. This is based on the total surface contact of the extractor compared with other devices, such as the stent retriever. The arcs of the engagement panels form a nearly complete ring at the longitudinal locations. The space between longitudinal locations does not have a structure that contacts the vessel wall. The engagement panels are relatively thin. The engagement panels can be formed by a single wire. The engagement panels can be formed by a double or triple wire. The engagement panels thereby reduce the friction forces against the vessel wall. The engagement panels result in low pull force. In some embodiments, the low pull force is critical when retracting the extractor inside a neurovascular vessel. The low pull force can prevent sub-arachnoid hemorrhage. For example, the current stent retriever has high surface area contact against the vessel wall. This creates high friction and tension force. As a result, when the stent retriever is retracted, the stent retriever will pull the vessel more aggressively that will potentially damage the surrounding tissue and smaller blood vessels. Whereas the extractor or engager engagement panels have lower material to vessel wall surface contact thereby minimize the friction force and prevent the pulling of the blood vessels or lesser tension applies to the vessels. This will help keeping the vessels stable during the retraction of the device resulting in minimal damage to the blood vessels. In some embodiments, the engagement panels have minimal surface contact to vessel wall, based on device total surface area as compared to a conventional stent retriever. Thereby reducing the friction force against vessel wall result in low pull force. In some embodiments, this is an advantage when retracting the device inside the neurovascular vessel to prevent sub-arachnoid hemorrhage.

The extractor can include an arrays of movable engagement panels. The engagement panels can include an open-space radially inward from the perimeter of the engagement panels. The engagement panels can include an outlined perimeter and a pore therethrough. The engagement panels can be operably connected together. In some embodiments, the engagement panels can be separated longitudinally by the spacer. In some embodiments, the engagement panels can be separated longitudinally by the coil. In some embodiments, the engagement panels can be separated longitudinally by the connecting member. In some embodiments, the extractor or engager has arrays of movable engagement panels and open-space radially inward to the perimeter of the panels, all operably connected together, but separated longitudinally by a spacer.

The extractor can include a method of expansion of the engagement panels as compared to a conventional stent retriever. For example, when stent retriever deploys and expands, the length of the stent retriever is shortened or contracted when fully deploy. The engagement panels when deploy and expands, the length of the device is not shortened. The engagement panels can expand by radial expansion without axial movement. The engagement panels can expand radially outward. The engagement panels can expand or contract without stretching or shortening as compared to stent retrievers. The engagement panels can expand can radially expand or open. In some embodiments, the engagement panels are in a first, constrained position and the arcs of the engagement panels at the first longitudinal location are positioned distal to the eyelet at the first longitudinal location. In some embodiments, the engagement panels are in a first, constrained position and the legs of the engagement panels at the first longitudinal location are compressed and positioned next to each other. The legs of the engagement panels at the first longitudinal location can be coaxial with the catheter shaft or core wire. The legs of the engagement panels at the first longitudinal location can be positional longitudinally inline with the legs of the engagement panels at the second longitudinal location. As the loading tube assembly or sheath is retracted, the engagement panels at the first longitudinal location open, the arcs of the engagement panels at the first longitudinal location expand and the legs of the engagement panels at the first longitudinal location move farther apart. As the loading tube assembly or sheath continues to retract, the arcs of the engagement panels at the first longitudinal location continue to expand and the legs of the engagement panels at the first longitudinal location continue to move apart. In some embodiments, the engagement panels also revert or move proximally and radially outward. The arcs and legs of the engagement panels at the first longitudinal location are fully expanded at the second, expanded position and positioned relatively inline with the eyelet at the first longitudinal location. As the loading tube assembly or sheath is retracted, the engagement panels at the second longitudinal location expand and then the engagement panels at the third longitudinal location expand. In some embodiments, when the extractor is positioned at the distal end of the delivery catheter, the engagement panels are contained inside the delivery catheter and constrained. As the delivery catheter is retracted to deploy the engagement panels at the first longitudinal location, the engagement panels will expand outward radially while maintaining the same length and the eyelet relatively stay fixed and does move. As the engagement panels at the second longitudinal location are expanded, the previous deployed or expanded engagement panels at the first longitudinal location do not contract. The engagement panels at the second longitudinal location deploy and expand radially without shortening. Once the engagement panels at the second longitudinal location is expanded, the panels will stay relatively fixed to the first longitudinal location. As the delivery catheter is retracted to deploy or expand additional engagement panels, the extractor length does not shorten or contract. In some embodiments, the method of expansion includes radial expansion without axial movement. In some embodiments, the extractor expands or contracts without stretching or shortening as compare to stent retrievers. In some embodiments, engagement panel can radially expand or open.

The extractor can include engagement panels formed of a single layer. Each engagement panel can be formed of a single wire. The extractor can include engagement panels formed of a double layer. Each engagement panel can be formed of a double wire. The layers can be longitudinally aligned. The layers can be stacked. The layers can form the same profile or perimeter. The layers can be offset. The layers can be circumferentially twisted. Each engagement panel can be formed of a triple layer. There can be multiple sets of engagement panels at a longitudinal location. The engagement panels can be offset to each other by certain degrees including, e.g. about 0 degrees, 5 degrees, 10 degrees, 15 degrees, 20 degrees, 25 degrees, 30 degrees, 35 degrees, 40 degrees, 45 degrees, 50 degrees, 55 degrees, 60 degrees, 65 degrees, 70 degrees, 75 degrees, 80 degrees, 85 degrees, 90 degrees, between 0 and 20 degrees, between 0 and 45 degrees, between 0 and 179 degrees, more or less, or any range of two of the foregoing values. The engagement panels that are offset can reduce pore sizes. The engagement panels can bifurcate the opening through the engagement panel. In some embodiments, the extractor includes multiple sets of engagement panels between arrays (e.g. double layer design). In some embodiments, engagement panels can be offset to each other by certain degrees from 0 to 179 degrees. In some embodiments, offset engagement panels can be designed to reduce pore sizes.

In some embodiments, the extractor can include a distal plug or distal member. In some embodiments, the distal member can be located at the distal end. The distal member can be distal to all engagement panels. In some embodiments, the distal member can be near the distal end. The distal member can be distal to some, but not all, engagement panels. There can be one or more engagement panels distal to the distal member. There can be one or more engagement panels proximal to the distal member. In some embodiments, the distal member is located at the first longitudinal location. In some embodiments, the distal member is located at the second longitudinal location. In some embodiments, the distal member is located at the third longitudinal location. In some embodiments, the distal member is located at the fourth longitudinal location.

In some embodiments, the engagement panels can compress upon removal of the spacer. In some embodiments, the engagement panels may not have compressive strength. In some embodiments, the engagement panels comprise double wires. In some embodiments, the engagement panel is designed to reduce deflection force. In some embodiments, the engagement panel can be formed from a large diameter wire. In some embodiments, the engagement panel can be formed from two or more smaller diameter wires. In some embodiments, the engagement panel forms a pore. The pore can be along the longitudinal direction in the direction of blood flow. The pore can allow blood to flow through the extractor. The pore size can be smaller if the engagement panels comprise offset layers. The pore size or opening between the offset layers will enable the engagement panels to capture smaller clot size or prevent smaller clot size to pass through. In some embodiments, the engagement panels are formed from one or more wires. In some embodiments, the engagement panels and the eyelet are formed from loops bonded to a hypotube. In some embodiments, the engagement panels and the eyelet can be formed using polymer via extrusion. In some embodiments, the engagement panels and the eyelet can be formed from other method like molding. In some embodiments, the engagement panels can compress upon removal of the spacer. In some embodiments, the engagement panels may not have compressive strength.

In some embodiments, the extractor can be formed from a single wire. In some embodiments, the extractor can be formed from a double wire. In some embodiments, the double wire has a smaller diameter wire. In some embodiments, creating the diameter smaller reduces the deflection force.

In some embodiments, the device can include a stent retriever. The device can include a stent like structure. The stent retriever can include a distal member. In some embodiments, the extractor is deployed within the stent retriever. In some embodiments, the extractor is deployed distal to the stent retriever. In some embodiments, the extractor is deployed proximal to the stent retriever.

In some embodiments, the extractor can include an eyelet. In some embodiments, the eyelet can be formed from one or more partial arcs. In some embodiments, the eyelet can be formed from one or more complete arcs. In some embodiments, the eyelet can be formed from a helical wire. In some embodiments, the eyelet can be formed from a coil. In some embodiments, the eyelet can form a central hole.

In some embodiments, the extractor is formed from a wire. In some embodiments, the extractor can be formed from loops. In some embodiments, the extractor can be formed from loops bonded to a hypotube. In some embodiments, the extractor can be formed from extrusion. In some embodiments, the engagement panels and the eyelet can be produced using polymer via extrusion. In some embodiments, the engagement panels and the eyelet can be produced by other methods such as molding.

The extractor can be used to remove material, such as clot material. The extractor can be deployed at or near a treatment site. The treatment site can be in a blood vessel, including but not limited to a neurovascular blood vessel. The extractor can include engagement panels at a first longitudinal location and a second longitudinal location. The extractor can be easy to use compared to complex systems. The extractor can reduce trauma to the blood vessel. The extractor can be easy to navigate to the treatment site. The extractor can be cost effective to manufacture. The extractor can remove material on a first pass, reducing hospitalization and leading to quicker recovery. The extractor can target remove of specific material such as hardened or chronic material from the vasculature. The functional portion of the extractor can include spaced apart arrays of engagement panels. The engagement panels are not covered by material thereby allowing blood flow through the pores of the engagement panels. The engagement panels at a longitudinal location can be in substantially continuous contact with the vessel wall along a circumference of the vessel wall. The engagement panels can be pre-formed with legs and the arc. The engagement panels expand from a collapsed state to an expanded state. The engagement panels expand into engagement with the vessel wall.

The extractor can have column strength to move longitudinally within a vessel. The expanded engagement panels at the longitudinal location are approximately equal to the diameter of the vessel. The engagement panels are segments of the complete circumference. The expanded engagement panels at the longitudinal location have a diameter of, e.g. about 1 mm, 2 mm, 3 mm, 4 mm, 5 mm, 6 mm, 7 mm, 8 mm, 9 mm, 10 mm, 11 mm, 12 mm, 13 mm, 14 mm, 15 mm, more or less, or any range of two of the foregoing values.

The extractor can be pulled proximally without axially lengthening. The extractor can be pulled proximally without radially compressing. The extractor can be pulled proximally and the engagement panels can scrape along the surface of the vessel. The extractor can be pulled proximally to compress the material between engagement panels at the first longitudinal location and the second longitudinal location. The extractor can retain the material between engagement panels at the first longitudinal location and the second longitudinal location.

In some embodiments, a filter is provided. The filter can prevent downstream emboli and fragmented clot. In some embodiments, the filter can be formed of nitinol. In some embodiments, the filter can be formed of polymeric materials and/or metallic materials.

In some embodiments, the spacer is fixed. The spacer can be unable to move or slide along the length of catheter shaft. In some embodiments, the spacer is movable. The spacer is able to move or slide along the length of the catheter shaft creating a tension variation and/or release.

In some embodiments, a collection bag is provided. The collection bag can encapsulate captured clot for removal. In some embodiments, the collection bag can be formed from nitinol. In some embodiments, the collection bag can be formed from polymeric materials.

In some embodiments, the extractor has a one piece construction. In some embodiments, the extractor comprises distinct members. The extractor can comprise the engagement panels, the spacers, and/or the catheter shaft. The spacers can keep the engagement panels apart. The engagement panels can have distinct legs. The legs can be straight. In some embodiments, the legs do not overlap. The legs provide sufficient support without overlapping. The engagement panels can form a segment of a larger circular profile. In some embodiments, the engagement panels are not loops. The engagement panels can have straight or linear legs connected to the arc. The engagement panels can define an eyelet. The engagement panels can define a lumen. The eyelet can be centrally located among the engagement panels.

In some embodiments, the engagement panels can be dynamic. The engagement panels can move. The engagement panels can have tension. The engagement panels can be spring-like. The engagement panels can be biased to compress toward each other. The engagement panels can be biased to create a pinching force. The engagement panels can include the arc. The arc can be greater than an apex. The arc can provide more surface contact with the vessel wall. In some embodiments, the engagement panels do not stretch. In some embodiments, the engagement panels collapse for delivery. In some embodiments, the engagement panels open for clot engagement. In some embodiments, the engagement panels fold toward the catheter shaft.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while several variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the disclosed invention. For all the embodiments described above, the steps of the methods need not be performed sequentially. Thus, it is intended that the scope of the present invention herein disclosed should not be limited by the particular disclosed embodiments described above, but should be determined only by a fair reading of the claims that follow.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

What is claimed is:

1. A device for removing material from a patient, the device comprising:
    an extractor formed from one continuous wire, the extractor comprising a first array of engagement panels located at a first longitudinal location formed from the one continuous wire, wherein the first array of engagement panels is configured to extend radially outward from a first coiled eyelet formed from the one continuous wire when expanded within a blood vessel,
    a second array of engagement panels located at a second longitudinal location formed from the one continuous wire, wherein the second array of engagement panels is configured to extend radially outward from a second coiled eyelet formed from the one continuous wire when expanded within the blood vessel,
    a third array of engagement panels located at a third longitudinal location formed from the one continuous wire, wherein the third array of engagement panels is configured to extend radially outward from a third coiled eyelet formed from the one continuous wire when expanded within the blood vessel, the first longitudinal location is spaced apart from the second longitudinal location, wherein the second longitudinal location is spaced apart from the third longitudinal location,
    wherein when expanded within the blood vessel, the first array of engagement panels is configured to be positioned distal to a thrombus, the second array of engagement panels is configured to be positioned within the thrombus, and the third array of engagement panels is configured to be positioned proximal to the thrombus,
    wherein when expanded within the blood vessel, the first array of engagement panels, the second array of engagement panels, and the third array of engagement panels are configured to engage the thrombus between the first array of engagement panels, the second array of engagement panels, and the third array of engagement panels,
    wherein upon retraction of the extractor to remove the thrombus, the engagement panels are configured to act independently and do not stretch or elongate under tension thus securing the thrombus during transit.

2. The device of claim 1, wherein each engagement panel comprises a quadrant of a circle.

3. The device of claim 1, wherein each engagement panel comprises a fan shape.

4. The device of claim 1, wherein each engagement panel comprises two legs that extend radially outward from the respective coiled eyelet.

5. The device of claim 1, wherein each engagement panel comprises an arc configured to scrape along a wall of the blood vessel.

6. The device of claim 5, wherein the arc comprises a smooth and atraumatic edge.

7. The device of claim 1, wherein the first array of engagement panels located at the first longitudinal location form a relatively complete circle configured to be in contact with the blood vessel.

8. The device of claim 1, wherein the first array engagement panels at the first longitudinal location are configured to contact more than 80% of a circumference of a wall of the blood vessel.

9. The device of claim 1, wherein the first array engagement panels at the first longitudinal location are configured to contact more than 90% of a circumference of a wall of the blood vessel.

10. The device of claim 1, wherein the first array of engagement panels located at the first longitudinal location are configured form a generally circular profile similar to a circumference of a wall of the blood vessel.

11. The device of claim 1, further comprising a distal member distal to the first array of engagement panels, wherein the distal member is configured to prevent distal migration of the thrombus.

12. The device of claim 1, wherein the first coiled eyelet, the second coiled eyelet, and the third coiled eyelet are configured to receive a catheter shaft or core wire.

13. A method for removing material from a patient, the method comprising:
    expanding an extractor within a blood vessel, wherein the extractor is formed from one continuous wire, the extractor comprising a first array of engagement panels located at a first longitudinal location formed from the one continuous wire, wherein the first array of engagement panels extends radially outward from a first coiled eyelet formed from the one continuous wire when expanded within the blood vessel,
    a second array of engagement panels located at a second longitudinal location formed from the one continuous wire, wherein the second array of engagement panels extends radially outward from a second coiled eyelet formed from the one continuous wire when expanded within the blood vessel, a third array of engagement panels located at a third longitudinal location formed from the one continuous wire, wherein the third array of engagement panels extends radially outward from a third coiled eyelet formed from the one continuous wire when expanded within the blood vessel, wherein the first location is spaced apart from the second location, wherein the second location is spaced apart from the third location, wherein when expanded within the blood vessel, the first array of engagement panels is positioned distal to a thrombus, the second array of engagement panels is positioned within the thrombus, wherein the third array of engagement panels is positioned proximal to the thrombus, wherein when expanded within the blood vessel, the first array of engagement panels, the second array of engagement panels, and the third array of engagement panels engage the thrombus between the first array of engagement panels, the second array of engagement panels, and the third array of engagement panels, wherein upon retraction of the extractor to remove the thrombus, the engagement panels act independently and do not stretch or elongate under tension thus securing the thrombus during transit.

14. The method of claim 13, wherein the first array of engagement panels located at the first longitudinal location, the second array of engagement panels located at the second longitudinal location, and the third array of engagement panels located at the third longitudinal location engage the thrombus while additional engagement panels are collapsed within a sheath.

15. The method of claim 13, wherein the extractor is pulled proximally and the first array of engagement panels, the second array of engagement panels, and the third array of engagement panels scrape along a surface of the blood vessel.

16. The method of claim 13, wherein the blood vessel comprises a cerebral blood vessel.

17. The method of claim 13, wherein the thrombus is located within the middle cerebral artery.

18. The method of claim 13, wherein the extractor comprises a column strength to move longitudinally within the blood vessel.

19. The method of claim 13, wherein the first array of engagement panels located at the first longitudinal location, the second array of engagement panels located at the second longitudinal location, and the third array of engagement panels located at the third longitudinal location retain their shape when pulled.

20. The method of claim 13, wherein the extractor is expanded approximately equal to a diameter of the blood vessel.

* * * * *